United States Patent
Liu et al.

(10) Patent No.: US 10,696,678 B2
(45) Date of Patent: Jun. 30, 2020

(54) KINASE INHIBITOR, AND PREPARING METHOD AND PHARMACEUTICAL USE THEREOF

(71) Applicant: GAN & LEE PHARMACEUTICALS, Beijing (CN)

(72) Inventors: Wenjian Liu, Beijing (CN); Lei Yin, Beijing (CN); Heng Li, Beijing (CN)

(73) Assignee: GAN & LEE PHARMACEUTICALS, Beijing (CN)

( * ) Notice: Subject to any disclaimer, the term of this patent is extended or adjusted under 35 U.S.C. 154(b) by 0 days.

(21) Appl. No.: 15/768,953

(22) PCT Filed: Oct. 20, 2016

(86) PCT No.: PCT/CN2016/102703
§ 371 (c)(1),
(2) Date: Apr. 17, 2018

(87) PCT Pub. No.: WO2017/071516
PCT Pub. Date: May 4, 2017

(65) Prior Publication Data
US 2018/0305363 A1  Oct. 25, 2018

(30) Foreign Application Priority Data
Oct. 27, 2015 (CN) .......................... 2015 1 0708487

(51) Int. Cl.
| | |
|---|---|
| A61K 31/506 | (2006.01) |
| C07D 487/04 | (2006.01) |
| C07D 519/00 | (2006.01) |
| A61K 31/55 | (2006.01) |
| A61P 9/10 | (2006.01) |
| A61P 31/18 | (2006.01) |
| A61P 35/02 | (2006.01) |
| C07D 471/04 | (2006.01) |

(52) U.S. Cl.
CPC .......... *C07D 487/04* (2013.01); *A61K 31/506* (2013.01); *A61K 31/55* (2013.01); *A61P 9/10* (2018.01); *A61P 31/18* (2018.01); *A61P 35/02* (2018.01); *C07D 471/04* (2013.01); *C07D 519/00* (2013.01)

(58) Field of Classification Search
CPC .............................. C07D 487/04; A61K 31/506
See application file for complete search history.

(56) References Cited

FOREIGN PATENT DOCUMENTS

| | | |
|---|---|---|
| CN | 102264725 A | 11/2011 |
| CN | 104910137 A | 9/2015 |
| CN | 105153119 A | 12/2015 |
| WO | 2015086525 A1 | 6/2015 |
| WO | 2016014904 A1 | 1/2016 |
| WO | 2016173505 A1 | 11/2016 |

OTHER PUBLICATIONS

Golub, Science, vol. 286, p. 531-537. (Year: 1999).*
NCI—Targeted Cancer Therapies, retrieved from http://www.cancer.gov/aboutcancer/treatment/types/targetedtherapies/targetedtherapiesfactsheet on Dec. 8, 2015 (Year: 2015).*
International Search Report and Written Opinion, PCT/CN2016/102703 dated Jan. 10, 2017.

* cited by examiner

*Primary Examiner* — Karen Cheng
(74) *Attorney, Agent, or Firm* — Edwin S. Flores; Daniel J. Chalker; Chalker Flores, LLP

(57) ABSTRACT

The invention provides a compound of Formula I, or its tautomer, mesomer, racemate, enantiomer, diastereoisomer or a mixture thereof, or a pharmaceutically acceptable salt or solvate of the compound of Formula I, its tautomer, mesomer, racemate, enantiomer, or diastereoisomer. Ring A, $R_1$, $R_2$, $R_3$ and $R_4$ are as defined in the specification. The invention further provides a method for preparing the compound of Formula I and their use in the manufacture of a medicament for the treatment of a cell proliferative disorder.

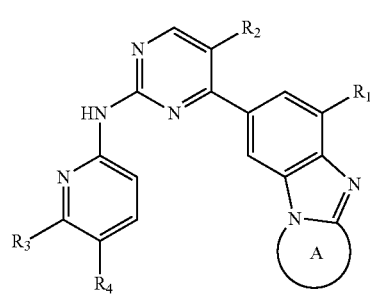

3 Claims, No Drawings

KINASE INHIBITOR, AND PREPARING METHOD AND PHARMACEUTICAL USE THEREOF

CROSS REFERENCE TO RELATED APPLICATIONS

This application is the National Stage of International Application No. PCT/CN2016/102703, filed on Oct. 20, 2016 claiming the priority of CN201510708487.3, filed on Oct. 27, 2015, the content of which is hereby incorporated by reference in its entirety.

FIELD OF THE INVENTION

The present invention belongs to the field of medicine, in particular relates to a series of substituted 2-(pyridin-2-yl) aminopyrimidine compounds having an inhibitory effect on protein kinases, preparation methods and medical uses thereof.

BACKGROUND OF THE INVENTION

Cell cycle is an important part of cell life activity. During normal cell growth, cell cycle progression depends on precise and tight regulation of cell cycle by regulatory factors at all levels. Among the regulatory factors, the core is cyclin dependent kinase (CDK) and its positive and negative regulatory factor—cyclin and cyclin dependent kinase inhibitor (CDI). CDK-cyclin complex formed by cyclin dependent kinase and cyclin is involved in cell growth, proliferation, dormancy or apoptosis. During cell cycle, cyclins are periodically and continuously expressed and degraded, and binds respectively to CDKs transiently activated by them. The promotion and transformation of different phases of the cell cycle are achieved by catalyzing the phosphorylation of different substrates through CDK activity.

Currently, there have been found 13 members of CDK family: CDK1-CDK13; among them, CDK1, CDK2, CDK3, CDK4 and CDK6 are involved in the regulation of cell proliferation, and CDK7, CDK8, CDK9, CDK11, CDK12 and CDK13 are involved in the regulation of transcription.

Cyclin is divided into cyclin A-L, different CDKs associate with different subtypes of cyclin. Among them, cyclin D family (cyclin D1, D2, D3) is expressed in the G1 phase, and binds and activates CDK4 and CDK6 to form a CDK4/6-cyclin D complex, which phosphorylates a series of substrates including retinoblastoma protein (Rb). Phosphorylated Rb releases proteins that bind to and are inhibited by it, mainly transcription factor E2F and others. E2F is activated and initiates transcription of some genes necessary for entry into the S phase (Ma. K., Advances in the Antitumor Effects of CDK4/6 inhibitor, World Notes on Antibiotics, 2013, 34(5): 197-202). If the balance is broken due to various factors, whether the signal for the promotion of cell proliferation is enhanced, or the signal for inhibition of cell proliferation is decreased to some extent, cell proliferation will be out of control, and then the tumor occurs. Studies have found that approximately 80% of human cancers have abnormalities in cyclin D-CDK4/6-INK4-Rb pathway (1. Malumbres M, Barbacid M., To cycle or not to cycle: a critical decision in cancer[J]. Nature Reviews Cancer, 2001, 1(3):222; 2. Shapiro G I., Cyclin-dependent kinase pathways as targets for cancer treatment[J]. J Clinical Oncology, 2006, 24(11):1770). Changes in this pathway accelerate the G1 phase progression, making tumor cell proliferation faster and gain survival advantage. Therefore, intervention on it has become a therapeutic strategy and CDK4/6 has therefore become one of the potential anti-tumor targets.

The advantage of CDK4/6 as an anti-tumor target is that: (1) most of the proliferating cells rely on CDK2 or CDK4/6 to proliferate, but CDK4/6 inhibitor does not exhibit similar cytotoxicity as a "pan-CDK inhibitor", such as myelosuppression and intestinal reaction; (2) preclinical experiments show that increase of the cell level of cyclin D or inactivation of p16INK4a can increase the drug sensitivity of cells, due to the above phenomenon exists in tumor cells relative to normal cells, the drug targeting is increased to some extent.

In addition to inhibition of tumor growth, CDK inhibitors are also used in the treatment of other disorders, such as cardiovascular disorders, including atherosclerosis, vascular restenosis after stent implantation and other cardiovascular disorders caused by abnormal cellular proliferation; diseases caused by fungi, protozoan parasite (such as *Plasmodium falciparum*) and DNA and RNA virus infections, including malaria, AIDS and the like. In addition, studies have also found that CDK inhibitors can also be used for autoimmune diseases (such as psoriasis, rheumatoid arthritis, glomerulonephritis and lupus erythematosus, etc.), to inhibit the proliferation of inflammatory cells.

Since WO9811095 disclosed a series of 2-pyrimidine amine compounds having cell kinase inhibitory activity, many of the compounds believed to have CDK4/6 inhibitory activity have been developed based on such a parent structure in the prior art, some of which have become promising candidate drugs, and even entered the phase III clinical trials. For example, compound PD0332991, disclosed in WO2003062236, is also known as Palbociclib. It has a structure as shown in Formula 1, and is developed by Pfizer Pharmaceuticals Ltd. PD0332991 inhibited CDK4 and CDK6 with IC50 being 11 nmol/L and 15 nmol/L, respectively; whereas in the case of inhibiting CDK2, CDK1 and CDK5, IC50 being greater than 10 μmol/L (Fry D W, Harvey P J, Keller P R, et al. Specific inhibition of cyclin-dependent kinase 4/6 by PD 0332991 and associated antitumor activity in human tumor xenografts [J]. Molecular Cancer Therapeutics, 2004, 3(11): 1427). Compound LEE011 (disclosed in WO2011101409) developed by Novartis Pharmaceuticals has a structure as shown in Formula 2. Compound LY2835219 (disclosed in WO2010075074), also known as Bemaciclib, has a structure as shown in Formula 3; it has been reported to inhibit CDK4 and CDK6 with IC50 being 2 nmol/L and 9.9 nmol/L respectively (Lawrence M. G., S. F. Cai, X. Lin et al. Preclinical characterization of the CDK4/6 inhibitor LY2835219: in-vivo cell cycle-dependent/independent anti-tumor activities alone/in combination with gemcitabine[J]. Invest New Drugs, (2014), 32: 825). Currently, Phase III clinical trials are being conducted by Eli Lilly and Company on LY2835219.

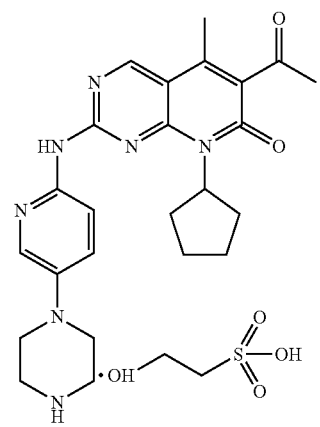

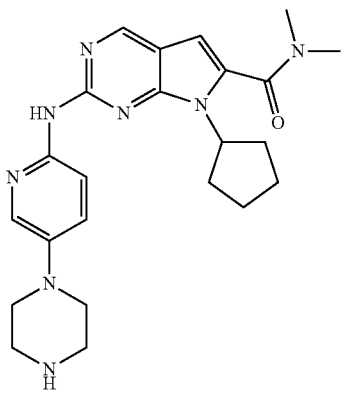

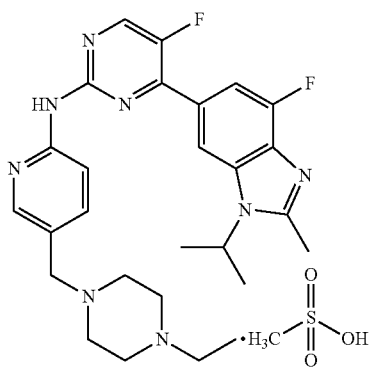

Due to the appearance of these compounds, CDK4/6 has become an explicit anti-tumor target. It is necessary and urgent to develop a CDK4/6 inhibitor with a better selectivity, activity and bioavailability, which may provide more clinical options for the treatment of diseases associated with abnormal cell proliferation, such as cancer.

SUMMARY OF THE INVENTION

For the above problems, an object of the present invention is to provide a novel substituted 2-aminopyrimidine compounds. The compound provided by the invention can selectively inhibit cell cycle protein kinase CDK4/6 and arrest cell cycle in G1 phase, thus can be used for treating cell proliferative disorders.

In order to achieve the above technical effect, the present invention employs the following technical solutions:

In one aspect, the invention provides a compound of Formula I, or its tautomer, mesomer, racemate, enantiomer, diastereoisomer or a mixture thereof, or a pharmaceutically acceptable salt or solvate of the compound of Formula I, its tautomer, mesomer, racemate, enantiomer or diastereoisomer,

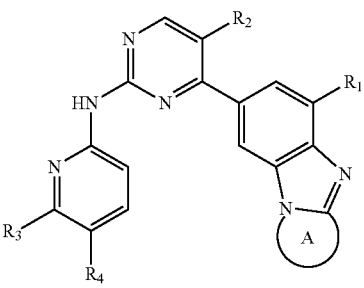

ring A is a 4- to 7-membered heterocyclic ring, which contains no other heteroatom except for a common N shared with imidazole, or ring A further contains one or more heteroatoms selected from N, O or S, and said ring A is substituted by one or more substituents selected from alkyl, cycloalkyl, haloalkyl, alkoxyl, hydroxyl, halogen, cyano, —NR$_5$R$_6$,

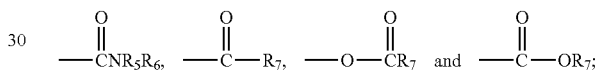

R$_1$ and R$_2$ are each independently selected from hydrogen and halogen, and at least one of R$_1$ and R$_2$ is halogen;

R$_3$ is selected from hydrogen, alkyl, alkoxyl and hydroxyl;

R$_4$ is

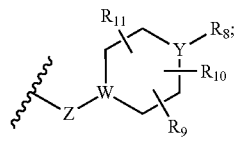

wherein, Z is carbonyl, O, S, imino, sulfonyl or

n is an integer—from 0 to 4; W and Y are each independently C, N, O or S, but W and Y can not both be C, and when Z is O or S, W is C; R$_8$, R$_9$, R$_{10}$ and R$_{11}$ are each independently selected from hydrogen, alkyl, cycloalkyl, hydroxyalkyl, haloalkyl, alkoxyl, hydroxyl, halogen, cyano, —NR$_5$R$_6$,

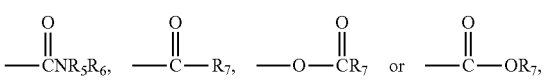

and when Y=N, R$_8$ is not —NR$_5$R$_6$;

or, R$_3$ and R$_4$ together with the C to which they are attached form a 5- to 7-membered heterocyclic ring which contains one or more heteroatoms selected from N, O or S, and said 5- to 7-membered heterocyclic ring is substituted by one or more substituents selected from alkyl, cycloalkyl, haloalkyl, alkoxyl, hydroxyalkyl, hydroxyl, halogen, cyano, —NR$_5$R$_6$,

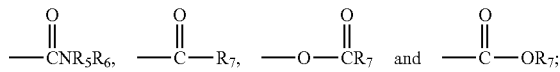

R$_5$, R$_6$ and R$_7$ are each independently selected from hydrogen, alkyl, hydroxyalkyl.

Preferably, ring A is a 5- to 7-membered heterocyclic ring.

More preferably, ring A is a 5- to 7-membered heterocyclic ring, and contains no other heteroatom except for a common N atom shared with imidazole.

Preferably, ring A is substituted by 1-4 substituents selected from alkyl, cycloalkyl, haloalkyl, alkoxyl and hydroxyl.

More preferably, ring A is substituted by 1-2 alkyl groups.

Preferably, ring A and the fused imidazole form the following chemical structures:

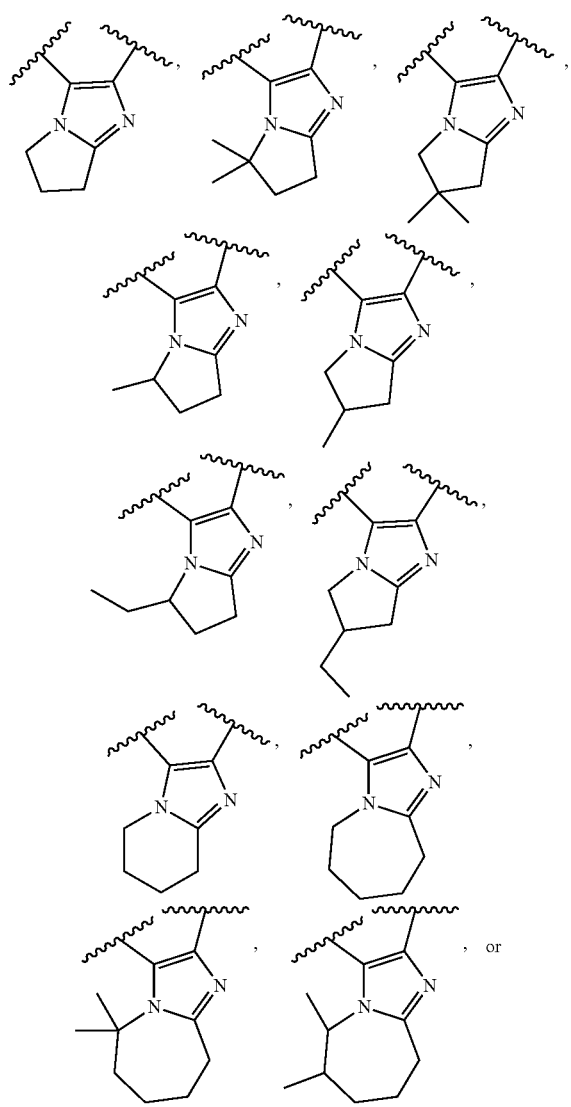

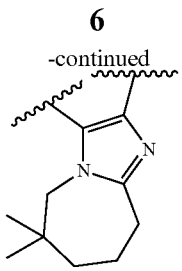

Preferably, R$_1$ and R$_2$ are each independently hydrogen, fluorine or chlorine, and at least one of R$_1$ and R$_2$ is fluorine or chlorine.

More preferably, R$_1$ and R$_2$ are each independently hydrogen or fluorine, and at least one of R$_1$ and R$_2$ is fluorine.

Most preferably, R$_1$ is hydrogen or fluorine, R$_2$ is fluorine.

Preferably, R$_3$ is selected from hydrogen or alkyl.

Preferably, Z is carbonyl, O or

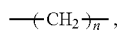

n is an integer from 0 to 4.

More preferably, Z is

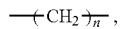

n is an integer from 0 to 2, further preferably, n=0 or 1.

Preferably, W and Y are each independently selected from C or N, but W and Y are not both C.

Preferably, R$_8$, R$_9$, R$_{10}$ and R$_{11}$ are each independently selected from hydrogen, alkyl, cycloalkyl, haloalkyl, hydroxyalkyl, alkoxyl, hydroxyl or —NR$_5$R$_6$, wherein, R$_5$ and R$_6$ are each independently selected from hydrogen and alkyl.

Further preferably, R$_4$ is selected from a substituent of the following structures:

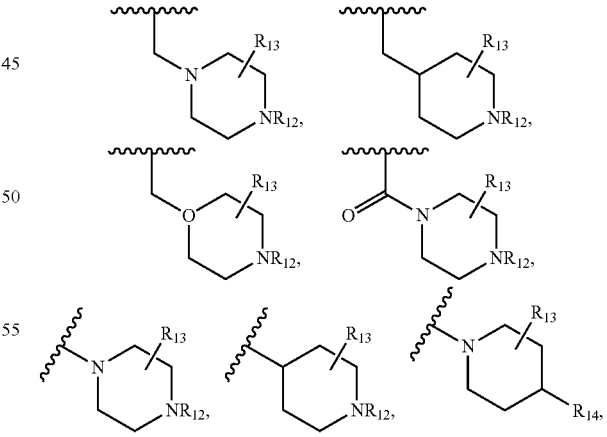

wherein,

R$_{12}$ and R$_{13}$ are each independently selected from hydrogen, alkyl, cycloalkyl, haloalkyl, hydroxyalkyl, alkoxyl or hydroxyl, R$_{14}$ is selected from hydrogen, alkyl, cycloalkyl, haloalkyl, hydroxyalkyl, alkoxyl, hydroxyl or —NR$_5$R$_6$, R$_5$ and R$_6$ are each independently selected from hydrogen and alkyl.

Preferably, $R_3$ and $R_4$ together with the C to which they are attached form a 6-membered heterocyclic ring which contains one or more heteroatoms selected from N, O or S.

More preferably, $R_3$ and $R_4$ together with the C to which they are attached form a 6-membered heterocyclic ring which contains one N atom.

Further preferably, $R_3$ and $R_4$ together with the C to which they are attached form the following chemical structure:

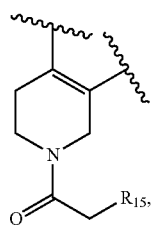

wherein $R_{15}$ is selected from hydroxyl or alkoxyl; more preferably, $R_{15}$ is hydroxyl.

In a preferred embodiment, the present invention further provides a compound of Formula II, III, IV or V, or its tautomer, mesomer, racemate, enantiomer, diastereoisomer or a mixture thereof, or a pharmaceutically acceptable salt or solvate of the compound of Formula II, III, IV or V, its tautomer, mesomer, racemate, enantiomer or diastereoisomer.

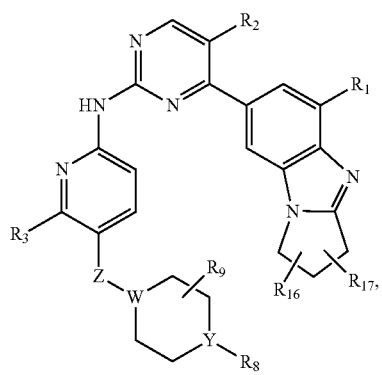

II

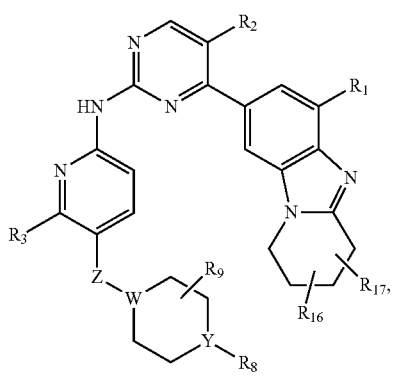

III

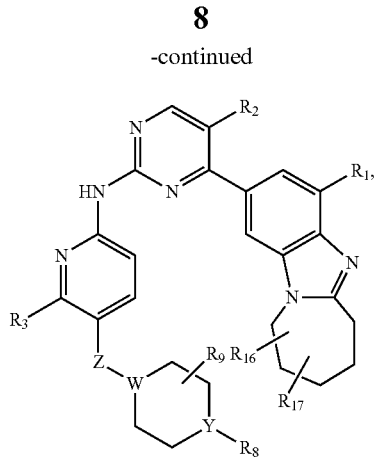

IV

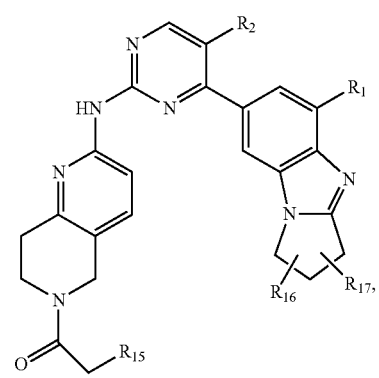

V wherein, Z, W, Y, $R_1$, $R_2$, $R_3$, $R_8$, $R_9$ and $R_{15}$ are as defined above, and $R_{16}$ and $R_{17}$ are each independently selected from hydrogen, alkyl, alkoxyl or haloalkyl.

In a more preferred embodiment, the present invention provides a compound of the following structures, or a pharmaceutically acceptable salt, solvate or polymorph thereof,

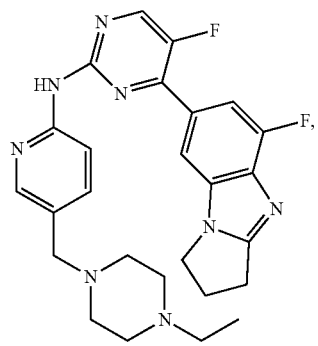

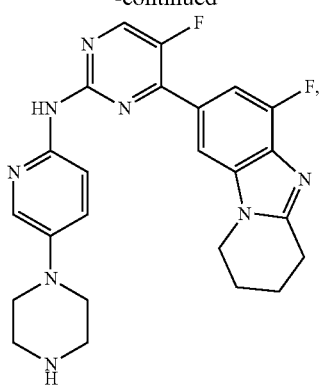
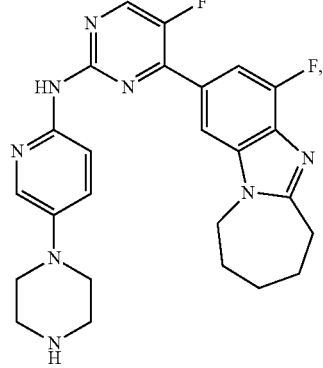
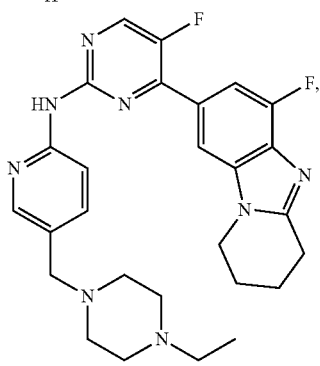
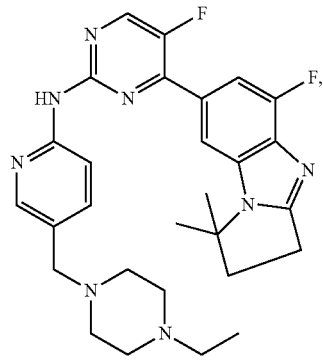
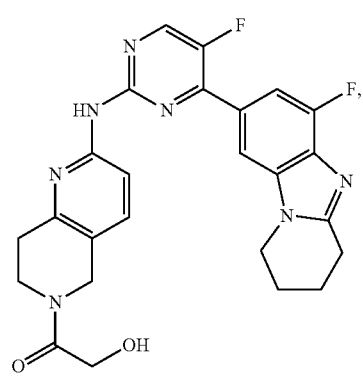
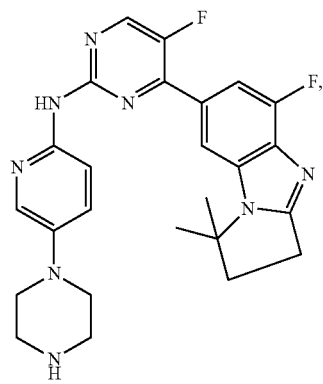
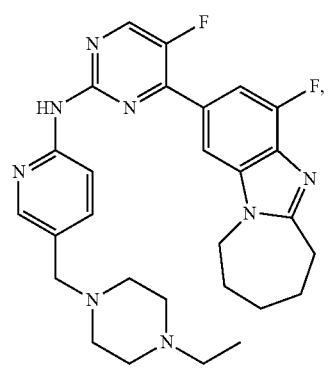
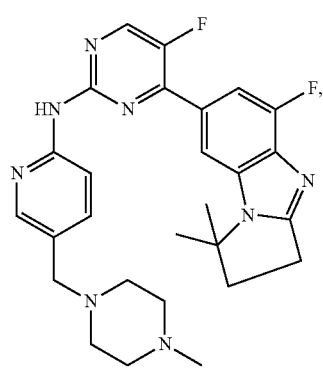

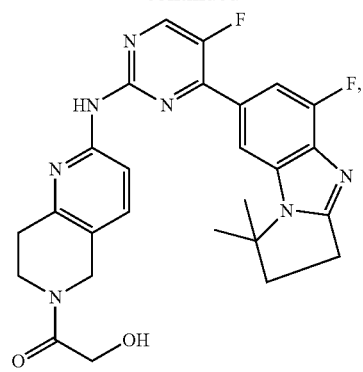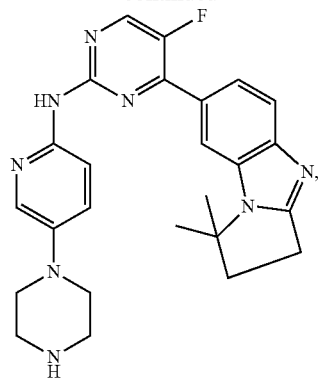

-continued
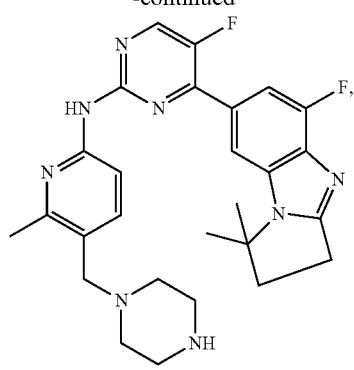
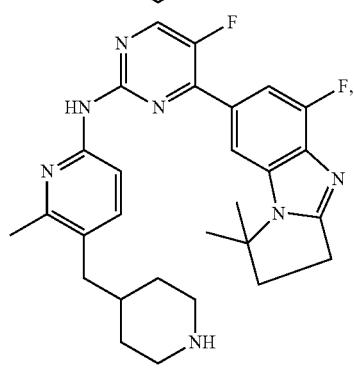
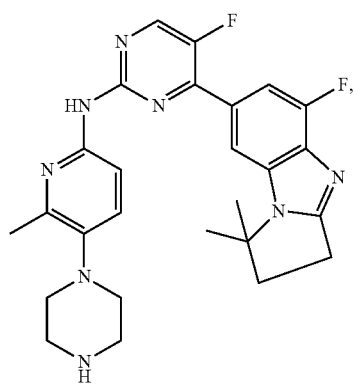
-continued
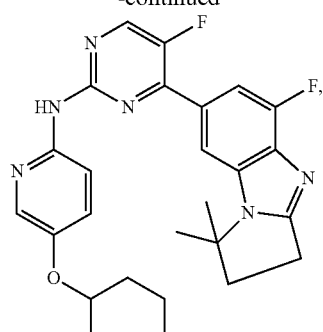
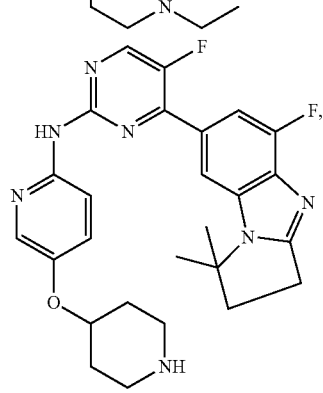
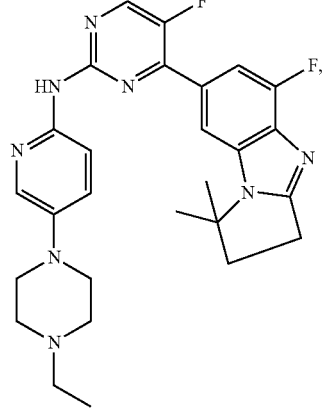

-continued
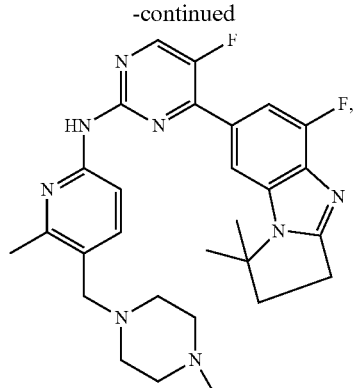
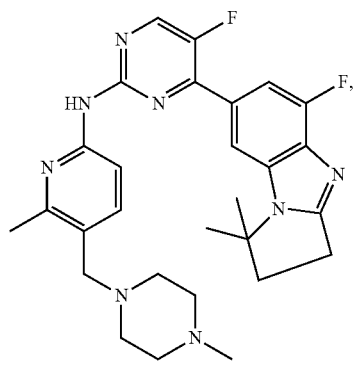
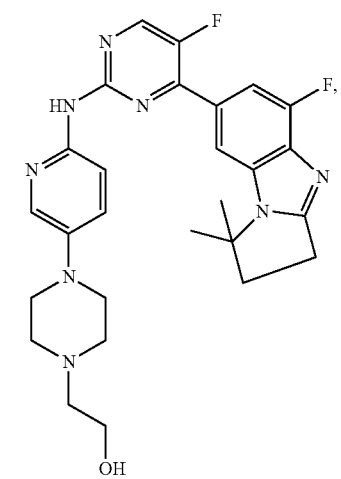
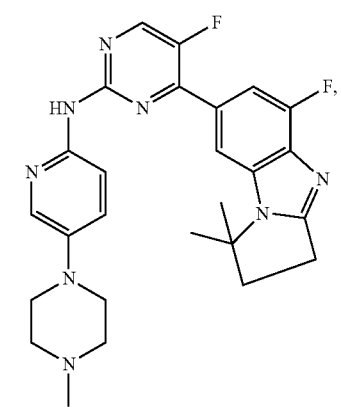
-continued
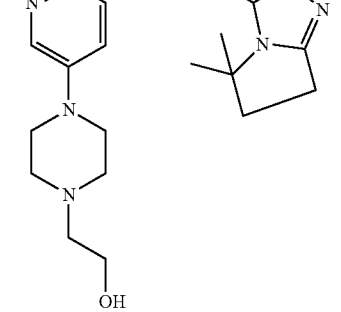
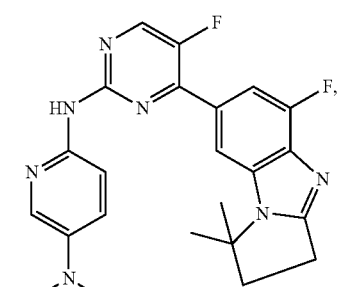

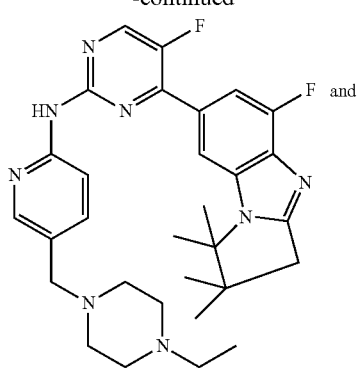
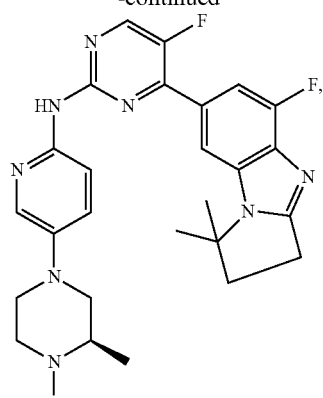
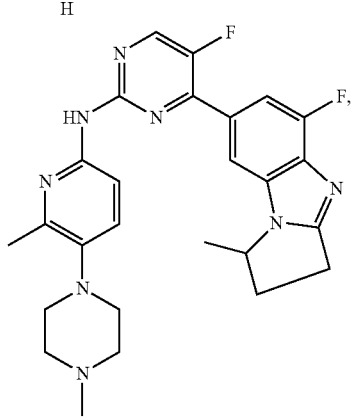
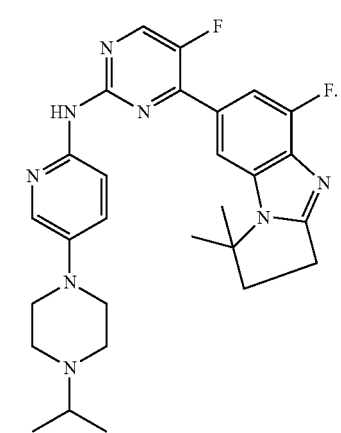
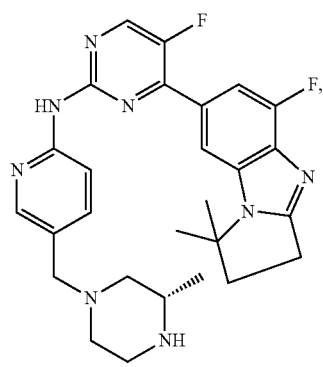
In a still more preferred embodiment, the present invention provides a compound of the following structures, or its tautomer, mesomer, racemate, enantiomer, diastereoisomer or a mixture thereof, or a pharmaceutically acceptable salt or solvate of said compound, its tautomer, mesomer, racemate, enantiomer, or diastereoisomer,
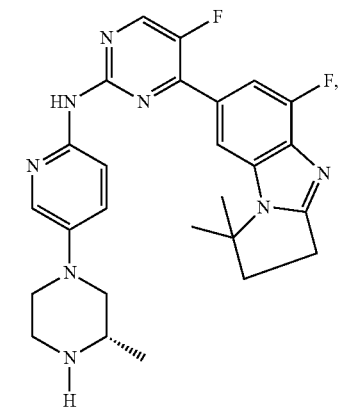
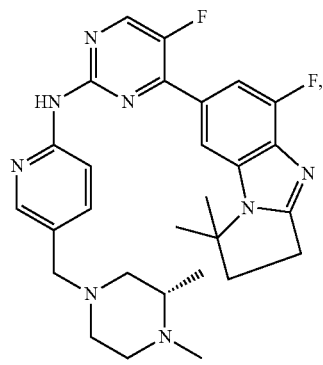

-continued
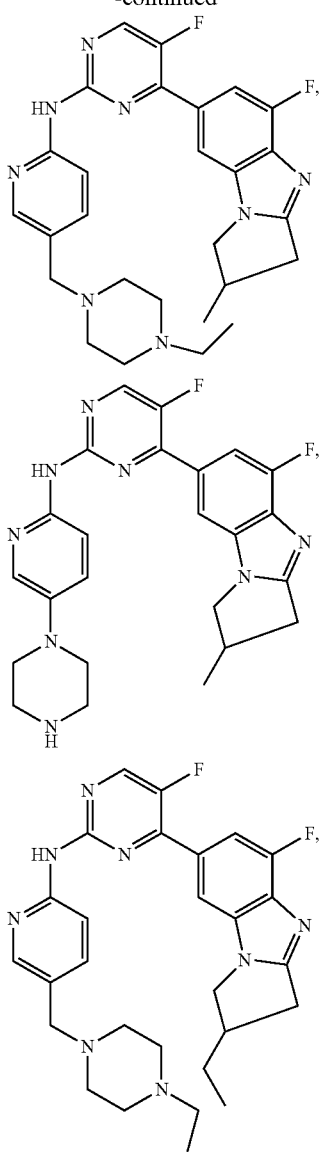
-continued
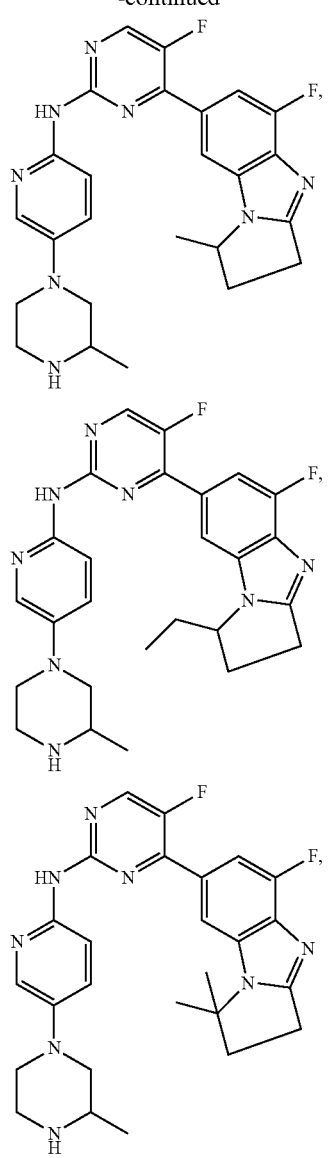
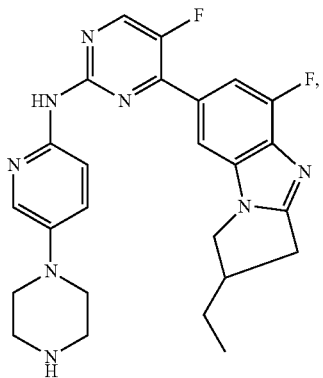
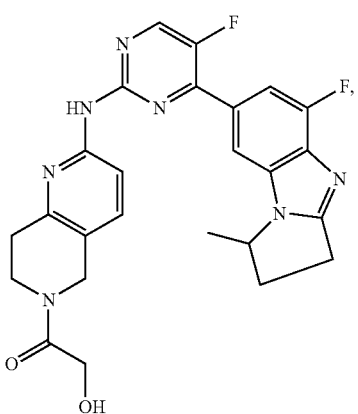

-continued
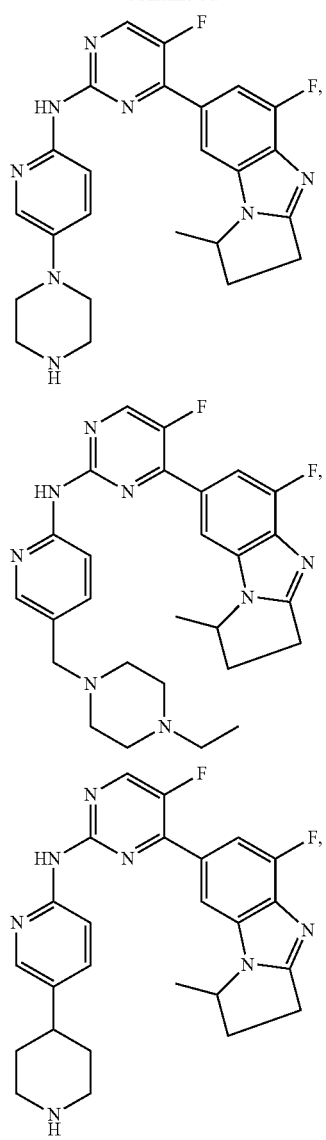
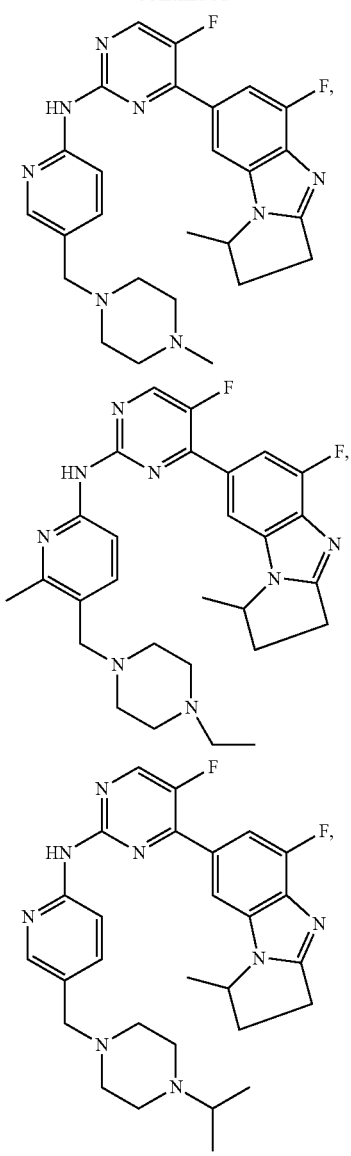
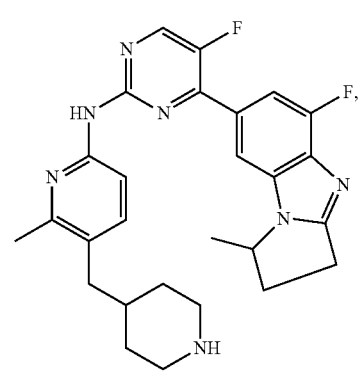
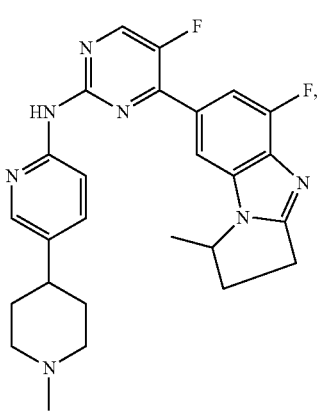

23
-continued
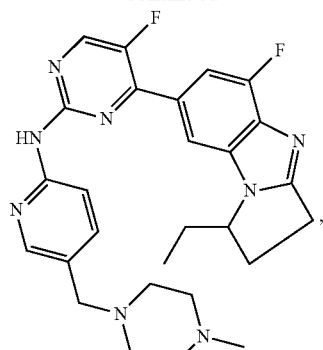
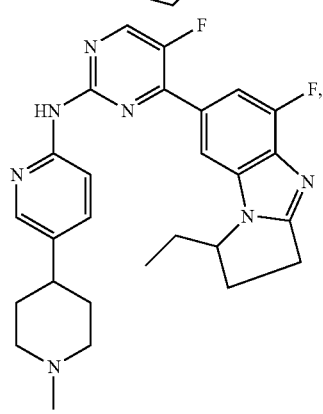
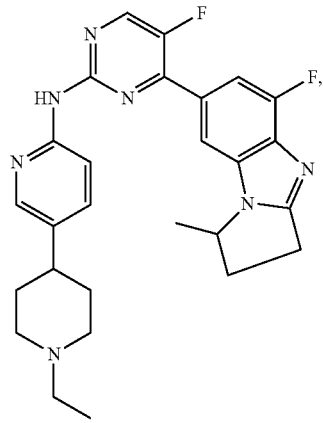
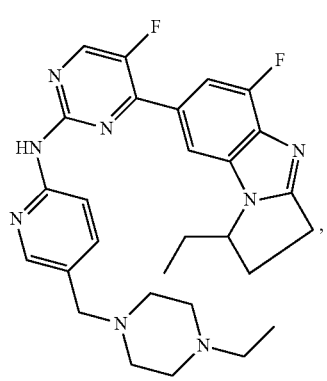
24
-continued
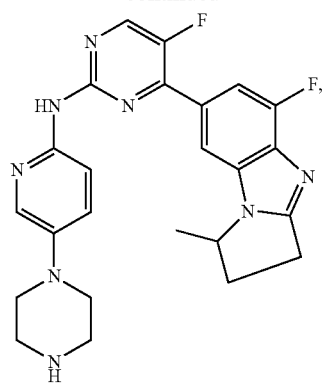
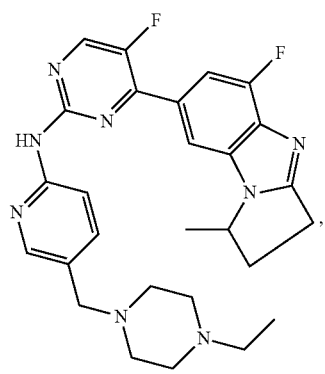 [SMILES: CCC1CCc2nc3c(F)cc(-c4nc(Nc5ccc(CN6CCN(CC)CC6)cn5)ncc4F)cc3n21 ; ","]
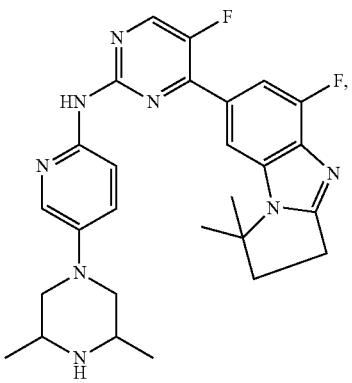
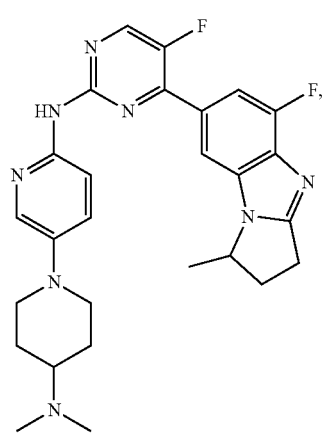

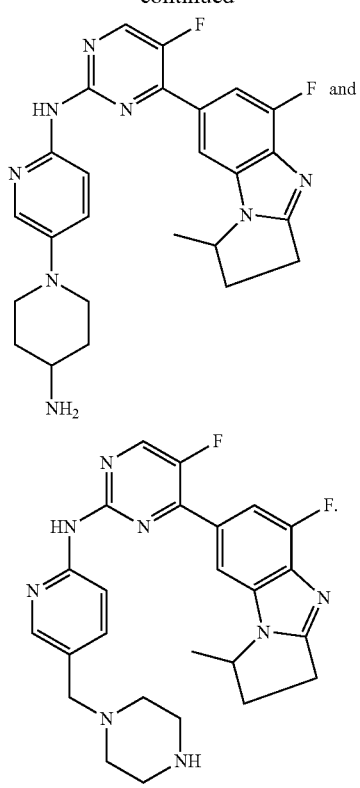

The compounds described in the present invention also include all the above-mentioned isotopically-labeled compounds.

In another aspect, the invention also provides a compound of Formula VI, or its tautomer, mesomer, racemate, enantiomer, diastereoisomer or a mixture thereof, or a pharmaceutically acceptable salt or solvate of the compound of Formula VI, its tautomer, mesomer, racemate, enantiomer, or diastereoisomer,

VI wherein, ring A, $R_1$ and $R_2$ are as defined above, and X is a leaving group or amino.

Preferably, X is halogen or amino, more preferably, X is fluorine, chlorine or amino.

In yet another aspect, the present invention provides a method for preparing the compounds of Formula I-V, comprising a step of obtaining the compound of Formula I via a palladium-catalyzed coupling reaction of a compound of Formula VI and a compound of VII in an aprotic solvent,

VI + VII →

I wherein, ring A, $R_1$, $R_2$, $R_3$ and $R_4$ are as defined above, X and M are each independently a leaving group or amino, only one of X and M is amino, and one of X and M have to be amino;

preferably, said leaving group is halogen;

more preferably, said leaving group is fluorine or chlorine.

Wherein, the above-mentioned preparation method may further include a step of deprotection.

Wherein, the above-mentioned preparation method may further include product separation and purification, and the separation and/or purification may be carried out by methods generally used in organic synthesis, such as filtration, extraction, washing, concentration, chromatography and the like in an appropriate combination.

In still another aspect, the invention provides the use of the compounds of Formula I-V, or their tautomers, mesomers, racemates, enantiomers, diastereoisomers or the mixture thereof, or the pharmaceutically acceptable salts or solvates of the compounds of Formula I-V, their tautomers, mesomers, racemates, enantiomers, or diastereoisomers in the manufacture of a pharmaceutical preparation for the treatment of a cell proliferative disorder.

Preferably, said pharmaceutical preparation comprises a pharmaceutically acceptable excipient.

Preferably, said cell proliferative disorder is cancer in a mammal or a human, more preferably, said cell proliferative disorder is cancer in a human, including malignant solid tumor and malignant non-solid tumor, including but not limited to breast cancer, lung cancer, prostate cancer, leukemia, brain cancer, stomach cancer and the like.

Preferably, said cell proliferative disorder may also refer to AIDS, atherosclerosis and vascular restenosis after stent implantation.

Preferably, the above-mentioned use refers to the use of the compounds of Formula I-V, or their tautomers, mesomers, racemates, enantiomers, diastereoisomers or the mixture thereof, or the pharmaceutically acceptable salts or solvates of the compounds of Formula I-V, their tautomers, mesomers, racemates, enantiomers, or diastereoisomers as the only active ingredient or in combination with an additional biologically active substance in the manufacture of a pharmaceutical preparation for the treatment of a cell proliferative disorder.

Said additional biologically active substance includes, but not limited to anticancer agent, immunosuppressive agent, antiviral agent and the like. Among them, said anticancer agent is selected from alkylating agent (such as cyclophosphamide, ifosfamide, thiotepa, semustine, mechlorethamine hydrochloride, busulfan, chlorambucil, sarcolysine, nitrocaphane, formylmerphalan, carmustine, lomustine, altretamine, dibromannitol and the like), antimetabolic antitumor agent (cytarabine, fluorouracil, methotrexate, hydroxyurea, tegafur, meisoindigotin, mercaptopurine and the like), platinum complex (such as cisplatin, carboplatin, oxaliplatin and the like), antitumor antibiotic (actinomycin D, mitomycin, adriamycin, pingyangmycin, epirubicin, pirarubicin, daunorubicin, bleomycin and the like), antitumor agent derived from natural sources (homoharringtonine and its derivatives, vincristine and its derivatives, hydroxycamptothecine and its derivatives, etoposide and its derivatives, vindesine and its derivatives, vinblastine and its derivatives, vinorelbine bitartrate, paclitaxel and its derivatives, colchicine and its derivatives, elemene and its derivatives and the like), hormonal antineoplastic (such as aminoglutethimide, tamoxifen, dexamethasone, dutasteride, flutamide, gonadorelin, leuprorelin acetate, letrozole and the like), VEGFR or EGFR inhibitor (such as sunitinib, sorafenib, imatinib, gefitinib, erlotinib, vandetinib, pazopanib, lapatinib, canertinib, afatinib, mubritinib, dasatinib, neratinib and the like), anti-tumor antibody (such as trastuzumab, pertuzumab, rituximab, panitumumab, bevacizumab, ipilimumab, ofatumumab, ramucirumab and the like), mTOR inhibitor (such as everolimus, sirolimus, zotarolimus and the like), and so on.

In yet another aspect, the present invention provides a combination for the treatment of a cell proliferative disorder, said combination comprises one or more of compounds selected from the compound of Formula I-V, or its tautomer, mesomer, racemate, enantiomer, diastereoisomer and/or a mixture thereof, or a pharmaceutically acceptable salt or solvate of the compound of Formula I-V, its tautomer, mesomer, racemate, enantiomer, or diastereoisomer.

Preferably, said combination further comprises a pharmaceutically acceptable excipient, and/or said combination is a kit.

In another aspect, the present invention provides a method for treating a cell proliferative disorder, comprises administering via an oral or parenteral route said patient an effective amount of the compound of the present invention, or its tautomer, mesomer, racemate, enantiomer, diastereoisomer and/or the mixture thereof, the pharmaceutically acceptable salt or solvate of the compound, its tautomer, mesomer, racemate, enantiomer, or diastereoisomer, or the combination described above.

Preferably, the above-mentioned method for treating a cell proliferative disorder, comprises administering via an oral or parenteral route an effective amount of the compound of the present invention and an additional biologically active substance to said patient. Said additional biologically active substance includes, but not limited to anticancer agent, immunosuppressive agent, antiviral agent and the like. Among them, said anticancer agent is selected from alkylating agent (such as cyclophosphamide, ifosfamide, thiotepa, semustine, mechlorethamine hydrochloride, busulfan, chlorambucil, sarcolysine, nitrocaphane, formylmerphalan, carmustine, lomustine, altretamine, dibromannitol and the like), antimetabolic antitumor agent (cytarabine, fluorouracil, methotrexate, hydroxyurea, tegafur, meisoindigotin, mercaptopurine and the like), platinum complex (such as cisplatin, carboplatin, oxaliplatin and the like), antitumor antibiotic (actinomycin D, mitomycin, adriamycin, pingyangmycin, epirubicin, pirarubicin, daunorubicin, bleomycin and the like), antitumor agent derived from natural sources (homoharringtonine and its derivatives, vincristine and its derivatives, hydroxycamptothecine and its derivatives, etoposide and its derivatives, vindesine and its derivatives, vinblastine and its derivatives, vinorelbine bitartrate, paclitaxel and its derivatives, colchicine and its derivatives, elemene and its derivatives and the like), hormonal antineoplastic (such as aminoglutethimide, tamoxifen, dexamethasone, dutasteride, flutamide, gonadorelin, leuprorelin acetate, letrozole and the like), VEGFR or EGFR inhibitor (such as sunitinib, sorafenib, imatinib, gefitinib, erlotinib, vandetinib, pazopanib, lapatinib, canertinib, afatinib, mubritinib, dasatinib, neratinib and the like), anti-tumor antibody (such as trastuzumab, pertuzumab, rituximab, panitumumab, bevacizumab, ipilimumab, ofatumumab, ramucirumab and the like), mTOR inhibitor such as everolimus, sirolimus, zotarolimus and the like), and so on.

The oral or parenteral route can refer to delivery to the patient by oral, injection, patch, spray, and one or more of other well-known ways. The effective amount may include an amount effective to treat, reduce, moderate, alleviate or eliminate one or more symptoms of a condition, the condition seeks to be treated or, alternatively, the condition seeks to be avoided, or otherwise there are clinically identifiable and beneficial changes in the condition or effect thereof.

In yet another aspect, the present invention provides a compound, or its tautomer, mesomer, racemate, enantiomer, diastereoisomer or a mixture thereof, or a pharmaceutically acceptable salt or solvate of the compound, its tautomer, mesomer, racemate, enantiomer or diastereoisomer for the treatment of a cell proliferative disorder, characterized in that, the formula of the compound is selected from one or more of Formula I-V.

Preferably, said cell proliferative disorder is cancer in a mammal or a human, more preferably, said cell proliferative disorder is cancer in a human, including malignant solid tumor and malignant non-solid tumor, including but not limited to breast cancer, lung cancer, prostate cancer, leukemia, brain cancer and stomach cancer.

Preferably, said cell proliferative disorder may further be selected from one or more of AIDS, atherosclerosis and vascular restenosis after stent implantation.

In the specification of the present invention, unless otherwise specified, "alkyl" refers to a $C_1$-$C_6$ linear or branched alkyl, preferably a $C_1$-$C_4$ linear or branched alkyl, more preferably methyl, ethyl, propyl or isopropyl. "Alkoxyl" refers to a $C_1$-$C_6$ linear or branched alkoxyl, preferably a $C_1$-$C_4$ linear or branched alkoxyl, more preferably methoxy, ethoxy, propoxy or 2-methylethoxy. "Cycloalkyl" refers to a $C_3$-$C_7$ cycloalkyl which is unsubstituted or substituted by alkyl or alkoxyl, preferably a $C_3$-$C_6$ cycloalkyl which is unsubstituted or substituted by alkyl or alkoxyl, more preferably cyclopropyl, cyclobutyl, methylcyclopropyl, cyclopentyl or cyclohexyl. "Halogen" refers to chlorine or fluorine. "Haloalkyl" refers to a linear or branched $C_1$-$C_6$ alkyl substituted by chlorine or fluorine, preferably a linear or branched $C_1$-$C_4$ alkyl substituted by chlorine or fluorine, more preferably fluoromethyl, difluoromethyl, trifluoromethyl, chloromethyl, dichloromethyl, trichloromethyl, 1-fluoroethyl, 1-chloroethyl, 1-chloropropyl.

Existing researches suggest that the toxicity of CDKs inhibitors is mainly related to their inhibitory effects on CDK1. Therefore, as a CDKs inhibitor, it is desired that the difference between its effects on CDK4/CDK6 and CDK1 is significant, that is, CDK4/CDK6 is selectively inhibited. In a parallel experiment, the compounds of the present invention showed better CDK4/CDK6 selectivity than LY2835219 disclosed in the prior art (disclosed in WO2010075074, also known as Bemaciclib). $IC_{50}$ (CDK4)/$IC_{50}$ (CDK1) and $IC_{50}$ (CDK6)/$IC_{50}$ (CDK1) may reflect the compound's selectivity for CDKs—the smaller the value, the better the selectivity for CDK4/6, indicating the toxicity of the compound regarding pan CDK inhibition may be smaller. For the control compound (LY2835219), $IC_{50}$ (CDK4)/$IC_{50}$ (CDK1)≈0.03, and $IC_{50}$ (CDK6)/$IC_{50}$ (CDK1)≈0.139; all of the compounds of Example 17, 18, 19, 20, 24, 25, 27, 28, 30, 31, 35, 36, 37, 39, 40, 41, 42, 43, 46, 47, 53, 55, 57, 59, 60, 65, 72, 74 of the present invention exhibited better selectivity for CDK4/6 than the control compound, as shown in Table 2 in detail. Pharmacokinetic experiments in rats and mice also showed that the representative compounds of the present invention have good oral absorption, long half-life and significant effect of oral absorption.

BRIEF DESCRIPTION OF THE DRAWINGS

None.

DETAILED DESCRIPTION OF THE INVENTION

The present invention is described below with reference to specific examples. It will be understood by those skilled in the art that these examples are merely illustrative of the invention and do not limit the scope of the invention in any way.

Compound of Formula VI of the present invention is a key intermediate for the synthesis of compound of Formula I, which is obtained via a palladium-catalyzed coupling reaction of the compound of Formula VI and compound of Formula VII in an aprotic solvent.

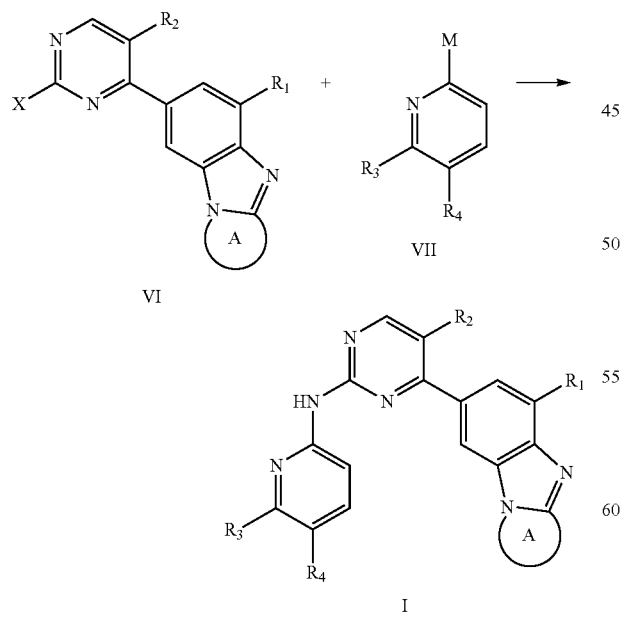

Wherein, the meanings of ring A, $R_1$, $R_2$, $R_3$, $R_4$, X and M are as defined above.

Preferably, ring A is a 5- to 7-membered heterocyclic ring, which contains no other heteroatom except for a common N shared with imidazole, and said ring A is preferably unsubstituted or substituted by 1-2 $C_1$-$C_3$ linear or branched alkyl.

$R_1$ and $R_2$ are each independently hydrogen or fluorine, and at least one of $R_1$ and $R_2$ is fluorine.

$R_3$ is preferably $C_1$-$C_3$ linear or branched alkyl, more preferably methyl or ethyl.

$R_4$ is preferably selected from a substituent of the following structure:

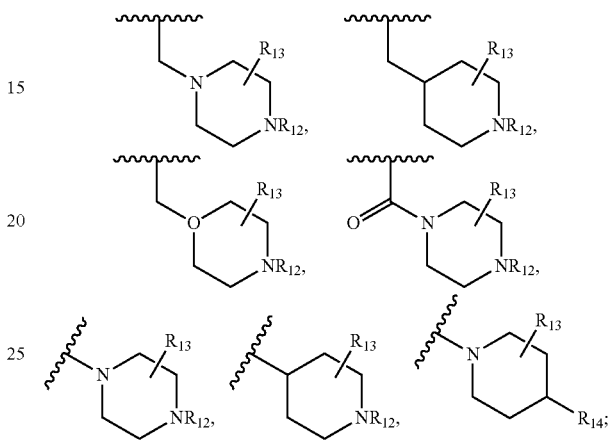

wherein, $R_{12}$ and $R_{13}$ are as defined above, more preferably, $R_{12}$ and $R_{13}$ are each independently selected from hydrogen, $C_1$-$C_3$ linear or branched alkyl, $C_3$-$C_6$ cycloalkyl, $C_1$-$C_3$ linear or branched alkyl substituted by hydroxyl or $C_1$-$C_3$ linear or branched alkyl substituted by halogen; $R_{14}$ is selected from hydrogen, $C_1$-$C_3$ linear or branched alkyl, $C_1$-$C_3$ linear or branched alkyl substituted by halogen or —$NR_5R_6$, $R_5$ and $R_6$ are independently selected from hydrogen, $C_1$-$C_3$ linear or branched alkyl.

or, further preferably, $R_3$ and $R_4$ together with the C to which they are attached form a following chemical structure:

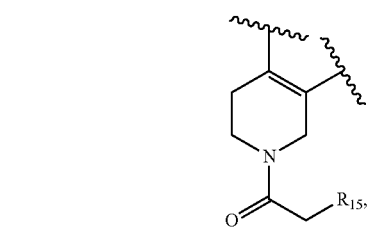

wherein $R_{15}$ is selected from hydroxyl or alkoxyl; further preferably, $R_{15}$ is hydroxyl.

Preferably, X is fluorine or chlorine, M is amino; or X is amino, M is fluorine or chlorine.

The following Examples 1-11 specifically describe the synthesis of compound of Formula VI as a key intermediate, Examples 12-74 specifically describe the synthesis of compounds of Formula I in which the above intermediates are involved.

The experimental methods in the following examples, unless otherwise specified, are conventional methods. The medicinal raw materials, reagent materials and the like used in the following examples are commercially available products, unless otherwise specified.

The above description of the specific embodiments of the present invention does not limit the present invention. Those skilled in the art may make various changes or modifications to the present invention without departing from the spirit of the present invention, which should fall within the scope of the appended claims.

Example 1

7-(2-Chloro-5-fluoropyrimidin-4-yl)-5-fluoro-1,1-dimethyl-2,3-dihydro-1H-benzo[d]pyrrolo[1,2-a]imidazole

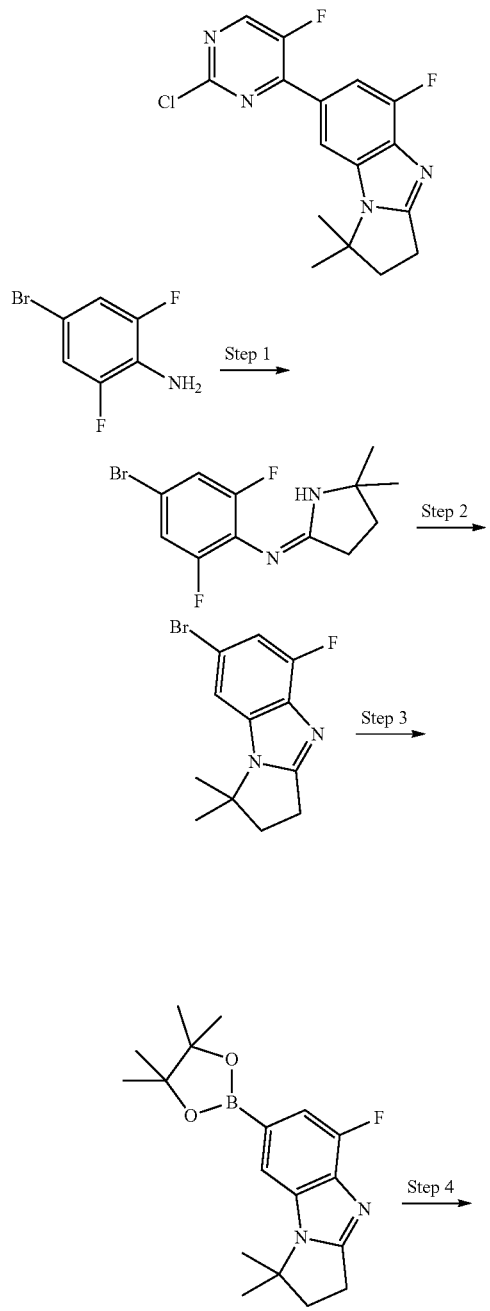

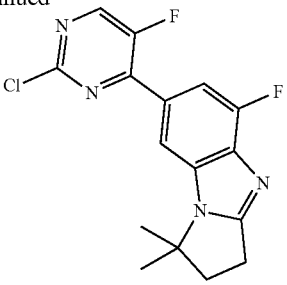

Step 1

(Z)—N-(4-Bromo-2,6-difluorophenyl)-5,5-dimethyl-pyrrolidin-2-imine

To a reaction flask was added 4-bromo-2,6-difluorobenzene (4.5 g, 21.6 mmol), 4,4-dimethylpyrrolidin-2-one (4.9 g, 43.3 mmol), triethylamine (3.3 g, 32.7 mmol), phosphorous oxychloride (5 g, 32.4 mmol) and toluene (100 mL), and the mixture was stirred for 3 hours under reflux to give rise to a reaction. The resulting mixture was cooled to room temperature and concentrated under reduced pressure. Dichloromethane (100 mL) was added, and the organic phase was washed with saturated aqueous sodium carbonate solution (30 mL×2). The organic layer was dried over anhydrous sodium sulfate, filtered with suction, and the filtrate was concentrated under reduced pressure. The resulting residue was purified by column chromatography on silica gel (DCM/MeOH=50/1) to give the title compound as a yellow solid (3.2 g, yield 49%).

MS m/z (ESI): 303.0, 305.0 (M+H)

Step 2

7-Bromo-5-fluoro-1,1-dimethyl-2,3-dihydro-1H-benzo[d]pyrrolo[1,2-a]imidazole

To a microwave reaction flask was added (Z)—N-(4-bromo-2,6-difluorophenyl)-5,5-dimethylpyrrolidin-2-imine (3.03 g, 10 mmol, prepared in Step 1), cesium carbonate (6.50 g, 20 mmol) and N,N-dimethylacetamide (30 mL), and the mixture was stirred at 210° C. for 30 minutes in the microwave to give rise to a reaction. The reaction liquid was cooled to room temperature, ethyl acetate (150 mL) was added, and the organic phase was washed with saturated sodium chloride (30 mL×3). The organic layer was dried over anhydrous sodium sulfate, filtered with suction, and the filtrate was concentrated under reduced pressure. The resulting residue was purified by column chromatography on silica gel (EtOAc/PE=1/1) to give the title compound as a yellow solid (1.50 g, yield 53%).

MS m/z (ESI): 283.0, 285.0 (M+H)

Step 3

5-Fluoro-1,1-dimethyl-7-(4,4,5,5-tetramethyl-1,3,2-dioxaborolan-2-yl)-2,3-dihydro-1H-benzo[d]pyrrolo[1,2-a]imidazole To a reaction flask was added 7-bromo-5-fluoro-1,1-dimethyl-2,3-dihydro-1H-benzo[d]pyrrolo[1,2-a]imidazole (1.5 g, 5.4 mmol, prepared in Step 2), bis(pinacolato)diboron (1.70 g, 6.5 mmol), Pd(dppf)Cl$_2$ (490 mg, 0.60 mmol), potassium acetate (1.10 g, 11 mmol) and dioxane (50 mL). The mixture was stirred at 100° C. for 12 hours under a nitrogen atmosphere to give rise to a reaction. The reaction liquid was cooled to room temperature and concentrated under reduced pressure. The resulting residue was purified by column chromatography on silica gel (EtOAc/PE=1/2) to give the title compound as a yellow solid (1.20 g, yield 67%).

MS m/z (ESI): 330.9 (M+H)

Step 4

7-(2-Chloro-5-fluoropyrimidin-4-yl)-5-fluoro-1,1-dimethyl-2,3-dihydro-1H-benzo[d]pyrrolo[1,2-a]imidazole To a reaction flask was added 5-fluoro-1,1-dimethyl-7-(4,4,5,5-tetramethyl-1,3,2-dioxaborolan-2-yl)-2,3-dihydro-1H-benzo[d]pyrrolo[1,2-a]imidazole (1.2 g, 3.6 mmol, prepared in Step 3), 2,4-dichloro-5-fluoropyrimidine (0.664 g, 4.0 mmol), Pd(PPh$_3$)$_2$Cl$_2$ (282 mg, 0.40 mmol), sodium carbonate (763 mg, 7.2 mmol) and DME/H$_2$O (40 mL/10 mL). The mixture was stirred at 80° C. for 3 hours under a nitrogen atmosphere to give rise to a reaction. The reaction liquid was cooled to room temperature and filtered with suction. The filtrate was concentrated in vacuo, and the resulting residue was purified by column chromatography on silica gel (EtOAc/PE=1/3) to give the title compound as a white solid (0.51 g, yield 42%).

MS m/z (ESI): 334.9 (M+H)

Example 2

7-(2-Chloro-5-fluoropyrimidin-4-yl)-5-fluoro-1-methyl-2,3-dihydro-1H-benzo[d]pyrrolo[1,2-a]imidazole

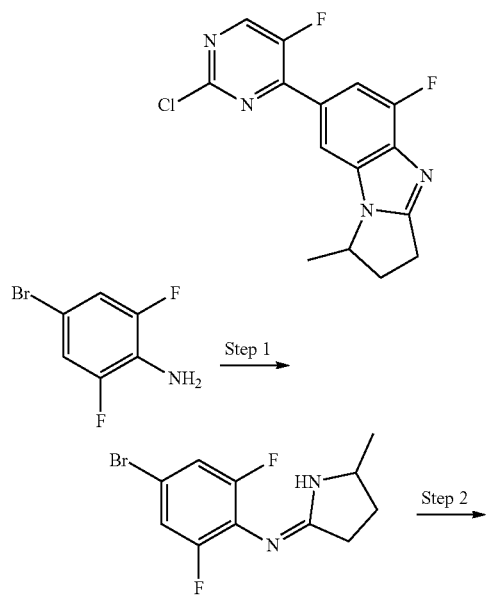

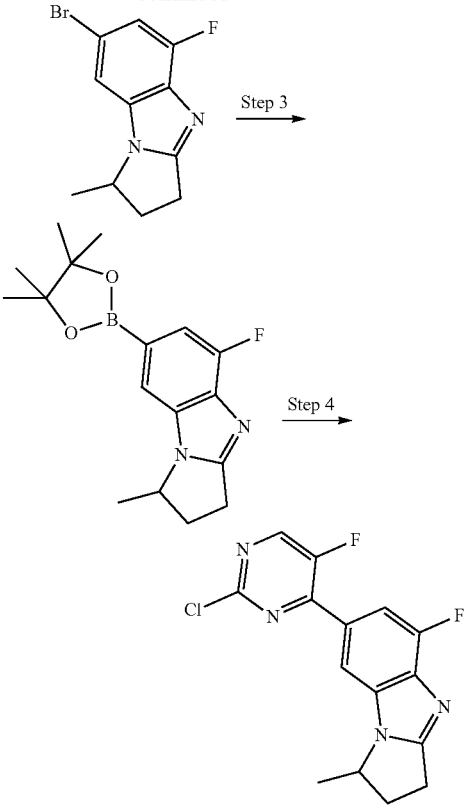

Step 1

(Z)—N-(4-Bromo-2,6-difluorophenyl)-5-methylpyrrolidin-2-imine

To a reaction flask was added 4-bromo-2,6-difluorobenzene (5 g, 24 mmol), 5-methylpyrrolidin-2-one (4.8 g, 48 mmol), triethylamine (7.2 g, 72 mmol), phosphorous oxychloride (11 g, 72 mmol) and toluene (50 mL), and the mixture was stirred for 3 hours under reflux to give rise to a reaction. The resulting mixture was cooled to room temperature and concentrated under reduced pressure. Dichloromethane (100 mL) was added, and the organic phase was washed with saturated aqueous sodium carbonate solution (50 mL×2). The organic layer was dried over anhydrous sodium sulfate, filtered with suction, and the filtrate was concentrated under reduced pressure. The resulting residue was purified by column chromatography on silica gel (DCM/MeOH=50/1) to give the title compound as a yellow solid (3 g, yield 43%).

MS m/z (ESI): 289.15 (M+H)

Step 2

7-Bromo-5-fluoro-1-methyl-2,3-dihydro-1H-benzo[d]pyrrolo[1,2-a]imidazole

To a microwave reaction flask was added (Z)—N-(4-bromo-2,6-difluorophenyl)-5-methylpyrrolidin-2-imine (2.89 g, 10 mmol), cesium carbonate (6.5 g, 20 mmol) and N,N-dimethylacetamide (20 mL), and the mixture was stirred for 2 hours in a microwave at 210° C. to give rise to a reaction. The reaction liquid was cooled to room temperature, ethyl acetate (150 mL) was added, and the organic phase was washed with saturated sodium chloride (100 mL×3). The organic layer was dried over anhydrous sodium sulfate, filtered with suction, and the filtrate was concentrated under reduced pressure. The resulting residue was purified by column chromatography on silica gel (EtOAc/PE=1/1) to give the title compound as a yellow solid (2.1 g, yield 78%).

MS m/z (ESI): 270.14 (M+H)

Step 3

5-Fluoro-1-methyl-7-(4,4,5,5-tetramethyl-1,3,2-dioxaborolan-2-yl)-2,3-dihydro-1H-benzo[d]pyrrolo[1,2-a]imidazole To a reaction flask was added 7-bromo-5-fluoro-1-methyl-2,3-dihydro-1H-benzo[d]pyrrolo[1,2-a]imidazole (1.5 g, 5.57 mmol, prepared in Step 2), bis(pinacolato)diboron (1.3 g, 5.57 mmol), Pd(dppf)Cl₂ (490 mg, 0.60 mmol), potassium acetate (1.10 g, 11 mmol) and dioxane (50 mL). The mixture was stirred at 100° C. for 12 hours under a nitrogen atmosphere to give rise to a reaction. The reaction liquid was cooled to room temperature and concentrated under reduced pressure. The resulting residue was purified by column chromatography on silica gel (EtOAc/PE=1/1) to give the title compound as a white solid (0.83 g, yield 47%).

MS m/z (ESI): 317.2 (M+H)

Step 4

7-(2-chloro-5-fluoropyrimidin-4-yl)-5-fluoro-1-methyl-2,3-dihydro-1H-benzo[d]pyrrolo[1,2-a]imidazole To a reaction flask was added 5-fluoro-1-methyl-7-(4,4,5,5-tetramethyl-1,3,2-dioxaborolan-2-yl)-2,3-dihydro-1H-benzo[d]pyrrolo[1,2-a]imidazole (0.83 g, 2.63 mmol, prepared in Step 3), 2,4-dichloro-5-fluoropyrimidine (0.44 g, 2.63 mmol), Pd(PPh₃)₄ (440 mg, 0.26 mmol), K₃PO₄ (1.1 g, 5.2 mmol) and DME/H₂O (40 mL/10 mL). The mixture was stirred at 100° C. for 12 hours under a nitrogen atmosphere to give rise to a reaction. When the reaction was complete, the resulting mixture was cooled to room temperature. Water (50 mL) was added, and the aqueous phase was extracted with ethyl acetate (50 mL×3). The organic layers were combined, washed with saturated sodium chloride (50 mL×3) and filtered with suction. The filtrate was dried over anhydrous sodium sulfate and concentrated in vacuo. The resulting residue was purified by column chromatography on silica gel (EtOAc/PE=1/1) to give the title compound as a white solid (0.3 g, yield 36%).

MS m/z (ESI): 321.75 (M+H)

Example 3

7-(2-Chloro-5-fluoropyrimidin-4-yl)-1-ethyl-5-fluoro-2,3-dihydro-1H-benzo[d]pyrrolo[1,2-a]imidazole

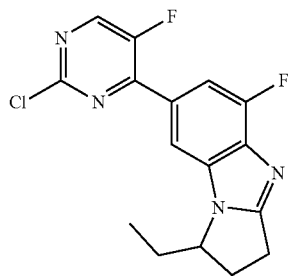 [SMILES: CCC1CCc2nc3c(F)cc(-c4nc(Cl)ncc4F)cc3n21]

The title compound was obtained by a procedure similar to those described in Example 1, using 5-ethylpyrrolidin-2-one as the starting material.

Example 4

7-(2-Chloro-5-fluoropyrimidin-4-yl)-5-fluoro-2,2-dimethyl-2,3-dihydro-1H-benzo[d]pyrrolo[1,2-a]imidazole

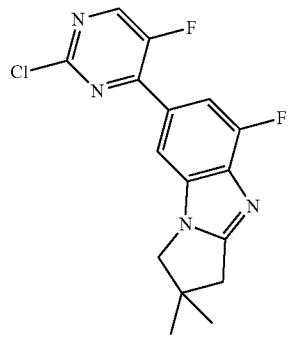 [SMILES: CC1(C)Cc2nc3c(F)cc(-c4nc(Cl)ncc4F)cc3n2C1]

The title compound was obtained by a procedure similar to those described in Example 1, using 4,4-dimethylpyrrolidin-2-one as the starting material.

Example 5

7-(2-Chloro-5-fluoropyrimidin-4-yl)-5-fluoro-2-methyl-2,3-dihydro-1H-benzo[d]pyrrolo[1,2-a]imidazole

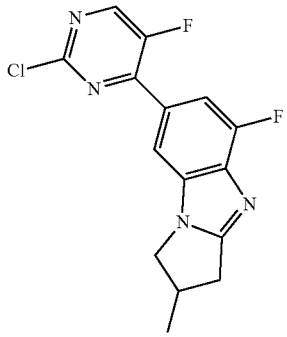 [SMILES: CC1Cc2nc3c(F)cc(-c4nc(Cl)ncc4F)cc3n2C1]

The title compound was obtained by a procedure similar to those described in Example 1, using 4-methylpyrrolidin-2-one as the starting material.

Example 6

7-(2-Chloro-5-fluoropyrimidin-4-yl)-5-fluoro-2-ethyl-2,3-dihydro-1H-benzo[d]pyrrolo[1,2-a]imidazole

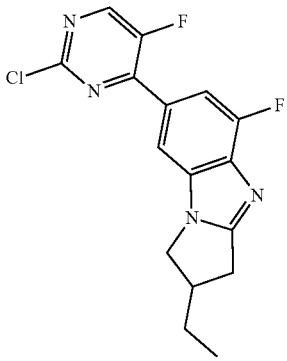 [SMILES: CCC1Cc2nc3c(F)cc(-c4nc(Cl)ncc4F)cc3n2C1]

The title compound was obtained by a procedure similar to those described in Example 1, using 4-ethylpyrrolidin-2-one as the starting material.

Example 7

8-(2-Chloro-5-fluoropyrimidin-4-yl)-6-fluoro-1,2,3,4-tetrahydrobenzo[4,5]imidazo[1,2-a]pyridine

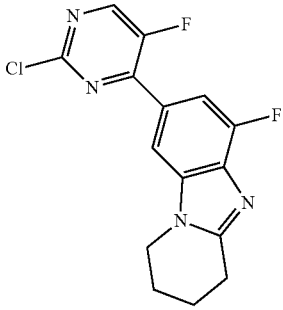 [SMILES: Fc1cnc(Cl)nc1-c1cc(F)c2nc3n(c2c1)CCCC3]

The title compound was obtained by a procedure similar to those described in Example 1, using piperidine-2-one as the starting material.

Example 8

2-(2-Chloro-5-fluoropyrimidin-4-yl)-4-fluoro-7,8,9,10-tetrahydro-6H-benzo[4,5]imidazo[1,2-a]azepane

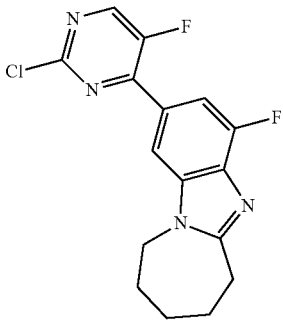 [SMILES: Fc1cnc(Cl)nc1-c1cc(F)c2nc3n(c2c1)CCCCC3]

The title compound was obtained by a procedure similar to those described in Example 1, using caprolactam as the starting material.

Example 9

7-(2-Chloropyrimidin-4-yl)-5-fluoro-1,1-dimethyl-2,3-dihydro-1H-benzo[d]pyrrolo[1,2-a]imidazole

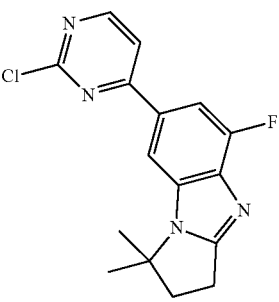 [SMILES: CC1(C)CCc2nc3c(F)cc(-c4ccnc(Cl)n4)cc3n21]

The title compound was obtained by a procedure similar to those described in Example 1, using 2,4-dichloropyrimidine as the starting material in Step 4.

Example 10

7-(2-Chloro-5-fluoropyrimidin-4-yl)-1,1-dimethyl-2,3-dihydro-1H-benzo[d]pyrrolo[1,2-a]imidazole

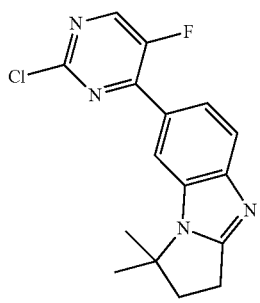 [SMILES: CC1(C)CCc2nc3ccc(-c4nc(Cl)ncc4F)cc3n21]

The title compound was obtained by a procedure similar to those described in Example 1, using 4-bromo-2-fluoroaniline as the starting material.

Example 11

7-(2-Chloro-5-fluoropyrimidin-4-yl)-5-fluoro-2,3-dihydro-1H-benzo[d]pyrrolo[1,2-a]imidazole

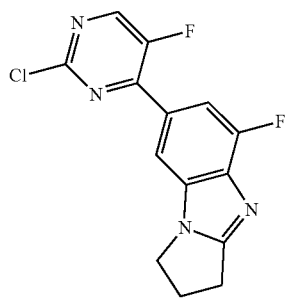 [SMILES: Fc1cnc(Cl)nc1-c1cc(F)c2nc3n(c2c1)CCC3]

The title compound was obtained by a procedure similar to those described in Example 1, using pyrrolidin-2-one as the starting material.

Example 12

N-(5-((4-Ethylpiperazin-1-yl)methyl)pyridin-2-yl)-5-fluoro-4-(5-fluoro-2,3-dihydro-1H-benzo[d]pyrrolo[1,2-a]imidazol-7-yl)pyrimidin-2-amine

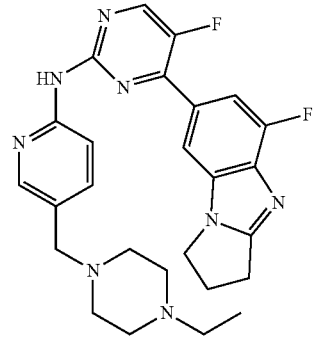

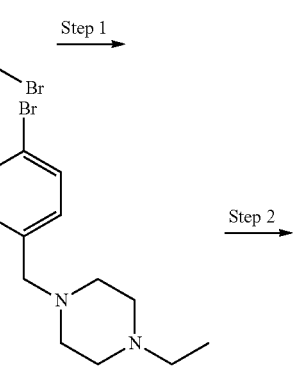

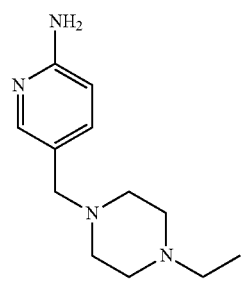

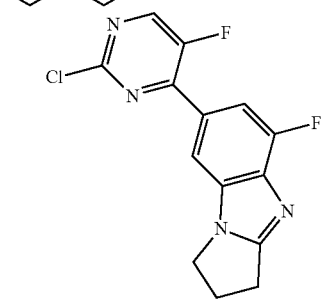

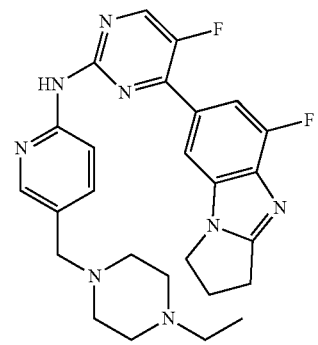

Step 1

1-((6-Bromopyridin-3-yl)methyl)-4-ethylpiperazine

To a reaction flask was added 1-ethylpiperazine (1.8 g, 16 mmol), 6-bromo-pyridine-3-carboxaldehyde (3 g, 16 mmol) and dichloromethane (50 mL), and sodium triacetoxyborohydride (3.7 g, 17.5 mmol) was added in portions under stirring. The mixture was stirred at room temperature for 12 hours to give rise to a reaction. To the reaction liquid were added dichloromethane (20 mL) and aqueous sodium hydroxide solution (2N, 15 mL). The aqueous phase was extracted with dichloromethane (20 mL×2) and the phases were separated. The organic phases were combined, washed with saturated sodium chloride solution (20 mL×2), dried over anhydrous sodium sulfate and filtered with suction. The filtrate was concentrated under reduced pressure to give the title compound as a yellow oil (3.6 g, yield 80%).

MS m/z (ESI): 285.2 (M+H)

Step 2

5-((4-Ethylpiperazin-1-yl)methyl)pyridin-2-amine

To a reaction flask was added 1-((6-bromopyridin-3-yl)methyl)-4-ethylpiperazine (2.84 g, 10 mmol, prepared in Step 1), 2-(dicyclohexylphosphino) biphenyl (0.7 g, 2 mmol), Pd$_2$(dba)$_3$ (915 mg, 1 mmol) and anhydrous toluene (30 mL). After the mixture was purged three times with nitrogen, LiHMDS (1M in THF, 20 mL, 20 mmol) was added. The mixture was stirred at 80° C. for 12 hours under a nitrogen atmosphere to give rise to a reaction. The resulting mixture was cooled to room temperature, water (50 mL) was added, and the aqueous phase was extracted with ethyl acetate (50 mL×2). The organic phases were combined, washed with saturated sodium chloride solution (20 mL×2), dried over anhydrous sodium sulfate and filtered with suction. The resulting residue was purified by column chromatography (DCM/MeOH/Et$_3$N=10:1:0.5%) to give the title compound as a brown solid (1.34 g, yield 61%).

MS m/z (ESI): 221.3 (M+H)

Step 3

N-(5-((4-Ethylpiperazin-1-yl)methyl)pyridin-2-yl)-5-fluoro-4-(5-fluoro-2,3-dihydro-1H-benzo[d]pyrrolo[1,2-a]imidazol-7-yl)pyrimidin-2-amine To a microwave reaction flask was added 7-(2-chloro-5-fluoropyrimidin-4-yl)-5-fluoro-2,3-dihydro-1H-benzo[d]pyrrolo[1,2-a]imidazole (100 mg, 0.33 mmol, prepared in Example 11), 5-((4-ethylpiperazin-1-yl)methyl)pyridin-2-amine (73 mg, 0.33 mmol, prepared in Step 2), sodium tert-butoxide (64 mg, 0.66 mmol), Pd$_2$(dba)$_3$ (30 mg, 0.033 mmol), XantPhos (38 mg, 0.066 mmol) and anhydrous 1,4-dioxane (5 mL), and the mixture was reacted for 1 hour in a microwave at 150° C. The resulting mixture was cooled to room temperature, water (10 mL) was added, and the aqueous phase was extracted with ethyl acetate (40 mL×3). The organic phases were combined, washed with saturated sodium chloride solution (40 mL×2), dried over anhydrous sodium sulfate and filtered with suction. The filtrate was concentrated under reduced pressure, and the resulting residue was purified by column chromatography (DCM/MeOH=10:1) to give the title compound as a yellow solid (15 mg, yield 9.3%).

$^1$HNMR (DMSO, 400 MHz), δ 9.97 (s, 1H), 8.69 (d, J=3.6 Hz, 1H), 8.19 (s, 1H), 8.17 (s, 1H), 8.07 (s, 1H), 7.78-7.70 (m, 2H), 4.24 (t, J=6.8 Hz, 2H), 3.44 (s, 2H), 3.05-3.01 (m, 2H), 2.71-2.68 (m, 2H), 2.39-2.33 (m, 8H), 0.98 (t, J=7.2 Hz, 3H)

MS m/z (ESI): 491.1 (M+H)

Example 13

5-Fluoro-4-(6-fluoro-1,2,3,4-tetrahydrobenzo[4,5]imidazo[1,2-a]pyridin-8-yl)-N-(5-(piperazin-1-yl)pyridin-2-yl)pyrimidin-2-amine

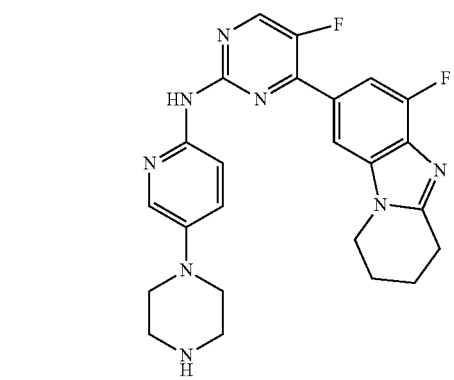

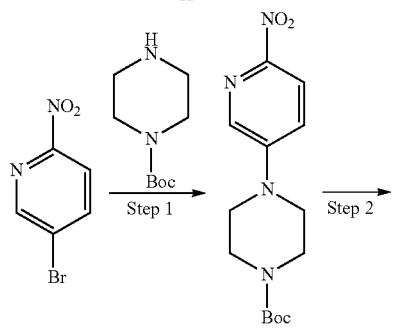

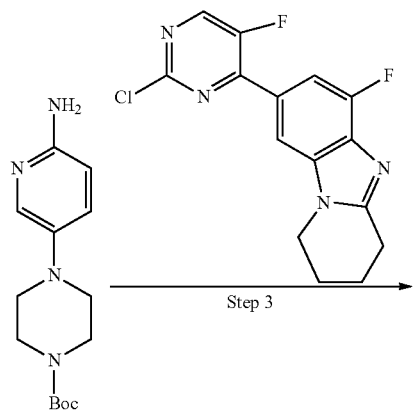

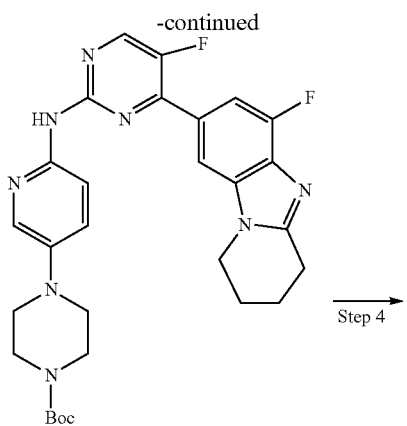

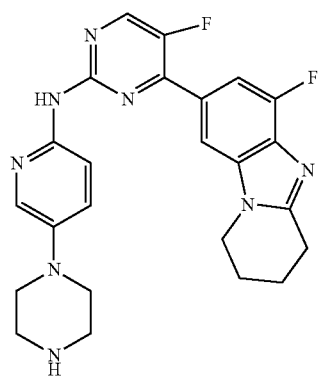

Step 1 tert-Butyl 4-(6-nitropyridin-3-yl)piperazine-1-carboxylate

To a reaction flask was added 5-bromo-2-nitropyridine (4.93 g, 24.3 mmol), tert-butyl piperazine-1-carboxylate (4.97 g, 26.7 mmol), diisopropylethylamine (4.65 mL, 26.7 mmol) and acetonitrile (60 mL). The mixture was stirred at 110° C. for 72 hours to give rise to a reaction. The resulting mixture was cooled to room temperature and concentrated under reduced pressure. The resulting residue was purified by column chromatography (DCM/MeOH=10/1) to give the title compound as a white solid (4.5 g, yield 60%).

MS m/z (ESI): 309.3 (M+H)

Step 2 tert-Butyl 4-(6-aminopyridin-3-yl)piperazine-1-carboxylate

To a reaction flask was added tert-butyl 4-(6-nitropyridin-3-yl)piperazine-1-carboxylate (3.4 g, 11 mmol, prepared in Step 1), palladium on carbon (10%, 400 mg), and ethyl acetate/ethanol (100 mL, 1:1). The mixture was stirred at room temperature for 12 hours under a hydrogen atmosphere to give rise to a reaction, and filtered with suction. The filtrate was concentrated under reduced pressure to give the title compound as a white solid (2.8 g, yield 93%).

MS m/z (ESI): 279.3 (M+H)

Step 3 tert-Butyl 4-(6-((5-fluoro-4-(6-fluoro-1,2,3,4-tetrahydrobenzo[4,5]imidazo[1,2-a]pyridin-8-yl)pyrimidin-2-yl)amino)pyridin-3-yl)piperazine-1-carboxylate To a reaction flask was added 8-(2-chloro-5-fluoropyrimidin-4-yl)-6-fluoro-1,2,3,4-tetrahydrobenzo[4,5]imidazo[1,2-a]pyridine (100 mg, 0.32 mmol, prepared in Example 7), tert-butyl 4-(6-aminopyridin-3-yl)piperazine-1-carboxylate (89 mg, 0.32 mmol, prepared in Step 2), cesium carbonate (195 mg, 0.6 mmol), Pd$_2$(dba)$_3$ (55 mg, 0.06 mmol), Xantphos (35 mg, 0.06 mmol) and anhydrous 1,4-dioxane (2 mL), and the mixture was reacted for 1 hour in a microwave at 150° C. The resulting mixture was cooled to room temperature and water (10 mL) was added. The aqueous phase was extracted with ethyl acetate (20 mL×3) and the phases were separated. The organic phases were combined, washed with saturated sodium chloride solution (20 mL×2), dried over anhydrous sodium sulfate, and filtered with suction. The filtrate was concentrated under reduced pressure, and the resulting residue was purified by column chromatography (DCM/MeOH=10:1) to give the title compound as a yellow oil (50 mg, yield 31%).

MS m/z (ESI): 563.2 (M+H)

Step 4

5-Fluoro-4-(6-fluoro-1,2,3,4-tetrahydrobenzo[4,5]imidazo[1,2-a]pyridin-8-yl)-N-(5-(piperazin-1-yl)pyridin-2-yl)pyrimidin-2-amine To a reaction flask was added tert-butyl 4-(6-((5-fluoro-4-(6-fluoro-1,2,3,4-tetrahydrobenzo[4,5]imidazo[1,2-a]pyridin-8-yl)pyrimidin-2-yl)amino)pyridin-3-yl)piperazine-1-carboxylate (50 mg, 0.089 mmol, prepared in Step 3), trifluoroacetic acid (0.5 mL) and dichloromethane (6 mL). The mixture was stirred at room temperature for 1 hour to give rise to a reaction, diluted with water (10 mL), and extracted with dichloromethane (20 mL×3). The organic layers were combined, washed with saturated sodium chloride (20 mL×2), dried over anhydrous sodium sulfate, and the filtrate was concentrated in vacuo. The resulting residue was purified by thin layer chromatography (DCM/MeOH=10:1) to give the title compound as a yellow solid (22 mg, yield 54%).

$^1$HNMR (DMSO, 400 MHz), δ 9.76 (s, 1H), 8.63 (s, 1H), 8.10 (s, 1H), 8.08 (s, 1H), 8.03 (s, 1H), 7.74 (d, J=12.4 Hz, 1H), 7.52 (d, J=8.8 Hz, 1H), 4.20 (s, 2H), 3.26 (brs, 8H), 3.02 (s, 2H), 2.08 (brs, 2H), 1.97 (brs, 2H)

MS m/z (ESI): 463.1 (M+H)

Example 14

N-(5-((4-Ethylpiperazin-1-yl)methyl)pyridin-2-yl)-5-fluoro-4-(6-fluoro-1,2,3,4-tetrahydrobenzo[4,5]imidazo[1,2-a]pyridin-8-yl)pyrimidin-2-amine

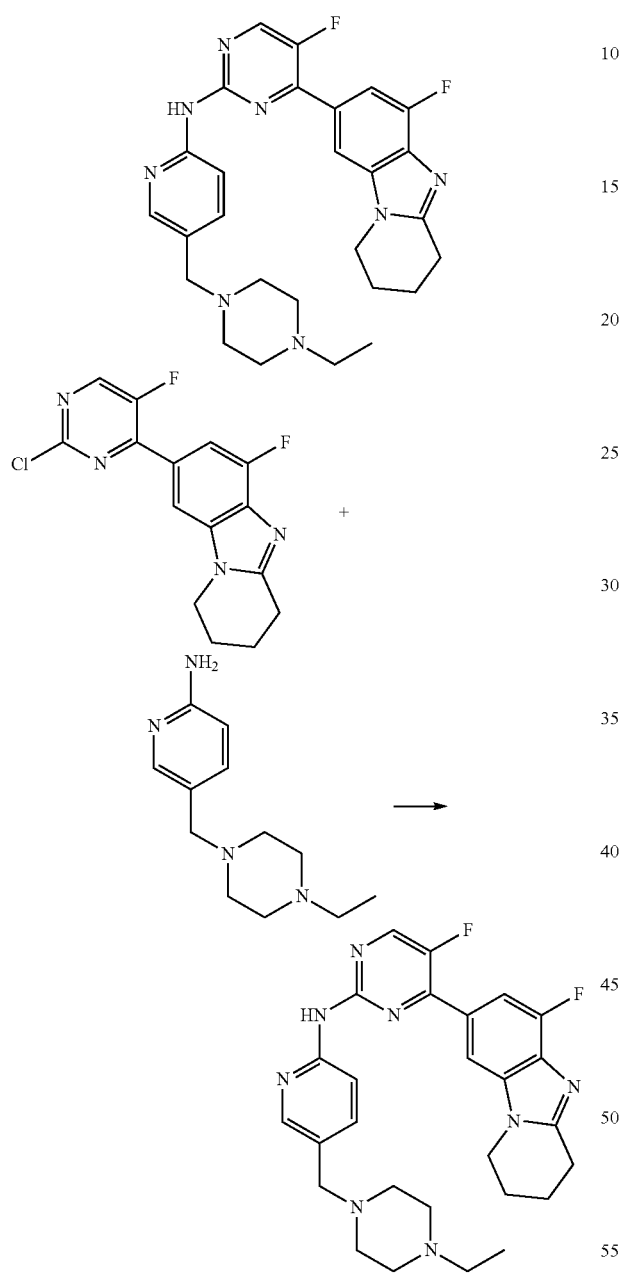

To a microwave reaction flask was added 8-(2-chloro-5-fluoropyrimidin-4-yl)-6-fluoro-1,2,3,4-tetrahydrobenzo[4,5]imidazo[1,2-a]pyridine (100 mg, 0.32 mmol, prepared in Example 7), 5-((4-ethylpiperazin-1-yl)methyl)pyridin-2-amine (68 mg, 0.32 mmol), $Cs_2CO_3$ (195 mg, 0.6 mmol), $Pd_2(dba)_3$ (55 mg, 0.06 mmol), Xantphos (35 mg, 0.06 mmol) and anhydrous 1,4-dioxane (2 mL), and the mixture was reacted for 1 hour in a microwave at 150° C. The resulting mixture was cooled to room temperature and water (10 mL) was added. The aqueous phase was extracted with ethyl acetate (20 mL×3) and the phases were separated. The organic phases were combined, washed with saturated sodium chloride solution (20 mL×2), dried over anhydrous sodium sulfate, and filtered with suction. The filtrate was concentrated under reduced pressure, and the resulting residue was purified by thin layer chromatography (DCM/MeOH=10:1) to give the title compound as a pale yellow solid (33 mg, yield 20.5%).

$^1$H NMR (DMSO, 400 MHz), δ 10.00 (s, 1H), 8.70 (s, 1H), 8.23 (s, 1H), 8.20 (s, 1H), 8.06 (s, 1H), 7.79-7.73 (m, 2H), 4.23-4.21 (m, 2H), 3.55 (s, 2H), 3.05-3.02 (m, 2H), 2.95-2.91 (m, 10H), 2.09-1.97 (m, 4H), 1.23-1.15 (m, 3H)

MS m/z (ESI): 505.1 (M+H)

Example 15

1-(2-((5-Fluoro-4-(6-fluoro-1,2,3,4-tetrahydrobenzo[4,5]imidazo[1,2-a]pyridin-8-yl)pyrimidin-2-yl)amino)-7,8-dihydro-1,6-naphthyridin-6(5H)-yl)-2-hydroxyethan-1-one

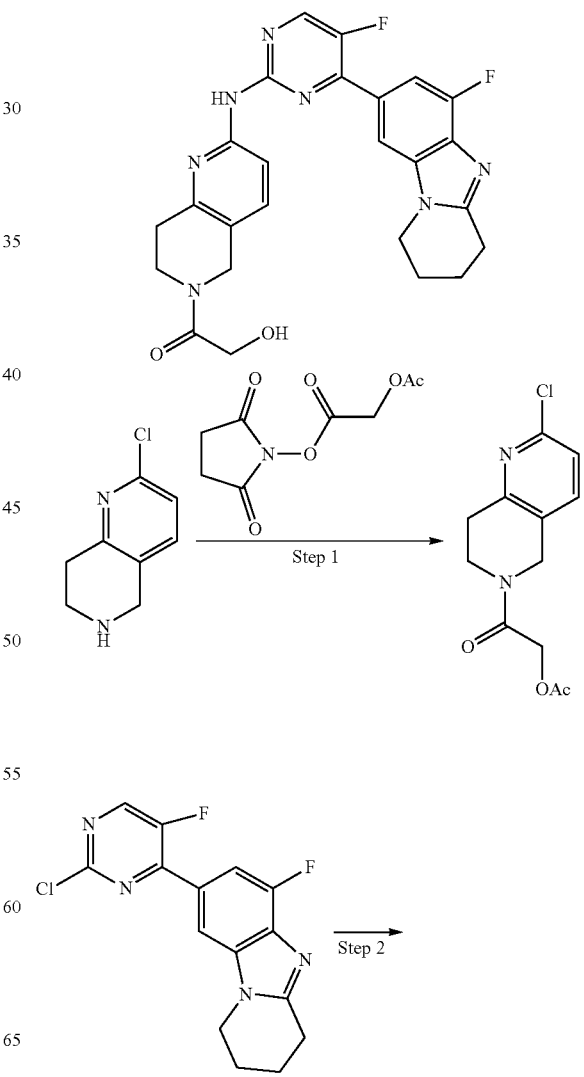

47
-continued

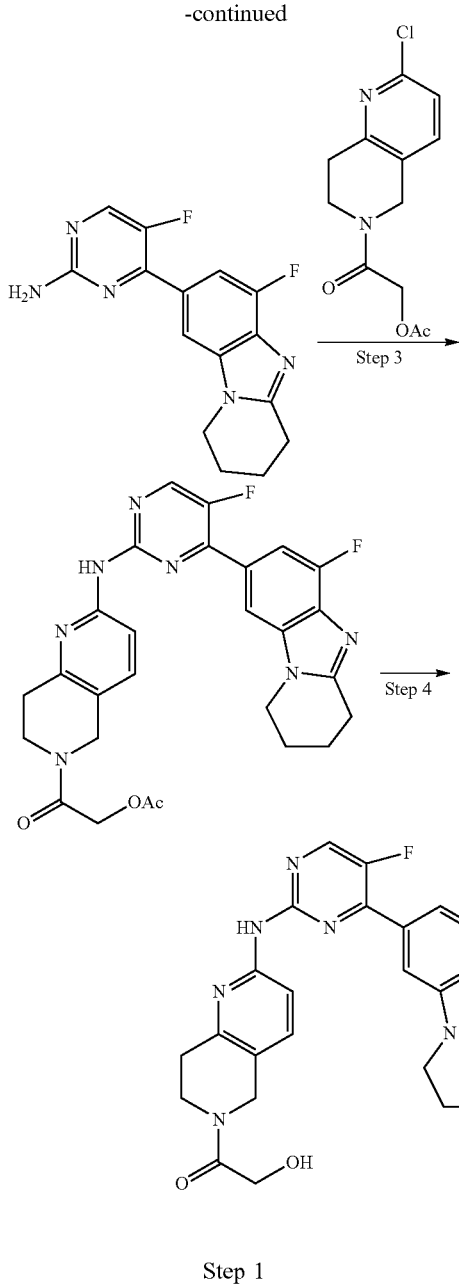

Step 1

2-(2-Chloro-7,8-dihydro-1,6-naphthyridin-6(5H)-yl)-2-oxoethyl acetate

To a reaction flask was added 2-chloro-5,6,7,8-tetrahydro-1,6-naphthyridine (1 g, 5.9 mmol), diisopropylethylamine (903 mg, 7 mmol), 2,5-dioxopyrrolidin-1-yl 2-acetoxyacetate (1.27 g, 5.9 mmol) and dichloromethane (20 mL). The mixture was stirred at room temperature for 1 hour under a nitrogen atmosphere, diluted with water (10 mL), and extracted with ethyl acetate (40 mL×3). The organic phases were combined and washed with saturated sodium chloride solution (40 mL×2), dried over anhydrous sodium sulfate, and filtered with suction. The filtrate was concentrated under reduced pressure, and the resulting residue was purified by column chromatography (DCM/MeOH=10:1) to give the title compound as a yellow solid (600 mg, yield 46%).

MS m/z (ESI): 267.2 (M+H)

48

Step 2

5-Fluoro-4-(6-fluoro-1,2,3,4-tetrahydrobenzo[4,5]imidazo[1,2-a]pyridin-8-yl)pyrimidin-2-amine To a reaction flask was added 8-(2-chloro-5-fluoropyrimidin-4-yl)-6-fluoro-1,2,3,4-tetrahydrobenzo[4,5]imidazo[1,2-a]pyridine (600 mg, 0.18 mmol, prepared in Example 7), aqueous ammonia (20 mL), and isopropanol (20 mL). The mixture was stirred at 110° C. for 12 hours under a nitrogen atmosphere, and concentrated under reduced pressure. The resulting residue was purified by column chromatography (DCM/MeOH=10:1) to give the title compound as a yellow solid (500 mg, yield 88%).

MS m/z (ESI): 302.1 (M+H)

Step 3

2-(2-((5-Fluoro-4-(6-fluoro-1,2,3,4-tetrahydrobenzo[4,5]imidazo[1,2-a]pyridin-8-yl)pyrimidin-2-yl)amino)-7,8-dihydro-1,6-naphthyridin-6(5H)-yl)-2-oxoethyl acetate To a microwave reaction flask was added 5-fluoro-4-(6-fluoro-1,2,3,4-tetrahydrobenzo[4,5]imidazo[1,2-a]pyridin-8-yl)pyrimidin-2-amine (100 mg, 0.33 mmol, prepared in Step 2), 2-(2-chloro-7,8-dihydro-1,6-naphthyridin-6(5H)-yl)-2-oxoethyl acetate (89 mg, 0.33 mmol, prepared in Step 1), cesium carbonate (215 mg, 0.66 mmol), Pd$_2$(dba)$_3$ (55 mg, 0.06 mmol), XantPhos (35 mg, 0.06 mmol) and 1,4-dioxane (2 mL), and the mixture was reacted for 1 hour in a microwave at 150° C. The resulting mixture was cooled to room temperature, diluted with water (10 mL) and extracted with ethyl acetate (40 mL×3). The organic phases were combined, washed with saturated sodium chloride solution (40 mL×2), dried over anhydrous sodium sulfate, and filtered with suction. The filtrate was concentrated under reduced pressure, and the resulting residue was purified by column chromatography (DCM/MeOH=20:1) to give the title compound as a yellow solid (20 mg, yield 19%).

MS m/z (ESI): 534.2 (M+H)

Step 4

1-(2-((5-Fluoro-4-(6-fluoro-1,2,3,4-tetrahydrobenzo[4,5]imidazo[1,2-a]pyridin-8-yl)pyrimidin-2-yl)amino)-7,8-dihydro-1,6-naphthyridin-6(5H)-yl)-2-hydroxyethan-1-one To a reaction flask was added 2-(2-((5-fluoro-4-(6-fluoro-1,2,3,4-tetrahydrobenzo[4,5]imidazo[1,2-a]pyridin-8-yl)pyrimidin-2-yl)amino)-7,8-dihydro-1,6-naphthyridin-6(5H)-yl)-2-oxoethyl acetate (10 mg, 0.018 mmol, prepared in Step 3), sodium methoxide (0.2 mL) and dichloromethane (6 mL). The mixture was stirred at room temperature for 1 hour to give rise to a reaction, diluted with water (10 mL), and extracted with dichloromethane (20 mL×2). The organic phases were combined, washed with saturated sodium chloride solution (40 mL×2), dried over anhydrous sodium sulfate, and filtered with suction. The filtrate was concentrated under reduced pressure, and the resulting residue was purified by column chromatography (DCM/MeOH=5:1) to give the title compound as a yellow solid (10 mg, yield 50%).

$^1$HNMR (DMSO, 400 MHz), δ 9.93 (s, 1H), 8.67 (s, 1H), 8.07 (s, 2H), 7.78 (d, J=12.4 Hz, 1H), 7.65 (d, J=8.8 Hz, 1H), 4.62-4.55 (m, 2H), 4.21-4.19 (m, 4H), 3.81-3.75 (m, 4H), 3.04-3.01 (m, 2H), 2.09-2.07 (m, 2H), 1.98-1.97 (m, 2H)

MS m/z (ESI): 492.1 (M+H)

Example 16

N-(5-((4-Ethylpiperazin-1-yl)methyl)pyridin-2-yl)-5-fluoro-4-(4-fluoro-7,8,9,10-tetrahydro-6H-benzo[4,5]imidazo[1,2-a]azepan-2-yl)pyrimidin-2-amine

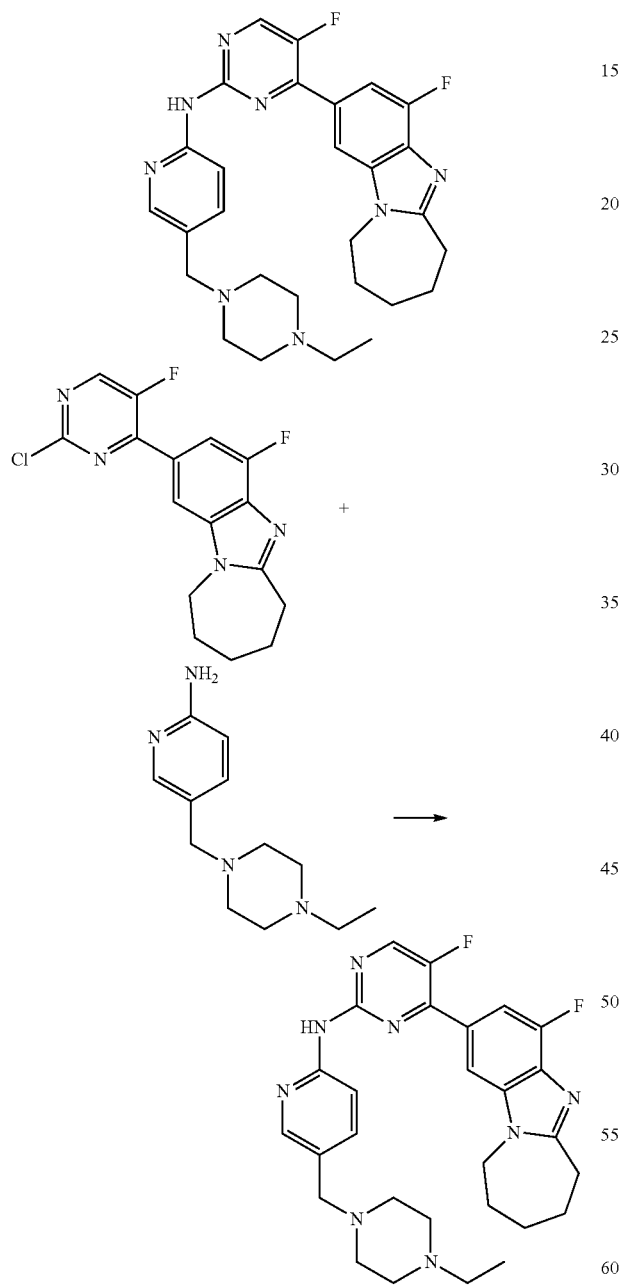

To a microwave reaction flask was added 2-(2-chloro-5-fluoropyrimidin-4-yl)-4-fluoro-7,8,9,10-tetrahydro-6H-benzo[4,5]imidazo[1,2-a]azepane (100 mg, 0.3 mmol, prepared in Example 8), 5-((4-ethylpiperazin-1-yl)methyl)pyridin-2-amine (66 mg, 0.3 mmol), $Cs_2CO_3$ (195 mg, 0.6 mmol), $Pd_2(dba)_3$ (55 mg, 0.06 mmol), Xantphos (35 mg, 0.06 mmol) and anhydrous 1,4-dioxane (2 mL), and the mixture was reacted for 1 hour in a microwave at 150° C. The resulting mixture was cooled to room temperature and water (10 mL) was added. The aqueous phase was extracted with ethyl acetate (20 mL×3) and the phases were separated. The organic phases were combined, washed with saturated sodium chloride solution (20 mL×2), dried over anhydrous sodium sulfate, and filtered with suction. The filtrate was concentrated under reduced pressure, and the resulting residue was purified by column chromatography (DCM/MeOH=20:1) to give the title compound as a yellow solid (20 mg, yield 13%).

¹HNMR (DMSO, 400 MHz), δ 10.09 (s, 1H), 8.71 (s, 1H), 8.27-8.20 (m, 2H), 8.07 (s, 1H), 7.79-7.73 (m, 2H), 4.23-4.20 (m, 2H), 3.52 (s, 2H), 3.12-2.85 (m, 10H), 2.39-2.37 (m, 2H), 2.09-2.08 (m, 2H), 1.98-1.96 (m, 2H), 1.15-1.06 (m, 5H)

MS m/z (ESI): 519.3 (M+H)

Example 17

5-Fluoro-4-(4-fluoro-7,8,9,10-tetrahydro-6H-benzo[4,5]imidazo[1,2-a]azepan-2-yl)-N-(5-(piperazin-1-yl)pyridin-2-yl)pyrimidin-2-amine

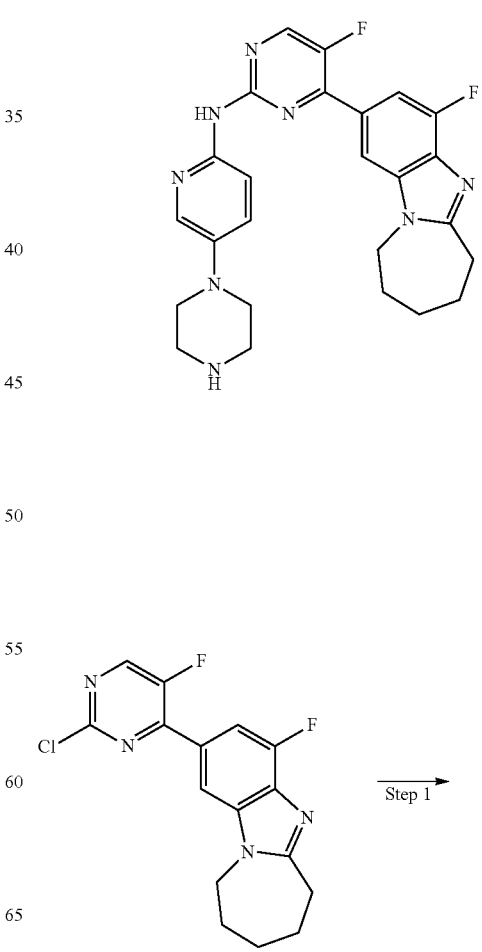

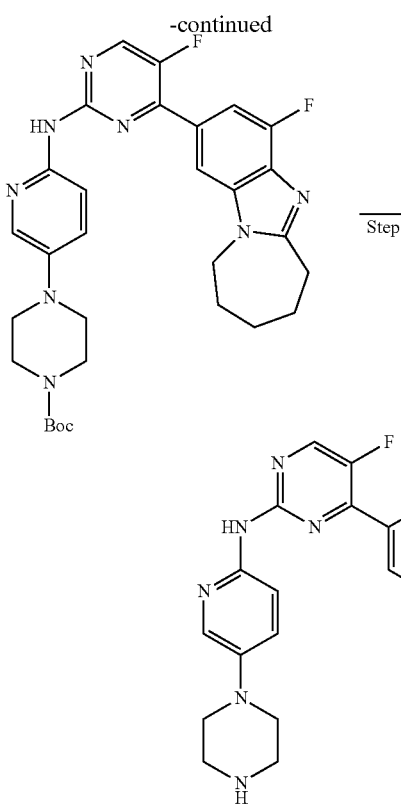

Step 1 tert-Butyl 4-(6-((5-fluoro-4-(4-fluoro-7,8,9,10-tetrahydro-6H-benzo[4,5]imidazo[1,2-a]azepan-2-yl)pyrimidin-2-yl)amino)pyridin-3-yl)piperazine-1-carboxylate To a reaction flask was added 2-(2-chloro-5-fluoropyrimidin-4-yl)-4-fluoro-7,8,9,10-tetrahydro-6H-benzo[4,5]imidazo[1,2-a]azepane (100 mg, 0.3 mmol, prepared in Example 8), tert-butyl 4-(6-aminopyridin-3-yl)piperazine-1-carboxylate (83 mg, 0.3 mmol), cesium carbonate (195 mg, 0.6 mmol), Pd₂(dba)₃ (55 mg, 0.06 mmol), Xantphos (35 mg, 0.06 mmol) and anhydrous 1,4-dioxane (2 mL), and the mixture was reacted for 1 hour in a microwave at 150° C. The resulting mixture was cooled to room temperature and water (10 mL) was added. The aqueous phase was extracted with ethyl acetate (20 mL×3) and the phases were separated. The organic phases were combined, washed with saturated sodium chloride solution (20 mL×2), dried over anhydrous sodium sulfate, and filtered with suction. The filtrate was concentrated under reduced pressure, and the resulting residue was purified by column chromatography (DCM/MeOH=10:1) to give the title compound as a yellow oil (45 mg, yield 26%).

MS m/z (ESI): 577.3 (M+H)

Step 2

5-Fluoro-4-(4-fluoro-7,8,9,10-tetrahydro-6H-benzo[4,5]imidazo[1,2-a]azepan-2-yl)-N-(5-(piperazin-1-yl)pyridin-2-yl)pyrimidin-2-amine To a reaction flask was added tert-butyl 4-(6-((5-fluoro-4-(4-fluoro-7,8,9,10-tetrahydro-6H-benzo[4,5]imidazo[1,2-a]azepan-2-yl)pyrimidin-2-yl)amino)pyridin-3-yl)piperazine-1-carboxylate (45 mg, 0.078 mmol, prepared in Step 1), trifluoroacetic acid (0.5 mL) and dichloromethane (6 mL). The mixture was stirred at room temperature for 1 hour to give rise to a reaction, diluted with water (10 mL), and extracted with dichloromethane (10 mL×3). The organic layers were combined, washed with saturated sodium chloride (10 mL×2), and dried over anhydrous sodium sulfate. The filtrate was concentrated in vacuo, and the resulting residue was purified by thin layer chromatography (DCM/MeOH=10:1) to give the title compound as a yellow solid (10 mg, yield 27%).

¹HNMR (DMSO, 400 MHz), δ 9.85 (s, 1H), 8.65 (s, 1H), 8.10-8.08 (m, 3H), 7.69 (d, J=12.4 Hz, 1H), 7.53-7.50 (m, 1H), 4.35 (s, 2H), 3.56-3.50 (m, 4H), 3.28-3.23 (m, 4H), 3.04-3.03 (m, 2H), 1.98 (s, 2H), 1.90 (s, 2H), 1.78 (s, 2H)

MS m/z (ESI): 477.3 (M+H)

Example 18

N-(5-((4-Ethylpiperazin-1-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine

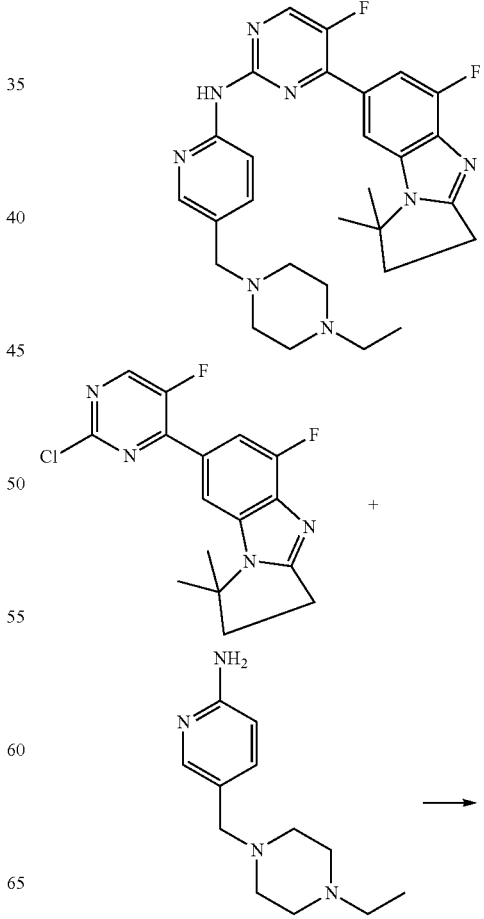

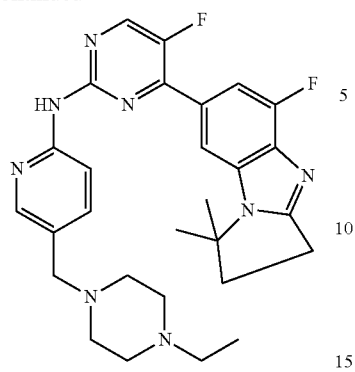

To a reaction flask was added 7-(2-chloro-5-fluoropyrimidin-4-yl)-5-fluoro-1,1-dimethyl-2,3-dihydro-1H-benzo[d]pyrrolo[1,2-a]imidazole (100 mg, 0.3 mmol, prepared in Example 1), 5-((4-ethylpiperazin-1-yl)methyl)pyridin-2-amine (66 mg, 0.3 mmol), cesium carbonate (195 mg, 0.6 mmol), Pd$_2$(dba)$_3$ (55 mg, 0.06 mmol), XantPhos (35 mg, 0.06 mmol) and anhydrous 1,4-dioxane (5 mL). The mixture was stirred at 120° C. for 12 hours to give rise to a reaction. The resulting mixture was cooled to room temperature and water (10 mL) was added. The aqueous phase was extracted with ethyl acetate (20 mL×3) and the phases were separated. The organic phases were combined, washed with saturated sodium chloride solution (20 mL×2), dried over anhydrous sodium sulfate, and filtered with suction. The filtrate was concentrated under reduced pressure, and the resulting residue was purified by column chromatography (DCM/MeOH=10:1) to give the title compound as a white solid (50 mg, yield 32%).

$^1$HNMR (DMSO, 400 MHz) δ 10.14 (s, 1H), 8.71 (d, J=3.6 Hz, 1H), 8.23-8.20 (m, 3H), 7.73-7.70 (m, 2H), 3.54 (brs, 2H), 3.13-3.09 (m, 3H), 2.92-2.90 (m, 4H), 2.59-2.56 (m, 4H), 2.50-2.48 (m, 2H), 1.67 (s, 6H), 1.23-1.20 (m, 4H)

MS m/z (ESI): 519.6 (M+H)

Example 19

5-Fluoro-4-(5-fluoro-1,1-dimethyl-2,3-dihydro-1H-benzo[d]pyrrolo[1,2-a]imidazol-7-yl)-N-(5-(piperazin-1-yl)pyridin-2-yl)pyrimidin-2-amine

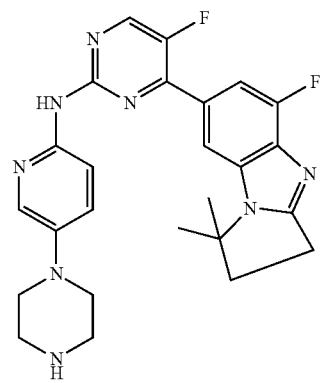 [SMILES: CC1(C)CCc2nc3c(F)cc(-c4nc(Nc5ccc(N6CCNCC6)cn5)ncc4F)cc3n21]

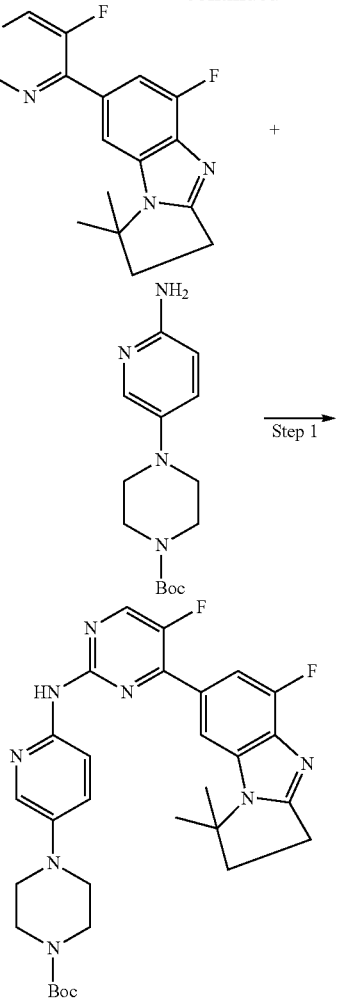

Step 1 tert-Butyl 4-(6-((5-fluoro-4-(5-fluoro-1,1-dimethyl-2,3-dihydro-1H-benzo[d]pyrrolo[1,2-a]imidazol-7-yl)pyrimidin-2-yl)amino)pyridin-3-yl)piperazine-1-carboxylate To a reaction flask was added 7-(2-chloro-5-fluoropyrimidin-4-yl)-5-fluoro-1,1-dimethyl-2,3-dihydro-1H-benzo[d]pyrrolo[1,2-a]imidazole (100 mg, 0.3 mmol, prepared in Example 1), tert-butyl 4-(6-aminopyridin-3-yl)piperazine-1-carboxylate (83 mg, 0.3 mmol), cesium carbonate (195 mg, 0.6 mmol), Pd$_2$(dba)$_3$ (55 mg, 0.06 mmol), Xantphos (35 mg, 0.06 mmol) and anhydrous 1,4-dioxane (2 mL), and the mixture was reacted for 1 hour in a microwave at 150° C. The resulting mixture was cooled to room temperature and water (10 mL) was added. The aqueous phase was extracted with ethyl acetate (20 mL×3) and the phases were separated. The organic phases were combined, washed with saturated sodium chloride solution (20 mL×2), dried over anhydrous sodium sulfate, and filtered with suction. The filtrate was concentrated under reduced pressure, and the resulting residue was purified by column chromatography (DCM/MeOH=10:1) to give the title compound as a yellow solid (92 mg, yield 53%).

MS m/z (ESI): 577.3 (M+H)

Step 2

5-Fluoro-4-(5-fluoro-1,1-dimethyl-2,3-dihydro-1H-benzo[d]pyrrolo[1,2-a]imidazol-7-yl)-N-(5-(piperazin-1-yl)pyridin-2-yl)pyrimidin-2-amine To a reaction flask was added tert-butyl 4-(6-((5-fluoro-4-(5-fluoro-1,1-dimethyl-2,3-dihydro-1H-benzo[d]pyrrolo[1,2-a]imidazol-7-yl)pyrimidin-2-yl)amino)pyridin-3-yl)piperazine-1-carboxylate (92 mg, 0.16 mmol, prepared in Step 1), trifluoroacetic acid (0.5 mL) and dichloromethane (6 mL). The mixture was stirred at room temperature for 1 hour to give rise to a reaction, diluted with water (10 mL), and extracted with dichloromethane (20 mL×3). The organic layers were combined, washed with saturated sodium chloride (20 mL×2), and dried over anhydrous sodium sulfate. The filtrate was concentrated in vacuo, and the resulting residue was purified by thin layer chromatography (DCM/MeOH=10:1) to give the title compound as a yellow solid (37 mg, yield 49%).

$^1$HNMR (MeOD, 400 MHz), δ 8.50 (s, 1H), 8.22 (s, 1H), 8.19 (s, 1H), 8.04 (d, J=2.8 Hz, 1H), 7.82 (d, J=12.4 Hz, 1H), 7.53 (dd, J1=2.8 Hz, J2=8.4 Hz, 1H), 3.23-3.16 (m, 10H), 2.68 (t, J=7.6 Hz, 2H), 1.76 (s, 6H)

MS m/z (ESI): 477.2 (M+H)

Example 20

5-Fluoro-4-(5-fluoro-1,1-dimethyl-2,3-dihydro-1H-benzo[d]pyrrolo[1,2-a]imidazol-7-yl)-N-(5-(piperazin-1-yl)pyridin-2-yl)pyrimidin-2-amine

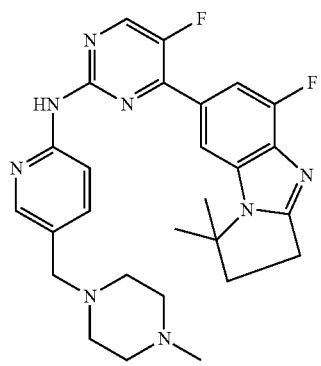

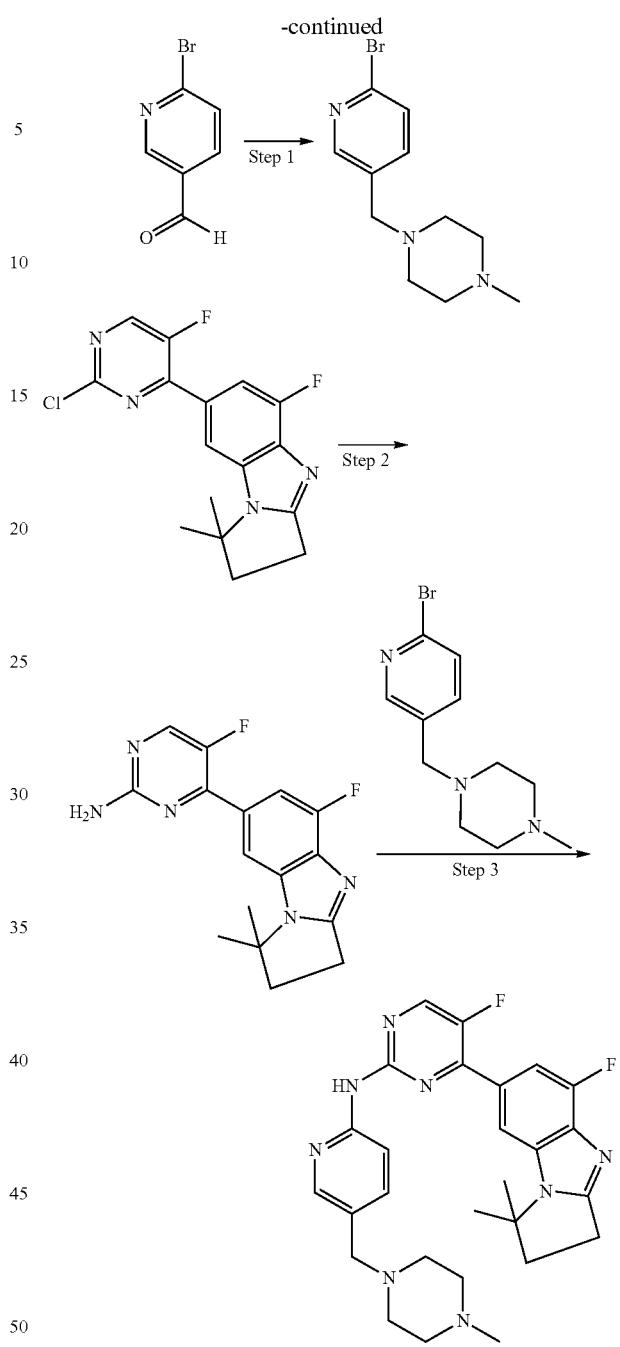

Step 1

1-((6-Bromopyridin-3-yl)methyl)-4-methylpiperazine

To a reaction flask was added 6-bromo-pyridine-3-carboxaldehyde (10 g, 53.7 mmol), 1-bromopiperazine (7.0 g, 70 mmol) and dichloromethane (100 mL), and sodium triacetoxyborohydride (17 g, 81 mmol) was added in portions under stirring. The mixture was stirred at room temperature for 12 hours to give rise to a reaction. Then dichloromethane (50 mL) and aqueous sodium hydroxide solution (2N, 15 mL) were added to the reaction liquid. The phases were separated and the aqueous phase was extracted with dichloromethane (50 mL×2). The organic phases were combined, washed with saturated sodium chloride solution (50 mL×2), dried over anhydrous sodium sulfate, and filtered with suction. The filtrate was concentrated under reduced pressure to give the title compound as a yellow oil (12.3 g, yield 85%).

MS m/z (ESI): 271.2 (M+H)

Step 2

5-Fluoro-4-(5-fluoro-1,1-dimethyl-2,3-dihydro-1H-benzo[d]pyrrolo[1,2-a]imidazol-7-yl)pyrimidin-2-amine To a reaction flask was added 7-(2-chloro-5-fluoropyrimidin-4-yl)-5-fluoro-1,1-dimethyl-2,3-dihydro-1H-benzo[d]pyrrolo[1,2-a]imidazole (500 mg, 1.5 mmol), aqueous ammonia (5 mL) and isopropanol (5 mL), and the mixture was reacted for 12 hours in a sealed autoclave at 100° C. The reaction liquid was cooled to room temperature, and concentrated under reduced pressure to give a crude product of the title compound as a yellow oil (450 mg), which was used directly in the next reaction step.

MS m/z (ESI): 316.1 (M+H)

Step 3

5-Fluoro-4-(5-fluoro-1,1-dimethyl-2,3-dihydro-1H-benzo[d]pyrrolo[1,2-a]imidazol-7-yl)-N-(5-(piperazin-1-yl)pyridin-2-yl)pyrimidin-2-amine To a reaction flask was added 5-fluoro-4-(5-fluoro-1,1-dimethyl-2,3-dihydro-1H-benzo[d]pyrrolo[1,2-a]imidazol-7-yl)pyrimidin-2-amine (100 mg, 0.31 mmol, prepared in Step 2), 1-((6-bromopyridin-3-yl)methyl)-4-methylpiperazine (88 mg, 0.31 mmol), cesium carbonate (194 mg, 0.6 mmol), $Pd_2(dba)_3$ (55 mg, 0.06 mmol), XantPhos (35 mg, 0.06 mmol) and anhydrous 1,4-dioxane (2 mL), and the mixture was reacted for 1 hour in a microwave at 150° C. The resulting mixture was cooled to room temperature, water (10 mL) was added, and the aqueous phase was extracted with ethyl acetate (20 mL×3). The organic phases were combined, washed with saturated sodium chloride solution (20 mL×2), dried over anhydrous sodium sulfate, and filtered with suction. The filtrate was concentrated under reduced pressure, and the resulting residue was purified by column chromatography (DCM/MeOH=10:1) to give the title compound as a white solid (65 mg, yield 42%).

$^1$HNMR (DMSO, 400 MHz), δ 10.09 (s, 1H), 8.70 (d, J=3.6 Hz, 1H), 8.23-8.21 (m, 3H), 7.73-7.68 (m, 2H), 3.53 (s, 2H), 3.12-3.09 (m, 2H), 2.97-2.95 (m, 4H), 2.66-2.50 (m, 9H), 1.67 (s, 6H)

MS m/z (ESI): 505.2 (M+H)

Example 21

1-(2-((5-Fluoro-4-(5-fluoro-1,1-dimethyl-2,3-dihydro-1H-benzo[d]pyrrolo[1,2-a]imidazol-7-yl)pyrimidin-2-yl)amino)-7,8-dihydro-1,6-naphthyridin-6(5H)-yl)-2-hydroxyethan-1-one

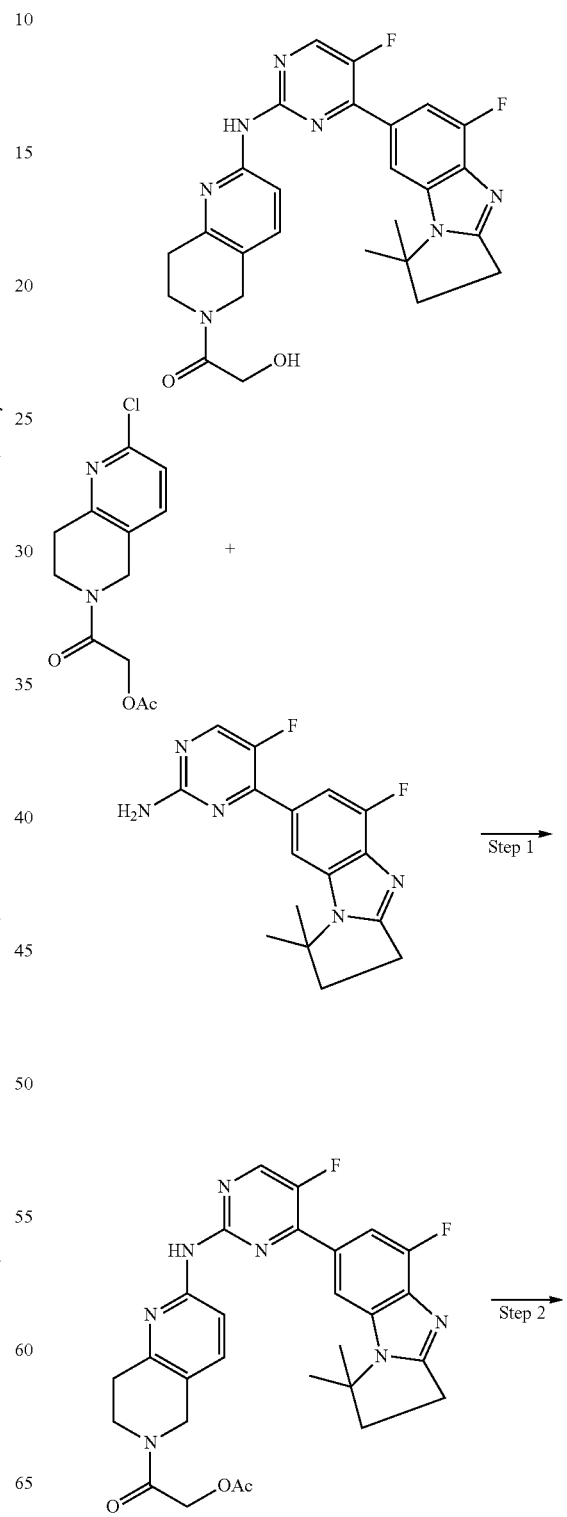

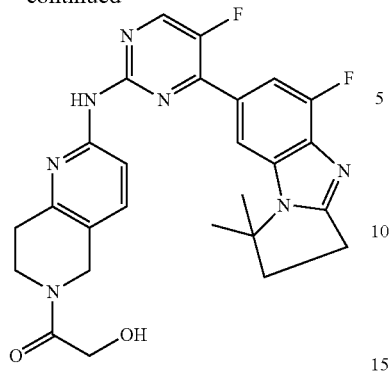

Step 1

2-(2-((5-Fluoro-4-(5-fluoro-1,1-dimethyl-2,3-dihydro-1H-benzo[d]pyrrolo[1,2-a]imidazol-7-yl)pyrimidin-2-yl)amino)-7,8-dihydro-1,6-naphthyridin-6(5H)-yl)-2-oxoethyl acetate To a reaction flask was added 2-(2-chloro-7,8-dihydro-1,6-naphthyridin-6(5H)-yl)-2-oxoethyl acetate (85 mg, 0.32 mmol), 5-fluoro-4-(5-fluoro-1,1-dimethyl-2,3-dihydro-1H-benzo[d]pyrrolo[1,2-a]imidazol-7-yl)pyrimidin-2-amine (100 mg, 0.32 mmol), Cs₂CO₃ (208 mg, 0.64 mmol), Pd₂(dba)₃ (55 mg, 0.06 mmol), Xantphos (35 mg, 0.06 mmol) and 1,4-dioxane (2 mL), and the mixture was reacted for 1 hour in a microwave at 150° C. The resulting mixture was cooled to room temperature, water (10 mL) was added, and the aqueous phase was extracted with ethyl acetate (20 mL×3). The organic phases were combined, washed with saturated sodium chloride solution (20 mL×2), dried over anhydrous sodium sulfate, and filtered with suction. The filtrate was concentrated under reduced pressure, and the resulting residue was purified by column chromatography (DCM/MeOH=10:1) to give the title compound as a yellow oil (20 mg, yield 11%).

MS m/z (ESI): 548.0 (M+H)

Step 2

1-(2-((5-Fluoro-4-(5-fluoro-1,1-dimethyl-2,3-dihydro-1H-benzo[d]pyrrolo[1,2-a]imidazol-7-yl)pyrimidin-2-yl)amino)-7,8-dihydro-1,6-naphthyridin-6(5H)-yl)-2-hydroxyethan-1-one To a reaction flask was added 2-(2-((5-fluoro-4-(5-fluoro-1,1-dimethyl-2,3-dihydro-1H-benzo[d]pyrrolo[1,2-a]imidazol-7-yl)pyrimidin-2-yl)amino)-7,8-dihydro-1,6-naphthyridin-6(5H)-yl)-2-oxoethyl acetate (20 mg, 0.37 mmol, prepared in Step 1), sodium methoxide (1M in methanol, 2 mL) and dichloromethane (6 mL). The mixture was stirred at room temperature for 1 hour under a nitrogen atmosphere. Water (10 mL) was added, and the aqueous phase was extracted with ethyl acetate (10 mL×3). The organic phases were combined, washed with saturated sodium chloride (40 mL), dried over anhydrous sodium sulfate, and filtered with suction. The filtrate was concentrated under reduced pressure, and the resulting residue was purified by thin layer chromatography (DCM/MeOH=10:1) to give the title compound as a yellow solid (10 mg, yield 54%).

¹HNMR (DMSO, 400 MHz), δ 9.99 (s, 1H), 8.68 (s, 1H), 8.23 (s, 1H), 8.11 (d, J=8.4 Hz, 1H), 7.72 (d, J=12.4 Hz, 1H), 7.63-7.55 (m, 1H), 4.66-4.56 (m, 2H), 4.21 (brs, 2H), 3.82-3.70 (m, 2H), 3.11 (t, J=7.2 Hz, 2H), 2.89-2.82 (m, 2H), 2.57 (t, J=7.6 Hz, 2H), 1.68 (s, 6H)

MS m/z (ESI): 506.1 (M+H)

Example 22

N-(5-((4-Ethylpiperazin-1-yl)methyl)pyridin-2-yl)-4-(5-fluoro-1,1-dimethyl-2,3-dihydro-1H-benzo[d]pyrrolo[1,2-a]imidazol-7-yl)pyrimidin-2-amine

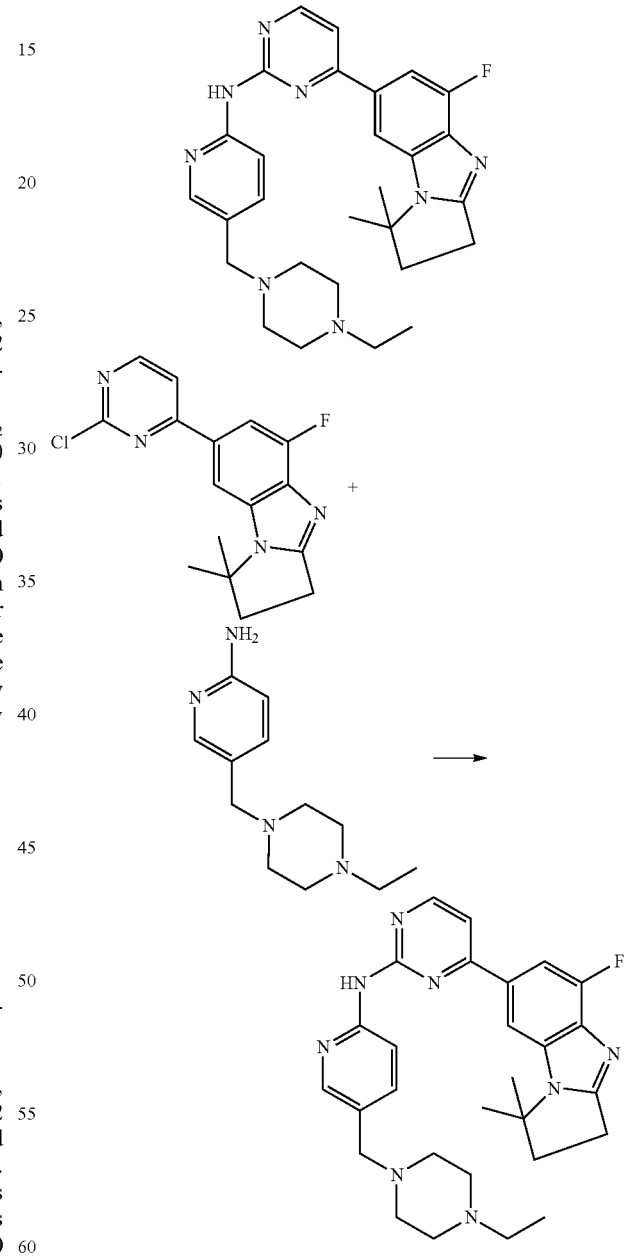

To a reaction flask was added 7-(2-chloro-5-fluoropyrimidin-4-yl)-5-fluoro-1,1-dimethyl-2,3-dihydro-1H-benzo[d]pyrrolo[1,2-a]imidazole (100 mg, 0.32 mmol, prepared in Example 9), 5-((4-ethylpiperazin-1-yl)methyl)pyridin-2-amine (70 mg, 0.32 mmol), cesium carbonate (208 mg, 0.64 mmol), Pd₂(dba)₃ (55 mg, 0.06 mmol), XantPhos (35 mg, 0.06 mmol) and anhydrous 1,4-dioxane (2 mL), and the mixture was reacted for 1 hour in a microwave at 150° C. The resulting mixture was cooled to room temperature, water (10 mL) was added, and the aqueous phase was extracted with ethyl acetate (20 mL×3). The organic phases were combined, washed with saturated sodium chloride solution (20 mL×2), dried over anhydrous sodium sulfate, and filtered with suction. The filtrate was concentrated under reduced pressure, and the resulting residue was purified by column chromatography (DCM/MeOH=20:1) to give the title compound as a pale yellow solid (16 mg, yield 10%).

¹HNMR (DMSO, 400 MHz), δ 9.89 (s, 1H), 8.61 (d, J=5.2 Hz, 1H), 8.35 (s, 1H), 8.33 (s, 1H), 8.24 (s, 1H), 7.89 (d, J=12.8 Hz, 1H), 7.74-7.72 (m, 2H), 3.56 (s, 2H), 3.09 (t, J=7.2 Hz, 2H), 2.93-2.90 (m, 4H), 2.57-2.54 (m, 4H), 2.39-2.35 (m, 2H), 1.70 (s, 6H), 0.86-0.83 (m, 5H)

MS m/z (ESI): 501.2 (M+H)

Example 23

4-(5-Fluoro-1,1-dimethyl-2,3-dihydro-1H-benzo[d] pyrrolo[1,2-a]imidazol-7-yl)-N-(5-(piperazin-1-yl) pyridin-2-yl)pyrimidin-2-amine

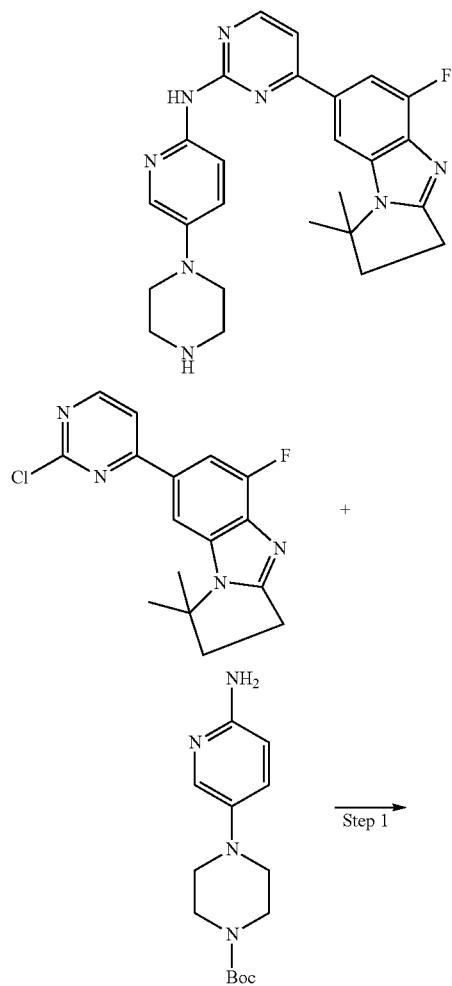

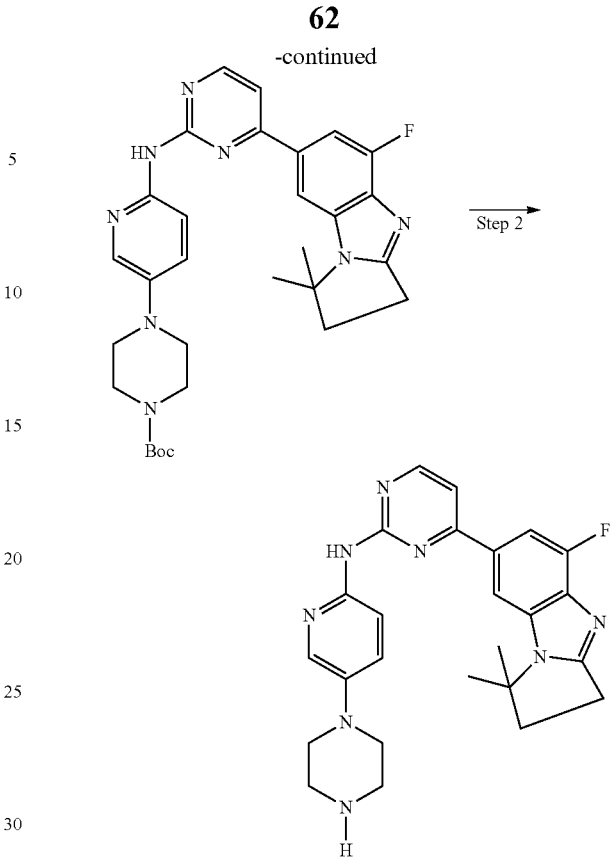

Step 1 tert-Butyl 4-(6-((4-(5-fluoro-1,1-dimethyl-2,3-dihydro-1H-benzo[d]pyrrolo[1,2-a]imidazol-7-yl)pyrimidin-2-yl)amino)pyridin-3-yl)piperazine-1-carboxylate To a reaction flask was added 7-(2-chloro-5-fluoropyrimidin-4-yl)-5-fluoro-1,1-dimethyl-2,3-dihydro-1H-benzo[d] pyrrolo[1,2-a]imidazole (100 mg, 0.32 mmol, prepared in Example 9), tert-butyl 4-(6-aminopyridin-3-yl)piperazine-1-carboxylate (89 mg, 0.32 mmol), cesium carbonate (208 mg, 0.64 mmol), Pd₂(dba)₃ (55 mg, 0.06 mmol), Xantphos (35 mg, 0.06 mmol) and anhydrous 1,4-dioxane (2 mL), and the mixture was reacted for 1 hour in a microwave at 150° C. The resulting mixture was cooled to room temperature and water (10 mL) was added. The aqueous phase was extracted with ethyl acetate (20 mL×3) and the phases were separated. The organic phases were combined, washed with saturated sodium chloride solution (20 mL×2), dried over anhydrous sodium sulfate, and filtered with suction. The filtrate was concentrated under reduced pressure, and the resulting residue was purified by column chromatography (DCM/MeOH=10:1) to give the title compound as a yellow oil (45 mg, yield 25%).

MS m/z (ESI): 559.1 (M+H)

Step 2

4-(5-Fluoro-1,1-dimethyl-2,3-dihydro-1H-benzo[d] pyrrolo[1,2-a]imidazol-7-yl)-N-(5-(piperazin-1-yl) pyridin-2-yl)pyrimidin-2-amine To a reaction flask was added tert-butyl 4-(6-((4-(5-fluoro-1,1-dimethyl-2,3-dihydro-1H-benzo[d]pyrrolo[1,2- a]imidazol-7-yl)pyrimidin-2-yl)amino)pyridin-3-yl)piperazine-1-carboxylate (45 mg, 0.08 mmol, prepared in Step 1), trifluoroacetic acid (0.5 mL) and dichloromethane (6 mL). The mixture was stirred at room temperature for 1 hour to give rise to a reaction, diluted with water (10 mL), and extracted with dichloromethane (20 mL×3). The organic layers were combined, washed with saturated sodium chloride (20 mL×2), and dried over anhydrous sodium sulfate. The filtrate was concentrated in vacuo, and the resulting residue was purified by thin layer chromatography (DCM/MeOH=10:1) to give the title compound as a yellow solid (18 mg, yield 49%).

$^1$HNMR (DMSO, 400 MHz), δ 9.62 (s, 1H), 8.55 (d, J=5.6 Hz, 1H), 8.30 (s, 1H), 8.18 (d, J=9.2 Hz, 1H), 8.05 (s, 1H), 7.87 (d, J=12.4 Hz, 1H), 7.65 (d, J=5.2 Hz, 1H), 7.48-7.46 (m, 1H), 3.22 (brs, 4H), 3.10-3.06 (m, 6H), 2.57-2.54 (m, 3H), 1.69 (s, 6H)

MS m/z (ESI): 459.2 (M+H)

Example 24

4-(1,1-Dimethyl-2,3-dihydro-1H-benzo[d]pyrrolo[1,2-a]imidazol-7-yl)-N-(5-((4-ethylpiperazin-1-yl)methyl)pyridin-2-yl)-5-fluoropyrimidin-2-amine

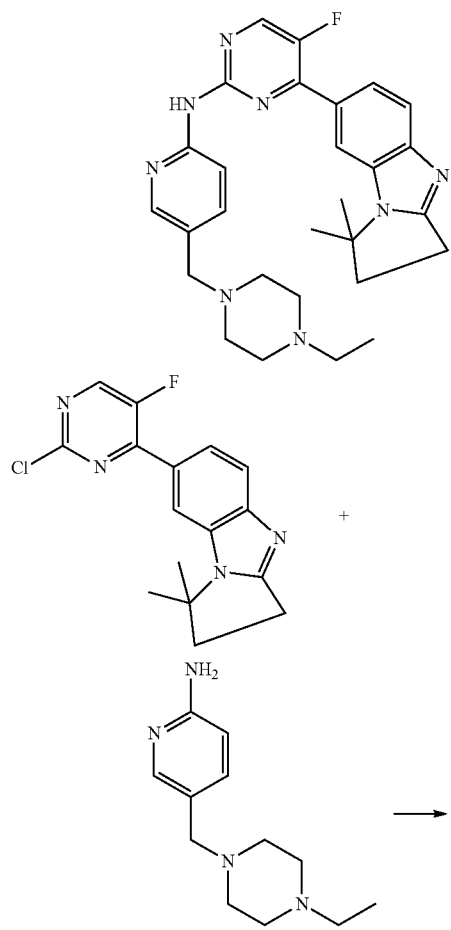

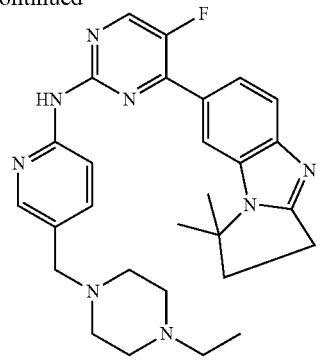

To a microwave reaction flask was added 7-(2-chloro-5-fluoropyrimidin-4-yl)-1,1-dimethyl-2,3-dihydro-1H-benzo[d]pyrrolo[1,2-a]imidazole (200 mg, 0.63 mmol, prepared according to the procedure of Example 10), 5-((4-ethylpiperazin-1-yl)methyl)pyridin-2-amine (139 mg, 0.63 mmol), cesium carbonate (410 mg, 1.26 mmol), Pd$_2$(dba)$_3$ (55 mg, 0.06 mmol), BINAP (37 mg, 0.06 mmol) and anhydrous 1,4-dioxane (5 mL), and the mixture was reacted for 1 hour in a microwave at 120° C. The resulting mixture was cooled to room temperature, water (10 mL) was added, and the aqueous phase was extracted with ethyl acetate (20 mL×3). The organic phases were combined, washed with saturated sodium chloride solution (20 mL×2), dried over anhydrous sodium sulfate, and filtered with suction. The filtrate was concentrated under reduced pressure, and the resulting residue was purified by column chromatography (DCM/MeOH=10:1) to give the title compound as a pale yellow solid (134 mg, yield 43%).

$^1$HNMR (DMSO, 400 MHz), δ 10.08 (s, 1H), 8.67 (s, 1H), 8.39 (s, 1H), 8.28-8.23 (m, 2H), 7.92 (d, J=8.8 Hz, 1H), 7.72-7.67 (m, 2H), 3.55 (s, 2H), 3.42-3.39 (m, 2H), 3.10-3.07 (m, 4H), 2.93-2.90 (m, 4H), 2.56-2.52 (m, 2H), 2.43-2.41 (m, 2H), 1.67 (s, 6H), 1.21 (t, J=6.8 Hz, 3H)

MS m/z (ESI): 501.1 (M+H)

Example 25

4-(1,1-Dimethyl-2,3-dihydro-1H-benzo[d]pyrrolo[1,2-a]imidazol-7-yl)-5-fluoro-N-(5-(piperazin-1-yl)pyridin-2-yl)pyrimidin-2-amine

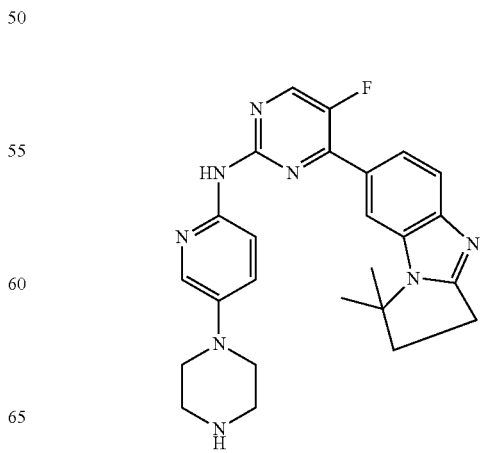

-continued

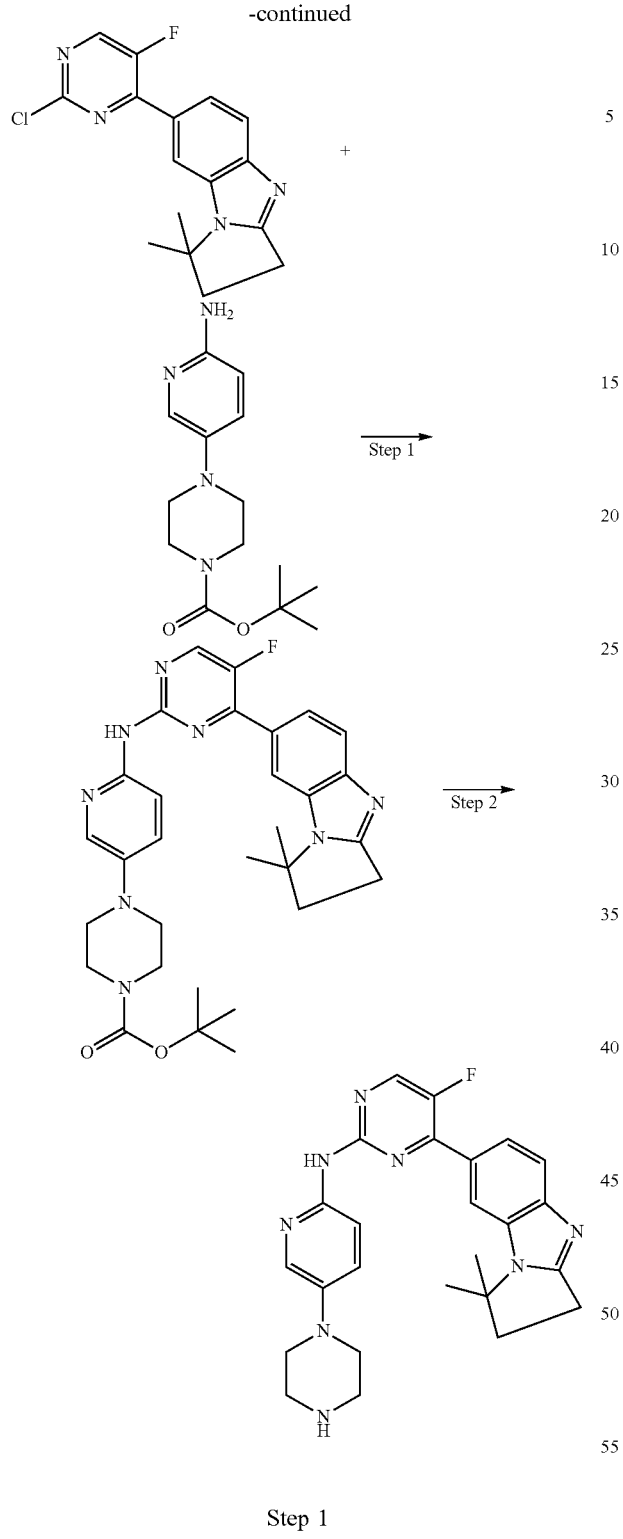

the procedure of Example 10), tert-butyl 4-(6-aminopyridin-3-yl)piperazine-1-carboxylate (264 mg, 0.95 mmol), cesium carbonate (618 mg, 1.9 mmol), Pd$_2$(dba)$_3$ (87 mg, 0.095 mmol), BINAP (124 mg, 0.2 mmol) and anhydrous 1,4-dioxane (4 mL), and the mixture was reacted for 1 hour in a microwave at 120° C. The resulting mixture was cooled to room temperature, water (10 mL) was added, and the aqueous phase was extracted with ethyl acetate (20 mL×3). The organic phases were combined, washed with saturated sodium chloride solution (20 mL×2), dried over anhydrous sodium sulfate, and filtered with suction. The filtrate was concentrated under reduced pressure, and the resulting residue was purified by column chromatography (DCM/MeOH=10:1) to give the title compound as a yellow solid (50 mg, yield 9.4%).

MS m/z (ESI): 559.3 (M+H)

Step 2

4-(1,1-Dimethyl-2,3-dihydro-1H-benzo[d]pyrrolo[1,2-a]imidazol-7-yl)-5-fluoro-N-(5-(piperazin-1-yl)pyridin-2-yl)pyrimidin-2-amine To a reaction flask was added 4-(1,1-dimethyl-2,3-dihydro-1H-benzo[d]pyrrolo[1,2-a]imidazol-7-yl)-5-fluoro-N-(5-(piperazin-1-yl)pyridin-2-yl)pyrimidin-2-amine (50 mg, 0.09 mmol, prepared in Step 1), trifluoroacetic acid (1 mL) and dichloromethane (5 mL). The mixture was stirred at room temperature for 3 hours to give rise to a reaction, diluted with water (10 mL), and extracted with dichloromethane (20 mL×3). The organic layers were combined, washed with saturated sodium chloride (20 mL×2), and dried over anhydrous sodium sulfate. The filtrate was concentrated in vacuo and the resulting residue was purified by thin layer chromatography (DCM/MeOH=10:1) to give the title compound as a yellow solid (22 mg, yield 54%).

$^1$HNMR (DMSO, 400 MHz), δ 10.31 (s, 1H), 8.71 (s, 1H), 8.43 (s, 1H), 8.06-8.02 (m, 3H), 7.93 (d, J=7.2 Hz, 1H), 7.62 (d, J=8.4 Hz, 1H), 4.75 (brs, 1H), 3.40-3.28 (m, 10H), 2.63-2.59 (m, 2H), 1.73 (s, 6H)

MS m/z (ESI): 477.1 (M+H)

Example 26

5-Fluoro-4-(5-fluoro-1,1-dimethyl-2,3-dihydro-1H-benzo[d]pyrrolo[1,2-a]imidazol-7-yl)-N-(5-(piperazine-4-yl)pyridin-2-yl)pyrimidin-2-amine

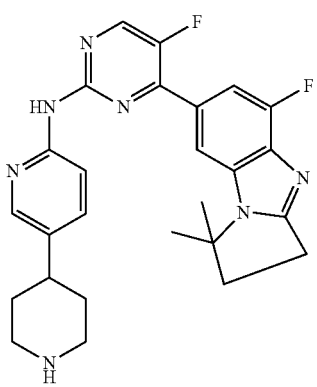 [SMILES: CC1(C)CCc2nc3c(F)cc(-c4nc(Nc5ccc(C6CCNCC6)cn5)ncc4F)cc3n21]

Step 1 tert-Butyl 4-(6-((4-(1,1-dimethyl-2,3-dihydro-1H-benzo[d]pyrrolo[1,2-a]imidazol-7-yl)-5-fluoropyrimidin-2-yl)amino)pyridin-3-yl)piperazine-1-carboxylate To a reaction flask was added 7-(2-chloro-5-fluoropyrimidin-4-yl)-1,1-dimethyl-2,3-dihydro-1H-benzo[d]pyrrolo[1,2-a]imidazole (300 mg, 0.95 mmol, prepared according to

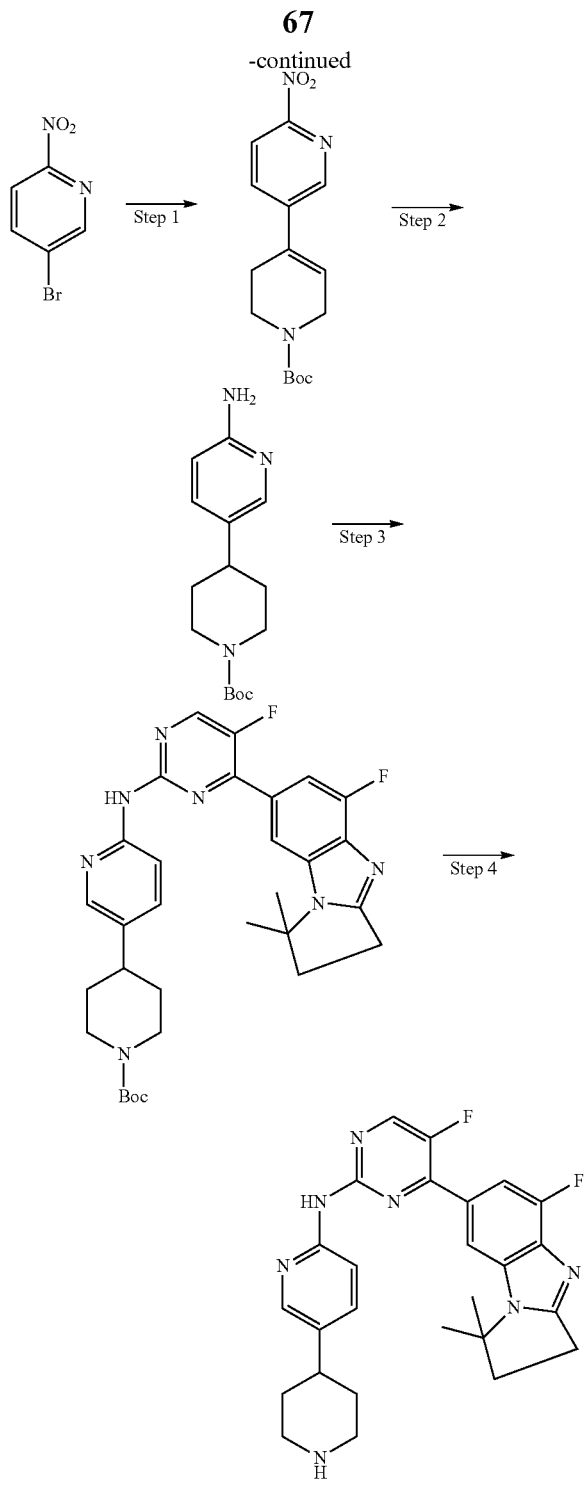

and the mixture was stirred at 85° C. for 12 hours to give rise to a reaction. The resulting mixture was cooled to room temperature and concentrated under reduced pressure. The resulting residue was purified by column chromatography (PE/EtOAc=1:1) to give the title compound as a white solid (11 g, yield 36%).

MS m/z (ESI): 306.1 (M+H)

Step 2 tert-Butyl 4-(6-aminopyridin-3-yl)piperidine-1-carboxylate

To a reaction flask was added tert-butyl 6-nitro-3',6'-dihydro-[3,4'-bipyridine]-1'(2'H)-carboxylate (0.9 g, 3 mmol, prepared in Step 1), palladium on carbon (10%, 90 mg) and ethyl acetate/methanol (10 mL/10 mL), and the mixture was stirred for 12 hours under a hydrogen atmosphere to give rise to a reaction. The resulting mixture was filtered, and the filtrate was directly concentrated to give the title compound as a white solid (790 mg, yield 95%).

MS m/z (ESI): 278.2 (M+H)

Step 3 tert-Butyl 4-(6-((5-fluoro-4-(5-fluoro-1,1-dimethyl-2,3-dihydro-1H-benzo[d]pyrrolo[1,2-a]imidazol-7-yl)pyrimidin-2-yl)amino)pyridin-3-yl)piperidine-1-carboxylate To a reaction flask was added 7-(2-chloro-5-fluoropyrimidin-4-yl)-5-fluoro-1,1-dimethyl-2,3-dihydro-1H-benzo[d]pyrrolo[1,2-a]imidazole (100 mg, 0.3 mmol, prepared according to the procedure of Example 1), tert-butyl 4-(6-aminopyridin-3-yl)piperidine-1-carboxylate (83 mg, 0.3 mmol), cesium carbonate (195 mg, 0.6 mmol), Pd₂(dba)₃ (55 mg, 0.06 mmol), Xantphos (35 mg, 0.06 mmol) and anhydrous 1,4-dioxane (2 mL), and the mixture was reacted for 1 hour in a microwave at 150° C. The resulting mixture was cooled to room temperature, water (10 mL) was added, and the aqueous phase was extracted with ethyl acetate (20 mL×3). The organic phases were combined, washed with saturated sodium chloride solution (20 mL), dried over anhydrous sodium sulfate, and filtered with suction. The filtrate was concentrated under reduced pressure, and the resulting residue was purified by column chromatography (DCM/MeOH=20:1) to give the title compound as a yellow solid (45 mg, yield 26%).

MS m/z (ESI): 576.2 (M+H)

Step 4

5-Fluoro-4-(5-fluoro-1,1-dimethyl-2,3-dihydro-1H-benzo[d]pyrrolo[1,2-a]imidazol-7-yl)-N-(5-(piperazine-4-yl)pyridin-2-yl)pyrimidin-2-amine To a reaction flask was added tert-butyl 4-(6-((5-fluoro-4-(5-fluoro-1,1-dimethyl-2,3-dihydro-1H-benzo[d]pyrrolo[1,2-a]imidazol-7-yl)pyrimidin-2-yl)amino)pyridin-3-yl)piperidine-1-carboxylate (45 mg, 0.078 mmol, prepared in Step 3), trifluoroacetic acid (0.5 mL) and dichloromethane (6 mL). The mixture was stirred at room temperature for 1 hour to give rise to a reaction, diluted with water (10 mL), and extracted with dichloromethane (10 mL×3). The organic layers were combined, washed with saturated sodium chloride (10 mL), and dried over anhydrous sodium sulfate. The filtrate was concentrated in vacuo and the resulting residue Step 1 tert-Butyl 6-nitro-3',6'-dihydro-[3,4'-bipyridine]-1' (2'H)-carboxylate

To a reaction flask was added 5-bromo-2-nitropyridine (20.3 g, 0.1 mol), tert-butyl 4-(4,4,5,5-tetramethyl-1,3,2-dioxaborolan-2-yl)-5,6-dihydropyridine-1(2H)-carboxylate (30.9 g, 0.1 mol), cesium carbonate (65 g, 0.2 mol), Pd(dppf)Cl₂ (7.33 g, 0.01 mol) and dioxane/water (250 mL/30 mL), was purified by thin layer chromatography (DCM/MeOH=10:1) to give the title compound as a yellow solid (25 mg, yield 68%).

¹HNMR (DMSO, 400 MHz), δ 10.06 (s, 1H), 8.69 (s, 1H), 8.20-8.17 (m, 3H), 7.72 (d, J=12.4 Hz, 1H), 7.63 (d, J=8.8 Hz, 1H), 3.12-3.09 (m, 2H), 3.03-3.01 (m, 2H), 2.98-2.95 (m, 3H), 2.58-2.55 (m, 2H), 1.97-1.94 (m, 2H), 1.85-1.82 (m, 2H), 1.67 (s, 6H)

MS m/z (ESI): 476.1 (M+H)

Example 27

5-Fluoro-4-(5-fluoro-1,1-dimethyl-2,3-dihydro-1H-benzo[d]pyrrolo[1,2-a]imidazol-7-yl)-N-(5-(piperazin-1-ylmethyl)pyridin-2-yl)pyrimidin-2-amine

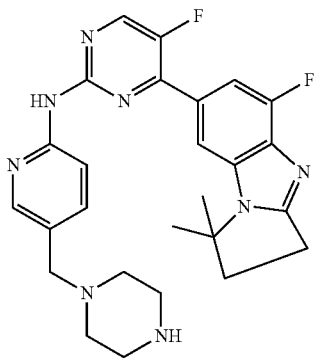

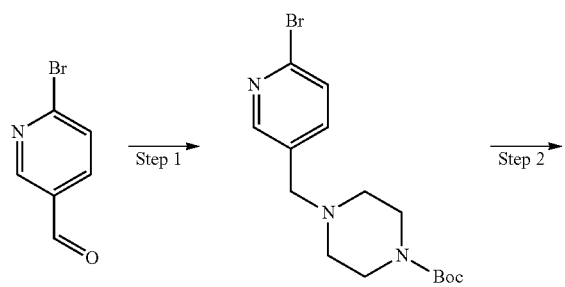

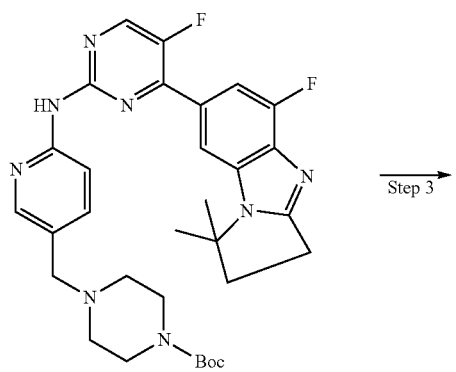

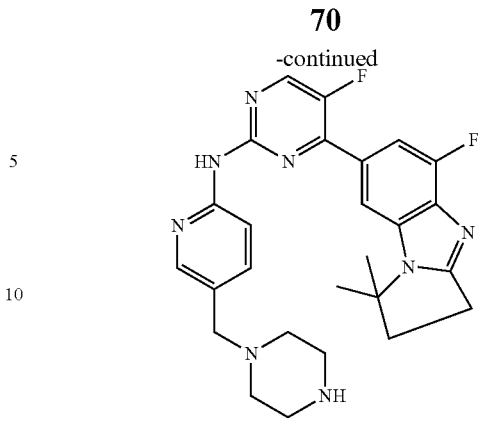

Step 1 tert-Butyl 4-((6-bromopyridin-3-yl)methyl)piperazine-1-carboxylate

To a reaction flask was added 6-bromo-3-formylpyridine (5.0 g, 26.88 mmol), tert-butyl piperazine-1-carboxylate (6.5 g, 35 mmol) and dichloromethane (30 mL), then sodium triacetoxyborohydride (8.6 g, 40 mmol) was added in portions. The mixture was stirred at room temperature for 12 hours to give rise to a reaction, saturated sodium carbonate solution (15 mL) was added, and the aqueous phase was extracted with dichloromethane (20 mL×3). The organic layers were combined, washed with saturated sodium chloride (10 mL), and dried over anhydrous sodium sulfate. The filtrate was concentrated in vacuo, and the resulting residue was purified by column chromatography (DCM/MeOH=20:1) to give the title compound as a pale yellow solid (3.4 g, yield 36%).

MS m/z (ESI): 357.2 (M+H)

Step 2 tert-Butyl 4-((6-((5-fluoro-4-(5-fluoro-1,1-dimethyl-2,3-dihydro-1H-benzo[d]pyrrolo[1,2-a]imidazol-7-yl)pyrimidin-2-yl)amino)pyridin-3-yl)methyl)piperazine-1-carboxylate To a microwave reaction flask was added 5-fluoro-4-(5-fluoro-1,1-dimethyl-2,3-dihydro-1H-benzo[d]pyrrolo[1,2-a]imidazol-7-yl)pyrimidin-2-amine (95 mg, 0.3 mmol, prepared according to the procedure of Example 1), tert-butyl 4-((6-bromopyridin-3-yl)methyl)piperazine-1-carboxylate (107 mg, 0.3 mmol), cesium carbonate (195 mg, 0.6 mmol), Pd₂(dba)₃ (55 mg, 0.06 mmol), Xant-phos (35 mg, 0.06 mmol) and 1,4-dioxane (2 mL), and the mixture was reacted for 1 hour in a microwave at 120° C. The resulting mixture was cooled to room temperature and water (10 mL) was added. The aqueous phase was extracted with dichloromethane (10 mL×3) and the phases were separated. The organic phases were combined and washed with saturated sodium chloride solution (10 mL), dried over anhydrous sodium sulfate, filtered with suction, was concentrated under reduced pressure. The resulting residue was purified by column chromatography (DCM/MeOH=10:1) to give the title compound (62 mg, as a yellow oil), yield 35%.

MS m/z (ESI): 591.2 (M+H)

Step 3

5-Fluoro-4-(5-fluoro-1,1-dimethyl-2,3-dihydro-1H-benzo[d]pyrrolo[1,2-a]imidazol-7-yl)-N-(5-(piperazin-1-ylmethyl)pyridin-2-yl)pyrimidin-2-amine To a reaction flask was added tert-butyl 4-((6-((5-fluoro-4-(5-fluoro-1,1-dimethyl-2,3-dihydro-1H-benzo[d]pyrrolo[1,2-a]imidazol-7-yl)pyrimidin-2-yl)amino)pyridin-3-yl)methyl)piperazine-1-carboxylate (62 mg, 0.1 mmol, prepared in Step 2), hydrochloric acid (2N, 2 mL) and 1,4-dioxane (2 mL). The mixture was stirred at room temperature for 2 hours to give rise to a reaction, diluted with water (10 mL), and extracted with dichloromethane (5 mL×3). The organic layers were combined, washed with saturated sodium chloride (10 mL), and dried over anhydrous sodium sulfate. The filtrate was concentrated in vacuo, and the resulting residue was purified by thin layer chromatography (DCM/MeOH=10:1) to give the title compound as a yellow solid (22 mg, yield 45%).

$^1$H-NMR (DMSO-d6, 400 MHz), δ 10.08 (s, 1H), 8.69 (s, 1H), 8.23-8.2 (m, 3H), 7.73-7.68 (m, 2H), 3.54 (s, 2H), 3.12-3.06 (m, 6H), 2.58-2.55 (m, 6H), 1.68 (s, 6H)

MS m/z (ESI): 491.1 (M+H)

Example 28

N-(5-(4-Aminopiperidine-1-yl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine

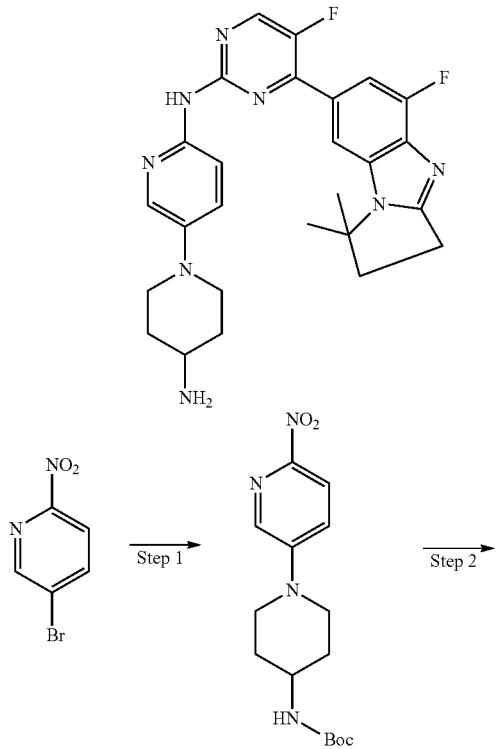

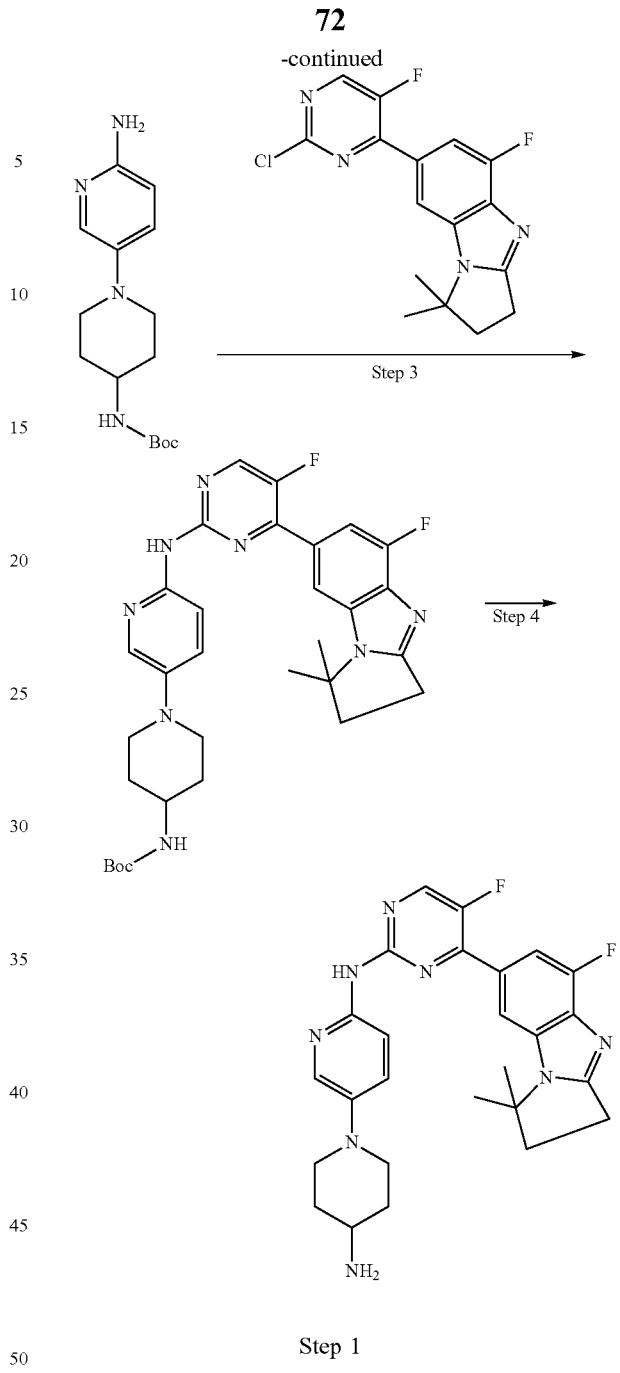

Step 1 tert-Butyl (1-(6-nitropyridin-3-yl)piperidine-4-yl)carbamate

To a reaction flask was added 5-bromo-2-nitropyridine (2.0 g, 9.9 mmol), tert-butyl piperidine-4-ylcarbamate (1.98 g, 9.9 mmol), triethylamine (1.31 g, 12.87 mmol) and dimethyl sulfoxide (8 mL), and the mixture was reacted for 1.5 hours in a microwave at 120° C. The resulting mixture was cooled to room temperature, and was extracted with ethyl acetate (25 mL×3). The organic phases were combined, washed with saturated sodium chloride (25 mL), dried over anhydrous sodium sulfate, and filtered with suction. The filtrate was concentrated under reduced pressure, and the resulting residue was purified by column chromatography (EtOAc/PE=1/5) to give the title compound as a yellow solid (1.4 g, yield 44.1%).

MS m/z (ESI): 323.1 (M+H)

Step 2 tert-Butyl (1-(6-aminopyridin-3-yl) piperidine-4-yl) carbamate

To a reaction flask was added tert-butyl (1-(6-nitropyridin-3-yl)piperidine-4-yl)carbamate (1.0 g, 3.1 mmol, prepared in Step 1), Pd/C (0.1 g), ethyl acetate (2 mL) and ethanol (8 mL), and the mixture was stirred at room temperature for 12 hours under a hydrogen atmosphere to give rise to a reaction. The reaction liquid was filtered with suction, and the filter cake was washed with ethyl acetate (20 mL). The organic phases were combined and concentrated. The resulting residue was purified by column chromatography (DCM/MeOH=50/1) to give the title compound as an off-white solid (0.87 g, yield 95%).

MS m/z (ESI): 293.2 (M+H)

Step 3 tert-Butyl (1-(6-((5-fluoro-4-(5-fluoro-1,1-dimethyl-2,3-dihydro-1H-benzo[d]pyrrolo[1,2-a]imidazol-7-yl)pyrimidin-2-yl)amino)pyridin-3-yl)piperidine-4-yl) carbamate To a microwave reaction flask was added 7-(2-chloro-5-fluoropyrimidin-4-yl)-5-fluoro-2,3-dihydro-1H-benzo[d]pyrrolo[1,2-a]imidazole (150 mg, 0.45 mmol, prepared in Example 1), tert-butyl (1-(6-aminopyridin-3-yl)piperidine-4-yl) carbamate (131 mg, 0.45 mmol), cesium carbonate (292 mg, 0.90 mmol), Pd$_2$(dba)$_3$ (41 mg, 0.045 mmol), Xant-phos (26 mg, 0.045 mmol) and 1,4-dioxane (10 mL), and the mixture was reacted for 1 hour in a microwave at 120° C. The resulting mixture was cooled to room temperature and water (10 mL) was added. The aqueous phase was extracted with dichloromethane (10 mL×3) and the phases were separated. The organic phases were combined, washed with saturated sodium chloride solution (10 mL), dried over anhydrous sodium sulfate, and filtered with suction. The filtrate was concentrated under reduced pressure. The resulting residue was purified by column chromatography (DCM/MeOH=10:1) to give the title compound as a yellow oil (39 mg, yield 14.7%).

MS m/z (ESI): 591.3 (M+H)

Step 4

N-(5-(4-Aminopiperidine-1-yl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine To a reaction flask was added tert-butyl (1-(6-((5-fluoro-4-(5-fluoro-1,1-dimethyl-2,3-dihydro-1H-benzo[d]pyrrolo[1,2-a]imidazol-7-yl)pyrimidin-2-yl)amino)pyridin-3-yl)piperidine-4-yl)carbamate (30.0 mg, 0.05 mmol, prepared in Step 3), hydrochloric acid (2N, 2 mL) and 1,4-dioxane (2 mL). The mixture was stirred at room temperature for 2 hours to give rise to a reaction, diluted with water (10 mL), and extracted with dichloromethane (5 mL×3). The organic layers were combined, washed with saturated sodium chloride (10 mL), and dried over anhydrous sodium sulfate. The filtrate was concentrated in vacuo, and the resulting residue was purified by thin layer chromatography (DCM/MeOH=10:1) to give the title compound as a yellow solid (18 mg yield 73%).

$^1$H-NMR (DMSO-d6, 400 MHz), δ 11.06 (s, 1H), 8.78 (d, J=2.4 Hz, 1H), 8.16 (s, 1H), 8.04-8.01 (m, 2H), 7.94-7.91 (m, 2H), 7.82 (d, J=6.9 Hz, 1H), 7.72 (d, J=9.0 Hz, 1H), 3.74 (d, J=9.0 Hz, 2H), 3.22-3.20 (m, 1H), 3.13 (t, J=5.4 Hz, 2H), 2.86 (t, J=8.4 Hz, 2H), 2.58 ((t, J=5.7 Hz, 2H), 2.00-1.98 (m, 2H), 1.66-1.60 (m, 8H)

MS m/z (ESI): 491.2 (M+H)

Example 29

5-Fluoro-4-(5-fluoro-1,1-dimethyl-2,3-dihydro-1H-benzo[d]pyrrolo[1,2-a]imidazol-7-yl)-N-(6-m ethyl-5-(piperazin-1-ylmethyl)pyridin-2-yl)pyrimidin-2-amine

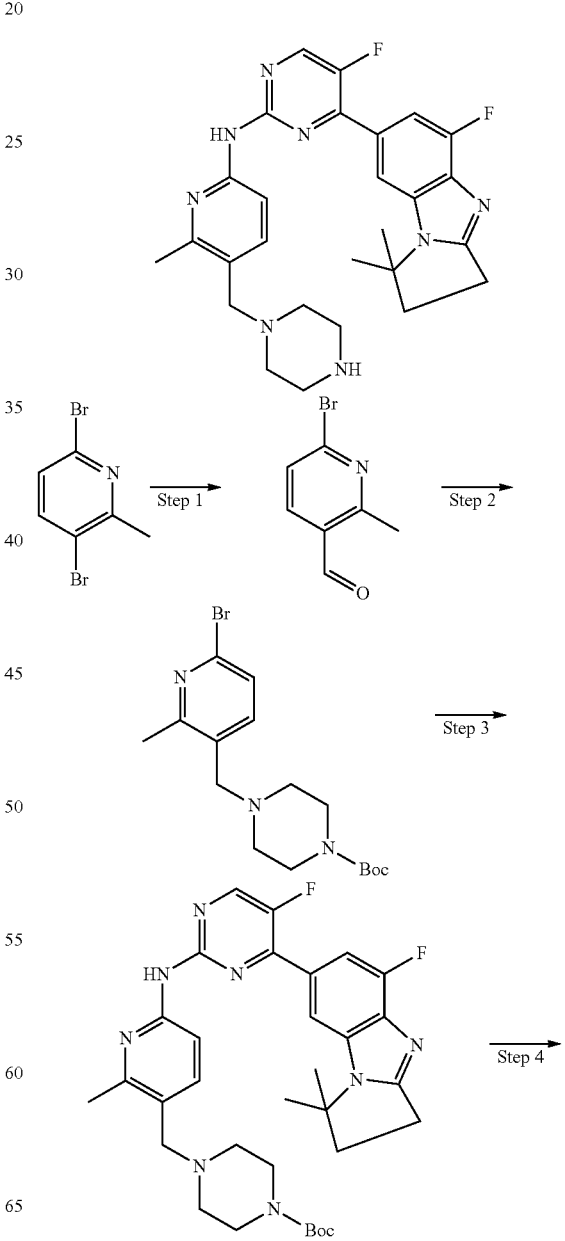

-continued

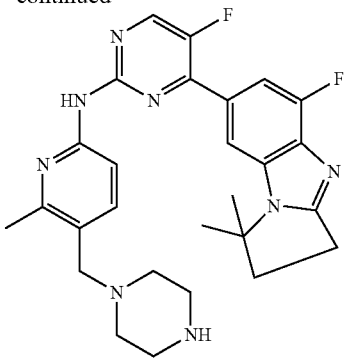

Step 1

6-Bromo-2-methyl-3-formylpyridine

To a reaction flask was added 3,6-dibromo-2-methylpyridine (1.0 g, 3.9 mmol) and anhydrous diethyl ether (10 mL), and the mixture was cooled to −78° C. n-BuLi (1.6M in hexanes, 2.4 mL, 3.9 mmol) was added dropwise and stirred for 1 hour. Anhydrous DMF (307 mg, 4.2 mmol) was added, and the mixture was stirred at room temperature for 1 hour to give rise to a reaction. Saturated ammonium chloride solution (10 mL) was added, and the aqueous phase was extracted with ethyl acetate (20 mL×3). The organic phases were combined, washed with saturated sodium chloride solution (20 mL), dried over anhydrous sodium sulfate, and filtered with suction. The filtrate was concentrated under reduced pressure and the resulting residue was purified by column chromatography (EtOAc/PE=1:10) to give the title compound as a white solid (0.4 g, yield 51%).

MS m/z (ESI): 202.1 (M+H)

Step 2 tert-Butyl 4-((6-bromo-2-methylpyridin-3-yl)methyl)piperazine-1-carboxylate To a reaction flask was added 6-bromo-2-methyl-3-formylpyridine (0.4 g, 2 mmol, prepared in Step 1), tert-butyl piperazine-1-carboxylate (0.37 g, 2 mmol), sodium triacetoxyborohydride (0.53 g, 2.5 mmol) and dichloromethane (35 mL). The mixture was stirred at room temperature for 1 hour to give rise to a reaction, diluted with water (10 mL), and extracted with dichloromethane (20 mL×3). The organic layers were combined, washed with saturated sodium chloride (10 mL), and dried over anhydrous sodium sulfate. The filtrate was concentrated in vacuo, and the resulting residue was purified by column chromatography (DCM/MeOH=20:1) to give the title compound as a white solid (500 mg, yield 75%).

MS m/z (ESI): 372.2 (M+H)

Step 3 tert-Butyl 4-((6-((5-fluoro-4-(5-fluoro-1,1-dimethyl-2,3-dihydro-1H-benzo[d]pyrrolo[1,2-a]imidazol-7-yl)pyrimidin-2-yl)amino)-2-methylpyridin-3-yl)methyl)piperazine-1-carboxylate To a reaction flask was added 5-fluoro-4-(5-fluoro-1,1-dimethyl-2,3-dihydro-1H-benzo[d]pyrrolo[1,2-a]imidazol-7-yl)pyrimidin-2-amine (95 mg, 0.3 mmol, prepared according to Step 2 of Example 20), tert-butyl 4-((6-bromo-2-methylpyridin-3-yl)methyl)piperazine-1-carboxylate (111 mg, 0.3 mmol), cesium carbonate (195 mg, 0.6 mmol), Pd$_2$(dba)$_3$ (55 mg, 0.06 mmol), XantPhos (35 mg, 0.06 mmol) and anhydrous 1,4-dioxane (2 mL), and the mixture was reacted for 1 hour in a microwave at 150° C. The resulting mixture was cooled to room temperature, water (10 mL) was added, and the aqueous phase was extracted with ethyl acetate (20 mL×3). The organic phases were combined, washed with saturated sodium chloride solution (10 mL), dried over anhydrous sodium sulfate, and filtered with suction. The filtrate was concentrated under reduced pressure. The resulting residue was purified by column chromatography (DCM/MeOH=20:1) to give the title compound as a yellow solid (30 mg, yield 17%).

MS m/z (ESI): 605.3 (M+H)

Step 4

5-Fluoro-4-(5-fluoro-1,1-dimethyl-2,3-dihydro-1H-benzo[d]pyrrolo[1,2-a]imidazol-7-yl)-N-(6-methyl-5-(piperazin-1-ylmethyl)pyridin-2-yl)pyrimidin-2-amine To a reaction flask was added tert-butyl 4-((6-((5-fluoro-4-(5-fluoro-1,1-dimethyl-2,3-dihydro-1H-benzo[d]pyrrolo[1,2-a]imidazol-7-yl)pyrimidin-2-yl)amino)-2-methylpyridin-3-yl)methyl)piperazine-1-carboxylate (30 mg, 0.05 mmol, prepared in Step 3), trifluoroacetic acid (0.5 mL) and dichloromethane (4 mL). The mixture was stirred at room temperature for 1 hour to give rise to a reaction, diluted with water (10 mL), and extracted with dichloromethane (10 mL×3). The organic layers were combined, washed with saturated sodium chloride (10 mL), and dried over anhydrous sodium sulfate. The filtrate was concentrated in vacuo, and the resulting residue was purified by thin layer chromatography (DCM/MeOH=10:1) to give the title compound as a yellow solid (17 mg, yield 68%).

$^1$HNMR (DMSO, 400 MHz), δ 9.96 (s, 1H), 8.67 (s, 1H), 8.24 (s, 1H), 8.04 (d, J=8.0 Hz, 1H), 7.72 (d, J=12.8 Hz, 1H), 7.57 (d, J=8.8 Hz, 1H), 3.42 (s, 2H), 3.21-3.18 (m, 2H), 2.87 (brs, 4H), 2.72 (brs, 2H), 2.58-2.54 (m, 2H), 2.38 (s, 3H), 2.34-2.32 (m, 2H), 1.68 (s, 6H)

MS m/z (ESI): 505.3 (M+H)

Example 30

5-Fluoro-4-(5-fluoro-1,1-dimethyl-2,3-dihydro-1H-benzo[d]pyrrolo[1,2-a]imidazol-7-yl)-N-(6-methyl-5-(piperidine-4-ylmethyl)pyridin-2-yl)pyrimidin-2-amine

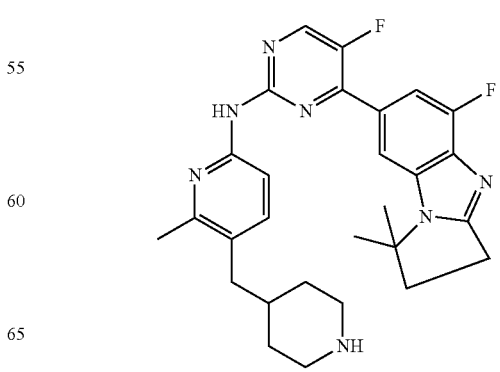

77
-continued

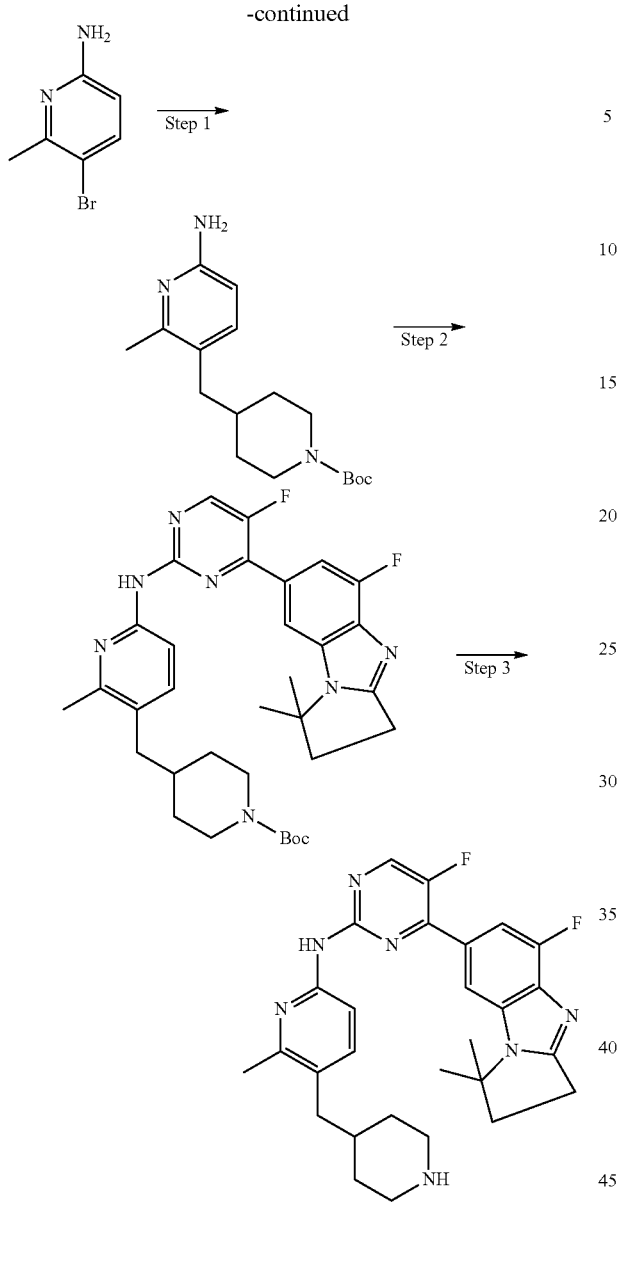

Step 1 tert-Butyl 4-((6-amino-2-methylpyridin-3-yl)methyl)
piperidine-1-carboxylate

To a reaction flask was added tert-butyl 4-methylenepiperidine-1-carboxylate (1.0 g, 5 mmol) and tetrahydrofuran (10 mL), then added 9-BBN (0.5M in THF, 15 mL, 7.5 mmol), and the mixture is stirred at 75° C. for 1 hour. The resulting mixture was cooled to room temperature, and then 5-bromo-6-methylpyridin-2-amine (748 mg, 4 mmol), potassium carbonate (0.8 g, 5.5 mmol), DMF (10 mL) and water (1 mL) were added. The mixture was stirred at 60° C. for 4 hours to give rise to a reaction, diluted with water (10 mL), and extracted with ethyl acetate (20 mL×3). The organic layers were combined, washed with saturated sodium chloride (10 mL), and dried over anhydrous sodium sulfate. The filtrate was concentrated in vacuo and the resulting residue was purified by column chromatography (DCM/MeOH=20:1) to give the title compound as a yellow solid (1 g, yield 84%).

MS m/z (ESI): 306.2 (M+H)

Step 2 tert-Butyl 4-((6-((5-fluoro-4-(5-fluoro-1,1-dimethyl-2,3-dihydro-1H-benzo[d]pyrrolo[1,2-a]imidazol-7-yl)pyrimidin-2-yl)amino)-2-methylpyridin-3-yl)methyl)piperidine-1-carboxylate To a microwave reaction flask was added 7-(2-chloro-5-fluoropyrimidin-4-yl)-5-fluoro-2,3-dihydro-1H-benzo[d]pyrrolo[1,2-a]imidazole (100 mg, 0.3 mmol, prepared according to the procedure of Example 1), tert-butyl 4-((6-amino-2-methylpyridin-3-yl)methyl)piperidine-1-carboxylate (92 mg, 0.3 mmol, prepared in Step 1), cesium carbonate (195 mg, 0.6 mmol), Pd$_2$(dba)$_3$ (27 mg, 0.03 mmol), XantPhos (35 mg, 0.06 mmol) and anhydrous 1,4-dioxane (2 mL), and the mixture was reacted for 1 hour in a microwave at 150° C. The resulting mixture was cooled to room temperature, water (10 mL) was added, and the aqueous phase was extracted with ethyl acetate (20 mL×3). The organic phases were combined, washed with saturated sodium chloride solution (10 mL), dried over anhydrous sodium sulfate, and filtered with suction. The filtrate was concentrated under reduced pressure, and the resulting residue was purified by column chromatography (DCM/MeOH=10:1) to give the title compound as a yellow solid (65 mg, yield 36%).

MS m/z (ESI): 604.2 (M+H)

Step 3

5-Fluoro-4-(5-fluoro-1,1-dimethyl-2,3-dihydro-1H-benzo[d]pyrrolo[1,2-a]imidazol-7-yl)-N-(6-methyl-5-(piperidine-4-ylmethyl)pyridin-2-yl)pyrimidin-2-amine To a reaction flask was added tert-butyl 4-((6-((5-fluoro-4-(5-fluoro-1,1-dimethyl-2,3-dihydro-1H-benzo[d]pyrrolo[1,2-a]imidazol-7-yl)pyrimidin-2-yl)amino)-2-methylpyridin-3-yl)methyl)piperidine-1-carboxylate (65 mg, 0.1 mmol, prepared in Step 2), trifluoroacetic acid (1 mL) and dichloromethane (4 mL). The mixture was stirred at room temperature for 1 hour to give rise to a reaction, diluted with water (10 mL), and extracted with dichloromethane (10 mL×3). The organic layers were combined, washed with saturated sodium chloride (10 mL), and dried over anhydrous sodium sulfate. The filtrate was concentrated in vacuo and the resulting residue was purified by thin layer chromatography (DCM/MeOH=10:1) to give the title compound as a yellow solid (25 mg, yield 50%).

$^1$HNMR (DMSO, 400 MHz), δ 9.92 (s, 1H), 8.83 (brs, 1H), 8.67 (s, 1H), 8.23 (s, 1H), 8.01 (d, J=8.4 Hz, 1H), 7.72 (d, J=12.8 Hz, 1H), 7.47 (d, J=8.0 Hz, 1H), 3.35 (s, 2H), 3.24-3.21 (m, 2H), 3.12-3.10 (m, 2H), 2.58-2.53 (m, 4H), 2.43 (s, 3H), 1.78-1.74 (m, 3H), 1.67 (s, 6H), 1.43-1.40 (m, 2H)

MS m/z (ESI): 505.2 (M+H)

Example 31

5-Fluoro-4-(5-fluoro-1,1-dimethyl-2,3-dihydro-1H-benzo[d]pyrrolo[1,2-a]imidazol-7-yl)-N-(6-methyl-5-(piperidine-1-yl)pyridin-2-yl)pyrimidin-2-amine

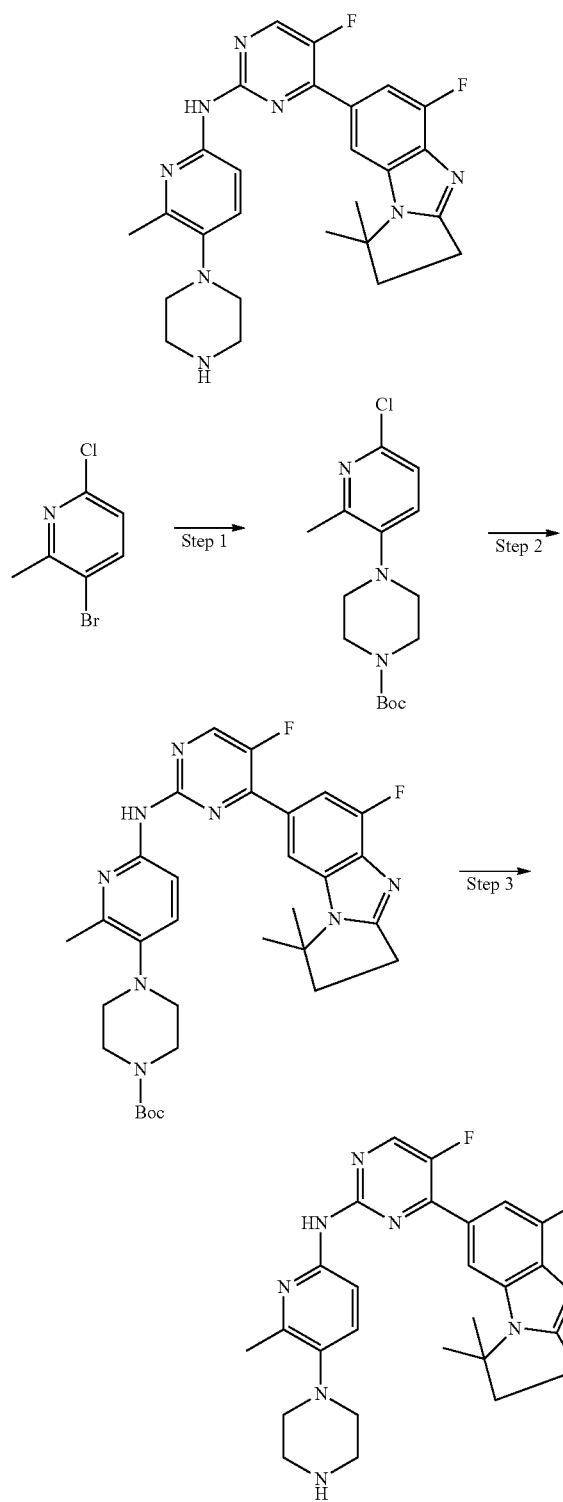

Step 1 tert-Butyl 4-(6-chloro-2-methylpyridin-3-yl)piperazine-1-carboxylate

To a reaction flask was added 3-bromo-6-chloro-2-methylpyridine (1.5 g, 7.2 mmol), tert-butyl piperazine-1-carboxylate (1.2 g, 6.4 mmol), sodium tert-butoxide (1.4 g, 14.4 mmol), Pd$_2$(dba)$_3$ (659 mg, 0.72 mmol), Xantphos (832 mg, 1.44 mmol) and toluene (20 mL), and the mixture was stirred under heating at 100° C. for 16 hours to give rise to a reaction. The resulting mixture was cooled to room temperature and filtered. The filtrate was concentrated and the resulting residue was purified by column chromatography (EtOAc/PE=1:5) to give the title compound as a yellow oil (698 mg, yield 31%).

MS m/z (ESI): 312.3 (M+H)

Step 2 tert-Butyl 4-(6-((5-fluoro-4-(5-fluoro-1,1-dimethyl-2,3-dihydro-1H-benzo[d]pyrrolo[1,2-a]imidazol-7-yl)pyrimidin-2-yl)amino)-2-methylpyridin-3-yl)piperazine-1-carboxylate To a reaction flask was added 5-fluoro-4-(5-fluoro-1,1-dimethyl-2,3-dihydro-1H-benzo[d]pyrrolo[1,2-a]imidazol-7-yl)pyrimidin-2-amine (95 mg, 0.3 mmol, prepared according to Step 2 of Example 20), tert-butyl 4-(6-chloro-2-methylpyridin-3-yl)piperazine-1-carboxylate (93 mg, 0.3 mmol), cesium carbonate (195 mg, 0.6 mmol), Pd$_2$(dba)$_3$ (55 mg, 0.06 mmol), XantPhos (69 mg, 0.12 mmol) and 1,4-dioxane (2 mL), and the mixture was reacted for 1 hour in a microwave at 150° C. The resulting mixture was cooled to room temperature, water (10 mL) was added, and the aqueous phase was extracted with ethyl acetate (20 mL×3). The organic phases were combined, washed with saturated sodium chloride solution (10 mL), dried over anhydrous sodium sulfate, and filtered with suction. The filtrate was concentrated under reduced pressure, and the resulting residue was purified by column chromatography (DCM/MeOH=20:1) to give the title compound as a yellow solid (56 mg, yield 32%).

MS m/z (ESI): 591.3 (M+H)

Step 3

5-Fluoro-4-(5-fluoro-1,1-dimethyl-2,3-dihydro-1H-benzo[d]pyrrolo[1,2-a]imidazol-7-yl)-N-(6-methyl-5-(piperidine-1-yl)pyridin-2-yl)pyrimidin-2-amine To a reaction flask was added tert-butyl 4-(6-((5-fluoro-4-(5-fluoro-1,1-dimethyl-2,3-dihydro-1H-benzo[d]pyrrolo[1,2-a]imidazol-7-yl)pyrimidin-2-yl)amino)-2-methylpyridin-3-yl)piperazine-1-carboxylate (56 mg, 0.095 mmol), trifluoroacetic acid (0.5 mL) and dichloromethane (4 mL). The mixture was stirred at room temperature for 1 hour to give rise to a reaction, diluted with water (10 mL), and extracted with dichloromethane (10 mL×3). The organic layers were combined, washed with saturated sodium chloride (10 mL), and dried over anhydrous sodium sulfate. The filtrate was concentrated in vacuo, and the resulting residue was purified by thin layer chromatography (DCM/MeOH=10:1) to give the title compound as a yellow solid (25 mg, yield 54%).

$^1$HNMR (DMSO, 400 MHz), δ 10.43 (s, 1H), 8.94 (brs, 1H), 8.73 (s, 1H), 8.22 (s, 1H), 7.96 (d, J=8.8 Hz, 1H), 7.74-7.65 (m, 2H), 3.28 (brs, 4H), 3.13-3.09 (m, 2H), 3.09-3.05 (m, 4H), 2.56 (t, J=7.6 Hz, 2H), 2.48 (s, 3H), 1.67 (s, 6H)

MS m/z (ESI): 491.3 (M+H)

Example 32

(4-Ethylpiperazin-1-yl)(6-((5-fluoro-4-(5-fluoro-1,1-dimethyl-2,3-dihydro-1H-benzo[d]pyrrolo[1,2-a]imidazol-7-yl)pyrimidin-2-yl)amino)pyridin-3-yl) methyl ketone

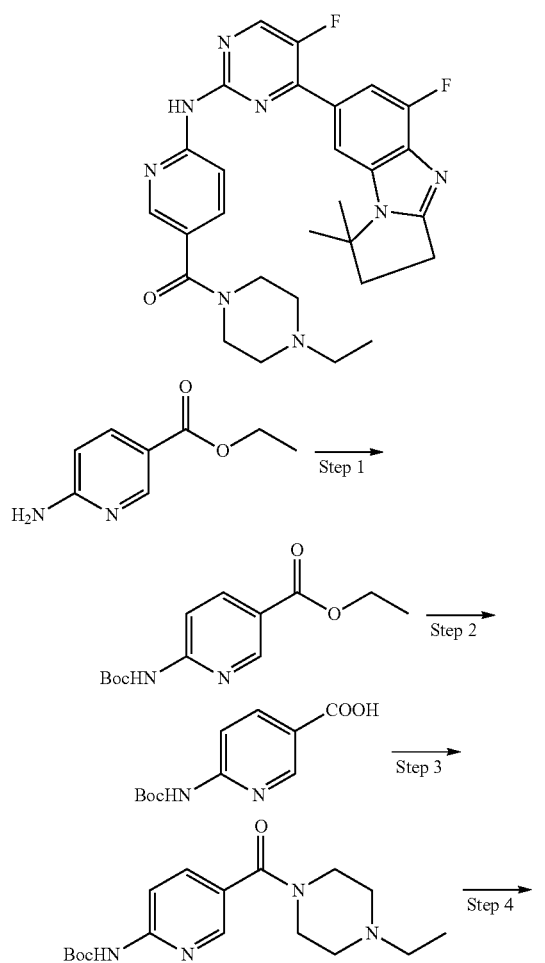

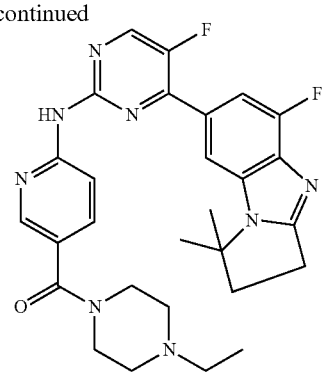

Step 1

Ethyl 6-((tert-Butyloxycarbonyl)amino)nicotinate

To a reaction flask was added ethyl 6-aminonicotinate (10 g, 60 mmol), DMAP (0.72 g, 6 mmol), (Boc)$_2$O (19.5 g, 90 mmol) and tetrahydrofuran (600 mL), and the mixture was stirred at room temperature for 12 hours to give rise to a reaction. Dichloromethane (100 mL) was added, the organic phase was washed with hydrochloric acid (0.5N, 20 mL), dried over anhydrous sodium sulfate, and filtered with suction. The filtrate was concentrated to give the title compound as a white solid (15 g, yield 94%).

MS m/z (ESI): 267.2 (M+H)

Step 2

6-((tert-Butyloxycarbonyl)amino)nicotinic acid

To a reaction flask was added ethyl 6-((tert-butyloxycarbonyl)amino) nicotinate (10 g, 37.6 mmol, prepared in Step 1), sodium hydroxide solution (1M, 75 mL) and MeOH (100 mL). The mixture was stirred at room temperature for 12 hours to give rise to a reaction and concentrated under reduced pressure. The resulting residue was neutralized with hydrochloric acid (2N) to pH 3 and filtered to give the title compound as a white solid (6.5 g, yield 73%).

MS m/z (ESI): 239.2 (M+H)

Step 3 tert-Butyl (5-(4-ethylpiperazin-1-carbonyl)pyridin-2-yl)carbamate

To a reaction flask was added 6-((tert-butyloxycarbonyl)amino)nicotinic acid (5 g, 21 mmol, prepared in Step 2), 1-ethylpiperazine (4.8 g, 42 mmol), HOBt (4.3 g, 31.5 mmol), triethylamine (6.4 g, 63 mmol), EDCI (6.0 g, 31.5 mmol) and DMF (100 mL), and the mixture was stirred at room temperature for 12 hours to give rise to a reaction. The reaction liquid was concentrated, dichloromethane (50 mL) was added, and the organic phase was washed with hydrochloric acid (0.1N, 10 mL). The organic phases were combined, washed with saturated sodium chloride (20 mL), dried over anhydrous sodium sulfate, and filtered with suction. The filtrate was concentrated to give the title compound as a white solid (4.0 g, yield 57%).

MS m/z (ESI): 335.2 (M+H)

83

Step 4

(6-Aminopyridin-3-yl)(4-ethylpiperazin-1-yl)methyl ketone

To a reaction flask was added tert-butyl (5-(4-ethylpiperazin-1-carbonyl) pyridin-2-yl)carbamate (2 g, 6 mmol, prepared in Step 3), trifluoroacetic acid (5 mL) and DMF (20 mL), and the mixture was stirred at room temperature for 12 hours to give rise to a reaction. Dichloromethane (20 mL) was added, the organic phase was washed with saturated sodium carbonate solution (20 mL), then washed with saturated sodium chloride (20 mL), dried over anhydrous sodium sulfate, and filtered with suction. The filtrate was concentrated to give the title compound as a white solid (1.0 g, yield 71%).

MS m/z (ESI): 235.1 (M+H)

Step 5

(4-Ehylpiperazin-1-yl)(6-((5-fluoro-4-(5-fluoro-1,1-dimethyl-2,3-dihydro-1H-benzo[d]pyrrolo[1,2-a]imidazol-7-yl)pyrimidin-2-yl)amino)pyridin-3-yl)methyl ketone To a reaction flask was added 7-(2-chloro-5-fluoropyrimidin-4-yl)-5-fluoro-2,3-dihydro-1H-benzo[d]pyrrolo[1,2-a]imidazole (200 mg, 0.6 mmol, prepared in Example 1), (6-aminopyridin-3-yl)(4-ethylpiperazin-1-yl)methyl ketone (140 mg, 0.6 mmol), cesium carbonate (391 mg, 1.2 mmol), $Pd_2(dba)_3$ (55 mg, 0.06 mmol), XantPhos (69 mg, 0.12 mmol) and anhydrous 1,4-dioxane (5 mL), and the mixture was reacted for 1 hour in a microwave at 120° C. The resulting mixture was cooled to room temperature, water (10 mL) was added, and the aqueous phase was extracted with ethyl acetate (20 mL×3). The organic phases were combined, washed with saturated sodium chloride solution (10 mL), dried over anhydrous sodium sulfate, and filtered with suction. The filtrate was concentrated under reduced pressure and the resulting residue was purified by column chromatography (DCM/MeOH=10:1) to give the title compound as a yellow solid (75 mg, yield 24%).

$^1$HNMR (DMSO, 400 MHz), δ 10.44 (s, 1H), 8.75 (s, 1H), 8.37 (s, 1H), 8.31 (d, J=8.8 Hz, 1H), 8.22 (s, 1H), 7.82-7.97 (m, 1H), 7.71 (d, 1H), 3.37-3.34 (m, 2H), 3.16-3.12 (m, 2H), 3.10-3.08 (m, 2H), 2.56 (q, J=7.6 Hz, 2H), 2.39-2.34 (m, 6H), 1.67 (s, 6H), 0.86 (t, J=7.6 Hz, 3H)

MS m/z (ESI): 533.3 (M+H)

84

Example 33

N-(5-((1-Ethylpiperidine-4-yl)oxy)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine

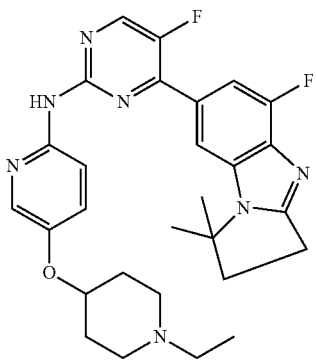

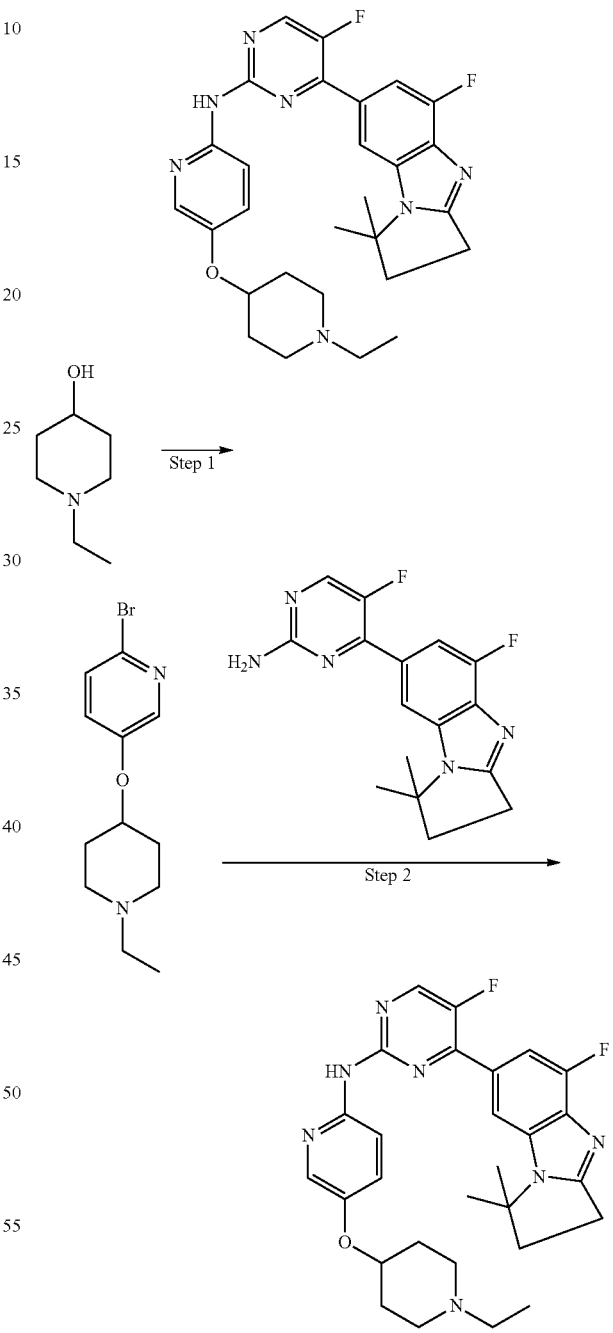

Step 1

2-Bromo-5-((1-ethylpiperidine-4-yl)oxy)pyridine

To a reaction flask was added 1-ethylpiperidin-4-ol (1.0 g, 7.7 mmol), 2,5-dibromopyridine (2 g, 8.5 mmol) and dimethyl sulfoxide (30 mL), then added sodium tert-butoxide (1.7 g, 15.4 mmol). The mixture was stirred at room temperature for 3 hours to give rise to a reaction, water (30 mL) was added, and the aqueous phase was extracted with dichloromethane (20 mL×3). The organic layers were combined, washed with saturated sodium chloride (20 mL), and dried over anhydrous sodium sulfate. The filtrate was concentrated in vacuo, and the resulting residue was purified by column chromatography (DCM/MeOH=10:1) to give the title compound as a black solid (702 mg, yield 32%).

MS m/z (ESI): 287.2 (M+H)

Step 2

N-(5-((1-Ethylpiperidine-4-yl)oxy)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine To a reaction flask was added 5-fluoro-4-(5-fluoro-1,1-dimethyl-2,3-dihydro-1H-benzo[d]pyrrolo[1,2-a]imidazol-7-yl)pyrimidin-2-amine (100 mg, 0.32 mmol, prepared according to Step 2 of Example 20), 2-bromo-5-((1-ethyl-piperidine-4-yl)oxy)pyridine (91 mg, 0.32 mmol), cesium carbonate (208 mg, 0.64 mmol), Pd$_2$(dba)$_3$ (55 mg, 0.06 mmol), XantPhos (35 mg, 0.06 mmol) and anhydrous 1,4-dioxane (5 mL), and the mixture was reacted for 1 hour in a microwave at 150° C. The resulting mixture was cooled to room temperature, water (10 mL) was added, and the aqueous phase was extracted with ethyl acetate (20 mL×3). The organic phases were combined, washed with saturated sodium chloride solution (20 mL), dried over anhydrous sodium sulfate, and filtered with suction. The filtrate was concentrated under reduced pressure and the resulting residue was purified by column chromatography (DCM/MeOH=10:1) to give the title compound as a white solid (50 mg, yield 30%).

$^1$HNMR (DMSO, 400 MHz) δ 9.67 (s, 1H), 8.61 (d, J=3.6 Hz, 1H), 8.57 (s, 1H), 8.12 (s, 1H), 8.00-7.97 (m, 1H), 7.64 (d, J=12.8 Hz, 1H), 4.94-4.91 (m, 1H), 3.10 (t, J=7.2 Hz, 2H), 2.73-2.71 (m, 2H), 2.58-2.56 (m, 2H), 2.37-2.32 (m, 2H), 2.17-2.13 (m, 2H), 1.99-1.97 (m, 2H), 1.66 (s, 6H), 1.62 (s, 2H), 1.02 t, J=6.4 Hz, 3H)

MS m/z (ESI): 520.3 (M+H)

Example 34

5-Fluoro-4-(5-fluoro-1,1-dimethyl-2,3-dihydro-1H-benzo[d]pyrrolo[1,2-a]imidazol-7-yl)-N-(5-(piperidine-4-yloxy)pyridin-2-yl)pyrimidin-2-amine

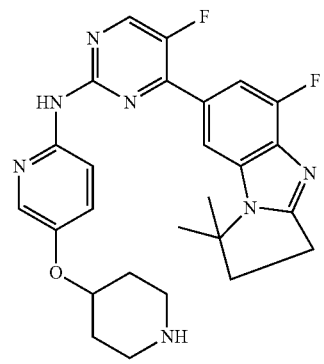

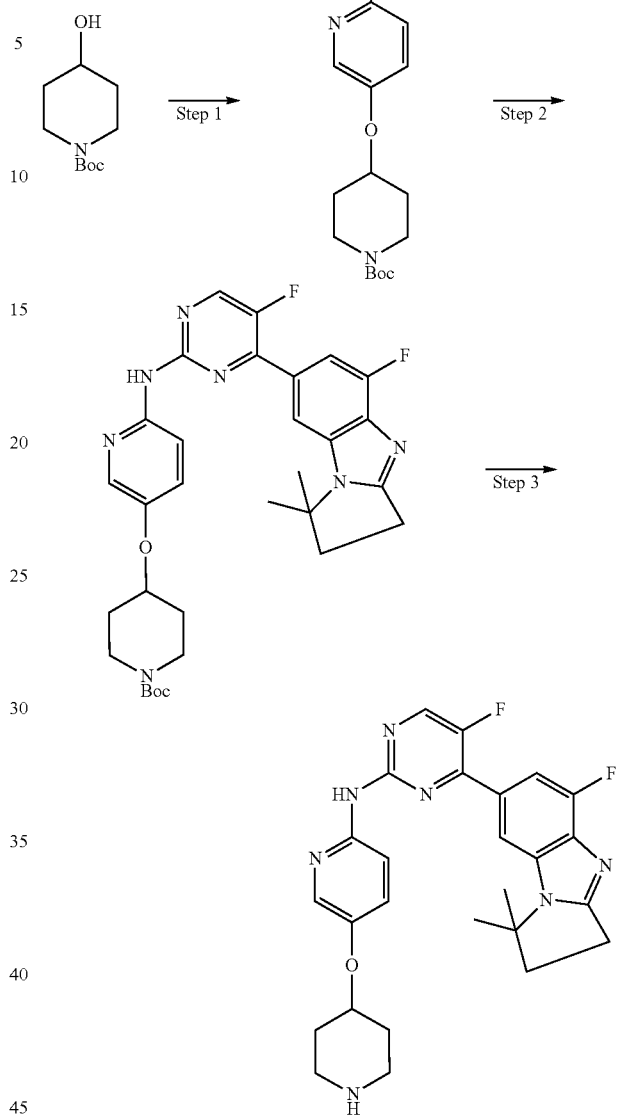

Step 1 tert-Butyl 4-((6-bromopyridin-3-yl)oxy)piperidine-1-carboxylate

To a reaction flask was added tert-butyl 4-hydroxypiperidine-1-carboxylate (1 g, 5 mmol), 2,5-dibromopyridine (1.2 g, 5 mmol), sodium tert-butoxide (0.72 g, 7.5 mmol) and DMSO (10 mL), and the mixture was stirred at room temperature for 3 hours to give rise to a reaction. Water (10 mL) and dichloromethane (30 mL) were added, and the organic phase was washed with saturated sodium chloride (20 mL), dried over anhydrous sodium sulfate, and filtered with suction. The filtrate was concentrated and the resulting residue was purified by column chromatography (PE/EtOAc=10/1) to give the title compound as a white solid (0.8 g, yield 45%).

MS m/z (ESI): 358.2 (M+H)

Step 2 tert-Butyl 4-((6-((5-Fluoro-4-(5-fluoro-1,1-dimethyl-2,3-dihydro-1H-benzo[d]pyrrolo[1,2-a]imidazol-7-yl) pyridin-2-yl)amino)pyridin-3-yl)oxy)piperidine-1-carboxylate To a reaction flask was added 5-fluoro-4-(5-fluoro-1,1-dimethyl-2,3-dihydro-1H-benzo[d]pyrrolo[1,2-a]imidazol-7-yl)pyrimidin-2-amine (200 mg, 0.64 mmol, prepared according to Step 2 of Example 20), tert-butyl 4-((6-bromopyridin-3-yl)oxy)piperidine-1-carboxylate (227 mg, 0.64 mmol, prepared in Step 1), sodium tert-butoxide (92 mg, 0.96 mmol), $Pd_2(dba)_3$ (59 mg, 0.064 mmol), XantPhos (74 mg, 0.128 mmol) and anhydrous 1,4-dioxane (5 mL), and the mixture was reacted for 1 hour in a microwave at 120° C. The resulting mixture was cooled to room temperature, water (10 mL) was added, and the aqueous phase was extracted with ethyl acetate (20 mL×3). The organic phases were combined, washed with saturated sodium chloride solution (10 mL), dried over anhydrous sodium sulfate, and filtered with suction. The filtrate was concentrated under reduced pressure, and the resulting residue was purified by column chromatography (DCM/MeOH=20:1) to give the title compound as a yellow solid (50 mg, yield 13.2%).

MS m/z (ESI): 592.3 (M+H)

Step 3

5-Fluoro-4-(5-fluoro-1,1-dimethyl-2,3-dihydro-1H-benzo[d]pyrrolo[1,2-a]imidazol-7-yl)-N-(5-(piperidine-4-yloxy)pyridin-2-yl)pyrimidin-2-amine To a reaction flask was added tert-butyl 4-((6-((5-fluoro-4-(5-fluoro-1,1-dimethyl-2,3-dihydro-1H-benzo[d]pyrrolo[1,2-a]imidazol-7-yl)pyridin-2-yl)amino)pyridin-3-yl)oxy)piperidine-1-carboxylate (50 mg, 0.084 mmol, prepared in Step 2), TFA (2 mL) and dichloromethane (6 mL), and the mixture was stirred at room temperature for 3 hours to give rise to a reaction. Then water (10 mL) was added, and the aqueous phase was extracted with dichloromethane (20 mL×2). The organic phases were combined, washed with saturated sodium chloride (20 mL), and dried over anhydrous sodium sulfate. The filtrate was concentrated under reduced pressure, and the resulting residue was purified by column chromatography (DCM/MeOH=10:1) to give the title compound as a yellow solid (25 mg, yield 60.5%).

$^1$HNMR (DMSO, 400 MHz), δ 9.73 (s, 1H), 8.63 (s, 1H), 8.61 (s, 1H), 8.10 (s, 1H), 8.06-8.03 (m, 1H), 7.65 (d, J=12.4 Hz, 1H), 6.82 (d, J=8.8 Hz, 1H), 5.16-5.13 (m, 1H), 3.26-3.24 (m, 3H), 3.12-3.05 (m, 4H), 2.58-2.50 (m, 2H), 2.11-2.09 (m, 2H), 1.98-1.96 (m, 2H), 1.81 (s, 6H)

MS m/z (ESI): 492.2 (M+H)

Example 35

N-(5-(4-Ethylpiperazin-1-yl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine

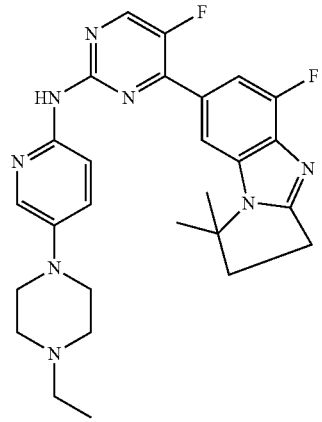

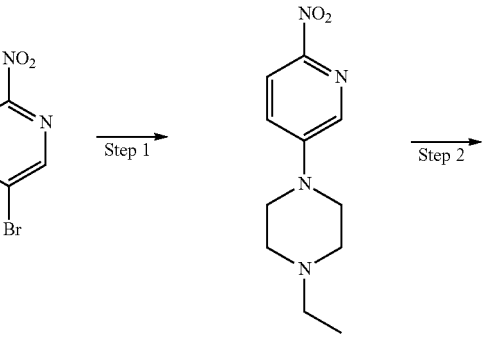

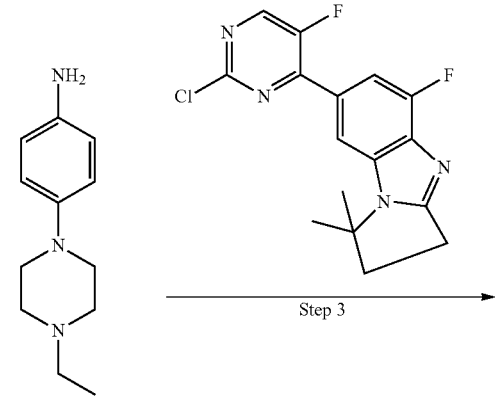

-continued

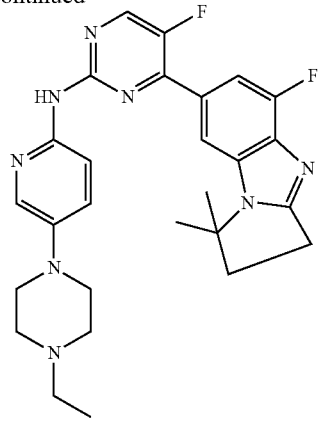

Step 1

1-Ethyl-4-(6-nitropyridin-3-yl)piperazine

To a reaction flask was added 5-bromo-2-nitropyridine (4.0 g, 19.7 mmol), 1-ethylpiperazine (3.4 g, 29.8 mmol), $K_2CO_3$ (4.1 g, 29.6 mmol), TBAI (0.42 g, 1.2 mmol) and dimethyl sulfoxide (40 mL), and the mixture was stirred under heating at 80° C. for 16 hours to give rise to a reaction. The reaction liquid was cooled to room temperature, poured into ice-water, and extracted with dichloromethane (20 mL×3). The organic layers were combined, washed with saturated sodium chloride (20 mL), and dried over anhydrous sodium sulfate. The filtrate was concentrated in vacuo, and the resulting residue was purified by column chromatography (DCM/MeOH=10:1) to give the title compound as a brown solid (3.59 g, yield 77%).

MS m/z (ESI): 237.1 (M+H)

Step 2

5-(4-Ethylpiperazin-1-yl)pyridin-2-amine

To a reaction flask was added 1-ethyl-4-(6-nitropyridin-3-yl)piperazine (0.9 g, 3.8 mmol, prepared in Step 1), palladium on carbon (10%, 18 mg) and ethyl acetate/methanol (9 mL/9 mL), and the mixture was stirred at room temperature for 12 hours under a hydrogen atmosphere to give rise to a reaction. The resulting mixture was filtered, and the filtrate was concentrated to give the title compound as a yellow solid (720 mg, yield 92%).

MS m/z (ESI): 207.1 (M+H)

Step 3

N-(5-(4-Ethylpiperazin-1-yl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine To a reaction flask was added 7-(2-chloro-5-fluoropyrimidin-4-yl)-5-fluoro-2,3-dihydro-1H-benzo[d]pyrrolo[1,2-a]imidazole (200 mg, 0.6 mmol, prepared according to the procedure of Example 1), 5-(4-ethylpiperazin-1-yl)pyridin-2-amine (123 mg, 0.6 mmol, prepared in Step 2), cesium carbonate (390 mg, 1.2 mmol), $Pd_2(dba)_3$ (55 mg, 0.06 mmol), XantPhos (35 mg, 0.06 mmol) and anhydrous 1,4-dioxane (5 mL), and the mixture was stirred at 120° C. for 12 hours to give rise to a reaction. The resulting mixture was cooled to room temperature and water (10 mL) was added. The aqueous phase was extracted with ethyl acetate (20 mL×3) and the phases were separated. The organic phases were combined, washed with saturated sodium chloride solution (20 mL), dried over anhydrous sodium sulfate, and filtered with suction. The filtrate was concentrated under reduced pressure. The resulting residue was purified by column chromatography (DCM/MeOH=10:1) to give the title compound as a white solid (50 mg, yield 17%).

$^1$HNMR (DMSO, 400 MHz) δ 9.80 (s, 1H), 8.62 (d, J=4.0 Hz, 1H), 8.18 (s, 1H), 8.05-8.02 (m, 2H), 7.68 (d, J=12.4 Hz, 1H), 7.42-7.39 (m, 1H), 3.11-3.08 (m, 6H), 2.57-2.50 (m, 6H), 2.40-2.39 (m, 2H), 1.66 (s, 6H), 0.86 (t, J=6.4 Hz, 1H)

MS m/z (ESI): 505.2 (M+H)

Example 36

5-Fluoro-4-(5-fluoro-1,1-dimethyl-2,3-dihydro-1H-benzo[d]pyrrolo[1,2-a]imidazol-7-yl)-N-(5-((4-(2-fluoroethyl)piperazin-1-yl)methyl)pyridin-2-yl)pyrimidin-2-amine

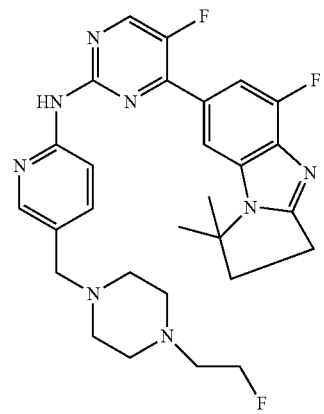 [SMILES: CC1(C)CCc2nc3c(F)cc(-c4nc(Nc5ccc(CN6CCN(CCF)CC6)cn5)ncc4F)cc3n21]

-continued

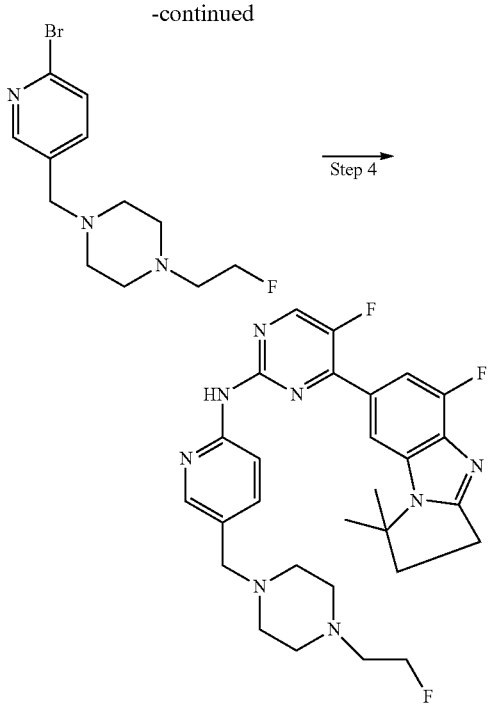

Step 1 tert-Butyl 4-((6-bromopyridin-3-yl)methyl)piperazine-1-carboxylate

To a reaction flask was added 2-bromo-5-formylpyridine (5.0 g, 27 mmol), tert-butyl piperazine-1-carboxylate (6.5 g, 35 mmol) and dichloromethane (30 mL), and sodium triacetoxyborohydride (8.6 g, 40 mmol) was added in portions. The mixture was stirred at room temperature for 12 hours to give rise to a reaction. Water (20 mL) was added, and the aqueous phase was extracted with dichloromethane (30 mL×3). The organic phases were combined, washed successively with saturated sodium carbonate solution (40 mL) and saturated sodium chloride solution (40 mL), dried over anhydrous sodium sulfate, and filtered with suction. The filtrate was concentrated, and the resulting residue was purified by column chromatography (DCM/MeOH=20:1) to give the title compound as a white solid (5.3 g, yield 55%).

MS m/z (ESI): 358.2 (M+H)

Step 2

1-(4-Bromophenyl)piperazine

To a reaction flask was added tert-butyl 4-((6-bromopyridin-3-yl)methyl) piperazine-1-carboxylate (5.3 g, 14.9 mmol, prepared in Step 1), trifluoroacetic acid (5 mL) and dichloromethane (30 mL), and the mixture was stirred at room temperature for 1 hour to give rise to a reaction. Saturated sodium carbonate solution (10 mL) was added, and the aqueous phase was extracted with dichloromethane (20 mL×3). The organic layers were combined, washed with saturated sodium chloride (10 mL), and dried over anhydrous sodium sulfate. The filtrate was concentrated in vacuo, and the resulting residue was purified by column chromatography (PE/EtOAc=5:1) to give the title compound as a yellow solid (3.1 g, yield 81%).

MS m/z (ESI): 257.2 (M+H)

Step 3

1-((6-Bromopyridin-3-yl)methyl)-4-(2-fluoroethyl)piperazine

To a reaction flask was added 1-(4-bromophenyl)piperazine (1.4 g, 5.4 mmol, prepared in Step 2), 1-bromo-2-fluoroethane (1.4 g, 10.8 mmol), potassium carbonate (3.0 g, 21.6 mmol) and acetonitrile (15 mL), and the mixture was stirred at 60° C. for 12 hours to give rise to a reaction. The resulting mixture was cooled to room temperature and filtered. The filter cake was washed with ethyl acetate, and the filtrate was concentrated to give the title compound as a white solid (813 mg, yield 50%).

MS m/z (ESI): 304.1 (M+H)

Step 4

5-Fluoro-4-(5-fluoro-1,1-dimethyl-2,3-dihydro-1H-benzo[d]pyrrolo[1,2-a]imidazol-7-yl)-N-(5-((4-(2-fluoroethyl)piperazin-1-yl)methyl)pyridin-2-yl)pyrimidin-2-amine To a reaction flask was added 5-fluoro-4-(5-fluoro-1,1-dimethyl-2,3-dihydro-1H-benzo[d]pyrrolo[1,2-a]imidazol-7-yl)pyrimidin-2-amine (200 mg, 0.63 mmol, prepared according to Step 2 of Example 20), 1-((6-bromopyridin-3-yl)methyl)-4-(2-fluoroethyl)piperazine (191 mg, 0.63 mmol), cesium carbonate (410 mg, 1.26 mmol), Pd$_2$(dba)$_3$ (58 mg, 0.063 mmol), BINAP (40 mg, 0.063 mmol) and 1,4-dioxane (4 mL), and the mixture was reacted for 1 hour in a microwave at 120° C. The resulting mixture was cooled to room temperature and filtered with suction. The filtrate was concentrated under reduced pressure and the resulting residue was purified by column chromatography (DCM/MeOH=10:1) to give the title compound as a white solid (78 mg, yield 23%).

$^1$HNMR (DMSO, 400 MHz), δ 10.12 (s, 1H), 8.69 (d, J=3.6 Hz, 1H), 8.21-8.19 (m, 3H), 7.72-7.65 (m, 2H), 4.58-4.44 (m, 2H), 3.45 (s, 2H), 3.34 (s, 2H), 3.10 (t, J=7.2 Hz, 2H), 2.57-2.44 (m, 10H), 1.67 (s, 6H)

MS m/z (ESI): 537.3 (M+H)

Example 37

N-(5-((4-Ethylpiperazin-1-yl)methyl)-6-methylpyridin-2-yl)-5-fluoro-4-(5-fluoro-1,1-dimethyl-2,3-dihydro-1H-benzo[d]pyrrolo[1,2-a]imidazol-7-yl)pyrimidin-2-amine

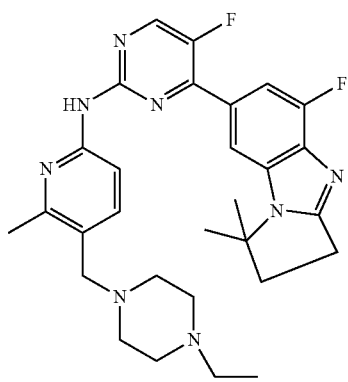

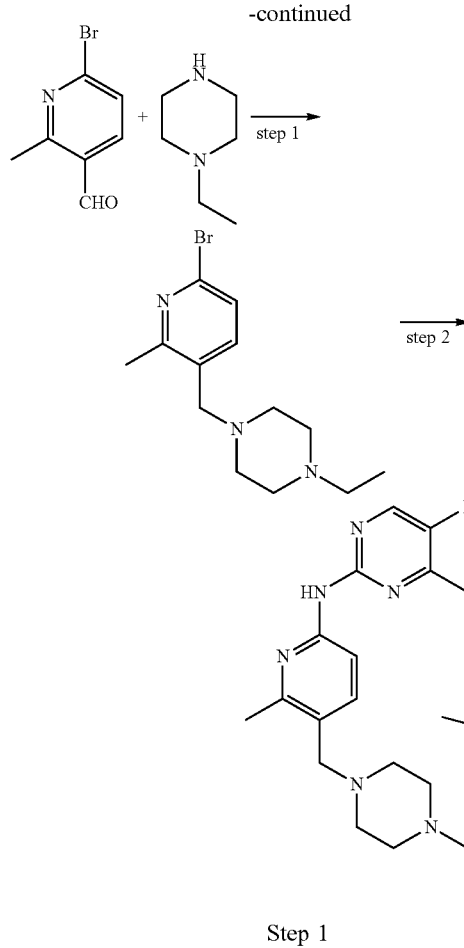

Step 1

1-((6-Bromo-2-methylpyridin-3-yl)methyl)-4-ethyl-piperazine

To a reaction flask was added 6-bromo-2-methyl-3-formylpyridine (1.5 g, 7.5 mmol), 1-ethylpiperazine (1.1 g, 9.7 mmol) and dichloromethane (15 mL), and sodium triacetoxyborohydride (2.4 g, 11.25 mmol) was added in portions. The mixture was stirred at room temperature for 12 hours to give rise to a reaction and filtered. The filtrate was concentrated and the resulting residue was purified by column chromatography (DCM/MeOH=20/1) to give the title compound as a white solid (782 mg, yield 35%).

MS m/z (ESI): 299.2 (M+H)

Step 2

N-(5-((4-Ethylpiperazin-1-yl)methyl)-6-methylpyridin-2-yl)-5-fluoro-4-(5-fluoro-1,1-dimethyl-2,3-dihydro-1H-benzo[d]pyrrolo[1,2-a]imidazol-7-yl)pyrimidin-2-amine To a microwave reaction flask was added 5-fluoro-4-(5-fluoro-1,1-dimethyl-2,3-dihydro-1H-benzo[d]pyrrolo[1,2-a]imidazol-7-yl)pyrimidin-2-amine (50 mg, 0.16 mmol, prepared according to Step 2 of Example 20), 1-((6-bromo-2-methylpyridin-3-yl)methyl)-4-ethylpiperazine (47 mg, 0.16 mmol), cesium carbonate (104 mg, 0.32 mmol), $Pd_2(dba)_3$ (29 mg, 0.032 mmol), BINAP (20 mg, 0.032 mmol) and anhydrous 1,4-dioxane (2 mL), and the mixture was reacted for 1 hour in a microwave at 120° C. The resulting mixture was cooled to room temperature and concentrated under reduced pressure. The resulting residue was purified by thin layer chromatography (DCM/MeOH=10:1) to give the title compound as a yellow solid (30 mg, yield 35%).

1HNMR (DMSO, 400 MHz), δ 9.95 (s, 1H), 8.67 (s, 1H), 8.23 (s, 1H), 8.05 (d, J=8.4 Hz, 1H), 7.72 (d, J=12.4 Hz, 1H), 7.58 (d, J=8.4 Hz, 1H), 3.51 (s, 2H), 3.35 (s, 2H), 3.12-3.08 (m, 4H), 2.91 (brs, 4H), 2.58-2.54 (m, 2H), 2.50-2.46 (m, 8H), 1.67 (s, 6H)

MS m/z (ESI): 533.3 (M+H)

Example 38

5-Fluoro-4-(5-fluoro-1,1-dimethyl-2,3-dihydro-1H-benzo[d]pyrrolo[1,2-a]imidazol-7-yl)-N-(6-methyl-5-((4-methylpiperazin-1-yl)methyl)pyridin-2-yl)pyrimidin-2-amine

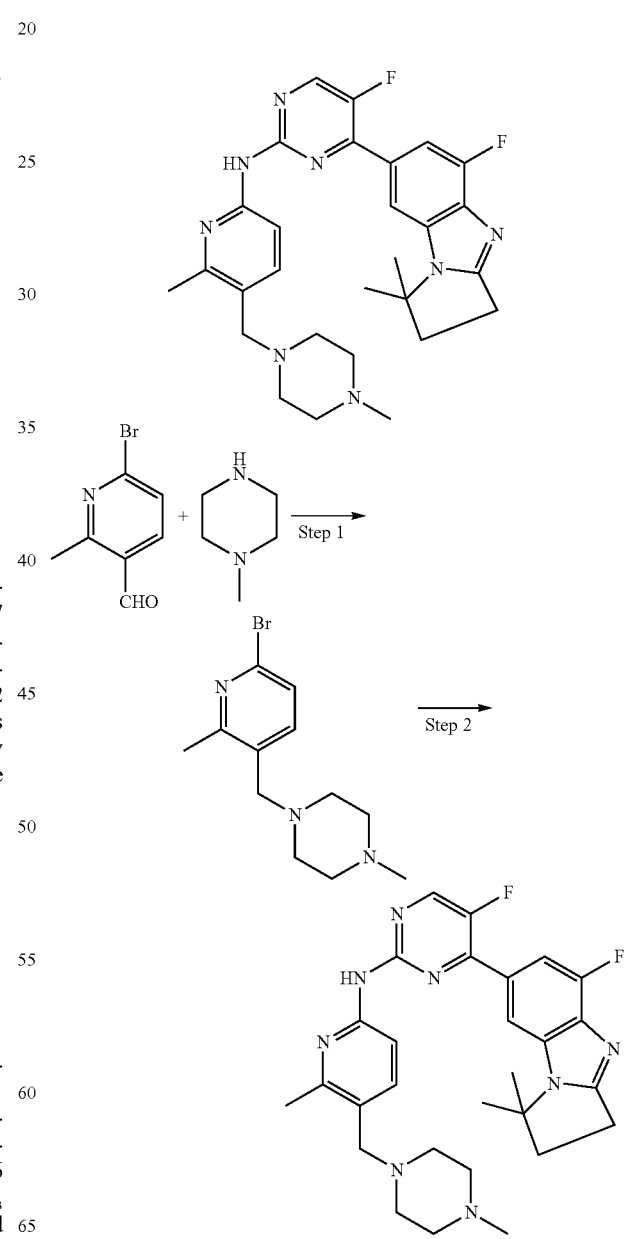

Step 1

1-((6-Bromo-2-methylpyridin-3-yl)methyl)-4-methylpiperazine

To a reaction flask was added 6-bromo-2-methyl-3-formylpyridine (1.5 g, 7.5 mmol), 1-methylpiperazine (0.97 g, 9.7 mmol) and dichloromethane (15 mL), and sodium triacetoxyborohydride (2.37 g, 11.25 mmol) was added in portions. The mixture was stirred at room temperature for 12 hours to give rise to a reaction. The resulting mixture was filtered and concentrated, and the resulting residue was purified by column chromatography (DCM/MeOH=20/1) to give the title compound as a white solid (809 mg, yield 38%).

MS m/z (ESI): 285.2 (M+H)

Step 2

5-Fluoro-4-(5-fluoro-1,1-dimethyl-2,3-dihydro-1H-benzo[d]pyrrolo[1,2-a]imidazol-7-yl)-N-(6-methyl-5-((4-methylpiperazin-1-yl)methyl)pyridin-2-yl)pyrimidin-2-amine To a reaction flask was added 5-fluoro-4-(5-fluoro-1,1-dimethyl-2,3-dihydro-1H-benzo[d]pyrrolo[1,2-a]imidazol-7-yl)pyrimidin-2-amine (50 mg, 0.16 mmol, prepared according to Step 2 of Example 20), 1-((6-bromo-2-methylpyridin-3-yl)methyl)-4-methylpiperazine (45 mg, 0.16 mmol, prepared in Step 1), Pd$_2$(dba)$_3$ (29 mg, 0.032 mmol), BINAP (20 mg, 0.032 mmol), Cs$_2$CO$_3$ (103 mg, 0.32 mmol) and 1,4-dioxane (2 mL), and the mixture was reacted for 1 hour in a microwave at 120° C. The resulting mixture was cooled to room temperature, and concentrated under reduced pressure. The resulting residue was purified by thin layer chromatography (DCM/MeOH=10:1) to give the title compound as a yellow solid (37 mg, yield 45%).

$^1$HNMR (DMSO, 400 MHz), δ 9.94 (s, 1H), 8.67 (s, 1H), 8.23 (s, 1H), 8.04 (d, J=8.4 Hz, 1H), 7.72 (d, J=12.4 Hz, 1H), 7.58 (d, J=8.4 Hz, 1H), 3.51 (s, 2H), 3.12-3.08 (m, 6H), 2.72 (s, 3H), 2.58-2.47 (m, 9H), 1.67 (s, 6H)

MS m/z (ESI): 519.3 (M+H)

Example 39

(S)-5-Fluoro-4-(5-fluoro-1,1-dimethyl-2,3-dihydro-1H-benzo[d]pyrrolo[1,2-a]imidazol-7-yl)-N-(5-(3-methylpiperazin-1-yl)pyridin-2-yl)pyrimidin-2-amine

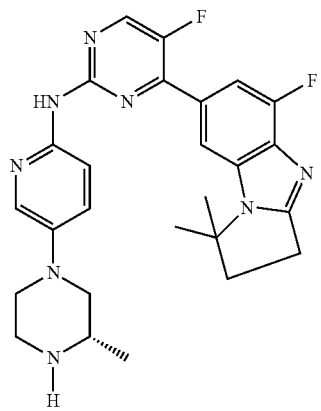 [SMILES: C[C@H]1CN(c2ccc(Nc3ncc(F)c(-c4cc(F)c5nc6n(c5c4)C(C)(C)CC6)n3)nc2)CCN1]

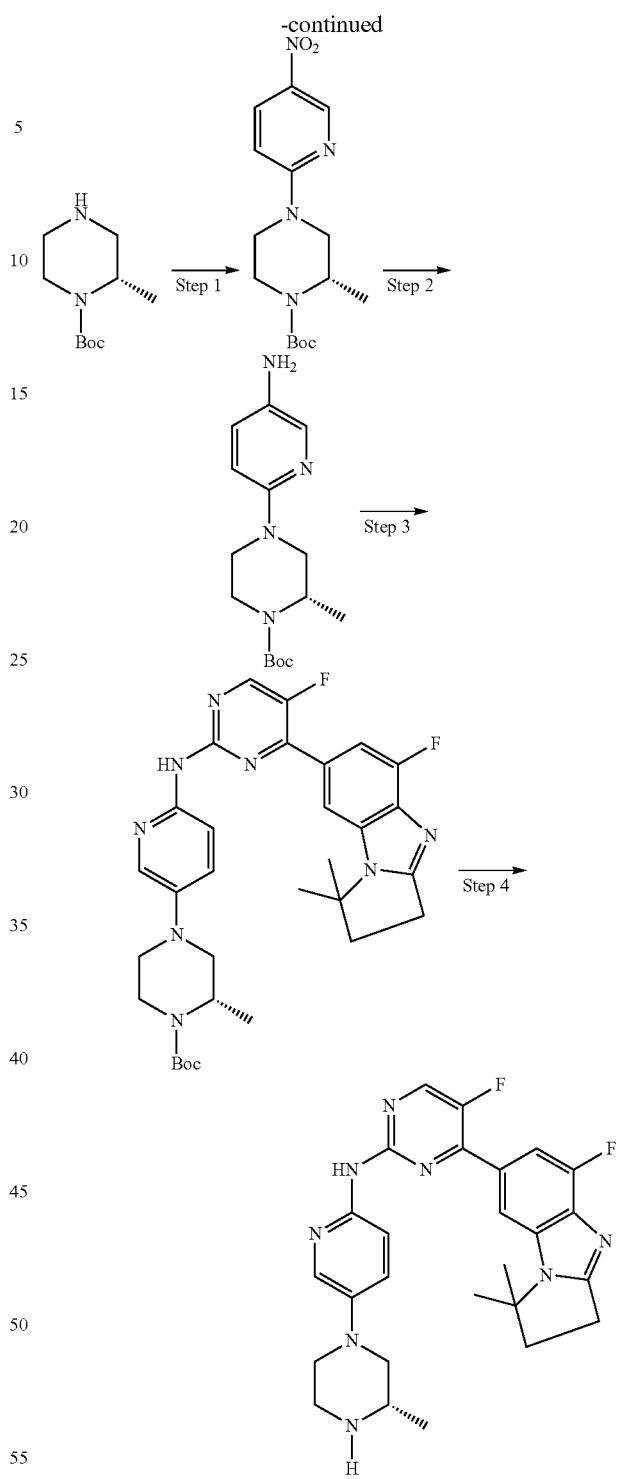

Step 1 tert-Butyl (S)-2-methyl-4-(6-nitropyridin-3-yl)piperazine-1-carboxylate

To a reaction flask was added 5-bromo-2-nitropyridine (4.0 g, 19.7 mmol), tert-butyl (S)-2-methylpiperazine-1-carboxylate (5.9 g, 29.6 mmol), potassium carbonate (4.1 g, 29.6 mmol), TBAI (0.42 g, 1.2 mmol) and DMSO (40 mL), and the mixture was stirred at 80° C. for 16 hours to give rise to a reaction. The reaction liquid was poured into ice-water, and extracted with dichloromethane (20 mL×3). The organic phases were combined, washed with saturated sodium chloride solution (20 mL), dried over anhydrous sodium sulfate, and filtered with suction. The filtrate was concentrated under reduced pressure, and the resulting residue was purified by column chromatography (DCM/MeOH=20:1) to give the title compound as a white solid (3.5 g, yield 55%).

MS m/z (ESI): 323.2 (M+H)

Step 2 tert-Butyl (S)-4-(6-aminopyridin-3-yl)-2-methylpiperazine-1-carboxylate

To a reaction flask was added tert-butyl (S)-2-methyl-4-(6-nitropyridin-3-yl) piperazine-1-carboxylate (0.9 g, 2.8 mmol, prepared in Step 1), palladium on carbon (10%, 90 mg) and ethyl acetate/methanol (9 mL/9 mL). The mixture was stirred at room temperature for 2 hours, filtered and the filtrate was concentrated to give the title compound as a white solid (776 mg, yield 95%).

MS m/z (ESI): 293.2 (M+H)

Step 3 tert-butyl (S)-4-(6-((5-Fluoro-4-(5-fluoro-1,1-dimethyl-2,3-dihydro-1H-benzo[d]pyrrolo[1,2-a]imidazol-7-yl)pyrimidin-2-yl)amino)pyridin-3-yl)-2-methylpiperazine-1-carboxylate To a reaction flask was added 7-(2-chloro-5-fluoropyrimidin-4-yl)-5-fluoro-1,1-dimethyl-2,3-dihydro-1H-benzo[d]pyrrolo[1,2-a]imidazole (150 mg, 0.45 mmol, prepared according to the procedure of Example 1), tert-butyl (S)-4-(5-aminopyridin-2-yl)-2-methylpiperazine-1-carboxylate (132 mg, 0.45 mmol, prepared in Step 2), Pd$_2$(dba)$_3$ (41 mg, 0.045 mmol), BINAP (56 mg, 0.09 mmol), cesium carbonate (294 mg, 0.9 mmol) and 1,4-dioxane (2 mL), and the mixture was reacted for 1 hour in a microwave at 120° C. The resulting mixture was cooled to room temperature and concentrated under reduced pressure. The resulting residue was purified by column chromatography (DCM/MeOH=20:1) to give the title compound as a yellow solid (65 mg, yield 25%).

MS m/z (ESI): 591.3 (M+H)

Step 4

(S)-5-Fluoro-4-(5-fluoro-1,1-dimethyl-2,3-dihydro-1H-benzo[d]pyrrolo[1,2-a]imidazol-7-yl)-N-(5-(3-methylpiperazin-1-yl)pyridin-2-yl)pyrimidin-2-amine To a reaction flask was added tert-butyl (S)-4-(6-((5-fluoro-4-(5-fluoro-1,1-dimethyl-2,3-dihydro-1H-benzo[d]pyrrolo[1,2-a]imidazol-7-yl)pyrimidin-2-yl)amino)pyridin-3-yl)-2-methylpiperazine-1-carboxylate (65 mg, 0.11 mmol, prepared in Step 3), TFA (1 mL) and dichloromethane (5 mL). The mixture was stirred at room temperature for 3 hours to give rise to a reaction, diluted with water (10 mL), and extracted with dichloromethane (10 mL×3). The organic layers were combined, washed with saturated sodium chloride (10 mL), and dried over anhydrous sodium sulfate. The filtrate was concentrated in vacuo, and the resulting residue was purified by thin layer chromatography (DCM/MeOH=10:1) to give the title compound as a pale yellow solid (30 mg, yield 56%).

$^1$HNMR (DMSO, 400 MHz), δ 9.76 (s, 1H), 8.63 (s, 1H), 8.18 (s, 1H), 8.04-8.01 (m, 2H), 7.69 (d, J=12 Hz, 1H), 7.39 (d, J=7.6 Hz, 1H), 3.49-3.43 (m, 2H), 3.12-3.08 (m, 2H), 2.97-2.95 (m, 1H), 2.84-2.78 (m, 2H), 2.58-2.54 (m, 4H), 2.22-2.17 (m, 1H), 1.67 (s, 6H), 1.02 (d, J=6.0 Hz, 3H)

MS m/z (ESI): 491.3 (M+H)

Example 40

(R)-5-Fluoro-4-(5-fluoro-1,1-dimethyl-2,3-dihydro-1H-benzo[d]pyrrolo[1,2-a]imidazol-7-yl)-N-(5-(3-methylpiperazin-1-yl)pyridin-2-yl)pyrimidin-2-amine

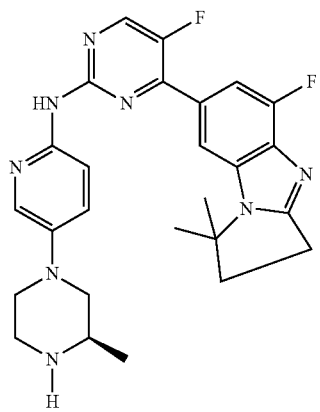 [SMILES: C[C@@H]1CN(c2ccc(Nc3ncc(F)c(-c4cc(F)c5nc6n(c5c4)C(C)(C)CC6)n3)nc2)CCN1]

The title compound, (R)-5-fluoro-4-(5-fluoro-1,1-dimethyl-2,3-dihydro-1H-benzo[d]pyrrolo[1,2-a]imidazol-7-yl)-N-(5-(3-methylpiperazin-1-yl)pyridin-2-yl)pyrimidin-2-amine, was obtained in a four-step procedure similar to those described in Example 39, using tert-butyl (S)-2-methylpiperazine-1-carboxylate as the starting material.

$^1$HNMR (DMSO, 400 MHz), δ 9.76 (s, 1H), 8.61 (s, 1H), 8.17 (s, 1H), 8.04-8.02 (m, 2H), 7.68 (d, J=12.4 Hz, 1H), 7.38 (d, J=6.4 Hz, 1H), 3.48-3.45 (m, 2H), 3.11-3.07 (m, 2H), 2.97-2.95 (m, 1H), 2.83-2.78 (m, 2H), 2.57-2.50 (m, 3H), 2.32-2.17 (m, 2H), 1.66 (s, 6H), 1.02 (d, J=6.0 Hz, 3H)

MS m/z (ESI): 491.2 (M+H)

Example 41

5-Fluoro-4-(5-fluoro-1-methyl-2,3-dihydro-1H-benzo[d]pyrrolo[1,2-a]imidazol-7-yl)-N-(6-methyl-5-(4-methylpiperazin-1-yl)pyridin-2-yl)pyrimidin-2-amine

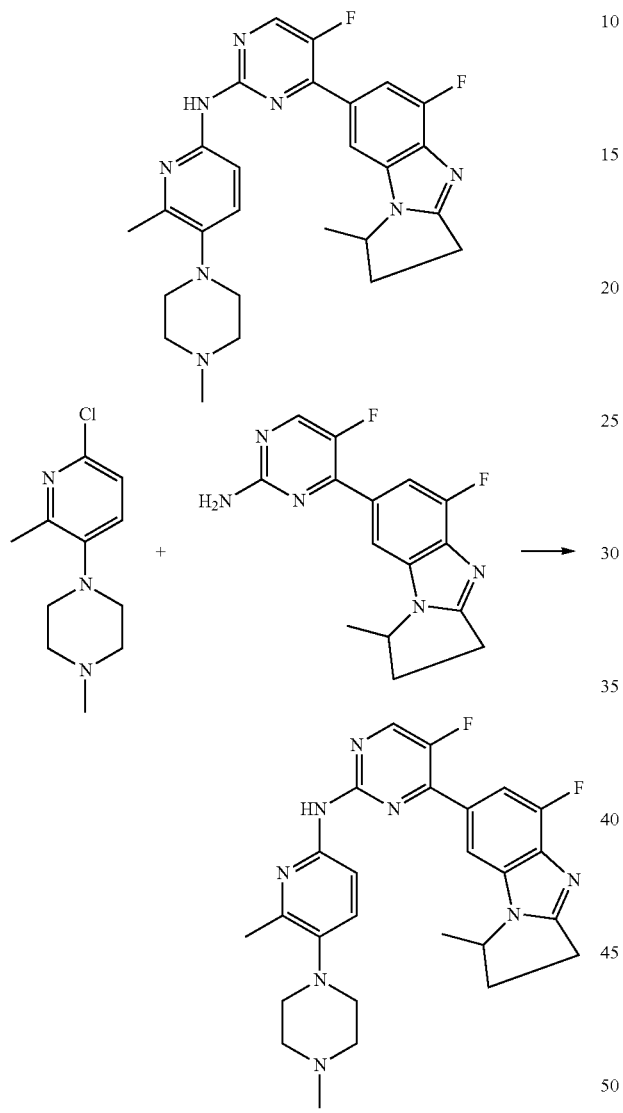

To a reaction flask was added 5-fluoro-4-(5-fluoro-1-methyl-2,3-dihydro-1H-benzo[d]pyrrolo[1,2-a]imidazol-7-yl)pyrimidin-2-amine (150 mg, 0.5 mmol, prepared according to Step 2 of Example 58, 1-(6-chloro-2-methylpyridin-3-yl)-4-methylpiperazine (135 mg, 0.5 mmol), Pd$_2$(dba)$_3$ (46 mg, 0.05 mmol), BINAP (62 mg, 0.1 mmol), sodium tert-butoxide (96 mg, 1.0 mmol) and 1,4-dioxane (2 mL), and the mixture was reacted for 1 hour in a microwave at 120° C. The resulting mixture was cooled to room temperature and water (10 mL) was added. The aqueous phase was extracted with ethyl acetate (20 mL×3) and the phases were separated. The organic phases were combined, washed with saturated sodium chloride solution (10 mL), dried over anhydrous sodium sulfate, and filtered with suction. The filtrate was concentrated under reduced pressure, and the resulting residue was purified by column chromatography (DCM/MeOH=10:1) to give the title compound as a yellow solid (113 mg, yield 46%).

$^1$HNMR (DMSO, 400 MHz), δ 9.70 (s, 1H), 8.63 (s, 1H), 8.16 (s, 1H), 7.98 (d, J=8.8 Hz, 1H), 7.72 (d, J=12.4 Hz, 1H), 7.47 (d, J=8.0 Hz, 1H), 4.78-4.74 (m, 1H), 3.14-3.08 (m, 4H), 2.97-2.92 (m, 5H), 2.40 (s, 3H), 2.38-2.29 (m, 6H), 1.58 (d, J=6.4 Hz, 3H)

MS m/z (ESI): 491.2 (M+H)

Example 42

2-(4-(6-((5-Fluoro-4-(5-fluoro-1,1-dimethyl-2,3-dihydro-1H-benzo[d]pyrrolo[1,2-a]imidazol-7-yl)pyrimidin-2-yl)amino)pyridin-3-yl)piperazin-1-yl)ethyl-1-ol

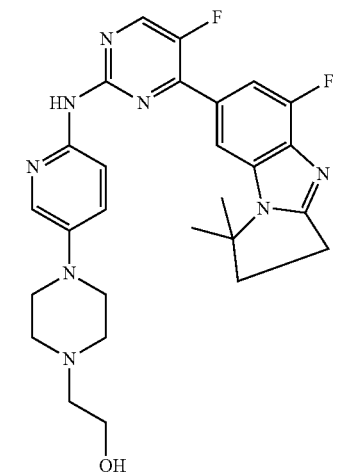

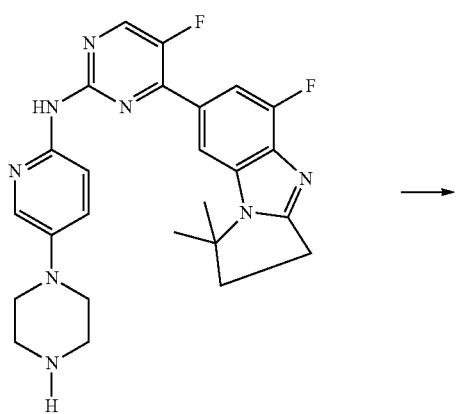

-continued

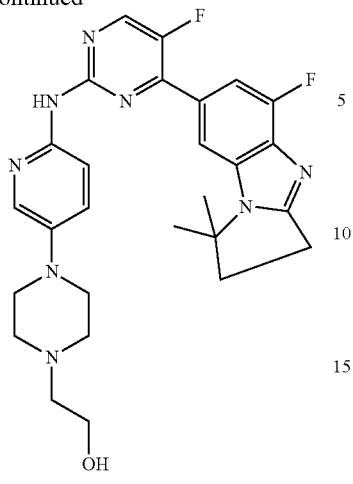

To a reaction flask was added 5-Fluoro-4-(5-fluoro-1,1-dimethyl-2,3-dihydro-1H-benzo[d]pyrrolo[1,2-a]imidazol-7-yl)-N-(5-(piperazin-1-yl)pyridin-2-yl)pyrimidin-2-amine (20 mg, 0.042 mmol, prepared according to Example 19), 2-bromoethanol (26 mg, 0.21 mmol), potassium carbonate (29 mg, 0.21 mmol) and DMF (2 mL), and the mixture was stirred at 90° C. for 2 hours to give rise to a reaction. The resulting mixture was cooled to room temperature, water was added (10 mL), and the aqueous phase was extracted with dichloromethane (5 mL×3). The organic phases were combined, washed with saturated sodium chloride solution (10 mL), dried over anhydrous sodium sulfate and filtered with suction. The filtrate was concentrated to give the title compound as a yellow solid (9 mg, yield 43%).

$^1$HNMR (D2O-ex, 400 MHz), δ 8.58 (d, J=3.6 Hz, 1H), 8.15 (s, 1H), 8.01 (s, 1H), 7.99 (s, 1H), 7.67 (d, J=12.4 Hz, 1H), 7.41-7.38 (m, 1H), 3.54 (t, J=6 Hz, 1H), 3.11-3.05 (m, 6H), 2.60-2.56 (m, 6H), 2.54-2.52 (m, 2H), 1.64 (s, 6H)

MS m/z (ESI): 521.3 (M+H)

Example 43

5-Fluoro-4-(5-fluoro-1,1-dimethyl-2,3-dihydro-1H-benzo[d]pyrrolo[1,2-a]imidazol-7-yl)-N-(5-(4-methylpiperazin-1-yl)pyridin-2-yl)pyrimidin-2-amine

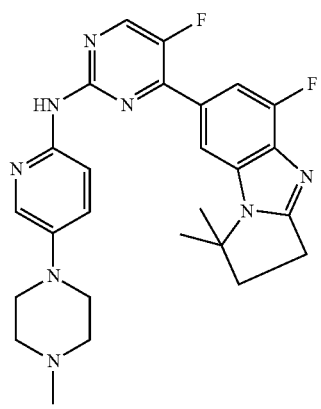 [SMILES: CN1CCN(c2ccc(Nc3ncc(F)c(-c4cc(F)c5nc6n(c5c4)C(C)(C)CC6)n3)nc2)CC1]

The title compound was obtained in a three-step procedure similar to those described in Example 39, using 5-bromo-2-nitropyridine and 1-methylpiperazine as the starting materials.

$^1$HNMR (DMSO, 400 MHz), δ 9.77 (s, 1H), 8.63 (d, J=3.6 Hz, 1H), 8.18 (s, 1H), 8.06 (s, 1H), 8.03 (s, 1H), 7.69 (d, J=12.4 Hz, 1H), 7.41 (d, J=8.4 Hz, 1H), 3.14-3.08 (m, 6H), 2.58-2.54 (m, 6H), 2.28 (s, 3H), 1.67 (s, 6H)

MS m/z (ESI): 491.3 (M+H)

Example 44

5-Fluoro-4-(5-fluoro-1,1-dimethyl-2,3-dihydro-1H-benzo[d]pyrrolo[1,2-a]imidazol-7-yl)-N-(5-(1-methylpiperidine-4-yl)pyridin-2-yl)pyrimidin-2-amine

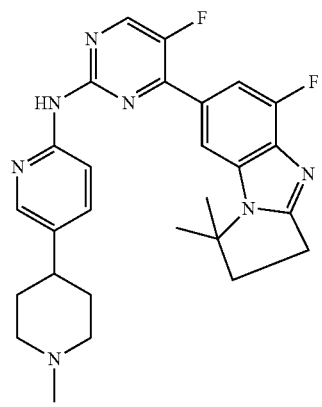

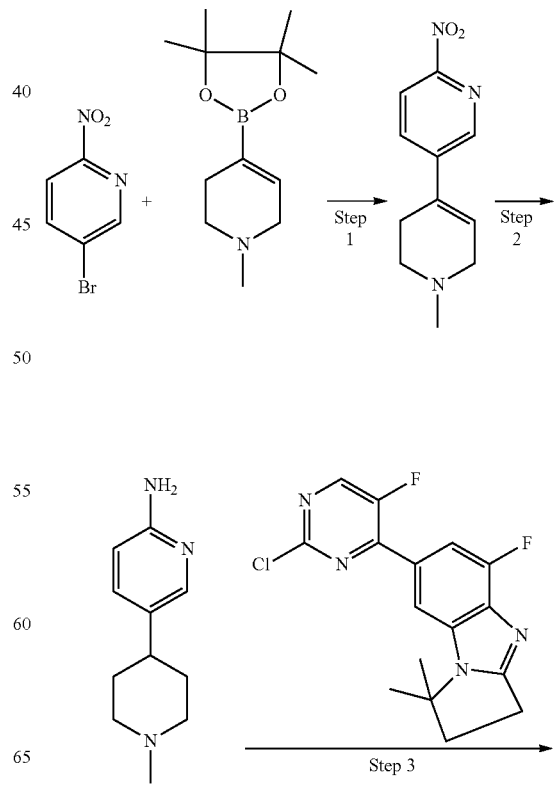

-continued

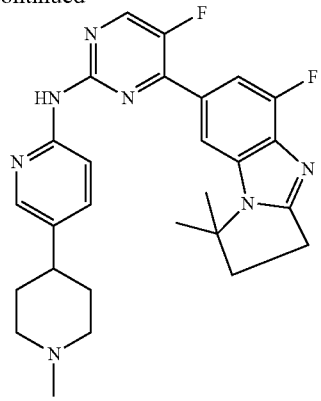

Step 1

1'-Methyl-6-nitro-1',2',3',6'-tetrahydro-3,4'-bipyridine

To a reaction flask was added 5-bromo-2-nitropyridine (20.3 g, 0.1 mol), 1-methyl-4-(4,4,5,5-tetramethyl-1,3,2-dioxaborolan-2-yl)-1,2,3,6-tetrahydropyridine (22.3 g, 0.1 mol), cesium carbonate (65 g, 0.2 mol), Pd(dppf)Cl$_2$ (7.33 g, 0.01 mol) and dioxane/water (250 mL/30 mL), and the mixture was stirred under heating at 85° C. for 12 hours to give rise to a reaction. The resulting mixture was cooled to room temperature and concentrated under reduced pressure. The resulting residue was purified by column chromatography (PE/EtOAc=1:1) to give the title compound as a white solid (5.7 g, yield 26%).

MS m/z (ESI): 220.2 (M+H)

Step 2

5-(1-Methylpiperidine-4-yl)pyridin-2-amine

To a reaction flask was added 1'-methyl-6-nitro-1',2',3',6'-tetrahydro-3,4'-bipyridine (657 mg, 3.0 mmol, prepared in Step 1), palladium on carbon (10%, 66 mg) and ethyl acetate/methanol (10 mL/10 mL). The mixture was stirred at room temperature for 2 hours under a hydrogen atmosphere to give rise to a reaction, filtered, and the filtrate was concentrated under reduced pressure to give the title compound as a white solid (550 mg, yield 96%).

MS m/z (ESI): 192.1 (M+H)

Step 3

5-Fluoro-4-(5-fluoro-1,1-dimethyl-2,3-dihydro-1H-benzo[d]pyrrolo[1,2-a]imidazol-7-yl)-N-(5-(1-methylpiperidine-4-yl)pyridin-2-yl)pyrimidin-2-amine To a reaction flask was added 7-(2-chloro-5-fluoropyrimidin-4-yl)-5-fluoro-1,1-dimethyl-2,3-dihydro-1H-benzo[d]pyrrolo[1,2-a]imidazole (150 mg, 0.45 mmol, prepared according to Example 1), 5-(1-methylpiperidine-4-yl)pyridin-2-amine (86 mg, 0.45 mmol), Pd$_2$(dba)$_3$ (42 mg, 0.045 mmol), BINAP (56 mg, 0.09 mmol), Cs$_2$CO$_3$ (293 mg, 0.9 mmol) and anhydrous 1,4-dioxane (4 mL). The mixture was reacted for 1 hour in a microwave at 150° C., cooled to room temperature, and concentrated under reduced pressure. The resulting residue was purified by column chromatography (DCM/MeOH=10:1) to give the title compound as a yellow solid (90 mg, yield 41%).

$^1$HNMR (DMSO, 400 MHz), δ 10.02 (s, 1H), 8.69 (s, 1H), 8.21-8.18 (m, 3H), 7.71 (d, J=12.8 Hz, 1H), 7.65 (d, J=6.8 Hz, 1H), 3.45 (s, 2H), 3.13-3.04 (m, 4H), 2.84-2.80 (m, 4H), 2.59-2.55 (m, 2H), 1.99-1.97 (m, 4H), 1.69 (s, 6H)

MS m/z (ESI): 490.3 (M+H)

Example 45

N-(5-(1-Ethylpiperidine-4-yl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine

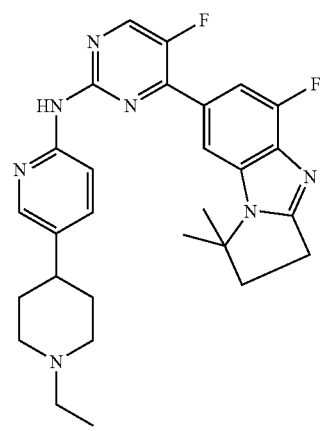 [SMILES: CCN1CCC(c2ccc(Nc3ncc(F)c(-c4cc(F)c5nc6n(c5c4)C(C)(C)CC6)n3)nc2)CC1]

The title compound was obtained in a three-step procedure similar to those described in Example 44, using 5-bromo-2-nitropyridine and 1-ethyl-4-(4,4,5,5-tetramethyl-1,3,2-dioxaborolan-2-yl)-1,2,3,6-tetrahydropyridine as the starting material.

$^1$HNMR (DMSO, 400 MHz), δ 10.07 (s, 1H), 8.69 (s, 1H), 8.27-8.19 (m, 3H), 7.71 (d, J=12.4 Hz, 1H), 7.65 (d, J=6.4 Hz, 1H), 3.57-3.54 (m, 2H), 3.12-3.09 (m, 4H), 2.99-2.97 (m, 3H), 2.58-2.55 (m, 2H), 2.03-2.01 (m, 4H), 1.69 (s, 6H), 1.28 (t, J=7.2 Hz, 3H)

MS m/z (ESI): 504.3 (M+H)

Example 46

(S)-5-Fluoro-4-(5-fluoro-1,1-dimethyl-2,3-dihydro-1H-benzo[d]pyrrolo[1,2-a]imidazol-7-yl)-N-(5-(3-methylpiperazin-1-yl)methyl)pyridin-2-yl)pyrimidin-2-amine

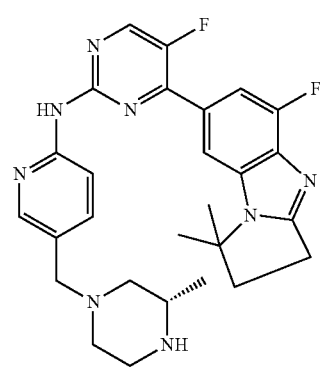

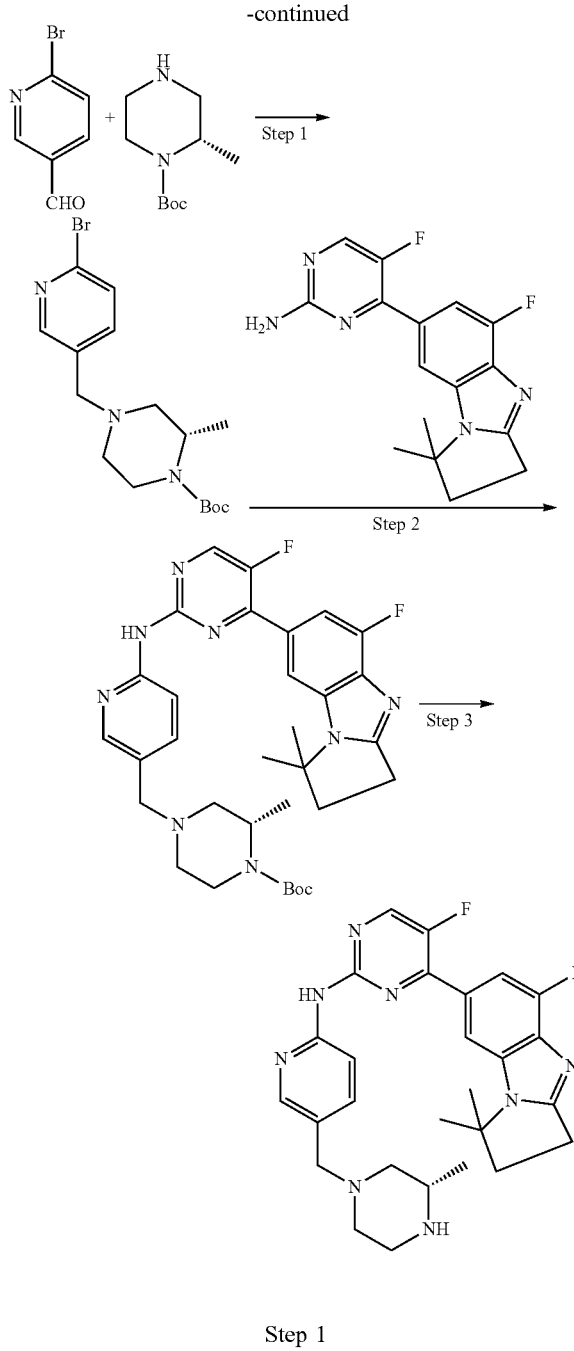

was concentrated under reduced pressure, and the resulting residue was purified by column chromatography (DCM/MeOH=20:1) to give the title compound as a white solid (2.2 g, yield 45%).

MS m/z (ESI): 372.1 (M+H)

Step 2 tert-Butyl (S)-4-((6-((5-fluoro-4-(5-fluoro-1,1-dimethyl-2,3-dihydro-1H-benzo[d]pyrrolo[1,2-a]imidazol-7-yl)pyrimidin-2-yl)amino)pyridin-3-yl)methyl)-2-methylpiperazine-1-carboxylate To a reaction flask was added 5-fluoro-4-(5-fluoro-1,1-dimethyl-2,3-dihydro-1H-benzo[d]pyrrolo[1,2-a]imidazol-7-yl)pyrimidin-2-amine (315 mg, 1 mmol, prepared according to Step 2 of Example 20), tert-butyl (S)-4-((6-bromopyridin-3-yl)methyl)-2-methylpiperazine-1-carboxylate (369 mg, 1 mmol prepared in Step 1), Pd$_2$(dba)$_3$ (92 mg, 0.1 mmol), BINAP (125 mg, 0.2 mmol), sodium tert-butoxide (200 mg, 2.0 mmol) and 1,4-dioxane (15 mL), and the mixture was stirred at 130° C. for 3 hours to give rise to a reaction. The resulting mixture was cooled to room temperature and concentrated under reduced pressure. The resulting residue was purified by column chromatography (DCM/MeOH=10:1) to give the title compound as a yellow oil (100 mg, yield 17%).

MS m/z (ESI): 605.3 (M+H)

Step 3

(S)-5-Fluoro-4-(5-fluoro-1,1-dimethyl-2,3-dihydro-1H-benzo[d]pyrrolo[1,2-a]imidazol-7-yl)-N-(5-(3-methylpiperazin-1-yl)methyl)pyridin-2-yl)pyrimidin-2-amine To a reaction flask was added tert-butyl (S)-4-((6-((5-fluoro-4-(5-fluoro-1,1-dimethyl-2,3-dihydro-1H-benzo[d]pyrrolo[1,2-a]imidazol-7-yl)pyrimidin-2-yl)amino)pyridin-3-yl)methyl)-2-methylpiperazine-1-carboxylate (100 mg, 0.17 mmol, prepared in Step 2), trifluoroacetic acid (1 mL) and dichloromethane (15 mL). The mixture was stirred at room temperature for 3 hours to give rise to a reaction, diluted with water (10 mL), and extracted with dichloromethane (20 mL×3). The organic layers were combined, washed with saturated sodium chloride (20 mL), and dried over anhydrous sodium sulfate. The filtrate was concentrated in vacuo, and the resulting residue was purified by thin layer chromatography (DCM/MeOH=10:1) to give the title compound as a yellow solid (55 mg, yield 64%).

$^1$HNMR (DMSO, 400 MHz), δ 10.03 (s, 1H), 8.69 (s, 1H), 8.22-8.18 (m, 3H), 7.73-7.65 (m, 2H), 3.41 (s, 2H), 3.12-3.08 (m, 2H), 2.80-2.77 (m, 1H), 2.68-2.63 (m, 4H), 2.59-2.55 (m, 2H), 1.93-1.87 (m, 2H), 1.67 (s, 6H), 1.59-1.54 (m, 1H), 0.89 (t, J=6.4 Hz, 3H)

MS m/z (ESI): 505.3 (M+H)

Step 1 tert-Butyl (S)-4-((6-bromopyridin-3-yl)methyl)-2-methylpiperazine-1-carboxylate

To a reaction flask was added 6-bromo-3-formylpyridine (2.43 g, 13 mmol) and tert-butyl (S)-2-methylpiperazine-1-carboxylate (2) (3.4 g, 17 mmol) and dichloromethane (30 mL), and sodium triacetoxyborohydride (4.3 g, 20 mmol) was added in portions. The mixture was stirred at room temperature for 12 hours to give rise to a reaction. Water (10 mL) was added, and the aqueous phase was extracted with dichloromethane (20 mL×3). The organic phase was washed with saturated Na$_2$CO$_3$ solution (40 mL) and then washed with saturated sodium chloride (40 mL), dried over anhydrous sodium sulfate, and filtered with suction. The filtrate

Example 47

(S)—N-(5-((3,4-Dimethylpiperazin-1-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine

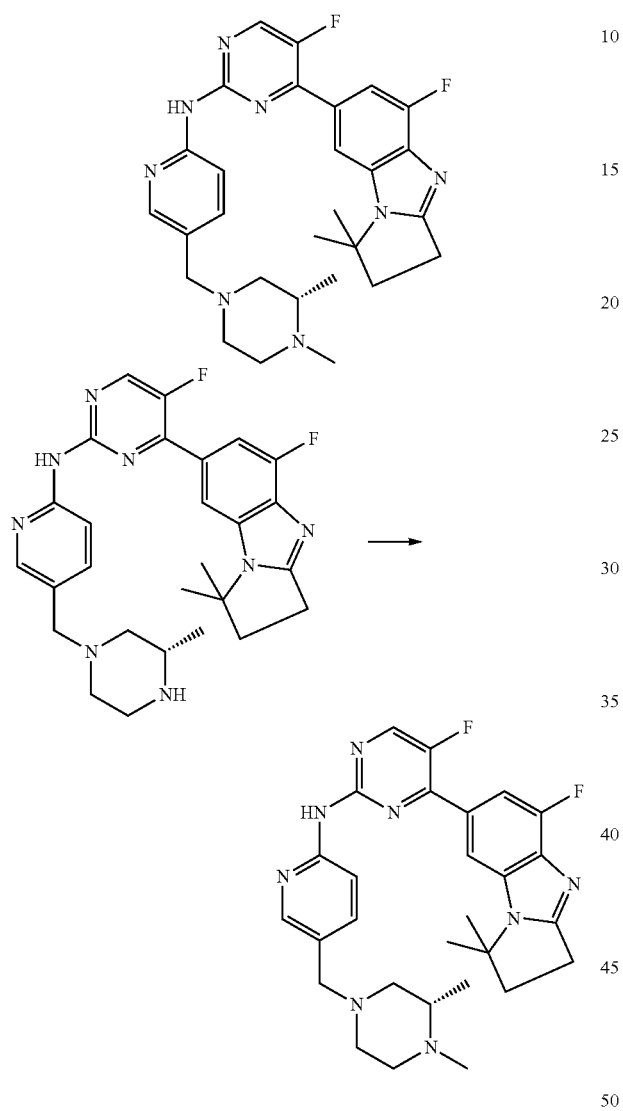

To a reaction flask was added (S)-5-fluoro-4-(5-fluoro-1,1-dimethyl-2,3-dihydro-1H-benzo[d]pyrrolo[1,2-a]imidazol-7-yl)-N-(5-(3-methylpiperazin-1-yl)methyl)pyri din-2-yl)pyrimidin-2-amine (51 mg, 0.1 mmol, prepared according to Example 46), formaldehyde (5 mg, 0.15 mmol), sodium triacetoxyborohydride (41 mg, 0.5 mmol) and dichloromethane (4 mL), and the mixture was stirred at room temperature for 3 hours to give rise to a reaction. Water (4 mL) was added, and the aqueous phase was extracted with dichloromethane (5 mL×3). The organic layers were combined, washed with saturated sodium chloride (10 mL), and dried over anhydrous sodium sulfate. The filtrate was concentrated in vacuo, and the resulting residue was purified by thin layer chromatography (DCM/MeOH=10:1) to give the title compound as a yellow solid (19 mg, yield 37%).

¹HNMR (DMSO, 400 MHz), δ 10.03 (s, 1H), 8.69 (s, 1H), 8.21-8.19 (m, 3H), 7.73-7.65 (m, 2H), 3.41 (s, 2H), 3.11 (t, J=7.6 Hz, 2H), 2.66-2.57 (m, 5H), 2.14-2.11 (m, 5H), 2.00 (brs, 1H), 1.79-1.74 (m, 1H), 1.68 (s, 6H), 0.92 (t, J=6.0 Hz, 3H)

MS m/z (ESI): 519.3 (M+H)

Example 48

N-(5-((4-Cyclopropylpiperazin-1-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine

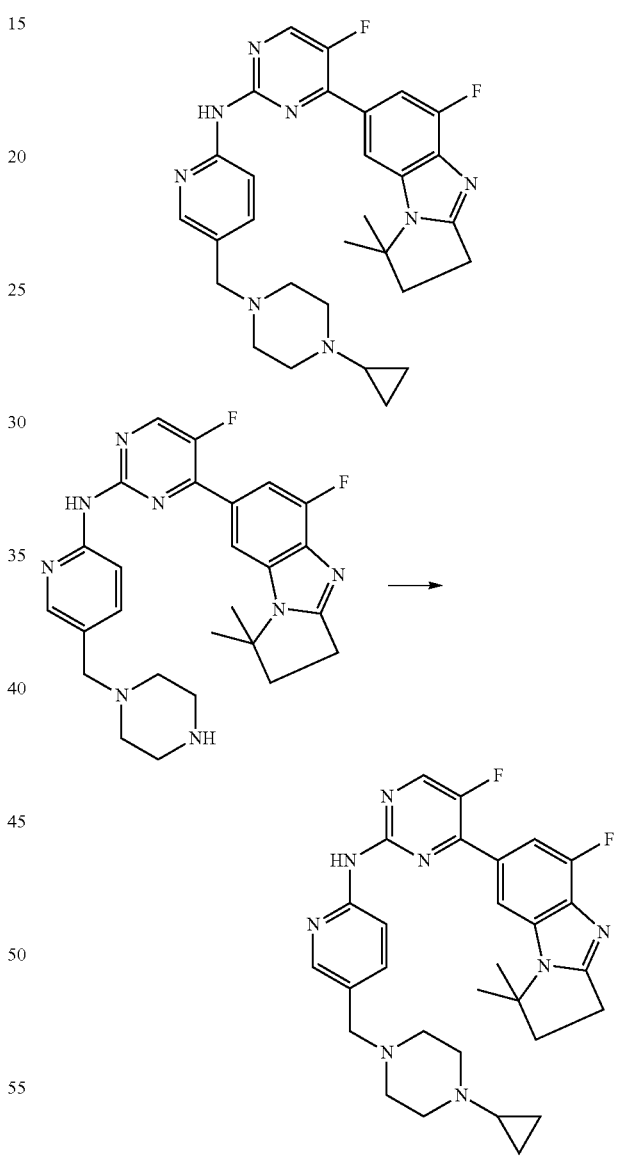

To a reaction flask was added 5-fluoro-4-(5-fluoro-1,1-1,1-dimethyl-2,3-dihydro-1H-benzo[d]pyrrolo[1,2-a]imidazol-7-yl)-N-(5-(piperazin-1-ylmethyl)pyridin-2-yl)pyrimidin-2-amine (50 mg, 0.1 mmol, prepared according to Example 27), potassium carbonate (71 mg, 0.51 mmol), cyclopropyl bromide (37 mg, 0.3 mmol) and DMF (4 mL), and the mixture was stirred at 50° C. for 5 hours to give rise to a reaction. The resulting mixture was cooled to room temperature, water was added (10 mL), and the aqueous phase was extracted with dichloromethane (10 mL×3). The organic phases were combined, washed with saturated sodium chloride solution (10 mL), dried over anhydrous sodium sulfate, and filtered with suction. The filtrate was concentrated under reduced pressure. The resulting residue was purified by thin layer chromatography (DCM/MeOH=10:1) to give the title compound as a yellow solid (17 mg, yield 32%).

$^1$HNMR (DMSO, 400 MHz), δ 10.032 (s, 1H), 8.69 (s, 1H), 8.22-8.19 (m, 3H), 7.73-7.65 (m, 2H), 5.84-5.74 (m, 1H), 5.18-5.09 (m, 2H), 3.45 (s, 2H), 3.11 (t, J=7.6 Hz, 2H), 2.92 (d, J=6.4 Hz, 2H), 2.59-2.55 (m, 3H), 2.39-2.37 (m, 7H), 1.68 (s, 6H)

MS m/z (ESI): 531.3 (M+H)

Example 49

N-(5-((4-Ethylpiperazin-1-yl)methyl)pyridin-2-yl)-5-fluoro-4-(5-fluoro-2-methyl-2,3-dihydro-1H-benzo[d]pyrrolo[1,2-a]imidazol-7-yl)pyrimidin-2-amine

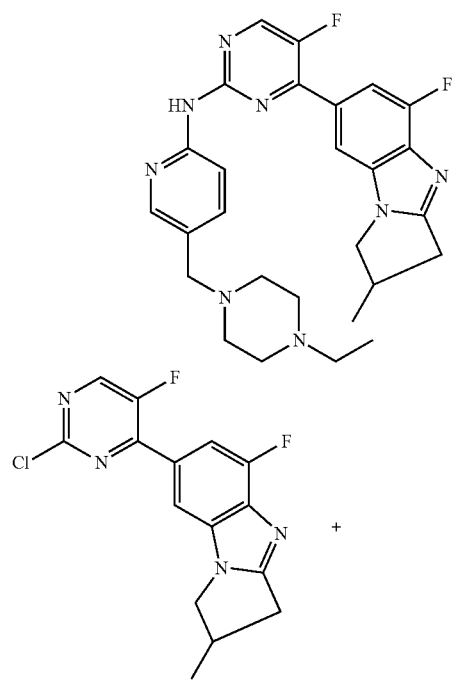

+

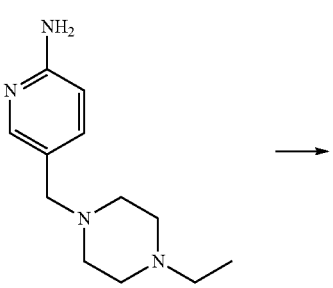

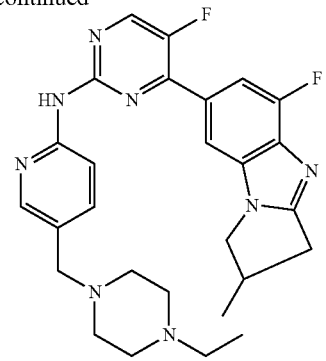

To a microwave reaction flask was added 7-(2-chloro-5-fluoropyrimidin-4-yl)-5-fluoro-2-methyl-2,3-dihydro-1H-benzo[d]pyrrolo[1,2-a]imidazole (96 mg, 0.3 mmol, prepared according to Example 5), 5-((4-ethylpiperazin-1-yl)methyl)pyridin-2-amine (66 mg, 0.3 mmol), cesium carbonate (195 mg, 0.6 mmol), Pd$_2$(dba)$_3$ (55 mg, 0.06 mmol), XantPhos (35 mg, 0.06 mmol) and anhydrous 1,4-dioxane (2 mL), and the mixture was reacted for 1 hour in a microwave at 150° C. The resulting mixture was cooled to room temperature, water was added (10 mL), and the aqueous phase was extracted with ethyl acetate (20 mL×3). The organic phases were combined, washed with saturated sodium chloride solution (20 mL), dried over anhydrous sodium sulfate, and filtered with suction. The filtrate was concentrated under reduced pressure and the resulting residue was purified by column chromatography (DCM/MeOH=20:1) to give the title compound amine as a yellow solid (30 mg, yield 20%).

$^1$HNMR (DMSO, 400 MHz), δ 10.01 (s, 1H), 8.70 (s, 1H), 8.20-8.18 (m, 2H), 8.05 (s, 1H), 7.78-7.71 (m, 2H), 4.44-4.40 (m, 1H), 3.83-3.78 (m, 1H), 3.48 (s, 2H), 3.25-3.20 (m, 3H), 2.72-2.65 (m, 3H), 2.37-2.32 (m, 6H), 1.29-1.23 (m, 7H)

MS m/z (ESI): 505.2 (M+H)

Example 50

5-Fluoro-4-(5-fluoro-2-methyl-2,3-dihydro-1H-benzo[d]pyrrolo[1,2-a]imidazol-7-yl)-N-(5-(piperazin-1-yl)pyridin-2-yl)pyrimidin-2-amine

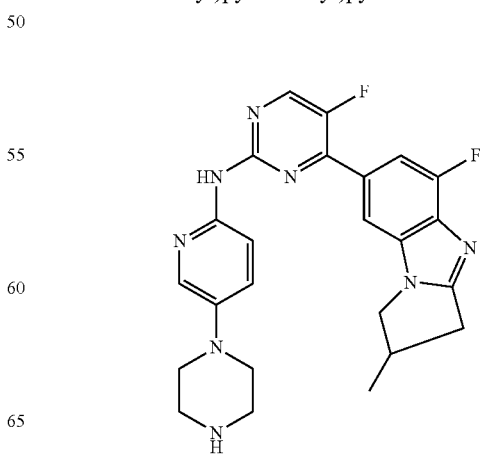

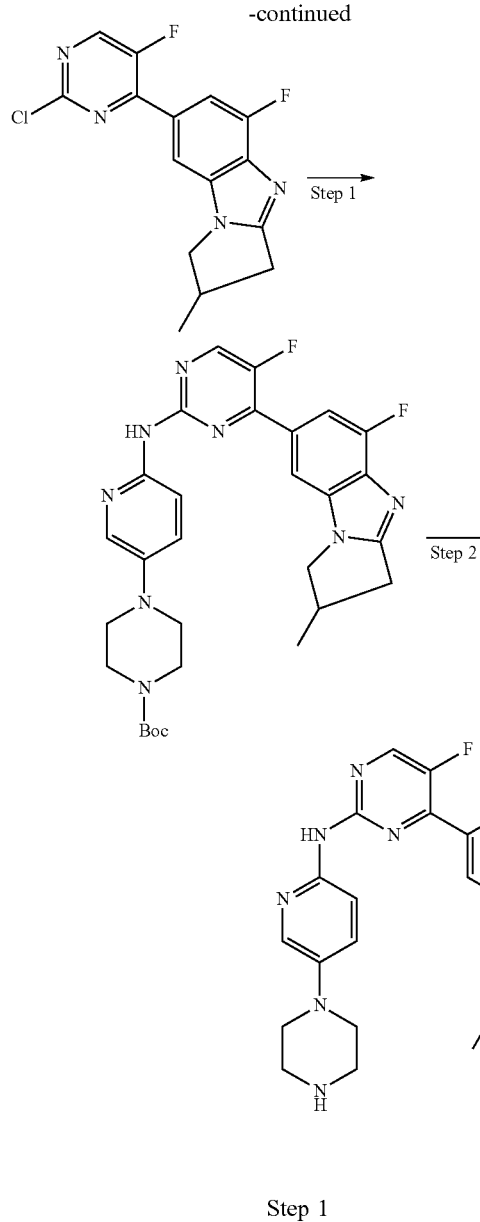

Step 1 tert-Butyl 4-(6-((5-fluoro-4-(5-fluoro-2-methyl-2,3-dihydro-1H-benzo[d]pyrrolo[1,2-a]imidazol-7-yl)pyrimidin-2-yl)amino)pyridin-3-yl)piperazine-1-carboxylate To a reaction flask was added tert-butyl 7-(2-chloro-5-fluoropyrimidin-4-yl)-5-fluoro-2-methyl-2,3-dihydro-1H-benzo[d]pyrrolo[1,2-a]imidazole (96 mg, 0.3 mmol), 4-(6-aminopyridin-3-yl)piperazine-1-carboxylate (84 mg, 0.3 mmol), cesium carbonate (195 mg, 0.6 mmol), Pd$_2$(dba)$_3$ (55 mg, 0.06 mmol), Xantphos (35 mg, 0.06 mmol) and 1,4-dioxane (2 mL), and the mixture was reacted for 1 hour in a microwave at 150° C. The resulting mixture was cooled to room temperature, water was added (10 mL), and the aqueous phase was extracted with ethyl acetate (20 mL×3). The organic phases were combined, washed with saturated sodium chloride solution (30 mL), dried over anhydrous sodium sulfate, and filtered with suction. The filtrate was concentrated under reduced pressure, and the resulting residue was purified by column chromatography (DCM/MeOH=10:1) to give the title compound as a yellow solid (28 mg, yield 17%).

MS m/z (ESI): 563.1 (M+H)

Step 2

5-Fluoro-4-(5-fluoro-2-methyl-2,3-dihydro-1H-benzo[d]pyrrolo[1,2-a]imidazol-7-yl)-N-(5-(piperazin-1-yl)pyridin-2-yl)pyrimidin-2-amine To a reaction flask was added tert-butyl 4-(6-((5-fluoro-4-(5-fluoro-2-methyl-2,3-dihydro-1H-benzo[d]pyrrolo[1,2-a]imidazol-7-yl)pyrimidin-2-yl)amino)pyridin-3-yl)piperazine-1-carboxylate (28 mg, 0.05 mmol, prepared in Step 1), trifluoroacetic acid (0.5 mL) and dichloromethane (4 mL). The mixture was stirred at room temperature for 1 hour to give rise to a reaction, diluted with water (10 mL), and extracted with dichloromethane (10 mL×3). The organic layers were combined, washed with saturated sodium chloride (10 mL), and dried over anhydrous sodium sulfate. The filtrate was concentrated in vacuo, and the resulting residue was purified by thin layer chromatography (DCM/MeOH=10:1) to give the title compound as a yellow solid (10 mg, yield 44%).

$^1$HNMR (DMSO, 400 MHz), δ 9.75 (s, 1H), 8.64 (s, 1H), 8.08-8.02 (m, 3H), 7.73 (d, J=12.4 Hz, 1H), 7.48 (d, J=12.4 Hz, 1H), 4.39 (q, J=6.4 Hz, 1H), 3.82-3.78 (m, 1H), 3.32-3.25 (m, 2H), 3.23-3.20 (m, 2H), 3.09-3.07 (m, 2H), 2.69-2.67 (m, 2H), 1.29-1.23 (m, 7H)

MS m/z (ESI): 463.1 M+H

Example 51

4-(2-Ethyl-5-fluoro-2,3-dihydro-1H-benzo[d]pyrrolo[1,2-a]imidazol-7-yl)-N-(5-(((4-ethylpiperazin-1-yl)methyl)pyridin-2-yl)-5-fluoropyrimidin-2-amine

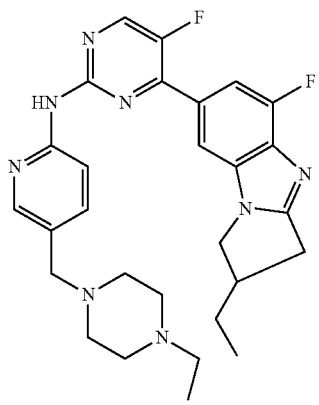

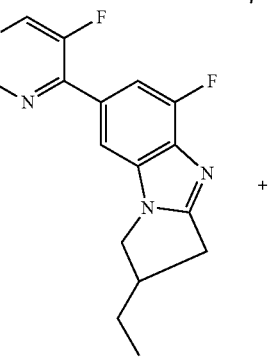

+

113

-continued

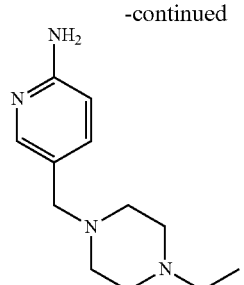

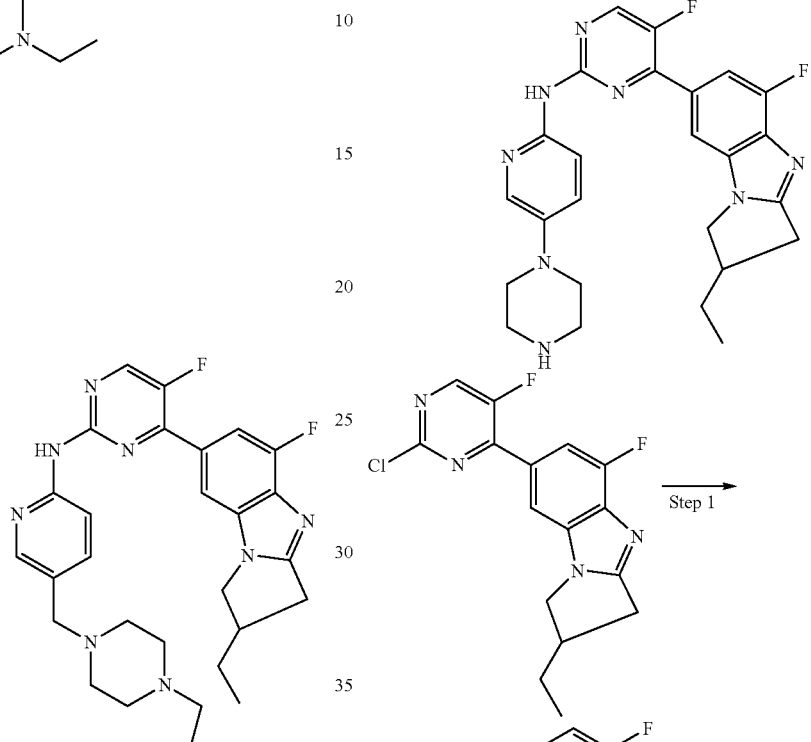

114

Example 52

4-(2-Ethyl-5-fluoro-2,3-dihydro-1H-benzo[d]pyrrolo[1,2-a]imidazol-7-yl)-5-fluoro-N-(5-(piperazin-1-yl)pyridin-2-yl)pyrimidin-2-amine To a reaction flask was added 7-(2-chloro-5-fluoropyrimidin-4-yl)-5-fluoro-2-methyl-2,3-dihydro-1H-benzo[d]pyrrolo[1,2-a]imidazole (100 mg, 0.3 mmol, prepared according to Example 6), 5-((4-ethylpiperazin-1-yl)methyl)pyridin-2-amine (66 mg, 0.3 mmol), cesium carbonate (195 mg, 0.6 mmol), $Pd_2(dba)_3$ (55 mg, 0.06 mmol), XantPhos (35 mg, 0.06 mmol) and 1,4-dioxane (2 mL), and the mixture was reacted for 1 hour in a microwave at 150° C. The resulting mixture was cooled to room temperature and water (10 mL) was added. The aqueous phase was extracted with ethyl acetate (20 mL×3) and the phases were separated. The organic phases were combined, washed with saturated sodium chloride solution (10 mL), dried over anhydrous sodium sulfate, and filtered with suction. The filtrate was concentrated under reduced pressure, and the resulting residue was purified by column chromatography (DCM/MeOH=20:1) to give the title compound as a yellow solid (30 mg, yield 20%).

$^1$HNMR (DMSO, 400 MHz), δ 9.96 (s, 1H), 8.68 (s, 1H), 8.19 (s, 1H), 8.17 (s, 1H), 8.05 (s, 1H), 7.77-7.07 (m, 2H), 4.44-4.40 (m, 1H), 3.88-3.84 (m, 1H), 3.46 (s, 2H), 3.23-3.21 (m, 3H), 3.08-3.04 (m, 2H), 2.76-2.70 (m, 2H), 2.35-2.32 (m, 6H), 1.68-1.63 (m, 2H), 1.00-0.97 (m, 6H)

MS m/z (ESI): 519.1 (M+H)

115

Step 1 tert-Butyl 4-(6-((4-(2-ethyl-5-fluoro-2,3-dihydro-1H-benzo[d]pyrrolo[1,2-a]imidazol-7-yl)-5-fluoro-pyrimidin-2-yl)amino)pyridin-3-yl)piperazine-1-carboxylate To a reaction flask was added tert-butyl 7-(2-chloro-5-fluoropyrimidin-4-yl)-5-fluoro-2-methyl-2,3-dihydro-1H-benzo[d]pyrrolo[1,2-a]imidazole (100 mg, 0.3 mmol, prepared according to Example 6), tert-butyl 4-(6-aminopyridin-3-yl) piperazine-1-carboxylate (83 mg, 0.3 mmol), cesium carbonate (195 mg, 0.6 mmol), $Pd_2(dba)_3$ (55 mg, 0.06 mmol), XantPhos (35 mg, 0.06 mmol) and 1,4-dioxane (2 mL), and the mixture was reacted for 1 hour in a microwave at 150° C. The resulting mixture was cooled to room temperature and water (10 mL) was added. The aqueous phase was extracted with ethyl acetate (20 mL×3) and the phases were separated. The organic phases were combined, washed with saturated sodium chloride solution (40 mL×2), dried over anhydrous sodium sulfate, and filtered with suction. The filtrate was concentrated under reduced pressure and the resulting residue was purified by column chromatography (DCM/MeOH=20:1) to give the title compound as a yellow solid (30 mg, yield 17.4%).

MS m/z (ESI): 577.2 (M+H)

Step 2

4-(2-Ethyl-5-fluoro-2,3-dihydro-1H-benzo[d]pyrrolo[1,2-a]imidazol-7-yl)-5-fluoro-N-(5-(piperazin-1-yl)pyridin-2-yl)pyrimidin-2-amine To a reaction flask was added tert-butyl 4-(6-((4-(2-ethyl-5-fluoro-2,3-dihydro-1H-benzo[d]pyrrolo[1,2-a]imidazol-7-yl)-5-fluoropyrimidine-2-yl)amino)pyridin-3-yl)piperazine-1-carboxylate (30 mg, 0.05 mmol, prepared in Step 1), TFA (0.5 mL) and dichloromethane (3 mL). The mixture was stirred at room temperature for 1 hour to give rise to a reaction, diluted with water (10 mL), and the aqueous phase was extracted with ethyl acetate (20 mL×3). The organic layers were combined, washed with saturated sodium chloride (10 mL), and dried over anhydrous sodium sulfate. The filtrate was concentrated in vacuo, and the resulting residue was purified by column chromatography (DCM/MeOH=10:1) to give the title compound as a white solid (15 mg, yield 63%).

$^1$HNMR (DMSO, 400 MHz), δ 10.52 (s, 1H), 8.78 (s, 1H), 8.73 (s, 1H), 8.06-8.03 (m, 2H), 7.95 (d, J=9.2 Hz, 1H), 7.77-7.74 (m, 2H), 4.44 (t, J=8.4 Hz, 1H), 3.87 (t, J=7.2 Hz, 1H), 3.36-3.28 (m, 4H), 3.24-3.22 (m, 4H), 3.20-3.18 (m, 1H), 3.10-3.06 (m, 1H), 2.77-2.71 (m, 1H), 1.70-1.63 (m, 2H), 0.99 (t, J=7.2 Hz, 3H)

m/z (ESI): 477.1 (M+H)

116

Example 53

5-Fluoro-4-(5-fluoro-1-methyl-2,3-dihydro-1H-benzo[d]pyrrolo[1,2-a]imidazol-7-yl)-N-(5-(3-3-methylpiperazin-1-yl)pyridin-2-yl)pyrimidin-2-amine

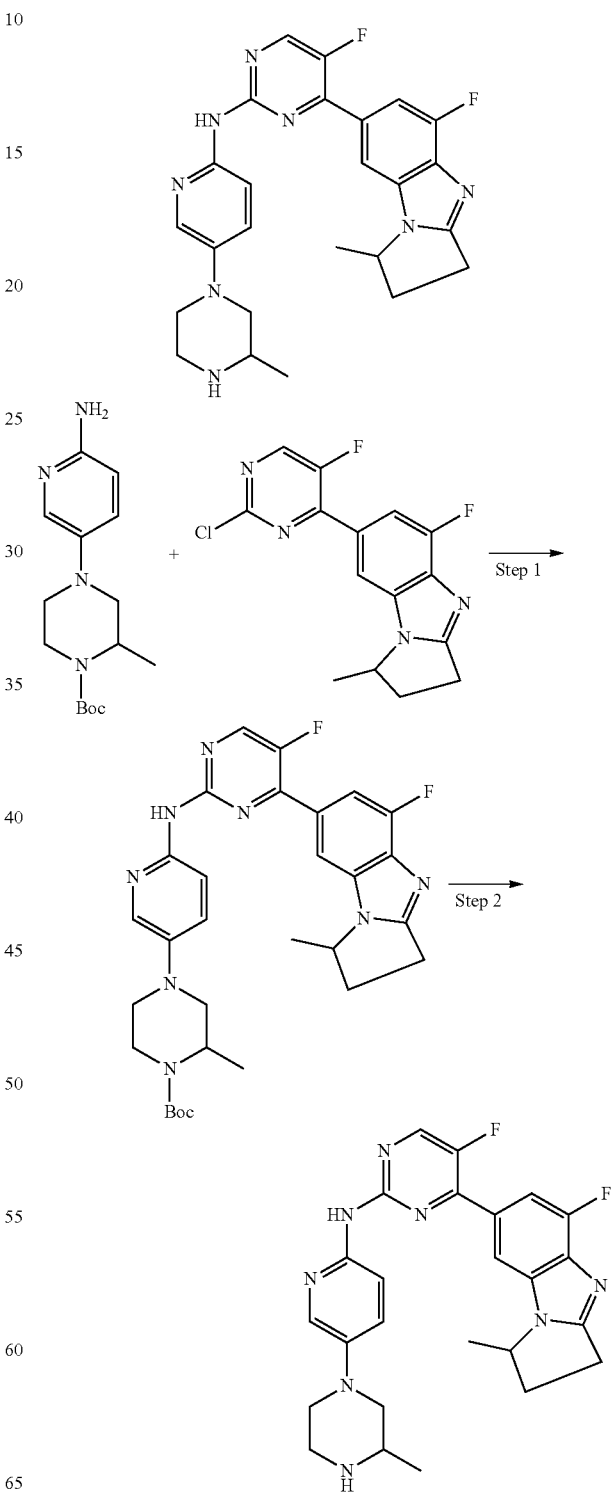

Step 1 tert-Butyl 4-(6-((5-fluoro-4-(5-fluoro-1-methyl-2,3-dihydro-1H-benzo[d]pyrrolo[1,2-a]imidazol-7-yl)pyrimidin-2-yl)amino)pyridin-3-yl)-2-methylpiperazine-1-carboxylate To a reaction flask was added 7-(2-chloro-5-fluoropyrimidin-4-yl)-5-fluoro-2-methyl-2,3-dihydro-1H-benzo[d]pyrrolo[1,2-a]imidazole (100 mg, 0.31 mmol, prepared according to Example 2), tert-butyl 4-(6-aminopyridin-3-yl)-2-methylpiperazine-1-carboxylate (91 mg, 0.31 mmol), cesium carbonate (202 mg, 0.62 mmol), Pd$_2$(dba)$_3$ (55 mg, 0.06 mmol), Xantphos (35 mg, 0.06 mmol) and 1,4-dioxane (2 mL), and the mixture was reacted for 1 hour in a microwave at 150° C. The resulting mixture was cooled to room temperature and water was added (10 mL). The aqueous phase was extracted with ethyl acetate (20 mL×3) and the phases were separated. The organic phases were combined, washed with saturated sodium chloride solution (10 mL), dried over anhydrous sodium sulfate, and filtered with suction. The filtrate was concentrated under reduced pressure, and the resulting residue was purified by column chromatography (DCM/MeOH=10:1) to give the title compound as a yellow solid (62 mg, yield 35%).

MS m/z (ESI): 577.6 (M+H)

Step 2

5-Fluoro-4-(5-fluoro-1-methyl-2,3-dihydro-1H-benzo[d]pyrrolo[1,2-a]imidazol-7-yl)-N-(5-(3-3-methylpiperazin-1-yl)pyridin-2-yl)pyrimidin-2-amine To a reaction flask was added tert-butyl 4-(6-((5-fluoro-4-(5-fluoro-1-methyl-2,3-dihydro-1H-benzo[d]pyrrolo[1,2-a]imidazol-7-yl)pyrimidin-2-yl)amino)pyridin-3-yl)-2-methylpiperazine-1-carboxylate (62 mg, 0.1 mmol, prepared in Step 1), trifluoroacetic acid (2 mL) and dichloromethane (6 mL). The mixture was stirred at room temperature for 1 hour to give rise to a reaction, diluted with water (10 mL), and the aqueous phase was extracted with ethyl acetate (10 mL×3). The organic layers were combined, washed with saturated sodium chloride (10 mL), and dried over anhydrous sodium sulfate. The filtrate was concentrated in vacuo, and the resulting residue was purified by column chromatography (DCM/MeOH=10:1) to give the title compound as a yellow solid (26 mg, yield 54.6%).

$^1$HNMR (DMSO, 400 MHz), δ 10.47 (s, 1H), 9.25 (s, 1H), 8.72 (s, 1H), 8.13 (s, 1H), 8.05 (s, 1H), 7.98 (d, J=8.8 Hz, 1H), 7.75-7.72 (m, 2H), 4.78-4.76 (m, 1H), 3.80-3.74 (m, 2H), 3.45-3.42 (m, 2H), 3.17-3.10 (m, 2H), 3.08-2.97 (m, 3H), 2.78-2.72 (m, 1H), 2.29-2.28 (m, 1H), 1.56 (d, J=6.4 Hz, 3H), 1.28 (d, J=6.4 Hz, 3H)

MS m/z (ESI): 477.5 (M+H)

Example 54

4-(1-Ethyl-5-fluoro-2,3-dihydro-1H-benzo[d]pyrrolo[1,2-a]imidazol-7-yl)-5-fluoro-N-(5-(piperazin-1-yl)pyridin-2-yl)pyrimidin-2-amine

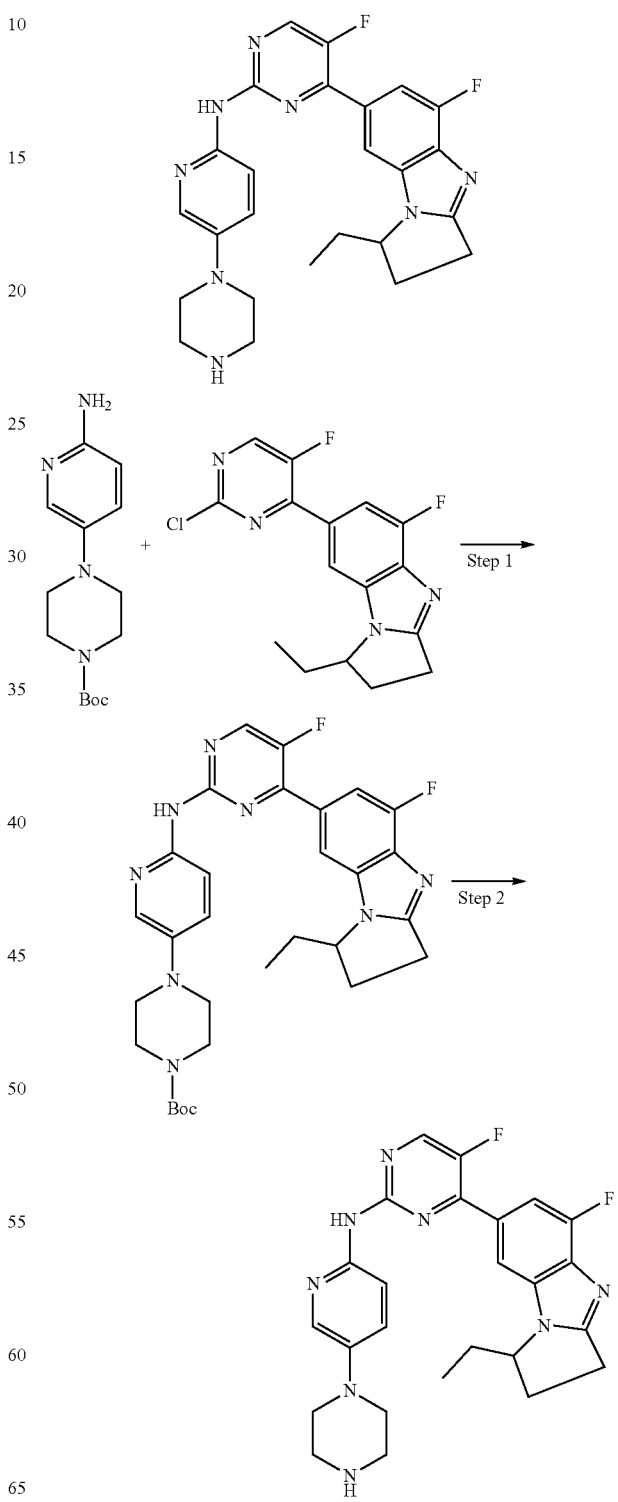

Step 1 tert-Butyl 4-(6-((4-(1-ethyl-5-fluoro-2,3-dihydro-1H-benzo[d]pyrrolo[1,2-a]imidazol-7-yl)-5-fluoropyrimidin-2-yl)amino)pyridin-3-yl)piperazine-1-carboxylate To a reaction flask was added 7-(2-chloro-5-fluoropyrimidin-4-yl)-1-ethyl-5-fluoro-2,3-dihydro-1H-benzo[d]pyrrolo[1,2-a]imidazole (100 mg, 0.30 mmol, prepared in Example 3), tert-butyl 4-(6-aminopyridin-3-yl)piperazine-1-carboxylate (83 mg, 0.30 mmol), cesium carbonate (195 mg, 0.6 mmol), $Pd_2(dba)_3$ (55 mg, 0.06 mmol), Xantphos (35 mg, 0.06 mmol) and 1,4-dioxane (2 mL), and the mixture was reacted for 1 hour in a microwave at 150° C. The resulting mixture was cooled to room temperature and water was added (10 mL). The aqueous phase was extracted with ethyl acetate (20 mL×3) and the phases were separated. The organic phases were combined, washed with saturated sodium chloride solution (10 mL), dried over anhydrous sodium sulfate, and filtered with suction. The filtrate was concentrated under reduced pressure, and the resulting residue was purified by column chromatography (DCM/MeOH=10:1) to give the title compound as a yellow solid (72 mg, yield 41.7%).

MS m/z (ESI): 577.61 (M+H)

Step 2

4-(1-Ethyl-5-fluoro-2,3-dihydro-1H-benzo[d]pyrrolo[1,2-a]imidazol-7-yl)-5-fluoro-N-(5-(piperazin-1-yl)pyridin-2-yl)pyrimidin-2-amine To a reaction flask was added tert-butyl 4-(6-((4-(1-ethyl-5-fluoro-2,3-dihydro-1H-benzo[d]pyrrolo[1,2-a]imidazol-7-yl)-5-fluoropyrimidin-2-yl)amino)pyridin-3-yl)piperazine-1-carboxylate (72 mg, 0.13 mmol, prepared in Step 1), trifluoroacetic acid (2 mL) and dichloromethane (6 mL). The mixture was stirred at room temperature for 1 hour to give rise to a reaction, diluted with water (10 mL), and the aqueous phase was extracted with ethyl acetate (40 mL×3). The organic layers were combined, washed with saturated sodium chloride (10 mL), and dried over anhydrous sodium sulfate. The filtrate was concentrated in vacuo, and the resulting residue was purified by column chromatography (DCM/MeOH=10:1) to give the title compound as a yellow solid (31 mg, yield 50%).

$^1$HNMR (DMSO, 400 MHz), δ 10.45 (s, 1H), 8.72 (s, 1H), 8.12 (s, 1H), 8.02 (s, 1H), 7.99-7.97 (m, 1H), 7.74-7.70 (m, 2H), 4.70-4.68 (m, 1H), 3.35-3.34 (m, 4H), 3.28-3.26 (m, 4H), 3.11-3.09 (m, 1H), 3.09-3.02 (m, 1H), 2.85-2.80 (m, 1H), 2.42-2.38 (m, 1H), 2.11-2.09 (m, 1H), 1.85-1.82 (m, 1H), 0.91 (t, J=7.2 Hz, 3H)

MS m/z (ESI): 477.3 (M+H)

Example 55

5-Fluoro-4-(5-fluoro-2,2-dimethyl-2,3-dihydro-1H-benzo[d]pyrrolo[1,2-a]imidazol-7-yl)-N-(5-(piperazin-1-yl)pyridin-2-yl)pyrimidin-2-amine

121

Step 1 tert-Butyl 4-(6-((5-fluoro-4-(5-fluoro-2,2-dimethyl-2,3-dihydro-1H-benzo[d]pyrrolo[1,2-a]imidazol-7-yl)pyrimidin-2-yl)amino)pyridin-3-yl)piperazine-1-carboxylate To a reaction flask was added 7-(2-chloro-5-fluoropyrimidin-4-yl)-5-fluoro-2,2-dimethyl-dihydro-1H-benzo[d]pyrrolo[1,2-a]imidazole (200 mg, 0.6 mmol, prepared according to Example 4), tert-butyl 4-(6-aminopyridin-3-yl)piperazine-1-carboxylate (167 mg, 0.6 mmol), cesium carbonate (390 mg, 1.2 mmol), Pd$_2$(dba)$_3$ (55 mg, 0.06 mmol), Xantphos (69 mg, 0.12 mmol) and 1,4-dioxane (4 mL), and the mixture was reacted for 45 minutes in a microwave at 150° C. The resulting mixture was cooled to room temperature and water was added (10 mL). The aqueous phase was extracted with ethyl acetate (20 mL×3) and the phases were separated. The organic phases were combined, washed with saturated sodium chloride solution (10 mL), dried over anhydrous sodium sulfate, and filtered with suction. The filtrate was concentrated under reduced pressure. The resulting residue was purified by column chromatography (DCM/MeOH=20:1) to give the title compound as a yellow solid (80 mg, yield 23%).

MS m/z (ESI): 577.2 (M+H)

Step 2

5-Fluoro-4-(5-fluoro-2,2-dimethyl-2,3-dihydro-1H-benzo[d]pyrrolo[1,2-a]imidazol-7-yl)-N-(5-(piperazin-1-yl)pyridin-2-yl)pyrimidin-2-amine To a reaction flask was added tert-butyl 4-(6-((5-fluoro-4-(5-fluoro-2,2-dimethyl-2,3-dihydro-1H-benzo[d]pyrrolo[1,2-a]imidazol-7-yl)pyrimidin-2-yl)amino)pyridin-3-yl)piperazine-1-carboxylate (80 mg, 0.14 mmol, prepared in Step 1), trifluoroacetic acid (2 mL) and dichloromethane (6 mL). The mixture was stirred at room temperature for 3 hours to give rise to a reaction, diluted with water (10 mL), and extracted with dichloromethane (20 mL×3). The organic layers were combined, washed with saturated sodium chloride (10 mL), and dried over anhydrous sodium sulfate. The filtrate was concentrated in vacuo, and the resulting residue was purified by column chromatography (DCM/MeOH=5:1) to give the title compound as a yellow solid (40 mg, yield 60%).

$^1$HNMR (DMSO, 400 MHz), δ 9.67 (s, 1H), 8.63 (s, 1H), 8.04-8.00 (m, 3H), 7.73 (d, J=12.4 Hz, 1H), 7.45-7.42 (m, 1H), 4.00 (s, 2H), 3.03-3.01 (m, 4H), 2.89 (s, 2H), 2 (m, 4H), 2.85 (brs, 4H), 1.30 (s, 6H)

MS m/z (ESI): 477.1 (M+H)

122

Example 56

N-(5-((4-Ethylpiperazin-1-yl)methyl)pyridin-2-yl)-5-fluoro-4-(5-fluoro-2,2-dimethyl-2,3-dihydro-1H-benzo[d]pyrrolo[1,2-a]imidazol-7-yl)pyrimidin-2-amine

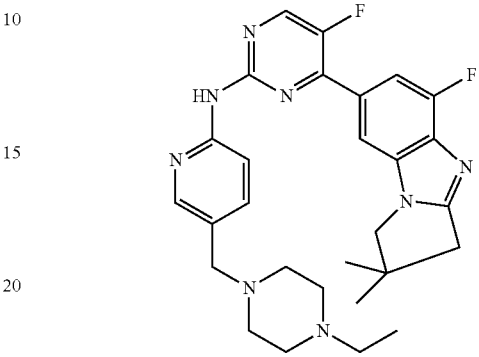

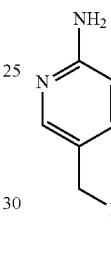

+

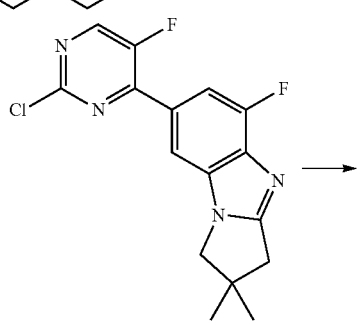

→

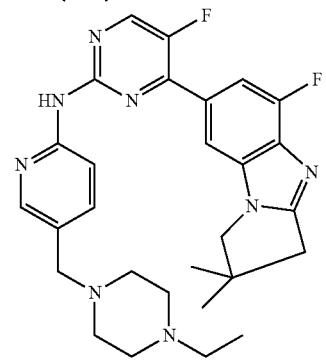

To a reaction flask was added 7-(2-chloro-5-fluoropyrimidin-4-yl)-5-fluoro-2,2-dimethyl-dihydro-1H-benzo[d]pyrrolo[1,2-a]imidazole (100 mg, 0.3 mmol, prepared according to Example 4), 5-((4-ethylpiperazin-1-yl)methyl)pyridin-2-amine (66 mg, 0.3 mmol), cesium carbonate (195 mg, 0.6 mmol), Pd$_2$(dba)$_3$ (27 mg, 0.03 mmol), XantPhos (35 mg, 0.06 mmol) and 1,4-dioxane (2 mL), and the mixture was reacted for 45 minutes in a microwave at 150°

C. The resulting mixture was cooled to room temperature and water was added (10 mL), The aqueous phase was extracted with ethyl acetate (20 mL×3) and the phases were separated. The organic phases were combined, washed with saturated sodium chloride solution (10 mL), dried over anhydrous sodium sulfate, and filtered with suction. The filtrate was concentrated under reduced pressure, and the resulting residue was purified by column chromatography (DCM/MeOH=10:1) to give the title compound as a yellow solid (20 mg, yield 14%).

¹HNMR (DMSO, 400 MHz), δ 9.94 (s, 1H), 8.69 (s, 1H), 8.19 (s, 1H), 8.17 (s, 1H), 8.04 (s, 1H), 7.78-7.70 (m, 2H), 4.02 (s, 2H), 3.44 (s, 2H), 2.90 (s, 2H), 2.33-2.29 (m, 10H), 1.31 (s, 6H), 0.97 (t, J=7.2 Hz, 3H)

MS m/z (ESI): 519.2 (M+H)

Example 57

5-Fluoro-4-(5-fluoro-1,1-dimethyl-2,3-dihydro-1H-benzo[d]pyrrolo[1,2-a]imidazol-7-yl)-N-(5-(3-methylpiperazin-1-yl)pyridin-2-yl)pyrimidin-2-amine

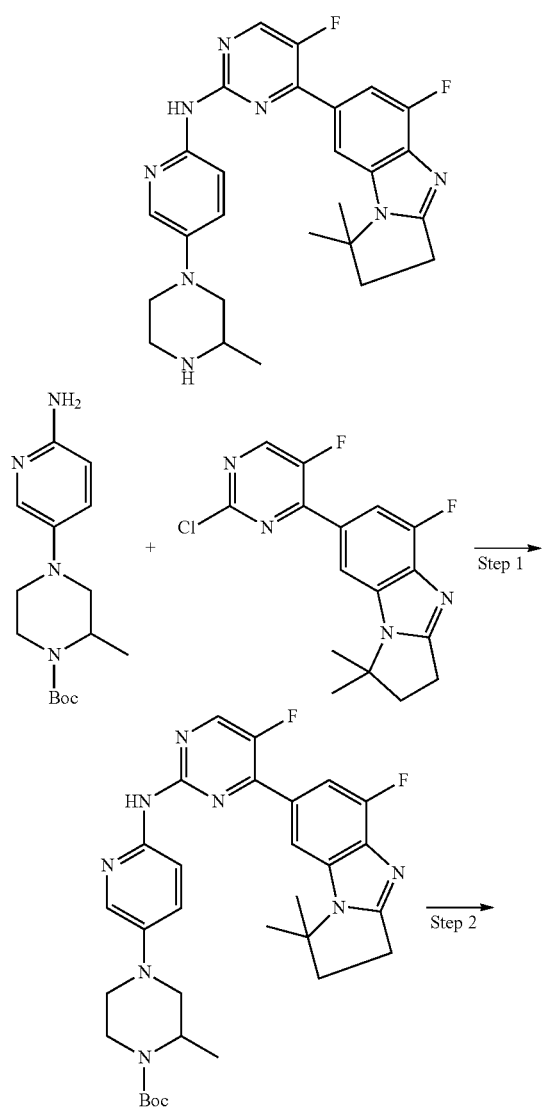

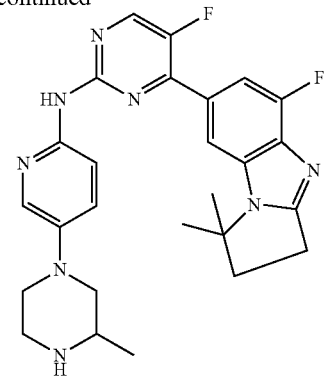

Step 1 tert-Butyl 4-(6-((5-fluoro-4-(5-fluoro-1,1-dimethyl-2,3-dihydro-1H-benzo[d]pyrrolo[1,2-a]imidazol-7-yl)pyrimidin-2-yl)amino)pyridin-3-yl)-2-methylpiperazine-1-carboxylate To a reaction flask was added 7-(2-chloro-5-fluoropyrimidin-4-yl)-5-fluoro-2,3-dihydro-1H-benzo[d]pyrrolo[1,2-a]imidazole (100 mg, 0.3 mmol, prepared according to Example 1), tert-butyl 4-(6-aminopyridin-3-yl)-2-methylpiperazine-1-carboxylate (88 mg, 0.3 mmol), cesium carbonate (195 mg, 0.6 mmol), Pd₂(dba)₃ (55 mg, 0.06 mmol), Xantphos (35 mg, 0.06 mmol) and 1,4-dioxane (2 mL), and the mixture was reacted for 1 hour in a microwave at 150° C. The resulting mixture was cooled to room temperature, water was added (10 mL), and the aqueous phase was extracted with ethyl acetate (40 mL×3). The organic phases were combined, washed with saturated sodium chloride solution (40 mL×2), dried over anhydrous sodium sulfate, and filtered with suction. The filtrate was concentrated under reduced pressure, and the resulting residue was purified by column chromatography (DCM/MeOH=10:1) to give the title compound as a yellow solid (52 mg, yield 29.4%).

MS m/z (ESI): 591.3 (M+H)

Step 2

5-Fluoro-4-(5-fluoro-1,1-dimethyl-2,3-dihydro-1H-benzo[d]pyrrolo[1,2-a]imidazol-7-yl)-N-(5-(3-methylpiperazin-1-yl)pyridin-2-yl)pyrimidin-2-amine To a reaction flask was added tert-butyl 4-(6-((5-fluoro-4-(5-fluoro-1,1-dimethyl-2,3-dihydro-1H-benzo[d]pyrrolo[1,2-a]imidazol-7-yl)pyrimidin-2-yl)amino)pyridin-3-yl)-2-methylpiperazine-1-carboxylate (52 mg, 0.09 mmol, prepared in Step 1), trifluoroacetic acid (2 mL) and dichloromethane (6 mL). The mixture was stirred at room temperature for 1 hour to give rise to a reaction, diluted with water (10 mL), and the aqueous phase was extracted with ethyl acetate (20 mL×3). The organic layers were combined, washed with saturated sodium chloride (10 mL), and dried over anhydrous sodium sulfate. The filtrate was concentrated in vacuo and the resulting residue was purified by column chromatography (DCM/MeOH=10:1) to give the title compound as a yellow solid (20 mg, yield 45.4%).

¹HNMR (DMSO, 400 MHz), δ 9.95 (s, 1H), 8.66 (s, 1H), 8.17 (s, 1H), 8.09-8.08 (m, 2H), 7.69 (d, J=12.4 Hz, 1H), 52-7.49 (m, 1H), 3.75-3.72 (m, 2H), 3.44-3.38 (m, 2H), 3.35-3.33 (m, 1H), 3.11-3.08 (m, 2H), 2.97-2.91 (m, 1H), 2.75-2.70 (m, 1H), 2.57-2.73 (m, 2H), 1.66 (s, 6H), 1.28 (d, J=6.4 Hz, 3H)

MS m/z (ESI): 491.3 (M+H)

Example 58

1-(2-((5-Fluoro-4-(5-fluoro-1-methyl-2,3-dihydro-1H-benzo[d]pyrrolo[1,2-a]imidazol-7-yl)pyrimidin-2-yl)amino)-7,8-dihydro-1,6-naphthyridin-6(5H)-yl)-2-hydroxyethan-1-one

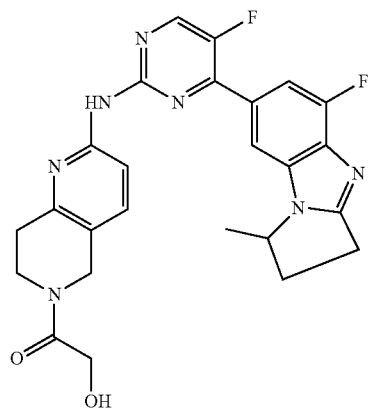 [SMILES: CC1CCc2nc3c(F)cc(-c4nc(Nc5ccc6c(n5)CCN(C(=O)CO)C6)ncc4F)cc3n21]

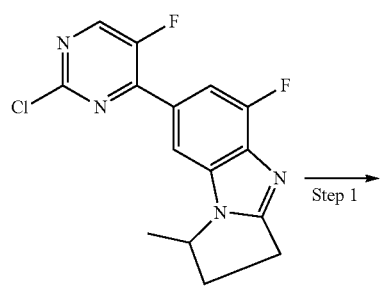

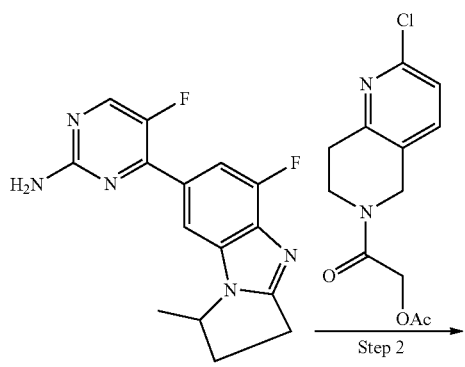

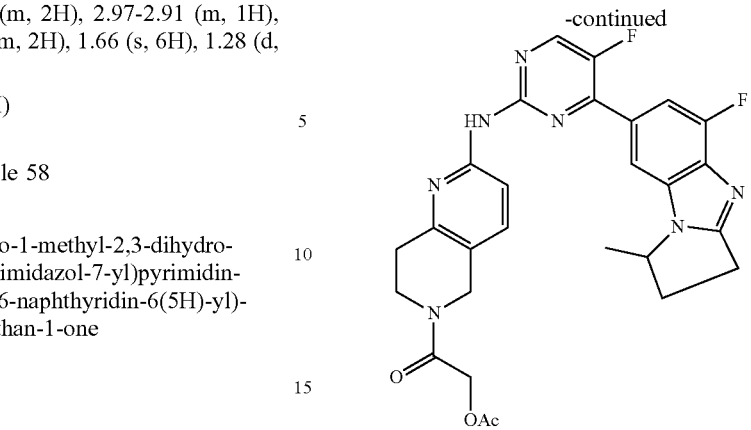

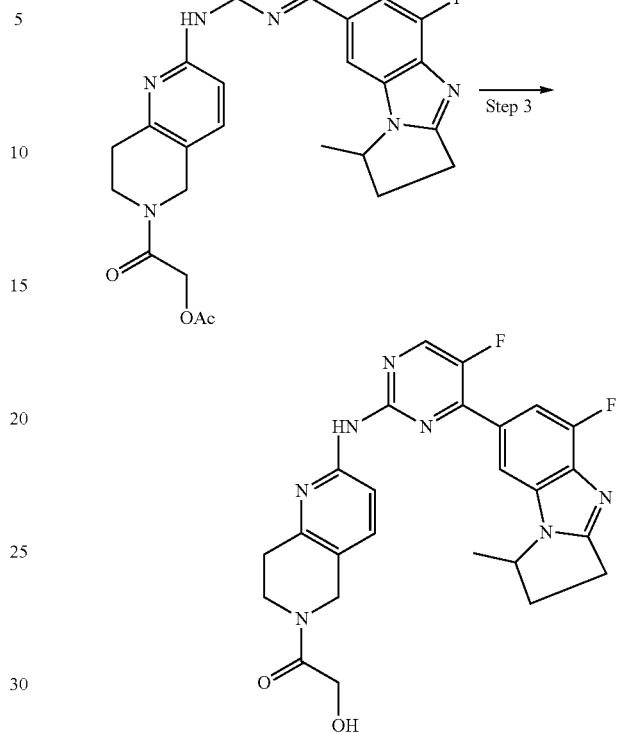

Step 1

5-Fluoro-4-(5-fluoro-1-methyl-2,3-dihydro-1H-benzo[d]pyrrolo[1,2-a]imidazol-7-yl)pyrimidin-2-amine To a reaction flask was added 7-(2-chloro-5-fluoropyrimidin-4-yl)-5-fluoro-1-methyl-2,3-dihydro-1H-benzo[d]pyrrolo[1,2-a]imidazole (500 mg, 1.56 mmol, prepared according to Example 2), aqueous ammonia (5 mL) and isopropanol (5 mL), and the mixture was reacted for 12 hours in a sealed autoclave at 100° C. The reaction liquid was cooled to room temperature and concentrated under reduced pressure to give a crude product of the title compound as a yellow oil (420 mg), which was used directly in the next reaction step.

MS m/z (ESI): 302.1 (M+H)

Step 2

2-(2-((5-Fluoro-4-(5-fluoro-1-methyl-2,3-dihydro-1H-benzo[d]pyrrolo[1,2-a]imidazol-7-yl)pyrimidin-2-yl)amino)-7,8-dihydro-1,6-naphthyridin-6(5H)-yl)-2-oxoethyl acetate To a reaction flask was added 5-fluoro-4-(5-fluoro-1-methyl-2,3-dihydro-1H-benzo[d]pyrrolo[1,2-a]imidazol-7-yl)pyrimidin-2-amine (200 mg, 0.66 mmol, prepared in Step 1), 2-(2-chloro-7,8-dihydro-1,6-naphthyridin-6(5H)-yl)-2-oxoethyl acetate (176 mg, 0.66 mmol), cesium carbonate (423 mg, 1.3 mmol), Pd₂(dba)₃ (55 mg, 0.06 mmol), Xant-Phos (35 mg, 0.06 mmol) and 1,4-dioxane (4 mL), and the mixture was reacted for 1 hour in a microwave at 150° C.

The resulting mixture was cooled to room temperature and water was added (10 mL). The aqueous phase was extracted with ethyl acetate (20 mL×3) and the phases were separated. The organic phases were combined, washed with saturated sodium chloride solution (10 mL), dried over anhydrous sodium sulfate, and filtered with suction. The filtrate was concentrated under reduced pressure, and the resulting residue was purified by column chromatography (DCM/MeOH=20:1) to give the title compound as a yellow solid (80 mg, yield 22.8%).

MS m/z (ESI): 534.1 (M+H)

Step 3

1-(2-((5-Fluoro-4-(5-fluoro-1-methyl-2,3-dihydro-1H-benzo[d]pyrrolo[1,2-a]imidazol-7-yl)pyrimidin-2-yl)amino)-7,8-dihydro-1,6-naphthyridin-6(5H)-yl)-2-hydroxyethan-1-one To a reaction flask was added 2-(2-((5-fluoro-4-(5-fluoro-1-methyl-2,3-dihydro-1H-benzo[d]pyrrolo[1,2-a]imidazol-7-yl)pyrimidin-2-yl)amino)-7,8-dihydro-1,6-naphthyridin-6(5H)-yl)-2-oxoethyl acetate (80 mg, 0.15 mmol, prepared in Step 2), sodium methoxide (0.2 mL) and dichloromethane (6 mL). The mixture was stirred at room temperature for 1 hour to give rise to a reaction, diluted with water (10 mL), and extracted with dichloromethane (20 mL×2). The organic phases were combined, washed with saturated sodium chloride solution (20 mL), dried over anhydrous sodium sulfate, and filtered with suction. The filtrate was concentrated under reduced pressure, and the resulting residue was purified by column chromatography (DCM/MeOH=5:1) to give the title compound as a yellow solid (20 mg, yield 27.4%).

¹HNMR (DMSO, 400 MHz), δ 9.98 (s, 1H), 8.68 (s, 1H), 8.17 (s, 1H), 8.09 (d, J=8.4 Hz, 1H), 7.75 (d, J=12.8 Hz, 1H), 7.65-7.57 (m, 1H), 4.79-4.56 (m, 4H), 4.22-4.19 (m, 2H), 3.82-3.69 (m, 2H), 3.11-2.81 (m, 5H), 1.58 (d, J=6.4 Hz, 3H)

MS m/z (ESI): 492.1 (M+H)

Example 59

5-Fluoro-4-(5-fluoro-1-methyl-2,3-dihydro-1H-benzo[d]pyrrolo[1,2-a]imidazol-7-yl)-N-(5-(piperazin-1-yl)pyridin-2-yl)pyrimidin-2-amine

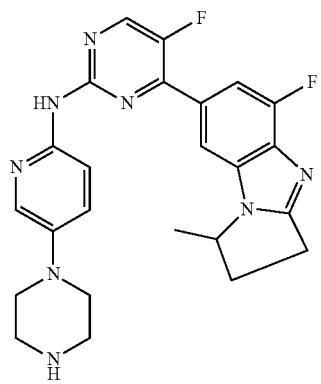

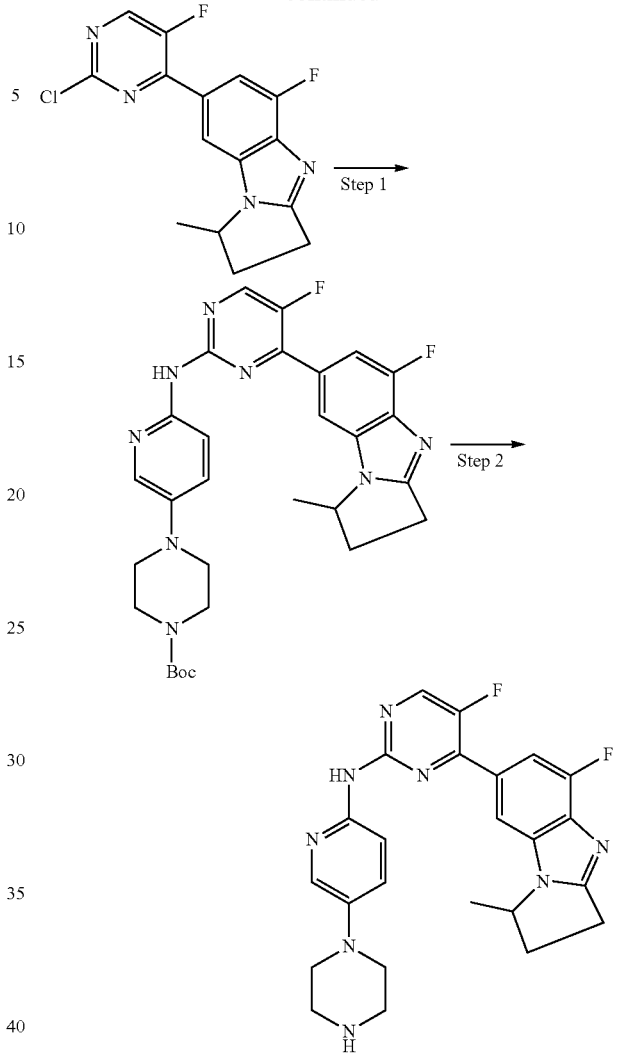

Step 1 tert-Butyl 4-(6-((5-fluoro-4-(5-fluoro-1-methyl-2,3-dihydro-1H-benzo[d]pyrrolo[1,2-a]imidazol-7-yl)pyrimidin-2-yl)amino)pyridin-3-yl)piperazine-1-carboxylate To a reaction flask was added 7-(2-chloro-5-fluoropyrimidin-4-yl)-5-fluoro-1-methyl-2,3-dihydro-1H-benzo[d]pyrrolo[1,2-a]imidazole (96 mg, 0.3 mmol, prepared in Example 2), tert-butyl 4-(6-aminopyridin-3-yl)piperazine-1-carboxylate (83 mg, 0.3 mmol), cesium carbonate (195 mg, 0.6 mmol), Pd₂(dba)₃ (55 mg, 0.06 mmol), Xantphos (35 mg, 0.06 mmol) and 1,4-dioxane (2 mL), and the mixture was reacted for 1 hour in a microwave at 150° C. The resulting mixture was cooled to room temperature and water (10 mL) was added. The aqueous phase was extracted with ethyl acetate (20 mL×3) and the phases were separated. The organic phases were combined, washed with saturated sodium chloride solution (20 mL), dried over anhydrous sodium sulfate, and filtered with suction. The filtrate was concentrated under reduced pressure, and the resulting residue was purified by column chromatography (DCM/MeOH=10:1) to give the title compound as a yellow solid (51 mg, yield 30%).

MS m/z (ESI): 563.2 (M+H)

Step 2

5-Fluoro-4-(5-fluoro-1-methyl-2,3-dihydro-1H-benzo[d]pyrrolo[1,2-a]imidazol-7-yl)-N-(5-(piperazin-1-yl)pyridin-2-yl)pyrimidin-2-amine To a reaction flask was added tert-butyl 4-(6-((5-fluoro-4-(5-fluoro-1-methyl-2,3-dihydro-1H-benzo[d]pyrrolo[1,2-a]imidazol-7-yl)pyrimidin-2-yl)amino)pyridin-3-yl) piperazine-1-carboxylate (51 mg, 0.09 mmol, prepared in Step 1), trifluoroacetic acid (1 mL) and dichloromethane (6 mL). The mixture was stirred at room temperature for 1 hour to give rise to a reaction, diluted with water (10 mL), and the aqueous phase was extracted with ethyl acetate (20 mL×3). The organic layers were combined, washed with saturated sodium chloride (10 mL), and dried over anhydrous sodium sulfate. The filtrate was concentrated in vacuo, and the resulting residue was purified by thin layer chromatography (DCM/MeOH=10:1) to give the title compound as a yellow solid (21 mg, yield 51.2%).

$^1$HNMR (DMSO, 300 MHz), δ 10.21 (s, 1H), 8.69 (s, 1H), 8.14 (s, 1H), 8.06-8.00 (m, 2H), 7.74 (d, J=12.4 Hz, 1H), 7.66-7.63 (m, 1H), 4.77 (q, J=6.4 Hz, 1H), 3.19-3.16 (m, 6H), 3.15-3.11 (m, 2H), 2.98-2.90 (m, 3H), 2.35-2.31 (m, 1H), 1.57 (d, J=4.5 Hz, 3H)

MS m/z (ESI): 463.1 (M+H)

Example 60

N-(5-((4-Ethylpiperazin-1-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine

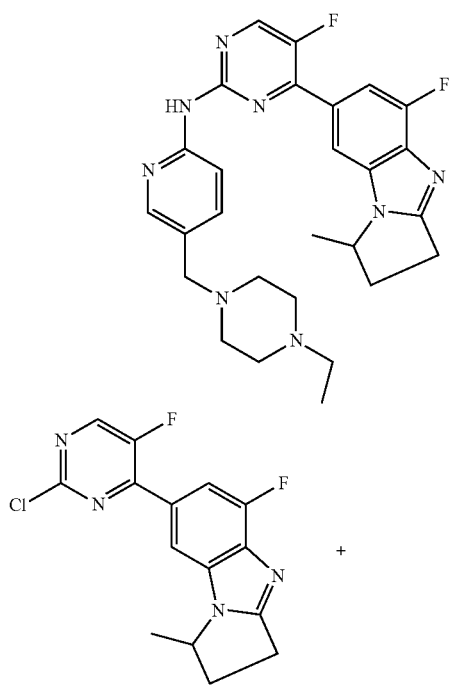

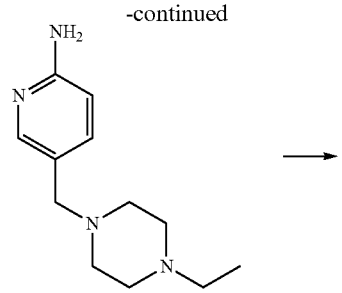

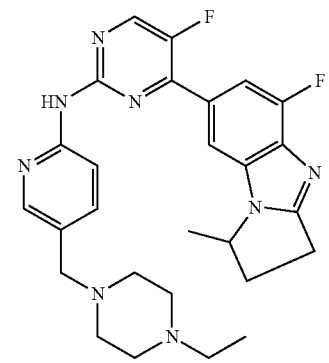

To a reaction flask was added 7-(2-chloro-5-fluoropyrimidin-4-yl)-5-fluoro-1-methyl-2,3-dihydro-1H-benzo[d]pyrrolo[1,2-a]imidazole (96 mg, 0.3 mmol, prepared in Example 2), 5-((4-ethylpiperazin-1-yl)methyl)pyridin-2-amine (66 mg, 0.3 mmol), cesium carbonate (195 mg, 0.6 mmol), Pd$_2$(dba)$_3$ (27 mg, 0.03 mmol), XantPhos (35 mg, 0.06 mmol) and 1,4-dioxane (2 mL), and the mixture was reacted for 1 hour in a microwave at 150° C. The resulting mixture was cooled to room temperature, water was added (10 mL), and the aqueous phase was extracted with ethyl acetate (20 mL×3). The organic phases were combined, washed with saturated sodium chloride solution (10 mL), dried over anhydrous sodium sulfate, and filtered with suction. The filtrate was concentrated under reduced pressure, and the resulting residue was purified by thin layer chromatography (DCM/MeOH=10:1) to give the title compound as a white solid (45 mg, yield 29.8%).

$^1$HNMR (DMSO, 400 MHz), δ 10.03 (s, 1H), 8.70 (d, J=4.0 Hz, 1H), 8.22 (s, 1H), 8.20 (s, 1H), 8.16 (s, 1H), 7.76-7.71 (m, 2H), 4.78 (q, J=6.4 Hz, 1H), 3.54 (s, 2H), 3.11-2.85 (m, 12H), 2.32-2.28 (m, 2H), 1.58 (d, J=6.4 Hz, 3H), 1.24 (s, 3H)

MS m/z (ESI): 505.1 (M+H)

Example 61

5-Fluoro-4-(5-fluoro-1-methyl-2,3-dihydro-1H-benzo[d]pyrrolo[1,2-a]imidazol-7-yl)-N-(5-(piperazine-4-yl)pyridin-2-yl)pyrimidin-2-amine

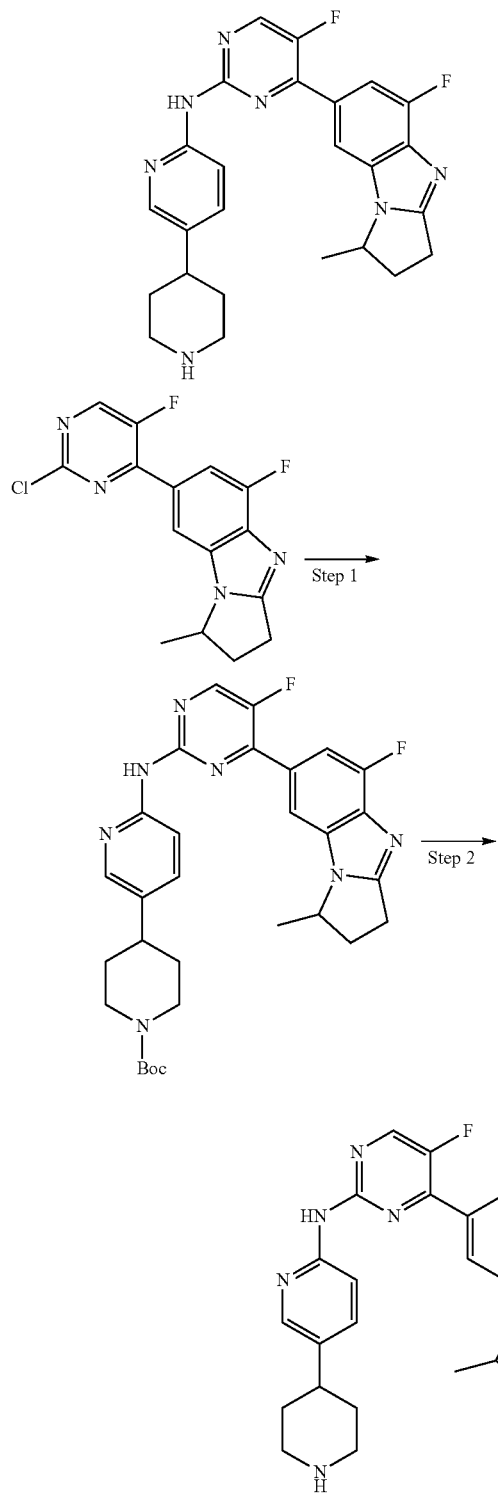

Step 1 tert-Butyl 4-(6-((5-fluoro-4-(5-fluoro-1-methyl-2,3-dihydro-1H-benzo[d]pyrrolo[1,2-a]imidazol-7-yl)pyrimidin-2-yl)amino)-3-yl)pyridin-3-yl)piperazine-1-carboxylate

To a reaction flask was added 7-(2-chloro-5-fluoropyrimidin-4-yl)-5-fluoro-1-methyl-2,3-dihydro-1H-benzo[d]pyrrolo[1,2-a]imidazole (100 mg, 0.31 mmol, prepared in Example 2), tert-butyl 4-(6-aminopyridin-3-yl)piperidine-1-carboxylate (85 mg, 0.31 mmol), cesium carbonate (201 mg, 0.62 mmol), Pd2(dba)3 (27 mg, 0.03 mmol), Xantphos (17 mg, 0.03 mmol) and anhydrous 1,4-dioxane (2 mL), and the mixture was reacted for 1 hour in a microwave at 150° C. The resulting mixture was cooled to room temperature and water (10 mL) was added. The aqueous phase was extracted with ethyl acetate (20 mL×3) and the phases were separated. The organic phases were combined, washed with saturated sodium chloride solution (20 mL×2), dried over anhydrous sodium sulfate, and filtered with suction. The filtrate was concentrated under reduced pressure, and the resulting residue was purified by column chromatography (DCM/MeOH=10:1) to give the title compound as a yellow solid (20 mg, yield 11.5%).

MS m/z (ESI): 562.1 (M+H)

Step 2

5-Fluoro-4-(5-fluoro-1-methyl-2,3-dihydro-1H-benzo[d]pyrrolo[1,2-a]imidazol-7-yl)-N-(5-(piperazine-4-yl)pyridin-2-yl)pyrimidin-2-amine

To a reaction flask was added tert-butyl 4-(6-((5-fluoro-4-(5-fluoro-1-methyl-2,3-dihydro-1H-benzo[d]pyrrolo[1,2-a]imidazol-7-yl)pyrimidin-2-yl)amino)-3-yl)pyridin-3-yl)piperazine-1-carboxylate (20 mg, 0.03 mmol, prepared in Step 1), TFA (0.5 mL) and dichloromethane (6 mL). The mixture was stirred at room temperature for 1 hour to give rise to a reaction, diluted with water (10 mL), and extracted with dichloromethane (10 mL×3). The organic layers were combined, washed with saturated sodium chloride (10 mL), and dried over anhydrous sodium sulfate. The filtrate was concentrated in vacuo, and the resulting residue was purified by thin layer chromatography (DCM/MeOH=10:1) to give the title compound as a yellow solid (15 mg, yield 91%).

$^1$HNMR (DMSO, 400 MHz), δ 9.98 (s, 1H), 8.69-8.68 (m, 1H), 8.29-8.16 (m, 3H), 7.75-7.64 (m, 2H), 4.79 (q, J=4 Hz, 1H), 3.32-3.03 (m, 2H), 3.01-2.93 (m, 1H), 2.93-2.86 (m, 3H), 2.50-2.32 (m, 1H), 2.32-2.30 (m, 2H), 2.30-1.92 (m, 2H), 1.92-1.88 (m, 2H), 1.80-1.77 (m, 3H)

MS m/z (ESI): 462.1 (M+H)

Example 62

5-Fluoro-4-(5-fluoro-1-methyl-2,3-dihydro-1H-benzo[d]pyrrolo[1,2-a]imidazol-7-yl)-N-(6-methyl-5-(piperidine-4-methylene)pyridin-2-yl)pyrimidin-2-amine

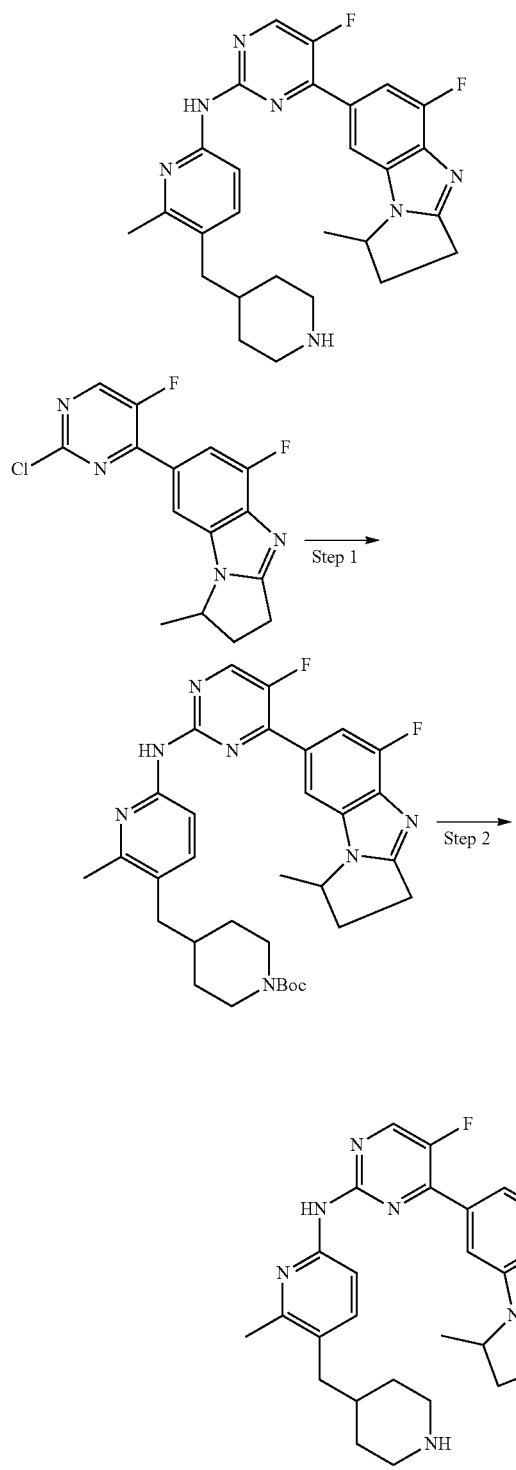

Step 1 tert-Butyl 4-((6-((5-fluoro-4-(5-fluoro-1-methyl-2,3-dihydro-1H-benzo[d]pyrrolo[1,2-a]imidazol-7-yl)pyrimidin-2-yl)amino)-2-methylpyridin-3-yl)methyl)piperidine-1-carboxylate To a reaction flask was added 7-(2-chloro-5-fluoropyrimidin-4-yl)-5-fluoro-1-methyl-2,3-dihydro-1H-benzo[d]pyrrolo[1,2-a]imidazole (100 mg, 0.31 mmol, prepared in Example 2), tert-butyl 4-((6-amino-2-methylpyridin-3-yl)methyl) piperazine-1-carboxylate (94 mg, 0.31 mmol), cesium carbonate (201 mg, 0.62 mmol), Pd$_2$(dba)$_3$ (55 mg, 0.06 mmol), Xantphos (35 mg, 0.06 mmol) and anhydrous 1,4-dioxane (2 mL), and the mixture was reacted for 1 hour in a microwave at 150° C. The resulting mixture was cooled to room temperature, water was added (10 mL), and the aqueous phase was extracted with ethyl acetate (30 mL×3). The organic phases were combined, washed with saturated sodium chloride solution (20 mL×2), dried over anhydrous sodium sulfate, and filtered with suction. The filtrate was concentrated under reduced pressure, and the resulting residue was purified by column chromatography (DCM/MeOH=10:1) to give the title compound as a yellow solid (18 mg, yield 10%).

MS m/z (ESI): 590.2 (M+H)

Step 2

5-Fluoro-4-(5-fluoro-1-methyl-2,3-dihydro-1H-benzo[d]pyrrolo[1,2-a]imidazol-7-yl)-N-(6-methyl-5-(piperidine-4-methylene)pyridin-2-yl)pyrimidin-2-amine To a reaction flask was added 5-fluoro-4-(5-fluoro-1-methyl-2,3-dihydro-1H-benzo[d]pyrrolo[1,2-a]imidazol-7-yl)-N-(6-methyl-5-(piperidine-4-methylene)pyridin-2-yl)pyrimidin-2-amine (18 mg, 0.03 mmol, prepared in Step 1), TFA (0.5 mL) and dichloromethane (3 mL). The mixture was stirred at room temperature for 1 hour to give rise to a reaction, diluted with water (10 mL), and extracted with dichloromethane (10 mL×3). The organic layers were combined, washed with saturated sodium chloride (10 mL×2), and dried over anhydrous sodium sulfate. The filtrate was concentrated in vacuo, and the resulting residue was purified by thin layer chromatography (DCM/MeOH=10:1) to give the title compound as a yellow solid (10 mg, yield 66%).

$^1$HNMR (DMSO, 400 MHz), δ 9.98 (s, 1H), 8.69-8.68 (m, 1H), 8.29-8.16 (m, 3H), 7.75-7.64 (m, 2H), 4.79 (q, J=4 Hz, 1H), 3.32-3.03 (m, 2H), 3.01-2.93 (m, 1H), 2.93-2.86 (m, 3H), 2.50-2.32 (m, 1H), 2.32-2.30 (m, 2H), 2.30-1.92 (m, 2H), 1.92-1.88 (m, 2H), 1.80-1.77 (m, 3H)

MS m/z (ESI): 490.2 (M+H)

Example 63

5-Fluoro-4-(5-fluoro-1-methyl-2,3-dihydro-1H-benzo[d]pyrrolo[1,2-a]imidazol-7-yl)-N-(5-((4-methylpiperazin-1-yl)methyl)pyridin-2-yl)pyrimidin-2-amine

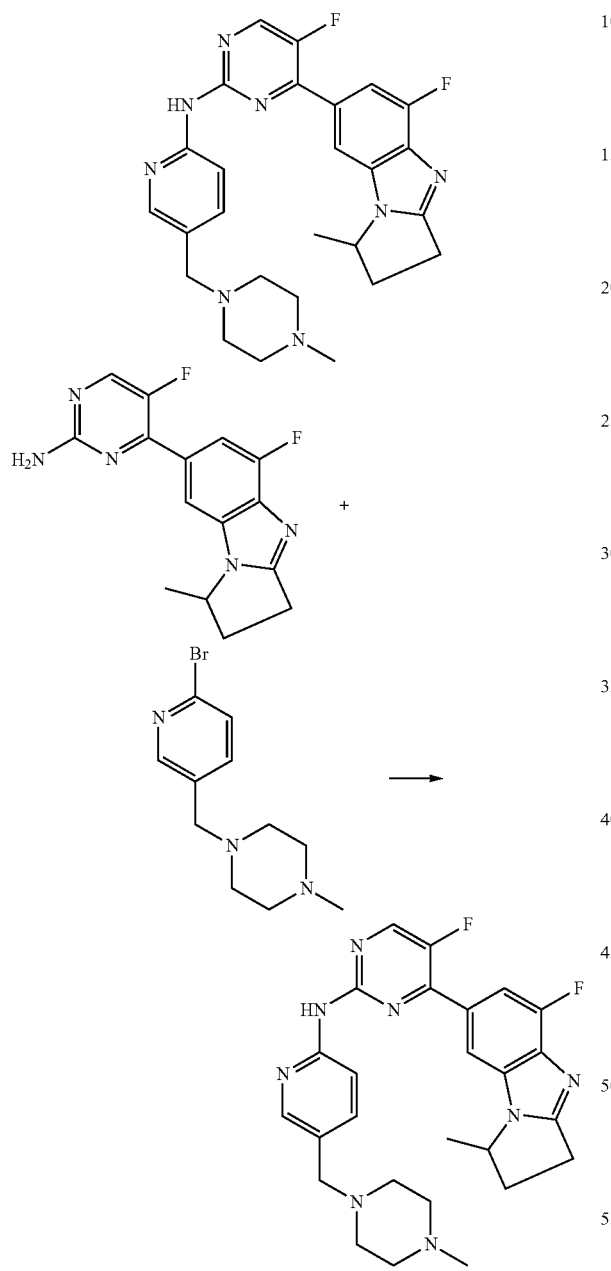

To a microwave reaction flask was added 5-fluoro-4-(5-fluoro-1-methyl-2,3-dihydro-1H-benzo[d]pyrrolo[1,2-a]imidazol-7-yl)pyrimidin-2-amine (100 mg, 0.33 mmol, prepared according to Step 1 of Example 58), 1-((6-bromopyridin-3-yl)methyl)-4-methylpiperazine (87.7 mg, 0.33 mmol), Cs2CO3 (214 mg, 0.66 mmol), Pd$_2$(dba)$_3$ (55 mg, 0.06 mmol), Xantphos (35 mg, 0.06 mmol) and anhydrous 1,4-dioxane (2 mL), and the mixture was reacted for 1 hour in a microwave at 150° C. The resulting mixture was cooled to room temperature, water was added (10 mL), and the aqueous phase was extracted with ethyl acetate (20 mL×3). The organic phases were combined, washed with saturated sodium chloride solution (20 mL×2), dried over anhydrous sodium sulfate, and filtered with suction. The filtrate was concentrated under reduced pressure, and the resulting residue was purified by column chromatography (DCM/MeOH=10:1) to give the title compound as a yellow solid (35 mg, yield 22%).

$^1$HNMR (DMSO, 400 MHz), δ 10.10 (s, 1H), 8.71-8.70 (m, 1H), 8.24-8.16 (m, 2H), 7.76-7.71 (m, 2H), 7.40-7.38 (m, 1H), 4.79 (q, J=4 Hz, 1H), 3.60-3.58 (m, 4H), 3.33-2.90 (m, 6H), 2.90-2.70 (m, 2H), 2.70-2.50 (m, 4H), 2.32-2.29 (m, 1H), 1.59-1.57 (m, 3H)

MS m/z (ESI): 491.2 (M+H)

Example 64

N-(5-((4-Ethylpiperazin-1-yl)methyl)-6-methylpyridin-2-yl)-5-fluoro-4-(5-fluoro-1-methyl-2,3-dihydro-1H-benzo[d]pyrrolo[1,2-a]imidazol-7-yl)pyrimidin-2-amine

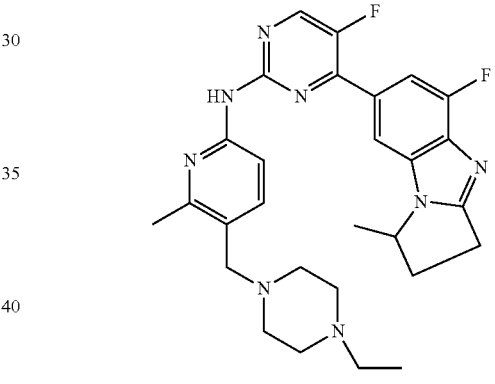

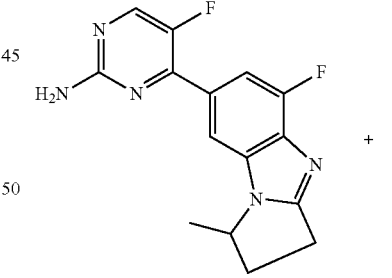

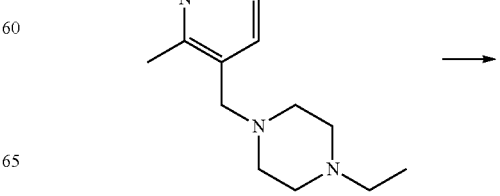

-continued

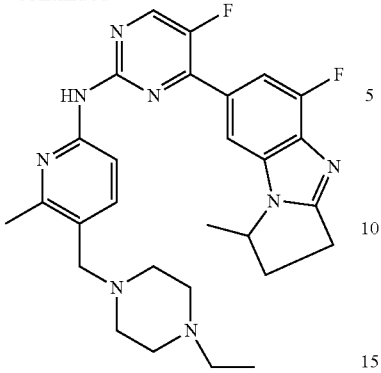

To a microwave reaction flask was added 5-fluoro-4-(5-fluoro-1-methyl-2,3-dihydro-1H-benzo[d]pyrrolo[1,2-a]imidazol-7-yl)pyrimidin-2-amine (200 mg, 0.66 mmol, prepared according to Step 1 of Example 58), 1-((6-bromo-2-methylpyridin-3-yl)methyl)-4-ethylpiperazine (198 mg, 0.66 mmol), Cs2CO3 (429 mg, 1.32 mmol), Pd$_2$(dba)$_3$ (118 mg, 0.13 mmol), Xantphos (75 mg, 0.13 mmol) and anhydrous 1,4-dioxane (4 mL), and the mixture was reacted for 1 hour in a microwave at 150° C. The resulting mixture was cooled to room temperature and water was added (10 mL). The aqueous phase was extracted with ethyl acetate (20 mL×3) and the phases were separated. The organic phases were combined, washed with saturated sodium chloride solution (20 mL×2), dried over anhydrous sodium sulfate, and filtered with suction. The filtrate was concentrated under reduced pressure, and the resulting residue was purified by column chromatography (DCM/MeOH=10:1) to give the title compound as a yellow solid (88 mg, yield 26%).

$^1$HNMR (DMSO, 400 MHz), δ 8.63 (s, 1H), 8.12-8.00 (m, 1H), 8.00-7.98 (m, 1H), 7.73-7.71 (m, 1H), 7.60-7.58 (m, 1H), 4.76 (q, J=6.5 Hz, 1H), 3.70 (s, 2H), 3.12-2.83 (m, 10H), 2.50 (s, 3H), 2.44-2.30 (m, 1H), 1.56-1.54 (m, 3H), 2.23-1.15 (m, 3H)

MS m/z (ESI): 519.2 (M+H)

Example 65

5-Fluoro-4-(5-fluoro-1-methyl-2,3-dihydro-1H-benzo[d]pyrrolo[1,2-a]imidazol-7-yl)-N-(5-((4-isopropylpiperazin-1-yl)methyl)pyridin-2-yl)pyrimidin-2-amine

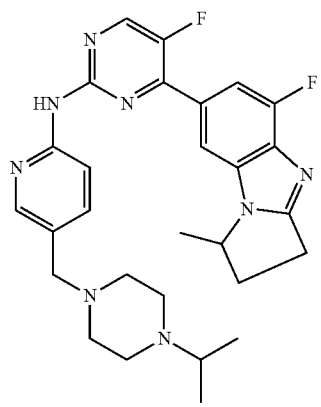

-continued

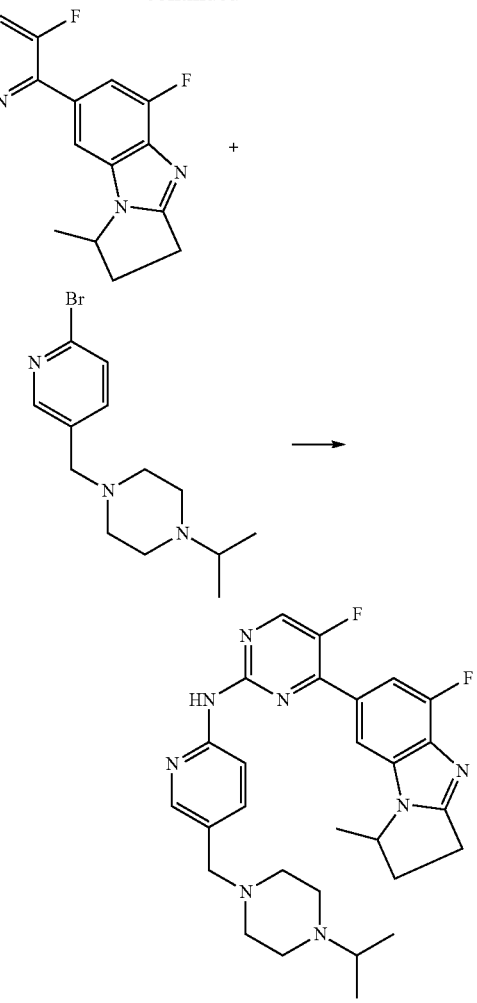

To a microwave reaction flask was added 5-fluoro-4-(5-fluoro-1-methyl-2,3-dihydro-1H-benzo[d]pyrrolo[1,2-a]imidazol-7-yl)pyrimidin-2-amine (150 mg, 0.5 mmol, prepared according to Step 1 of Example 58), 1-((6-bromopyridin-3-yl)methyl)-4-isopropylpiperazine (149 mg, 0.5 mmol), Cs$_2$CO$_3$ (325 mg, 1 mmol), Pd$_2$(dba)$_3$ (91 mg, 0.1 mmol), Xantphos (57 mg, 0.1 mmol) and anhydrous 1,4-dioxane (2 mL), and the mixture was reacted for 1 hour in a microwave at 150° C. The resulting mixture was cooled to room temperature, water was added (10 mL), and the aqueous phase was extracted with ethyl acetate (30 mL×3). The organic phases were combined, washed with saturated sodium chloride solution (20 mL×2), dried over anhydrous sodium sulfate, and filtered with suction. The filtrate was concentrated under reduced pressure, and the resulting residue was purified by column chromatography (DCM/MeOH=10:1) to give the title compound as a yellow solid (93 mg, yield 36%).

$^1$HNMR (DMSO, 400 MHz), δ 8.65 (s, 1H), 8.19-8.11 (m, 3H), 7.73-7.69 (m, 2H), 4.76 (q, J=6.6 Hz, 1H), 3.70-3.50 (m, 2H), 3.08-2.82 (m, 9H), 2.50-2.27 (m, 4H), 1.56-1.54 (m, 3H), 1.09-1.07 (m, 6H)

MS m/z (ESI): 519.3 (M+H)

Example 66

5-Fluoro-4-(5-fluoro-1-methyl-2,3-dihydro-1H-benzo[d]pyrrolo[1,2-a]imidazol-7-yl-N-(5-(1-methylpiperidine-4-yl)pyridin-2-yl)pyrimidin-2-amine

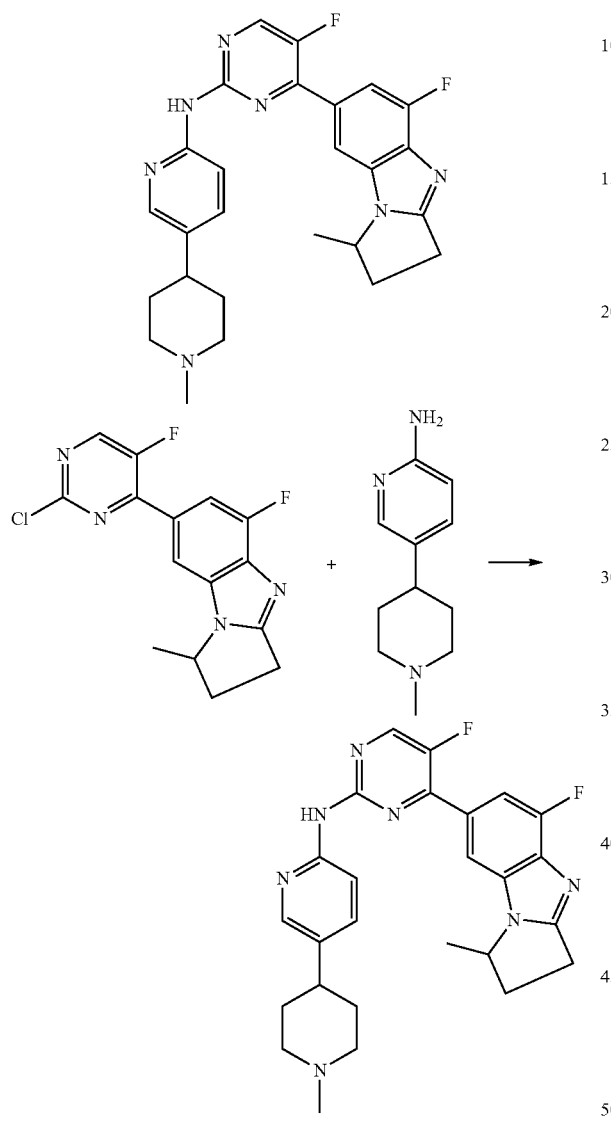

To a microwave reaction flask was added 7-(2-chloro-5-fluoropyrimidin-4-yl)-5-fluoro-1-methyl-2,3-dihydro-1H-benzo[d]pyrrolo[1,2-a]imidazole (200 mg, 0.63 mmol, prepared in Example 2), 5-(1-methylpiperidine-4-yl)pyridin-2-amine (120 mg, 0.63 mmol), Cs$_2$CO$_3$ (406 mg, 1.25 mmol), Pd$_2$(dba)$_3$ (119 mg, 0.13 mmol), Xantphos (75 mg, 0.13 mmol) and anhydrous 1,4-dioxane (2 mL), and the mixture was reacted for 1 hour in a microwave at 150° C. The resulting mixture was cooled to room temperature and water was added (10 mL). The aqueous phase was extracted with ethyl acetate (20 mL×3) and the phases were separated. The organic phases were combined, washed with saturated sodium chloride solution (20 mL×2), dried over anhydrous sodium sulfate, and filtered with suction. The filtrate was concentrated under reduced pressure, and the resulting residue was purified by column chromatography (DCM/MeOH=10:1) to give the title compound as a yellow solid (100 mg, yield 33%).

$^1$HNMR (DMSO, 400 MHz), δ 9.98 (s, 1H), 8.69-8.68 (m, 1H), 8.29-8.16 (m, 3H), 7.75-7.64 (m, 2H), 4.77 (q, J=4 Hz, 1H), 3.32-3.03 (m, 6H), 3.03-2.89 (m, 3H), 2.72-2.50 (m, 2H), 2.29-2.28 (m, 1H), 1.99-1.97 (m, 4H), 1.59-1.57 (m, 3H)

MS m/z (ESI): 476.3 (M+H)

Example 67

4-(1-Ethyl-5-fluoro-2,3-dihydro-1H-benzo[d]pyrrolo[1,2-a]imidazol-7-yl)-5-fluoro-N-(5-((4-methylpiperazin-1-yl)methyl)pyridin-2-yl)pyrimidin-2-amine

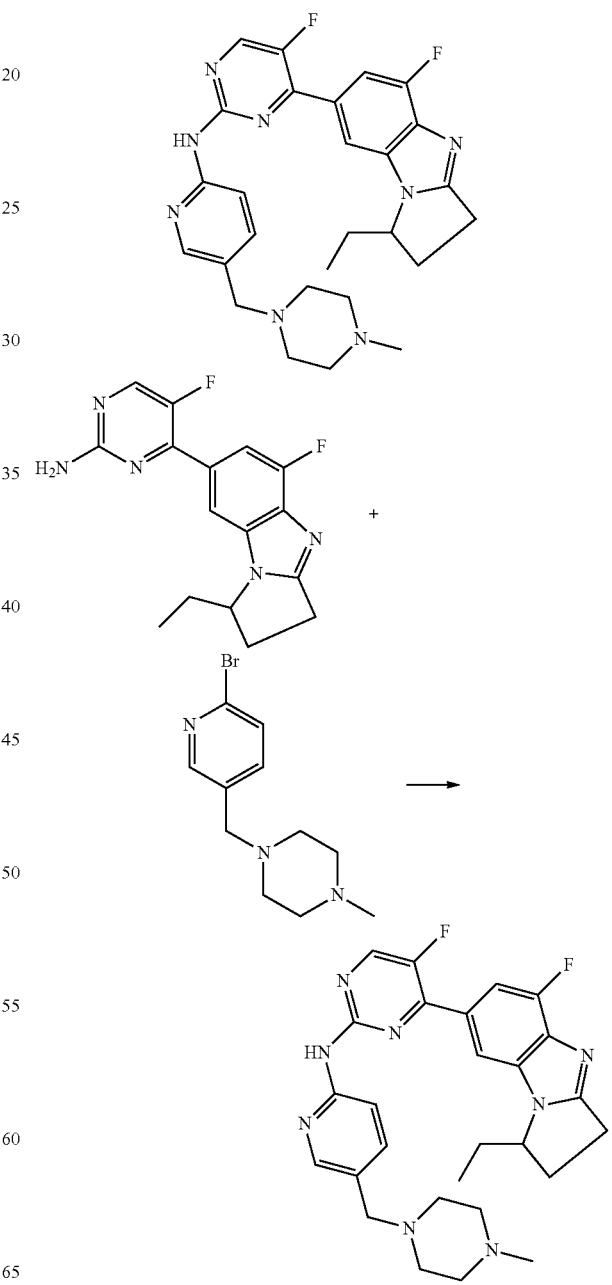

To a microwave reaction flask was added 5-fluoro-4-(5-fluoro-1-ethyl-2,3-dihydro-1H-benzo[d]pyrrolo[1,2-a]imidazol-7-yl)pyrimidin-2-amine (200 mg, 0.63 mmol), 1-((6-bromopyridin-3-yl)methyl)-4-methylpiperazine (171 mg, 0.63 mmol), Cs$_2$CO$_3$ (406 mg, 1.25 mmol), Pd$_2$(dba)$_3$ (119 mg, 0.13 mmol), Xantphos (75 mg, 0.13 mmol) and anhydrous 1,4-dioxane (2 mL), and the mixture was reacted for 1 hour in a microwave at 150° C. The resulting mixture was cooled to room temperature and water was added (10 mL). The aqueous phase was extracted with ethyl acetate (20 mL×3) and the phases were separated. The organic phases were combined and washed with saturated sodium chloride solution (20 mL×2), dried over anhydrous sodium sulfate, and filtered with suction. The filtrate was concentrated under reduced pressure, and the resulting residue was purified by thin layer chromatography (DCM/MeOH=10:1) to give the title compound as a yellow solid (80 mg, yield 25%).

$^1$HNMR (DMSO, 400 MHz), δ 10.06 (s, 1H), 8.70 (s, 1H), 8.23-8.21 (d, 2H), 8.15 (s, 1H), 7.77-7.71 (m, 2H), 4.70-4.68 (m, 1H), 3.56-3.33 (m, 4H), 3.15-2.97 (m, 6H), 2.86-2.81 (m, 2H), 2.97 (s, 4H), 2.43-2.39 (m, 1H), 1.87-1.83 (m, 1H), 0.95-0.91 (m, 3H)

MS m/z (ESI): 505.3 (M+H)

Example 68

4-(1-Ethyl-5-fluoro-2,3-dihydro-1H-benzo[d]pyrrolo[1,2-a]imidazole1-7-yl)-5-fluoro-N-(5-(1-methylpiperidine-4-yl)pyridin-2-yl)pyrimidin-2-amine

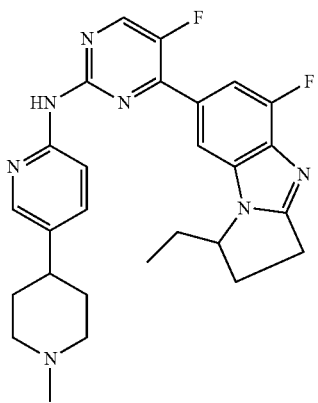

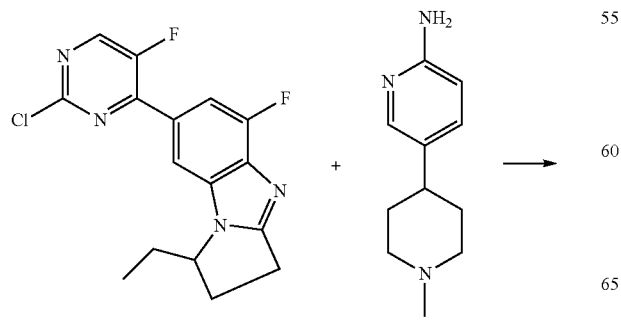

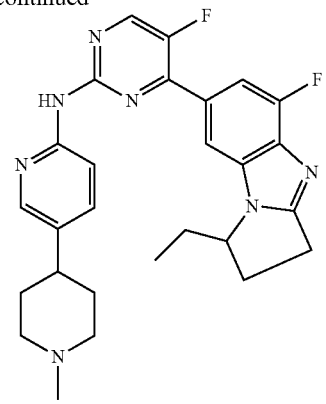

To a microwave reaction flask was added 7-(2-chloro-5-fluoropyrimidin-4-yl)-5-fluoro-1-ethyl-2,3-dihydro-1H-benzo[d]pyrrolo[1,2-a]imidazole (200 mg, 0.6 mmol, prepared according to Example 3), 5-(1-methylpiperidine-4-yl)pyridin-2-amine (114 mg, 0.6 mmol), Cs$_2$CO$_3$ (390 mg, 1.2 mmol), Pd$_2$(dba)$_3$ (110 mg, 0.12 mmol), Xantphos (69 mg, 0.12 mmol) and anhydrous 1,4-dioxane (2 mL), and the mixture was reacted for 1 hour in a microwave at 150° C. The resulting mixture was cooled to room temperature and water was added (10 mL). The aqueous phase was extracted with ethyl acetate (20 mL×3) and the phases were separated. The organic phases were combined, washed with saturated sodium chloride solution (20 mL×2), dried over anhydrous sodium sulfate, and filtered with suction. The filtrate was concentrated under reduced pressure, and the resulting residue was purified by column chromatography (DCM/MeOH=10:1) to give the title compound as a yellow solid (90 mg, yield 30%).

$^1$HNMR (DMSO, 400 MHz), δ 10.01 (s, 1H), 8.69 (s, 1H), 8.21-8.15 (m, 3H), 7.75-7.58 (m, 2H), 4.73-4.69 (m, 1H), 3.47-3.38 (m, 2H), 3.10-3.01 (m, 4H), 2.86-2.80 (m, 3H), 2.50-2.30 (d, 1H), 2.01-1.86 (d, 6H), 1.26-1.18 (m, 2H), 0.95-0.91 (m, 3H)

MS m/z (ESI): 490.2 (M+H)

Example 69

N-(5-(1-Ethylpiperidine-4-yl)pyridin-2-yl)-5-fluoro-4-(5-fluoro-1-methyl-2,3-dihydro-1H-benzo[d]pyrrolo[1,2-a]imidazol-7-yl)pyrimidin-2-amine

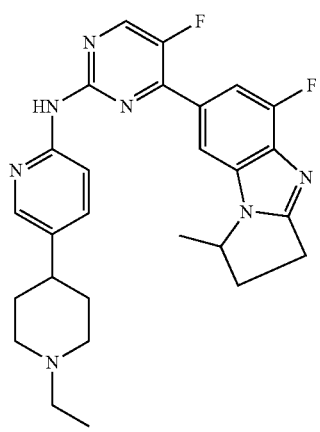

143
-continued

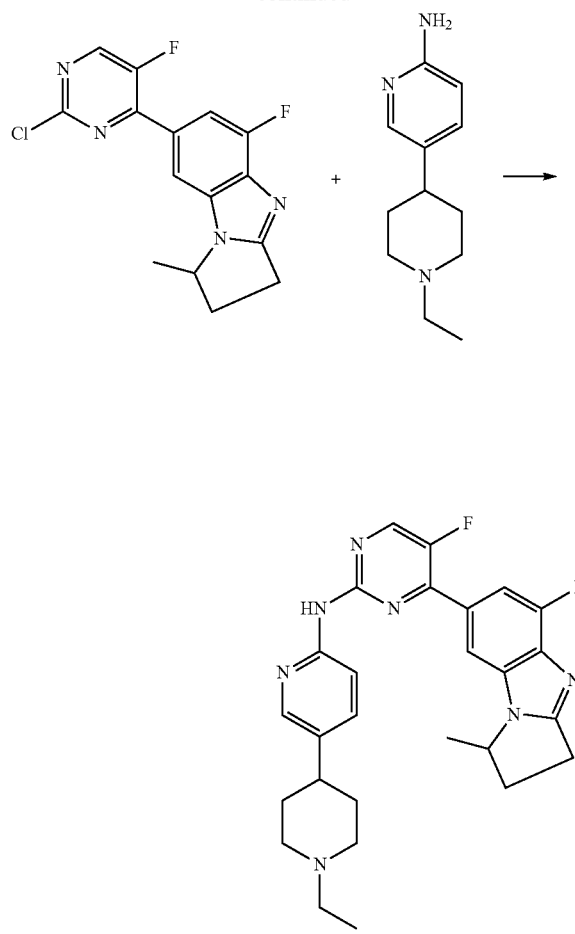

To a microwave reaction flask was added 7-(2-chloro-5-fluoropyrimidin-4-yl)-5-fluoro-1-methyl-2,3-dihydro-1H-benzo[d]pyrrolo[1,2-a]imidazole (50 mg, 0.16 mmol, prepared in Example 2), 5-(1-ethylpiperidine-4-yl)pyridin-2-amine (32 mg, 0.16 mmol), $Cs_2CO_3$ (104 mg, 0.32 mmol), $Pd_2(dba)_3$ (27 mg, 0.03 mmol), Xantphos (17 mg, 0.03 mmol) and anhydrous 1,4-dioxane (2 mL), and the mixture was reacted for 1 hour in a microwave at 150° C. The resulting mixture was cooled to room temperature, water was added (10 mL), and the aqueous phase was extracted with ethyl acetate (20 mL×3). The organic phases were combined, washed with saturated sodium chloride solution (20 mL×2), dried over anhydrous sodium sulfate, and filtered with suction. The filtrate was concentrated under reduced pressure, and the resulting residue was purified by column chromatography (DCM/MeOH=10:1) to give the title compound as a yellow solid (17 mg, yield 22%).

$^1$HNMR (DMSO, 400 MHz), δ 9.90 (s, 1H), 8.68-8.67 (m, 1H), 8.20-8.16 (m, 3H), 7.60-7.70 (m, 2H), 4.72-4.65 (s, 1H), 3.16-2.89 (m, 2H), 2.36-2.33 (m, 2H), 2.03-1.96 (m, 1H), 1.74 (s, 2H), 1.59-1.58 (m, 2H), 1.46-1.39 (m, 3H), 1.35-1.34 (m, 3H), 1.08-0.01 (m, 3H), 0.87-0.84 (m, 3H)

MS m/z (ESI): 490.2 (M+H)

144

Example 70

4-(1-Ethyl-5-fluoro-2,3-dihydro-1H-benzo[d]pyrrolo[1,2-a]imidazol-7-yl)-N-(5-((4-ethylpiperazin-1-yl)methyl)pyridin-2-yl)-5-fluoropyrimidin-2-amine

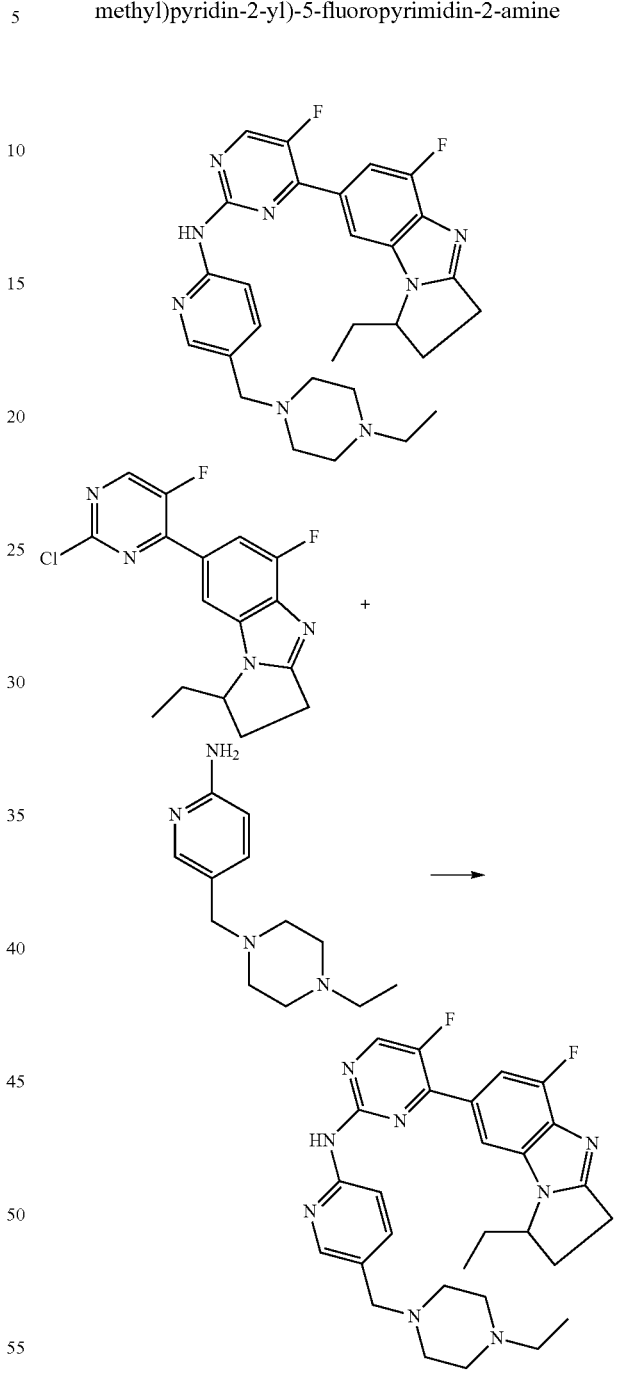

To a microwave reaction flask was added 7-(2-chloro-5-fluoropyrimidin-4-yl)-5-fluoro-1-ethyl-2,3-dihydro-1H-benzo[d]pyrrolo[1,2-a]imidazole (100 mg, 0.3 mmol, prepared in Example 3), 5-((4-ethylpiperazin-1-yl)methyl)pyridin-2-amine (66 mg, 0.3 mmol), $Cs_2CO_3$ (195 mg, 0.6 mmol), $Pd_2(dba)_3$ (55 mg, 0.06 mmol), Xantphos (35 mg, 0.06 mmol) and anhydrous 1,4-dioxane (2 mL), and the mixture was reacted for 1 hour in a microwave at 150° C. The resulting mixture was cooled to room temperature, water was added (10 mL), and the aqueous phase was extracted with ethyl acetate (20 mL×3). The organic phases were combined, washed with saturated sodium chloride solution (20 mL×2), dried over anhydrous sodium sulfate, and filtered with suction. The filtrate was concentrated under reduced pressure, and the resulting residue was purified by thin layer chromatography (DCM/MeOH=10:1) to give the title compound as a yellow solid (31 mg, yield 20%).

¹HNMR (DMSO, 400 MHz), δ 10.07 (s, 1H), 8.70 (s, 1H), 8.20-8.22 (m, 2H), 8.06 (s, 1H), 7.73-7.79 (m, 2H), 4.69 (q, J=4.8 Hz, 1H), 3.49-3.10 (m, 8H), 3.10-2.97 (m, 3H), 2.97-2.80 (m, 2H), 2.50-2.39 (m, 3H), 2.14-2.11 (m, 1H), 1.85-1.82 (m, 1H), 1.06-0.94 (m,H), 0.93-0.91 (m, 3H)

MS m/z (ESI): 519.3 (M+H)

Example 71

N-(5-(4-(Dimethylamino)piperidine-1-yl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine

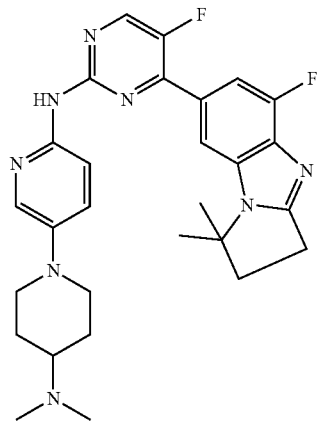

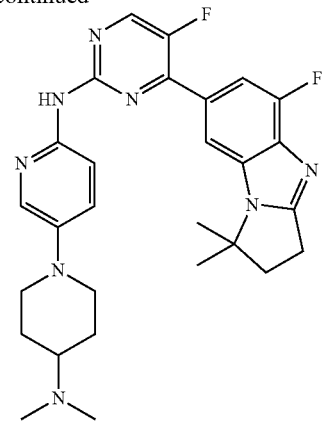

To a microwave reaction flask was added 7-(2-chloro-5-fluoropyrimidin-4-yl)-5-fluoro-1,1-dimethyl-2,3-dihydro-1H-benzo[d]pyrrolo[1,2-a]imidazole (100 mg, 0.3 mmol, prepared according to Example 1), 5-(4-(dimethylamino)-1-piperidinyl)pyridin-2-amine (66 mg, 0.3 mmol), Cs₂CO₃ (195 mg, 0.6 mmol), Pd₂(dba)₃ (55 mg, 0.06 mmol), Xantphos (35 mg, 0.06 mmol) and anhydrous 1,4-dioxane (2 mL), and the mixture was reacted for 1 hour in a microwave at 150° C. The resulting mixture was cooled to room temperature, water was added (10 mL), and the aqueous phase was extracted with ethyl acetate (20 mL×3). The organic phases were combined, washed with saturated sodium chloride solution (20 mL×2), dried over anhydrous sodium sulfate, and filtered with suction. The filtrate was concentrated under reduced pressure, and the resulting residue was purified by column chromatography (DCM/MeOH=10:1) to give the title compound as a yellow solid (30 mg, yield 20%).

¹HNMR (DMSO, 400 MHz), δ 9.84 (s, 1H), 8.64-8.63 (m, 1H), 8.17-8.11 (m, 1H), 8.06-8.04 (m, 2H), 7.70-7.67 (m, 1H), 7.46-7.43 (m, 1H), 3.78-3.75 (m, 2H), 3.36-3.08 (m, 4H), 2.69-2.57 (m, 8H), 2.55-2.54 (m, 2H), 2.07-1.90 (m, 2H), 1.74-1.66 (m, 7H)

MS m/z (ESI): 519.3 (M+H)

Example 72

4-(5-Fluoro-1-methyl-2,3-dihydro-1H-benzo[d]pyrrolo[1,2-a]imidazol-7-yl)-N-(5-(piperazin-1-yl)pyridin-2-yl)pyrimidin-2-amine

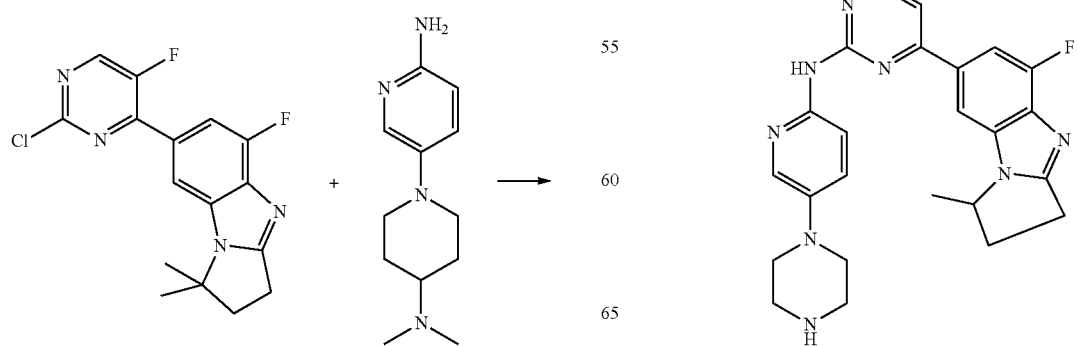

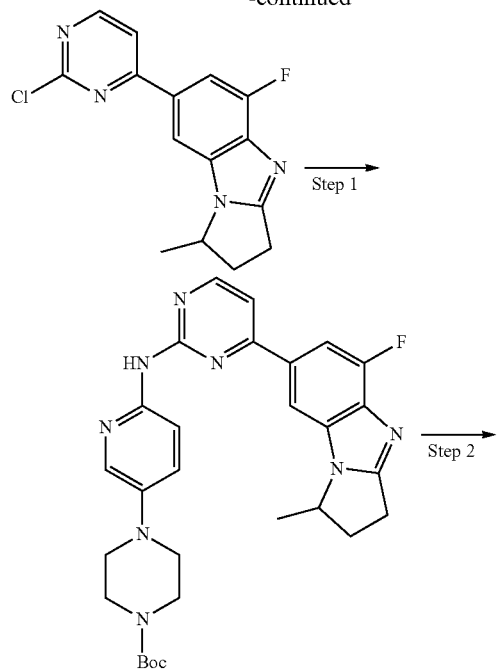

column chromatography (DCM/MeOH=10:1) to give the title compound as a yellow solid (30 mg, yield 16.5%).
MS m/z (ESI): 545.3 (M+H)

Step 2

4-(5-Fluoro-1-methyl-2,3-dihydro-1H-benzo[d]pyrrolo[1,2-a]imidazol-7-yl)-N-(5-(piperazin-1-yl)pyridin-2-yl)pyrimidin-2-amine To a reaction flask was added tert-butyl 4-(6-((4-(5-fluoro-1-methyl-2,3-dihydro-1H-benzo[d]pyrrolo[1,2-a]imidazol-7-yl)pyrimidin-2-yl)amino)pyridin-3-yl)piperazine-1-carboxylate (30 mg, 0.055 mmol, prepared in Step 1), TFA (0.5 mL) and dichloromethane (6 mL). The mixture was stirred at room temperature for 1 hour to give rise to a reaction, diluted with water (10 mL), and extracted with dichloromethane (10 mL×3). The organic layers were combined, washed with saturated sodium chloride (10 mL), and dried over anhydrous sodium sulfate. The filtrate was concentrated in vacuo, and the resulting residue was purified by thin layer chromatography (DCM/MeOH=10:1) to give the title compound as a yellow solid (15 mg, yield 63%).
$^1$HNMR (DMSO, 400 MHz), δ 10.77 (s, 1H), 8.90 (s, 2H), 8.64-8.31 (m, 2H), 8.04-8.03 (m, 1H), 7.94-7.79 (m, 4H), 4.77-4.72 (m, 1H), 3.38-3.30 (m, 8H), 3.13-2.81 (m, 3H), 2.29-2.26 (m, 1H), 1.61-1.60 (m, 3H)
MS m/z (ESI): 445.3 (M+H)

Example 73

N-(5-((4-Ethylpiperazin-1-yl)methyl)pyridin-2-yl)-4-(5-fluoro-1-methyl-2,3-dihydro-1H-benzo[d]pyrrolo[1,2-a]imidazol-7-yl)pyrimidin-2-amine

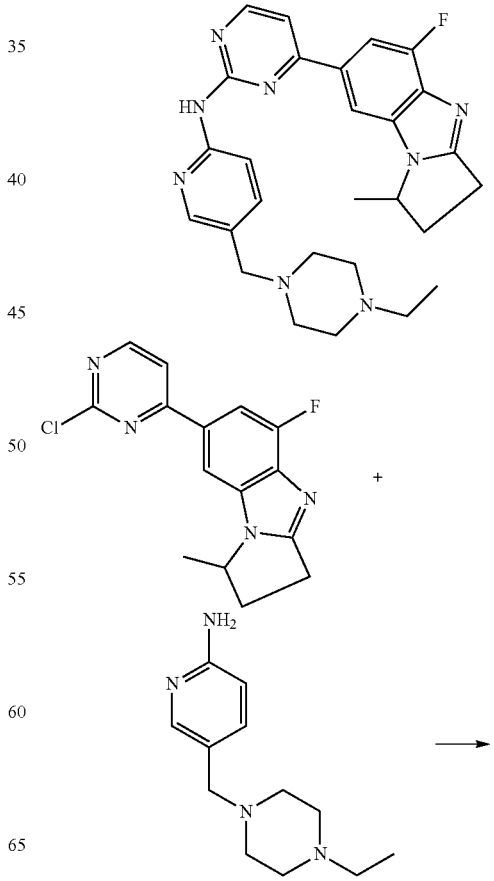

Step 1 tert-butyl 4-(6-((4-(5-fluoro-1-methyl-2,3-dihydro-1H-benzo[d]pyrrolo[1,2-a]imidazol-7-yl)pyrimidin-2-yl) amino)pyridin-3-yl)piperazine-1-carboxylate To a reaction flask was added 7-(2-chloro-pyrimidin-4-yl)-5-fluoro-1-methyl-2,3-dihydro-1H-benzo[d]pyrrolo[1,2-a]imidazole (100 mg, 0.33 mmol, prepared by a procedure similar to those described in Example 9), tert-butyl 4-(6-aminopyridin-3-yl)piperazine-1-carboxylate (92 mg, 0.33 mmol), cesium carbonate (215 mg, 0.66 mmol), Pd$_2$(dba)$_3$ (55 mg, 0.06 mmol), Xantphos (35 mg, 0.06 mmol) and anhydrous 1,4-dioxane (2 mL), and the mixture was reacted for 1 hour in a microwave at 150° C. The resulting mixture was cooled to room temperature and water was added (10 mL). The aqueous phase was extracted with ethyl acetate (20 mL×3) and the phases were separated. The organic phases were combined, washed with saturated sodium chloride solution (20 mL×2), dried over anhydrous sodium sulfate, and filtered with suction. The filtrate was concentrated under reduced pressure, and the resulting residue was purified by

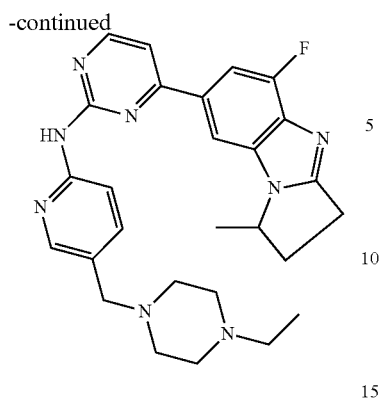

To a microwave reaction flask was added 7-(2-chloropyrimidin-4-yl)-5-fluoro-1-methyl-2,3-dihydro-1H-benzo[d]pyrrolo[1,2-a]imidazole (100 mg, 0.33 mmol, prepared by a procedure similar to those described in Example 9), 5-((4-ethylpiperazin-1-yl)methyl)pyridin-2-amine (73 mg, 0.33 mmol), $Cs_2CO_3$ (195 mg, 0.66 mmol), $Pd_2(dba)_3$ (55 mg, 0.06 mmol), Xantphos (35 mg, 0.06 mmol) and anhydrous 1,4-dioxane (2 mL), and the mixture was reacted for 1 hour in a microwave at 150° C. The resulting mixture was cooled to room temperature and water was added (10 mL). The aqueous phase was extracted with ethyl acetate (20 mL×3) and the phases were separated. The organic phases were combined, washed with saturated sodium chloride solution (20 mL×2), dried over anhydrous sodium sulfate, and filtered with suction. The filtrate was concentrated under reduced pressure, and the resulting residue was purified by column chromatography (DCM/MeOH=10:1) to give the title compound as a yellow solid (62 mg, yield 39%).

$^1$HNMR (DMSO, 400 MHz), δ 10.03 (s, 1H), 8.60 (s, 1H), 8.62-8.40 (m, 2H), 8.40-8.32 (m, 1H), 7.91-7.88 (m, 1H), 7.76-7.68 (m, 2H), 4.77-4.71 (m, 1H), 3.56-3.44 (m, 2H), 3.41-3.35 (m, 8H), 3.09-2.89 (m, 3H), 2.50-2.30 (m, 2H), 2.29-2.28 (m, 1H), 1.62-1.61 (m, 3H), 1.23-1.16 (m, 3H)

MS m/z (ESI): 487.3 (M+H)

Example 74

N-(5-(3,5-Dimethylpiperazin-1-yl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine

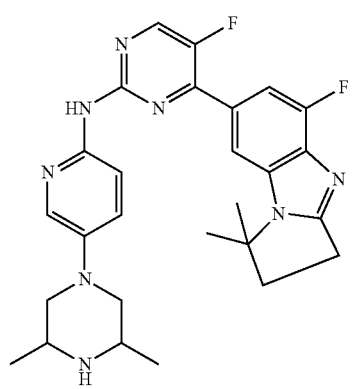 [SMILES: CC1CN(c2ccc(Nc3ncc(F)c(-c4cc(F)c5nc6n(c5c4)C(C)(C)CC6)n3)nc2)CC(C)N1]

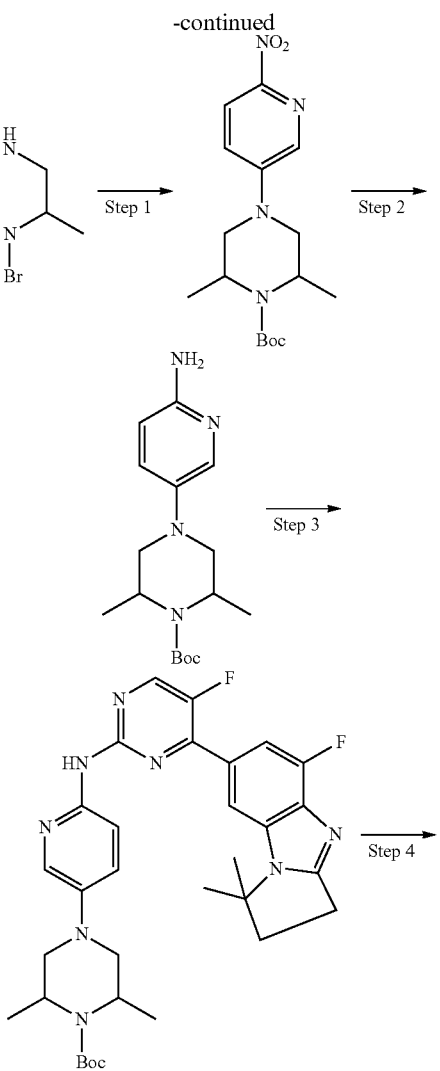

Step 1 tert-Butyl 2,6-dimethyl-4-(6-nitropyridin-3-yl)piperazine-1-carboxylate

To a reaction flask was added 5-bromo-2-nitropyridine (2.0 g, 9.33 mmol), tert-butyl 2,6-dimethylpiperazine-1-carboxylate (3.0 g, 14 mmol), potassium carbonate (2.0 g, 14 mmol), TBAI (0.22 g, 0.6 mmol) and dimethyl sulfoxide (20 mL), and the mixture was stirred at 80° C. for 16 hours to give rise to a reaction. The reaction liquid was cooled to room temperature, poured into ice-water, and extracted with dichloromethane (50 mL×3). The organic phases were combined, washed with saturated sodium chloride solution (20 mL), dried over anhydrous sodium sulfate, and filtered with suction. The filtrate was concentrated under reduced pressure, and the resulting residue was purified by column chromatography (DCM/MeOH=20:1), to give the title compound as a white solid (1.7 g, yield 54%).

MS m/z (ESI): 337.1 (M+H)

Step 2 tert-Butyl 4-(6-aminopyridin-3-yl)-2,6-dimethylpiperazine-1-carboxylate

To a reaction flask was added tert-butyl 2,6-dimethyl-4-(6-nitropyridin-3-yl)piperazine-1-carboxylate (1.0 g, 3.0 mmol, prepared in Step 1), palladium on carbon (10%, 0.1 g) and ethyl acetate/methanol (10 mL/10 mL), and the mixture was stirred at room temperature for 2 hours under a hydrogen atmosphere to give rise to a reaction. The resulting mixture was filtered, and the filtrate was concentrated to give the title compound as a white solid (872 mg, yield 95%).

MS m/z (ESI): 307.2 (M+H)

Step 3 tert-Butyl 4-(6-((5-fluoro-4-(5-fluoro-1,1-dimethyl-2,3-dihydro-1H-benzo[d]pyrrolo[1,2-a]imidazol-7-yl)pyrimidin-2-yl)amino)pyridin-3-yl)-2,6-dimethyl-piperazine-1-carboxylate To a reaction flask was added 7-(2-chloro-5-fluoropyrimidin-4-yl)-5-fluoro-1,1-dimethyl-2,3-dihydro-1H-benzo[d]pyrrolo[1,2-a]imidazole (200 mg, 0.6 mmol, prepared according to Example 1), tert-butyl 4-(6-aminopyridin-3-yl)-2,6-dimethylpiperazine-1-carboxylate (183 mg, 0.6 mmol, prepared in Step 2), cesium carbonate (390 mg, 1.2 mmol), $Pd_2(dba)_3$ (110 mg, 0.12 mmol), Xantphos (69 mg, 0.12 mmol) and anhydrous 1,4-dioxane (2 mL), and the mixture was reacted for 1 hour in a microwave at 150° C. The resulting mixture was cooled to room temperature and water was added (10 mL). The aqueous phase was extracted with ethyl acetate (40 mL×3) and the phases were separated. The organic phases were combined, washed with saturated sodium chloride solution (20 mL×2), dried over anhydrous sodium sulfate, and filtered with suction. The filtrate was concentrated under reduced pressure, and the resulting residue was purified by column chromatography (DCM/MeOH=10:1) to give the title compound as a yellow solid (50 mg, yield 13%).

MS m/z (ESI): 605.2 (M+H)

Step 4

N-(5-(3,5-Dimethylpiperazin-1-yl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine To a reaction flask was added tert-butyl 4-(6-((5-fluoro-4-(5-fluoro-1,1-dimethyl-2,3-dihydro-1H-benzo[d]pyrrolo[1,2-a]imidazol-7-yl)pyrimidin-2-yl)amino)pyridin-3-yl)-2,6-dimethylpiperazine-1-carboxylate (50 mg, 0.1 mmol, prepared in Step 3), TFA (0.5 mL) and dichloromethane (6 mL). The mixture was stirred at room temperature for 1 hour to give rise to a reaction, diluted with water (10 mL), and extracted with dichloromethane (10 mL×3). The organic layers were combined, washed with saturated sodium chloride (10 mL×2), and dried over anhydrous sodium sulfate. The filtrate was concentrated in vacuo, and the resulting residue was purified by column chromatography (DCM/MeOH=10:1) to give the title compound as a yellow solid (20 mg, yield 50%).

$^1$HNMR (DMSO, 400 MHz), δ 9.76 (s, 1H), 8.63 (s, 1H), 8.18 (s, 1H), 8.04-8.02 (d, 2H), 7.71-7.68 (d, 1H), 7.40-7.37 (m, 1H), 5.76 (s, 1H), 3.49-3.48 (d, 2H), 3.12-3.08 (m, 2H), 2.89-2.84 (m, 2H), 2.58-2.50 (m, 2H), 2.14-2.09 (m, 3H), 1.66 (s, 6H), 1.03-1.01 (m, 6H)

MS m/z (ESI): 505.3 (M+H)

The control used in the following experimental example, No. LY2835219, prepared according to the preparation method of PCT application publication No. WO 2010075074, has a formula as shown in the Formula 3 in the "Background Art" section.

Experimental Example 1. CDKs Inhibition Assay of the Compounds of the Present Invention In vitro inhibition of CDK (CDK1, CDK4, CDK6) activity by compounds of the present invention was tested by the following method.

Instrument and Kit Used in the Experimental Example

| Name | Model | Manufacturer |
| --- | --- | --- |
| Shaker | MTS2/4 | IKA |
| Microplate reader | M1000pro | TECAN |
| Centrifuge | Avanti J-26XP | Beckman Coulter |
| ADP-Glo ™ Kinase Assay + CDK1/CyclinA2 Kinase Enzyme System | V9211 | Promega |
| ADP-Glo ™ Kinase Assay + CDK4/CyclinE1 Kinase Enzyme System | V4489 | Promega |
| ADP-Glo ™ Kinase Assay + CDK6/CyclinD3 Kinase Enzyme System | V4511 | Promega |
| 5× Reaction Buffer A | V307A-C | Promega |

Experimental Preparation:

1. Preparation of kinase reaction buffer I: 5× Reaction Buffer A (Promega; V307A-C) provided in the kit was diluted with a mixture of Milli Q $H_2O$ and 0.1M DTT (dithiothreitol) to 4× kinase buffer; then Milli Q $H_2O$ was added in a proper proportion, to finally formulate into 1× kinase buffer.

Preparation of kinase reaction buffer II: 0.5% DMSO (dimethyl sulfoxide) was added into 1× kinase reaction buffer and uniformly mixed to obtain the title buffer.

2. Preparation of kinase solution: 100 ng/μl kinase stock solution was formulated with 1× kinase reaction buffer into kinase solution with the desired concentration for each reaction system.

3. Preparation of solution of test compound and LY2835219 as a control:

(1) Preparation of Solution of LY2835219 as a Control a. 1 μl of 10 mM standard stock solution was added respectively into 9 μl of kinase reaction buffer I and uniformly mixed; then 90 μl of kinase reaction buffer I was added and uniformly mixed; and then 100 μl of kinase reaction buffer I was added and uniformly mixed, to achieve a final concentration of 50 μM.

b. 40 μl of kinase reaction buffer II was added into Well B2-B10 of a 96-well plate; and 50 μl of above-mentioned solution was added into Well B1;

c. 10 µl of solution was taken from Well B1, added into Well B2 and uniformly mixed, then 10 µl of dilution was taken from Well B2 and added into Well B3, the serial dilution was continued up to B9, to obtain 5-fold serial dilutions of the reference solution.

(2) Preparation of Test Compound:

a. Test compounds at a certain concentration were taken respectively, and diluted with kinase reaction buffer I to compound solutions with a final concentration of 50 µM;

b. 40 µl of kinase reaction buffer II was added into Well H2-H10 of a 96-well plate; and 50 µl of above-mentioned solution was added into Well H1;

c. 10 µl of solution was taken from Well H1, added into Well H2 and uniformly mixed, then 10 µl of dilution was taken from Well H2 and added into Well H3, the serial dilution was continued up to H9, to obtain 5-fold serial dilutions of the test compound solution.

4. Preparation of reaction substrate and ATP mixed solution:

a. Preparation of ATP solution:

200 µl of 0.1 mM ATP solution: 2 µl of 10 mM ATP was added into 198 µl kinase reaction buffer I;

300 µl of 50 µl M ATP solution: 150 µl kinase reaction buffer I was added into 150 µl of above-mentioned 0.1 mM ATP solution;

b. Preparation of 300 µl reaction substrate solution:

150 µl of 1 µg/µl reaction substrate stock solution was added into 150 µl kinase reaction buffer I and uniformly mixed;

c. Above-mentioned a/b solutions were mixed to obtain mixed solutions respectively.

Experimental Procedure:

2 µl compound solution at each concentration was added into a 384-well plate respectively, and centrifuged for 3 min;

4 µl kinase solution was added into each well, centrifuged at 5000 rpm for 10 min at 18° C., and shaked well for 10 min on a shaker;

4 µl substrate and ATP mixed solution were added into each well, centrifuged at 5000 rpm for 10 min at 18° C., and shaked well for 90 min on a shaker at 37° C.;

The 384 well plate was removed and allow to achieve room temperature;

10 µl ADP-Glo reagent was added into each well, centrifuged at 5000 rpm for 10 min at 18° C., and shaked well for 40 min on a shaker at 25° C. to terminate the reaction;

20 µl kinase assay reagent was added into each well, centrifuged at 5000 rpm for 10 min at 18° C., and shaked well for 30 min on a shaker at 25° C.;

Fluorescence values were read by M1000pro microplate reader.

Data Processing:

The inhibition rate of each compound at each concentration point was calculated according to the following equation, and $IC_{50}$ value was calculated by curve fitting using GraphPad Prism 5 software.

Inhibition rate at each concentration point (inh %) =

$$\frac{\text{Fluorescence value at zero concentration point} - \text{Fluorescence value at each concentration point}}{\text{Fluorescence value at zero concentration point}} \times 100\%$$

Assay results: The inhibitory effects of LY2835219 disclosed in WO2010075074 and compounds of Example 12-74 on CDK4 and CDK6 are measured in $IC_{50}$ and the detailed results are shown in Table 1 below. The inhibitory effects of LY2835219 and the representative compounds of the present invention on CDK1 and CDK selectivity are shown in Table 2.

TABLE 1

Assay results of inhibitory activity on CDK ($IC_{50}$: nM)

| Example | $IC_{50}$ CDK4/D3 | $IC_{50}$ CDK6/D3 |
|---|---|---|
| LY2835219 | 1.7 | 7.8 |
| 12 | 18 | 244.1 |
| 13 | 18 | 62.7 |
| 14 | 6.8 | 45.6 |
| 15 | 28 | 68.6 |
| 16 | 147.3 | 247.8 |
| 17 | 235.6 | 1.9 |
| 18 | 7.4 | 0.9 |
| 19 | 4 | 0.4 |
| 20 | 0.8 | 4 |
| 21 | — | 17.6 |
| 22 | 1 | 17.4 |
| 23 | — | 90 |
| 24 | 1.7 | 15.8 |
| 25 | 0.6 | 2.8 |
| 26 | 3 | 82 |
| 27 | 0.6 | 3.7 |
| 28 | 2.8 | 1.4 |
| 29 | 89 | 18.7 |
| 30 | 1.2 | 12.2 |
| 31 | 2 | 55 |
| 32 | 49 | 13 |
| 33 | 3.2 | 7.6 |
| 34 | 3.9 | 3.8 |
| 35 | 6.9 | 5.3 |
| 36 | 5.7 | 11.2 |
| 37 | 16 | 46 |
| 38 | 25 | 271 |
| 39 | 0.2 | 0.2 |
| 40 | 0.6 | 0.2 |
| 41 | 28.5 | 57.8 |
| 42 | 0.3 | 0.9 |
| 43 | 13 | 0.3 |
| 44 | 14.5 | 16 |
| 45 | 7 | 21.7 |
| 46 | 1.7 | 8.6 |
| 47 | 2.4 | 3 |
| 48 | 9.7 | 19 |
| 49 | 15.8 | 392 |
| 50 | 17.6 | 368 |
| 51 | 49.7 | 339 |
| 52 | 60.7 | 143.6 |
| 53 | 1.8 | 3.6 |
| 54 | 19 | 9.6 |
| 55 | 4 | 18.7 |
| 56 | 20 | 36 |
| 57 | 0.2 | 4 |
| 58 | 28 | 47.3 |
| 59 | 9 | 20 |
| 60 | 27 | 28 |
| 61 | 3.9 | 80 |
| 62 | 1.7 | 34 |
| 63 | 5.7 | 275 |
| 64 | 39 | 178 |
| 65 | 0.6 | 12.7 |
| 66 | 4.3 | 21.4 |
| 67 | — | 2.4 |
| 68 | 9 | 6 |
| 69 | 40 | 24.4 |
| 70 | 14 | 22 |
| 71 | 1 | 14 |
| 72 | 15.8 | 9.9 |
| 73 | 17.6 | 752 |
| 74 | 0.28 | 0.6 |

TABLE 2

Inhibitory activity on CDK1 and CDKs selectivity of the representative compounds of the present invention

| Example | $IC_{50}$ (nM) CDK1/A2 | Ratio $IC_{50}$ (CDK4)/ $IC_{50}$ (CDK1) | Ratio $IC_{50}$ (CDK6)/ $IC_{50}$ (CDK1) |
|---|---|---|---|
| LY2835219 | 56 | 0.030 | 0.139 |
| 17 | 1301 | 0.181 | 0.001 |
| 18 | 2670 | 0.003 | 0.0003 |
| 19 | 86.6 | 0.046 | 0.005 |
| 20 | 353.9 | 0.002 | 0.011 |
| 24 | 610 | 0.003 | 0.026 |
| 25 | 109 | 0.006 | 0.026 |
| 27 | 1365 | 0.0004 | 0.003 |
| 28 | 64 | 0.044 | 0.022 |
| 30 | 744.4 | 0.002 | 0.016 |
| 31 | 351 | 0.006 | 0.157 |
| 35 | 376 | 0.018 | 0.014 |
| 36 | 1610 | 0.004 | 0.007 |
| 37 | 1914 | 0.008 | 0.024 |
| 39 | 241 | 0.001 | 0.001 |
| 40 | 275 | 0.002 | 0.001 |
| 41 | 1729 | 0.016 | 0.033 |
| 42 | 959 | 0.0003 | 0.001 |
| 43 | 732 | 0.018 | 0.0004 |
| 46 | 509.8 | 0.003 | 0.017 |
| 47 | 744.6 | 0.003 | 0.004 |
| 53 | 1397 | 0.001 | 0.003 |
| 55 | 6241 | 0.001 | 0.003 |
| 57 | 481.1 | 0.0004 | 0.008 |
| 59 | 1040 | 0.009 | 0.019 |
| 60 | 2189 | 0.012 | 0.013 |
| 65 | 3072 | 0.0002 | 0.004 |
| 72 | 693.3 | 0.023 | 0.014 |
| 74 | 94.8 | 0.003 | 0.006 |

Assay results: As can be seen from Table 1, the compounds of the present invention showed comparable inhibitory activity on CDK4 and CDK6 kinases as the control compound, and showed sufficient inhibitory activity.

$IC_{50}$ (CDK4)/$IC_{50}$ (CDK1) and $IC_{50}$ (CDK6)/$IC_{50}$ (CDK1) may reflect the compound's selectivity for CDKs: the smaller the value, the better the selectivity for CDK4/6, indicating the toxicity of the compound regarding pan CDKs inhibition may be smaller. For the control compound (LY2835219), $IC_{50}$ (CDK4)/$IC_{50}$ (CDK1)≈0.03, $IC_{50}$ (CDK6)/$IC_{50}$ (CDK1)≈0.139. All of the representative compounds of the present invention listed in Table 2 showed better selectivity for CDK4/6 than the control compound.

Experimental Example 2 Proliferation Inhibition Assay of the Compounds of the Present Invention on Human Breast Cancer Cell Line MDB-MA-231

Experimental materials: human breast cancer cell line MDA-MB-231 was purchased from Cell Resource Center (IBMS, CAMS/PUMC, Beijing, China), DAPI (5 mg/mL, Beyotime Biotechnology, c1002), 4% paraformaldehyde (Beijing dingguo changsheng biotech CO. LTD., AR-0211), 96-well plate with black transparent bottom (PE, 6005182), In Cell Analyzer 2200 (GE Healthcare)

Experimental Preparation:

1. Preparation of medium for human breast cancer cell line MDA-MB-231: RPIM1640+10% FBS+1% penicillin/streptomycin 2. Preparation of test compounds and standard LY2835219 solution:

(1) Preparation of standard LY2835219 and PD0332992 solution a. 3.6 µl of 10 mM standard stock solution was added respectively into 6.4 ul of medium and uniformly mixed; then 90 µl of medium was added and uniformly mixed; and then 200 µl of medium was added and uniformly mixed, to achieve a initial concentration of 20 µM.

b. 200 µl of medium containing 0.2% DMSO (dimethyl sulfoxide) was added into Well B2-B10 of a 96-well plate; 300 µl of above-mentioned solution was added into Well B1;

c. 100 µl of solution was taken from Well B1, added into Well B2 and uniformly mixed, then 100 µl of dilution was taken from Well B2 and added into Well B3, the serial dilution was continued up to B9, to obtain 3-fold serial dilutions of the standard solution.

(2) Preparation of test compound solution:

a. Test compound solutions at a certain concentration were taken respectively, and diluted with medium to compound solutions with a final concentration of 20 µM;

b. 200 µl of medium containing 0.2% DMSO (dimethyl sulfoxide) was added into Well H2-H10 of a 96-well plate; and 300 µl of above-mentioned solution was added into Well H1;

c. 100 µl of solution was taken from Well H1, added into Well H2 and uniformly mixed, then 100 µl of dilution was taken from Well H2 and added into Well H3, the serial dilution was continued up to H9, to obtain 3-fold serial dilutions of the test compound solution.

Experimental Procedure:

1. MDA-MB-231 cells were seeded at 4000 cells/100 ul/well to a 96-well plate with black transparent bottom, and cultured overnight at 37° C.;

2. The above-mentioned samples were added at 100 µl/well into culture plate seeded with cells, the plate was flicked to uniformly mix, and incubated for 72 h at 37° C.;

3. Fixation: the cell plate was taken, medium was removed, and 50 µl of 4% paraformaldehyde was added to each well and fixed 10 min;

4. 50 µl 0.1 M glycine was added to neutralize for 10 min;

5. The cells were washed twice with 1×PBS (phosphate buffer PH7.2);

6. Permeabilization: 50 ul of 0.2% TritonX-100 was added to each well and permeabilized at room temperature for 10 min;

7. The cells were washed twice with 1×PBS (phosphate buffer PH7.2);

8. 5 mg/mL DAPI stock solution was diluted at 1:5000 (final concentration 1 µg/ml) and the cells were stained at room temperature for 20 min.

9. The cells were washed three times with 1×PBS (phosphate buffer PH7.2);

10. The plate was scanned and analyzed on In cell analyser.

Data Processing:

1. The inhibition rate of each compound at each concentration point was calculated according to the following equation, and $IC_{50}$ value was calculated by curve fitting using GraphPad Prism 5 software.

Inhibition rate at each concentration point $(inh\ \%)$ =

$$\frac{\text{Fluorescence value at zero concentration point} - \text{Fluorescence value at each concentration point}}{\text{Fluorescence value at zero concentration point}} \times 100\%$$

Assay results: The cell viability of LY2835219 disclosed in WO2010075074 and compounds of Example 12-74 are measured in IC50 and the detailed results are shown in Table 3.

TABLE 3

$IC_{50}$ for inhibition of proliferation of human breast cancer cell line MDB-MA-231 by the compounds of the present invention (nM)

| Example | $IC_{50}$ |
|---|---|
| LY2835219 | 191 |
| 12 | 20276 |
| 13 | 1166 |
| 14 | 8882 |
| 15 | 1230 |
| 16 | 6620 |
| 17 | 555 |
| 18 | 402 |
| 19 | 74 |
| 20 | 217 |
| 21 | 92 |
| 22 | 483 |
| 23 | 543 |
| 24 | 251 |
| 25 | 145 |
| 26 | 214 |
| 27 | 768 |
| 28 | 100 |
| 29 | 2126 |
| 30 | 300 |
| 31 | 129 |
| 32 | 579 |
| 33 | 20 |
| 34 | 35 |
| 35 | 52 |
| 36 | 967 |
| 37 | 3303 |
| 38 | 2205 |
| 39 | 17 |
| 40 | 63 |
| 41 | 549 |
| 42 | 46 |
| 43 | 58 |
| 44 | 21 |
| 45 | 30 |
| 48 | 39 |
| 49 | 5879 |
| 50 | 3653 |
| 52 | 1678 |
| 53 | 600 |
| 54 | 252 |
| 55 | 377 |
| 57 | 39 |
| 58 | 458 |
| 59 | 1313 |
| 60 | 2108 |
| 61 | 1532 |
| 62 | 1320 |
| 63 | 3339 |
| 64 | 2682 |
| 65 | 1159 |
| 70 | 2527 |
| 71 | 46 |
| 72 | 817 |
| 73 | 3617 |
| 74 | 174 |

Assay conclusion: Most of the compounds of the present invention exhibit comparable or even stronger inhibitory activity against the proliferation of human breast cancer cell line MDB-MA-231 compared to the control compound.

Experimental Example 3 Pharmacokinetic Study of Compounds of Example 18, 20 and 24 in Rats 1. Experimental Summary SD rats were used as test animals, and drug concentration in plasma at different time points was determined by LC/MS/MS method after the rats were intragastrically administered the preferred compounds, to investigate the pharmacokinetics of the compounds of the present invention in rats and to evaluate their pharmacokinetic characteristics.

2. Experimental Protocol 2.1 Test Drugs:

Compounds prepared according to Example 18, 20 and 24 of the present invention;

Control drug LY2835219, self-made.

2.2 Test Animals:

6 to 8-week-old healthy adult male SD rats, weighing between 200-250 g (3 rats for each test compound), were purchased from JOINN Laboratories CO., LTD. (Suzhou), Animal Breeder License No.: SCXK(Su) 2013-0003

2.3 Preparation of Test Compounds

An appropriate amount of sample was weighed, then 0.1% hydroxyethyl cellulose/0.5% Tween 80 were added to final volume to obtain a solution of 1 mg/ml.

2.4 Test Drug Administration

Male SD rats, 3 for each test compound, were intragastrically administered test drugs at a dose of 5 mg/kg and a drug volume of 5 ml/kg after an overnight fast.

3. Experimental Operation

The carotid artery of the animal was catheterized and blood sample was removed prior to dosing and at 0.25, 0.5, 1, 2, 4, 8, 12 and 24 hours after dosing. Whole blood was anticoagulated with EDTA-K2, centrifuged to remove the supernatant, and cryopreserved at −20° C. until being analyzed. Plasma samples, which were pretreated using a protein precipitation method, were analyzed by LC-MS/MS, with a linear range of 1-2000 ng/ml and a minimum limit of quantitation of 1 ng/ml.

4. Pharmacokinetic Data Results

The pharmacokinetic parameters of the compounds of the invention are shown in Table 4

TABLE 4

Pharmacokinetic parameters of the compounds of the invention in rats

Pharmacokinetic study (5 mg/kg)

| Example No. | Plasma concentration Cmax (ng/mL) | Area under the curve AUC (ng/Ml*h) | Half-life T½ (h) | Retention time MRT (h) | Clearance CL/F (ml/min/kg) | Apparent volume of distribution Vz/F (ml/kg) |
|---|---|---|---|---|---|---|
| LY2835219 | 312 ± 33 | 3275 ± 731 | 4.07 ± 2.31 | 7.97 ± 1.17 | 24.2 | 8533 |
| 18 | 343 ± 67 | 3746 ± 697 | 4.62 ± 0.2 | 7.58 ± 0.15 | 21.9 ± 3.67 | 8751 ± 1657 |
| 20 | 463 ± 219 | 4945 ± 2217 | 6.41 ± 3.63 | 7.61 ± 1.19 | 17.9 ± 9.10 | 8016 ± 1450 |
| 24 | 567 ± 82 | 5311 ± 2030 | 3.46 ± 0.42 | 6.04 ± 1.17 | 17.0 ± 5.88 | 4950 ± 1199 |

5. Experimental conclusion: the preferred compounds of the present invention when administering at a dose of 5 mg/kg, have a better pharmacokinetic absorption in rats, longer half-life, and significant oral absorption effect compared to LY2835219.

Experimental Example 4 Pharmacokinetic Study of Compounds of Example 20 and 60 in Mice 1. Experimental Summary ICR mice were used as test animals, and drug concentration in plasma at different time points was determined by LC/MS/MS method after the mice were intragastrically administered the preferred compounds, to investigate the pharmacokinetics of the compounds of the present invention in mice and to evaluate their pharmacokinetic characteristics.

2. Experimental Protocol 2.1 Test Drugs:

Compounds prepared according to Example 20 and 60 of the present invention;

Control drug LY2835219, self-made.

2.2 Test Animals:

6 to 8-week-old healthy adult male ICR mice, weighing between 20-25 g (3 mice for each test compound which was administered intragastrically, and 3 mice for each test compound which was administered by intravenous injection), were purchased from JOINN Laboratories CO., LTD. (Suzhou), Animal Breeder License No.: SCXK(Su) 2013-0003

2.3 Preparation of Test Compounds

An appropriate amount of sample was weighed, then 0.1% hydroxyethyl cellulose/0.5% Tween 80 was added to final volume to obtain a solution of 0.5 mg/ml for intragastrical administration.

An appropriate amount of sample was weighed, then 10% N-methyl-2-pyrrolidone and 90% of 18% sulfobutyl-β-cyclodextrin were added to final volume to obtain a solution of 0.2 mg/ml for administration by intravenous injection.

2.4 Test Drug Administration

Male ICR mice, 3 for each test compound, were intragastrically administered test drugs at a dose of 5 mg/kg and a drug volume of 10 ml/kg after an overnight fast.

Male ICR mice, 3 for each test compound, were administered by intravenous injection test drugs at a dose of 2 mg/kg and a drug volume of 10 ml/kg after an overnight fast.

3. Experimental Operation

The carotid artery of the animal was catheterized and blood sample was removed prior to dosing and at 0.25, 0.5, 1, 2, 4, 8, 12 and 24 hours after dosing for intragastrical administration group. Whole blood was anticoagulated with EDTA-K2, centrifuged to remove the supernatant, and cryopreserved at −20° C. until being analyzed. The carotid artery of the animal was catheterized and blood sample was removed prior to dosing and at 0.083, 0.25, 0.5, 1, 2, 4, 8, 12 and 24 hours after dosing for i.v. administration group. Plasma sample treatment was the same as intragastrical administration group. Plasma samples, which were pretreated using a protein precipitation method, were analyzed by LC-MS/MS, with a linear range of 1-2000 ng/ml and a minimum limit of quantitation of 1 ng/ml.

4. Pharmacokinetic Data Results: See Table 5.

TABLE 5

Pharmacokinetic parameters of the compounds of the invention in mice

| Example | plasma concentration Cmax (ng/mL) | Area under the curve AUC (ng/mL*h) | Half-life T½ (h) | Retention time MRT (h) | Clearance CL/F (ml/min/kg) | Apparent volume of distribution Vz/F (ml/kg) | Bioavailability F (%) |
|---|---|---|---|---|---|---|---|
| LY2835219 | 154 ± 6.4 i.g. (5 mg/kg) | 756 ± 34 | 1.70 ± 0.02 | 3.08 ± 0.02 | 109 ± 4.97 | 16080 ± 963 | 45.10 |
|  | i.v. (2 mg/kg) | 674 ± 82.1 | 1.68 ± 0.1 | 1.64 ± 0.17 | 49.6 ± 5.72 | 7210 ± 1080 |  |
| 20 | 314 i.g. (5 mg/kg) | 1351 ± 465.2 | 2.23 | 3.36 ± 0.46 | 64.3 ± 18.6 | 12561 ± 5137 | 76.20 |
|  | i.v. (2 mg/kg) | 707 ± 221 | 2.86 ± 0.63 | 2.12 ± 0.60 | 49.9 ± 19.1 | 12800 ± 7220 |  |
| 60 | 186 ± 57.2 i.g. (5 mg/kg) | 1221 ± 123 | 4.77 ± 1.77 | 5.92 ± 0.88 | 66.0 ± 7.21 | 26820 ± 9211 | 80.70 |
|  | i.v. (2 mg/kg) | 611 ± 119.3 | 4.99 ± 0.59 | 5.11 ± 1.19 | 54.2 ± 10.64 | 23400 ± 5690 |  |

5. Experimental conclusion: the preferred compounds of the present invention when administering at a dose of 5 mg/kg, have a better pharmacokinetic absorption in mice and a better bioavailability compared to LY2835219.

In summary, the present invention provides a series of novel compounds with a selectively inhibitory activity on CDK4/6 kinase, which is comparable to activity of LY2835219, a candidate drug currently in Phase III clinical trials, with some compounds exhibiting even better selectivity. Moreover, the good oral absorption of the preferred compounds indicates that the compounds of the present invention are promising to be developed into new drugs for the treatment of diseases associated with cell proliferation, particularly malignancies, providing new options for clinicians and patients.

Kit

The present invention also provides a kit comprising a compound of Formula I-V or its tautomer, mesomer, racemate, enantiomer, diastereoisomer and/or a mixture thereof, or a pharmaceutically acceptable salt or solvate of the compound of Formula I-V, its tautomer, mesomer, racemate, enantiomer, or diastereoisomer.

In addition, said kit may further include instructions for use.

Pharmaceutical Composition

The present invention also relates to a combination for the treatment of a cell proliferative disorder, comprising a pharmaceutically acceptable carrier, and a compound of Formula I-V or its tautomer, mesomer, racemate, enantiomer, diastereoisomer and/or a mixture thereof, or a pharmaceutically acceptable salt or solvate of the compound of Formula I-V, its tautomer, mesomer, racemate, enantiomer, or diastereoisomer. The compound of Formula I-V or its tautomer, mesomer, racemate, enantiomer, diastereoisomer and/or a mixture thereof, or a pharmaceutically acceptable salt or solvate of the compound of Formula I-V, its tautomer, mesomer, racemate, enantiomer, or diastereoisomer may be present in the pharmaceutical composition at an effective amount or at a therapeutically effective amount.

As used herein, "effective amount" refers to an amount that may have function or activity on humans and/or animals and is acceptable to humans and/or animals.

As used herein, "pharmaceutically acceptable" ingredient refers to substances that are suitable for use in humans and/or animals (such as mammals or birds) without undue adverse side effects (such as toxicity, irritation and allergic response), and are commensurate with a reasonable benefit/risk ratio. "Pharmaceutically acceptable carrier" refers to carriers for administration and may include various excipients and diluents and the like. Such carriers may include but are not limited to, water, saline, liposome, lipid, protein, protein-antibody conjugate, peptide, cellulose, nanogel, buffer, dextrose, glycerol, ethanol, and combination thereof. The choice of carriers should generally be compatible with the mode of administration, which is well-known to those of ordinary skill in the art.

The effective amount of the present invention may vary depending on the mode of administration and the severity of the disease to be treated. The preferred effective amount can be determined by those of ordinary skill in the art based on various factors (such as, by clinical trials). Such factors include, but are not limited to, the pharmacokinetic parameters of the active ingredient, such as bioavailability, metabolism, half-life, etc.; the severity of the disease to be treated in the patient, the weight of the patient, the immune status of the patient, administration route and so on.

Therapeutic Method

The present invention also provides a method of treating a cell proliferative disorder, said method comprises administering via an oral or parenteral route to said patient an effective amount of the compound of Formula I-V, and/or its tautomer, mesomer, racemate, enantiomer, diastereoisomer or the mixture thereof, or the pharmaceutically acceptable salt or solvate of the compound of Formula I-V, its tautomer, mesomer, racemate, enantiomer, or diastereoisomer, or the pharmaceutical composition described above.

The oral or parenteral route may be administration via gastrointestinal tract, nasal cavity, trachea, lung, vein or epidermis of the nonlesion site, intradermal route, subcutaneous route, intracardiac route, intramuscular route, myeloid, intraperitoneal route, epidural route, buccal route, sublingual route, ocular route, rectal route, vaginal route, urethra, ear canal and other routes. Preferred mode of administration or mode of dosing includes oral administration, administration via respiratory tract, administration by injection, transdermal administration, mucosal administration, or administration via lumen.

Wherein, oral administration includes ingesting, buccal administration and the like. Administration via respiratory tract includes administration by inhalation, such as ultrasonic aerosol inhalation, oxygen atomization inhalation, hand-pressure inhalation and the like. Administration by injection includes arterial injection, intravenous injection, intramuscular injection, intracardiac injection, intradermal injection and the like. Transdermal administration or percutaneous includes iontophoresis, electroporation and the like. Mucosal administration includes nasal mucosal administration, oral mucosal administration, ophthalmic mucosal administration, rectal mucosal administration, uterine administration, vaginal mucosal administration and the like. Administration via lumen includes rectal administration, vaginal administration, urethral administration, nasal administration, ear canal administration and the like.

All references, including patent documents or non-patent documents, mentioned in the present invention are incorporated herein by reference as if each document was individually incorporated by reference.

While the invention has been illustrated to some extent, it will be apparent that suitable variations of the respective conditions may be made without departing from the spirit and scope of the invention. It is to be understood that the invention is not limited to the embodiments described, but defined by the scope of the claims, which includes equivalents to each described element.

The invention claimed is:

1. A compound, said compound is:

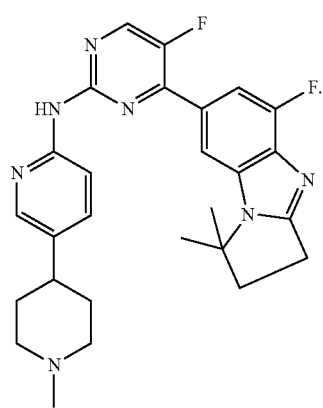 [SMILES: CN1CCC(c2ccc(Nc3ncc(F)c(-c4cc(F)c5nc6n(c5c4)C(C)(C)CC6)n3)nc2)CC1]

2. A combination for the treatment of a cell proliferative disorder mediated by an inhibitor of cell cycle protein kinase CDK4/6, characterized in that, said combination comprises the compound of claim 1 or its tautomer, mesomer, racemate, enantiomer, diastereoisomer and/or a mixture thereof, or a pharmaceutically acceptable salt or solvate of the compound of claim 1, its tautomer, mesomer, racemate, enantiomer, or diastereoisomer;

said combination further comprises a pharmaceutically acceptable excipient; and/or said combination is a kit.

3. The compound of claim 1, or its tautomer, mesomer, racemate, enantiomer, diastereoisomer or a mixture thereof, or a pharmaceutically acceptable salt or solvate of the compound, its tautomer, mesomer, racemate, enantiomer or diastereoisomer for the treatment of a cell proliferative disorder mediated by an inhibitor of cell cycle protein kinase CDK4/6;

said cell proliferative disorder is a malignant solid tumor and malignant non-solid tumor, breast cancer, lung cancer, prostate cancer, leukemia, brain cancer and stomach cancer; and/or said cell proliferative disorder is selected from one or more of AIDS, atherosclerosis and vascular restenosis after stent implantation.

\* \* \* \* \*